(12) United States Patent
Deng et al.

(10) Patent No.: US 9,624,166 B2
(45) Date of Patent: Apr. 18, 2017

(54) TETRACYCLINE COMPOUNDS

(75) Inventors: Yonghong Deng, Watertown, MA (US);
Louis Plamondon, Belmont, MA (US);
Cuixiang Sun, Watertown, MA (US);
Xiao-Yi Xiao, San Diego, CA (US);
Jingye Zhou, Belmont, MA (US);
Joyce A. Sutcliffe, Newton, MA (US);
Magnus P. Ronn, Melrose, MA (US)

(73) Assignee: Tetraphase Pharmaceuticals, Inc.,
Watertown, MA (US)

( * ) Notice: Subject to any disclaimer, the term of this patent is extended or adjusted under 35 U.S.C. 154(b) by 0 days.

(21) Appl. No.: 13/391,407

(22) PCT Filed: Aug. 27, 2010

(86) PCT No.: PCT/US2010/047035
§ 371 (c)(1),
(2), (4) Date: May 2, 2012

(87) PCT Pub. No.: WO2011/025982
PCT Pub. Date: Mar. 3, 2011

(65) Prior Publication Data
US 2012/0208788 A1  Aug. 16, 2012

Related U.S. Application Data

(60) Provisional application No. 61/275,507, filed on Aug. 28, 2009.

(51) Int. Cl.
| | | |
|---|---|---|
| A61K 31/65 | (2006.01) |
| A61P 31/04 | (2006.01) |
| C07C 237/26 | (2006.01) |
| C07C 311/08 | (2006.01) |
| C07C 307/10 | (2006.01) |
| C07C 311/09 | (2006.01) |
| C07C 311/13 | (2006.01) |
| C07C 311/21 | (2006.01) |
| C07C 311/29 | (2006.01) |
| C07C 311/44 | (2006.01) |
| C07D 205/04 | (2006.01) |
| C07D 207/12 | (2006.01) |
| C07D 207/16 | (2006.01) |
| C07D 209/44 | (2006.01) |
| C07D 209/52 | (2006.01) |
| C07D 211/54 | (2006.01) |
| C07D 211/60 | (2006.01) |

(Continued)

(52) U.S. Cl.
CPC .......... *C07C 311/08* (2013.01); *C07C 237/26* (2013.01); *C07C 307/10* (2013.01); *C07C 311/09* (2013.01); *C07C 311/13* (2013.01); *C07C 311/21* (2013.01); *C07C 311/29* (2013.01); *C07C 311/44* (2013.01); *C07D 205/04* (2013.01); *C07D 207/12* (2013.01); *C07D 207/16* (2013.01); *C07D 209/44* (2013.01); *C07D 209/52* (2013.01); *C07D 211/54* (2013.01); *C07D 211/60* (2013.01); *C07D 213/70* (2013.01); *C07D 213/74* (2013.01); *C07D 213/82* (2013.01); *C07D 223/06* (2013.01); *C07D 231/18* (2013.01); *C07D 233/60* (2013.01); *C07D 233/84* (2013.01); *C07D 295/15* (2013.01); *C07D 307/64* (2013.01); *C07C 2101/02* (2013.01); *C07C 2101/04* (2013.01); *C07C 2101/08* (2013.01); *C07C 2101/14* (2013.01); *C07C 2103/40* (2013.01); *C07C 2103/44* (2013.01)

(58) Field of Classification Search
USPC .......................... 514/152; 552/205, 202, 204
See application file for complete search history.

(56) References Cited

U.S. PATENT DOCUMENTS 3,338,963 A  8/1967  Petisi et al.
3,988,468 A  10/1976  Rogalski et al.
(Continued)

FOREIGN PATENT DOCUMENTS

CN  1072172 A  5/1993
CN  1087626 A  6/1994
(Continued)

OTHER PUBLICATIONS

Draper et al. (Abstract, US 20040242548, U.S. Pat. No. 8,088,820; HCAPLUS, AN 2004:2036703).*
(Continued)

*Primary Examiner* — Sabiha N Qazi
(74) *Attorney, Agent, or Firm* — Foley Hoag LLP

(57) ABSTRACT

The present invention is directed to a compound represented by Structural Formula (1): or a pharmaceutically acceptable salt thereof. The variables for Structural Formula (I) are defined herein. Also described is a pharmaceutical composition comprising the compound of Structural Formula (I) and its therapeutic use.

18 Claims, No Drawings

(51) Int. Cl.
*C07D 213/70* (2006.01)
*C07D 213/74* (2006.01)
*C07D 213/82* (2006.01)
*C07D 223/06* (2006.01)
*C07D 231/18* (2006.01)
*C07D 233/60* (2006.01)
*C07D 233/84* (2006.01)
*C07D 295/15* (2006.01)
*C07D 307/64* (2006.01)

(56) References Cited

U.S. PATENT DOCUMENTS

| | | |
|---|---|---|
| 5,284,963 A | 2/1994 | Sum et al. |
| 5,328,902 A | 7/1994 | Sum et al. |
| 5,380,888 A | 1/1995 | Sum et al. |
| 5,386,041 A | 1/1995 | Sum et al. |
| 5,401,729 A | 3/1995 | Sum et al. |
| 5,442,059 A | 8/1995 | Sum et al. |
| 5,466,684 A | 11/1995 | Sum et al. |
| 5,494,903 A | 2/1996 | Hlavka et al. |
| 5,495,031 A | 2/1996 | Sum et al. |
| 5,529,990 A | 6/1996 | Hlavka et al. |
| 5,530,117 A | 6/1996 | Hlavka et al. |
| 5,574,026 A | 11/1996 | Backer et al. |
| 6,841,546 B2 | 1/2005 | Draper et al. |
| 6,914,057 B1 | 7/2005 | Ryan et al. |
| 7,045,507 B2 | 5/2006 | Draper et al. |
| RE40,086 E | 2/2008 | Hlavka et al. |
| RE40,183 E | 3/2008 | Hlavka et al. |
| 7,763,735 B2 | 7/2010 | Myers et al. |
| 7,807,842 B2 | 10/2010 | Myers et al. |
| 7,820,641 B2 | 10/2010 | Nelson et al. |
| 7,825,105 B2 | 11/2010 | Bandarage et al. |
| 7,939,513 B2 * | 5/2011 | Takhi ............... C07D 205/04 514/152 |
| 8,088,820 B2 * | 1/2012 | Draper et al. ............... 514/464 |
| 8,367,654 B2 | 2/2013 | Clark et al. |
| 8,501,716 B2 * | 8/2013 | Zhou et al. ............... 514/152 |
| 8,796,245 B2 * | 8/2014 | Zhou et al. ............... 514/152 |
| 8,828,988 B2 * | 9/2014 | Clark et al. ............... 514/210.21 |
| 8,906,887 B2 * | 12/2014 | Zhou et al. ............... 514/152 |
| 9,315,451 B2 * | 4/2016 | Chen ............... C07C 237/26 |
| 2004/0063674 A1 | 4/2004 | Levy et al. |
| 2004/0092490 A1 | 5/2004 | Draper et al. |
| 2004/0214800 A1 | 10/2004 | Levy et al. |
| 2004/0242548 A1 * | 12/2004 | Draper et al. ............... 514/152 |
| 2005/0143352 A1 * | 6/2005 | Nelson ............... C07C 237/26 514/152 |
| 2006/0166944 A1 | 7/2006 | Berniac et al. |
| 2006/0183720 A1 | 8/2006 | Sum et al. |
| 2006/0194773 A1 | 8/2006 | Levy et al. |
| 2006/0281717 A1 | 12/2006 | Berniac et al. |
| 2007/0093455 A1 | 4/2007 | Abato et al. |
| 2008/0015169 A1 | 1/2008 | Nelson et al. |
| 2008/0070873 A1 | 3/2008 | Alekshun et al. |
| 2008/0118979 A1 * | 5/2008 | Draper et al. ............... 435/375 |
| 2009/0118269 A1 | 5/2009 | Berniac et al. |
| 2009/0257985 A1 * | 10/2009 | Nelson et al. ............... 424/93.7 |
| 2010/0022483 A1 | 1/2010 | Berniac et al. |
| 2010/0105671 A1 | 4/2010 | Zhou et al. |
| 2011/0009371 A1 | 1/2011 | Myers et al. |
| 2011/0269714 A1 | 11/2011 | Xiao-Yi et al. |
| 2012/0108569 A1 | 5/2012 | Clark et al. |
| 2012/0135968 A1 * | 5/2012 | Chen et al. ............... 514/152 |
| 2012/0208788 A1 | 8/2012 | Deng et al. |
| 2012/0302527 A1 | 11/2012 | Zhou et al. |
| 2013/0109657 A1 | 5/2013 | Zhou et al. |
| 2013/0345178 A1 | 12/2013 | Clark et al. |

FOREIGN PATENT DOCUMENTS

| | | |
|---|---|---|
| CN | 1090267 A | 8/1994 |
| CN | 1034216 C | 3/1997 |
| CN | 1653037 A | 8/2005 |
| CN | 1845897 A | 10/2006 |
| CN | 101027279 A | 8/2007 |
| EP | 0 536 515 | 4/1993 |
| EP | 0 582 789 A1 | 2/1994 |
| EP | 0 582 810 A1 | 2/1994 |
| EP | 0 618 190 A1 | 10/1994 |
| EP | 2301916 A2 | 3/2011 |
| GB | 935 384 | 8/1963 |
| GB | 1 034 933 | 7/1966 |
| JP | 51-41362 | 4/1976 |
| JP | 2004-502753 | 1/2004 |
| JP | 2005-520846 | 7/2005 |
| JP | 2008-530106 | 8/2008 |
| TW | 275616 B | 5/1996 |
| TW | I299038 B | 7/2008 |
| WO | WO 99/37307 A1 | 7/1999 |
| WO | WO 00/18353 | 4/2000 |
| WO | WO 01/98260 A1 | 12/2001 |
| WO | WO 02/04404 A2 | 1/2002 |
| WO | WO 02/04407 A2 | 1/2002 |
| WO | WO 02/072022 A2 | 9/2002 |
| WO | WO 02/072031 A2 | 9/2002 |
| WO | WO 02/085303 A2 | 10/2002 |
| WO | WO 03/005971 A2 | 1/2003 |
| WO | WO 03/079984 A2 | 10/2003 |
| WO | WO 2004/006850 A2 | 1/2004 |
| WO | WO 2004/038000 A2 | 5/2004 |
| WO | WO 2004/038001 A2 | 5/2004 |
| WO | WO 2005/009943 A2 | 2/2005 |
| WO | WO 2005/112945 A2 | 12/2005 |
| WO | WO 2006/047671 A2 | 5/2006 |
| WO | WO 2006/084265 A1 | 8/2006 |
| WO | WO 2006/088720 A2 | 8/2006 |
| WO | WO 2007/087416 A2 | 8/2007 |
| WO | WO 2007/117639 A2 | 10/2007 |
| WO | WO 2007/133798 A2 | 11/2007 |
| WO | WO-2008/045507 A2 | 4/2008 |
| WO | WO 2008/045507 A2 | 4/2008 |
| WO | WO 2008/127361 A2 | 10/2008 |
| WO | WO 2008/127722 A1 | 10/2008 |
| WO | WO 2009/073056 A1 | 6/2009 |
| WO | WO 2009/128913 A1 | 10/2009 |
| WO | WO 2010/017470 | 2/2010 |
| WO | WO 2010/126607 A2 | 11/2010 |
| WO | WO 2010/129055 | 11/2010 |
| WO | WO 2010/129057 | 11/2010 |
| WO | WO 2011/025982 | 3/2011 |
| WO | WO 2012/021712 | 2/2012 |
| WO | WO 2012/047907 A1 | 4/2012 |
| WO | WO 2014/036502 A2 | 3/2014 |

OTHER PUBLICATIONS

Nelson et al. (Abstract WO 2005009943, (US 2005/0143352), AN 2005:99455, HCAPLUS).*
Notice of Allowance, U.S. Appl. No. 13/570,837, Dated: Jun. 6, 2013.
Office Action dated Dec. 7, 2011 for U.S. Appl. No. 12/462,795.
Abbanat, D., et al., "New agents in development for the treatment of bacterial infections", *Current Opinion in Pharmacology*, 8(5): 582-592 (Oct. 1, 2008).
Charest, M.G., et al., "A Convergent Enantioselective Route to Structurally Diverse 6-Deoxytetracycline Antibiotics", *Science*, vol. 308, p. 395-398 (Apr. 15, 2005).
Hlavka, J.J., et al., "The 6-Deoxytetracyclines. IV. A Photochemical Displacement of a Diazonium Group," Organic Chemical Research Section, vol. 27, pp. 3674-3675 (1962).
International Preliminary Report on Patentability for International Application No. PCT/US2010/001350; Date Mailed: Nov. 9, 2011.
International Preliminary Report on Patentability for International Application No. PCT/US2010/047035; Date Mailed: Feb. 28, 2012.
Notification Concerning Transmittal of International Preliminary Report on Patentability for International Application No. PCT/US2009/053142 dated Feb. 17, 2011.

(56) References Cited

OTHER PUBLICATIONS

Notification of Transmittal of International Search Report and the Written Opinion of the International Search Authority, or the Declaration, in International Application No. PCT/US2010/047035; Date mailed: Jul. 22, 2011.
Notification of Transmittal of the International Search Report and the Written Opinion of the International Searching Authority, or the Declaration, in International Application No. PCT/US2010/001350, 13 pages, date of mailing Nov. 23, 2010.
Notification of Transmittal of the International Search Report and the Written Opinion of the International Searching Authority, or the Declaration, in International Application No. PCT/US2011/047428, 4 pages, date of mailing Jan. 6, 2012.
Podlogar, B., L., et al., "Patents on tetracycline and tetracyline derivatives as antimicrobials", *Expert Opin. Ther. Patents*, 13(4): 467-478 (2003).
Sato, F., et al. "Structure-Activity Relationship Investigation of Some New Tetracyclines by Electronic Index Methodology", *Los Alamos National Laboratory*, Quantitative Biology, 1-18 (Aug. 21, 2007).
Sun, C., et al., "A Robust Platform for the Synthesis of New Tetracycline Antibiotics,", *J. Am. Chem.Soc.*, 130:17913-17927 (2008).
Verma, A.K., et al., "Antibiotic and non-antibiotic tetracycline patents", *Expert Opin. Ther. Patents*, vol. 18, pp. 69-82 (2008).
Notification of Transmittal of the International Search Report and the Written Opinion of the International Searching Authority, or the Declaration for International Application No. PCT/US2009/053142; Date Mailed: Oct. 13, 2009.
Chopra, I. and Roberts, M., "Tetracycline Antibiotics: Mode of Action, Applications, Molecular Biology, and Epidemiology of Bacterial Resistance," Microbiology and Molecular Biology Reviews, 65(2): 232-260 (2001).
Office Action, U.S. Appl. No. 13/718,909, Dated: Jul. 9, 2013.
Office Action, U.S. Appl. No. 12/462,795, Dated: Sep. 23, 2013.
Charest, M.G., et al., "A Convergent Enantioselective Route to Structurally Diverse 6-Deoxytetracycline Antibiotics," Science, 308: 395-398 (2005).
Notification Concerning Transmittal of International Preliminary Report on Patentability for International Application No. PCT/US2011/047428; Date Mailed: Feb. 21, 2013.
Office Action, U.S. Appl. No. 12/462,795, Dated: Jan. 24, 2012.
Office Action, U.S. Appl. No. 12/462,795, Dated: Jul. 24, 2012.
Office Action, U.S. Appl. No. 13/570,837, Dated: Feb. 4, 2013.
Office Action, U.S. Appl. No. 13/718,909, Dated: Feb. 5, 2013.
Pre Appeal Brief Conference Decision, U.S. Appl. No. 12/462,795, Dated: Feb. 19, 2013.
Esse, R., et al., "Tetracycloxides. II. Transformations at the C-4 Position", Journal of the American Chemical Society, 86(18): 3875-3877 (Sep. 20, 1964).
International Search Report for International Application No. PCT/US2013/057690, "Tetracycline Compounds", Date of Mailing: Feb. 24, 2014.
Office Action dated Jan. 16, 2014 for U.S. Appl. No. 13/319,298, "Tetracycline Compounds".
Office Action dated Jan. 17, 2014 for U.S. Appl. No. 12/462,795, "C7-Fluoro Substituted Tetracycline Compounds".
Extended Search Report for European Patent Application No. 13172357.9 dated May 16, 2014 "C7-Fluoro Substituted Tetracycline Compounds".
International Preliminary Report on Patentability for International Application No. PCT/US2013/057690, "Tetracycline Compounds", Date of Issuance: Mar. 3, 2015.
Notice of Allowance, U.S. Appl. No. 12/462,795, entitled: "C7-Fluoro Substituted Tetracycline Compounds" Dated: Aug. 4, 2014.
Notice of Allowance dated Jun. 5, 2014 for U.S. Appl. No. 13/718,909, entitled "C7-Fluro Substituted Tetracycline Compounds".
Final Office Action dated Aug. 25, 2014 for U.S. Appl. No. 13/319,298 "Tetracycline Compounds".
Martin, W., et al., "Totalsynthese von d, 1-7-Chlor-6-desoxytetracyclinen und d, 1-7-Chlor-6-desmethyl-6-desoxytetracyclinen der naturlichen, der 5a-epi- und der 6-epi-Reihe", Tetrahedron Letters, pp. 3513-3516 (Dec. 31, 1975); and English translation.
Office Action, U.S. Appl. No. 13/319,298; Dated: Apr. 27, 2015.
Notice of Allowance dated Dec. 1, 2015 for U.S. Appl. No. 13/319,298, entitled "Tetracycline Compounds".
Office Action, U.S. Appl. No. 13/319,298, Dated: Aug. 25, 2014.
HCAPLUS, Accession No. 2004:1036703, Document No. 141:420412 (Apr. 24, 2002).
HCAPLUS, Accession No. 2005:99455, Document No. 142:197754 (Jun. 25, 2004).
Huel, Christiane, et al., "Synthesis of 1-Functionalized-6-hydroxy-4-methyl and 6, 11-Dihydroxy-4-methylnaphtho[2,3-g]isoquinoline-5, 12-quinoes," J. Heterocyclic Chem., 28:67-71 (1991).
Notice of Allowance, U.S. Appl. No. 13/731,753, Dated: May 1, 2014.
Notification Concerning Transmittal of International Preliminary Report on Patentability for International Application No. PCT/US2010/001348, Date of Mailing: Nov. 17, 2011.
International Search Report and Written Opinion of the International Searching Authority for International Application No. PCT/US2010/001348, Date of Mailing: Jul. 19, 2010.
Sun, C. et al., Synthesis and Antibacterial Activity of Pentacyclines: A Novel Class of Tetracycline Analogs. J. Med. Chem., Apr. 18, 2011, vol. 54, No. 11, pp. 3704-3731.

* cited by examiner

TETRACYCLINE COMPOUNDS

RELATED APPLICATION

This application is the U.S. National Stage of International Application No. PCT/US2010/047035, filed Aug. 27, 2010, which designates the U.S., published in English, and claims the benefit of U.S. Provisional Application No. 61/275,507, filed Aug. 28, 2009. The entire teachings of the above applications are incorporated herein by reference.

BACKGROUND OF THE INVENTION

The tetracyclines are broad spectrum anti-microbial agents that are widely used in human and veterinary medicine. The total production of tetracyclines by fermentation or semi-synthesis is measured in the thousands of metric tons per year.

The widespread use of tetracyclines for therapeutic purposes has led to the emergence of resistance to these antibiotics, even among highly susceptible bacterial species. Therefore, there is need for new tetracycline analogs with improved antibacterial activities and efficacies against other tetracycline responsive diseases or disorders.

SUMMARY OF THE INVENTION

One embodiment of the present invention is directed to a compound represented by Structural Formula (I):

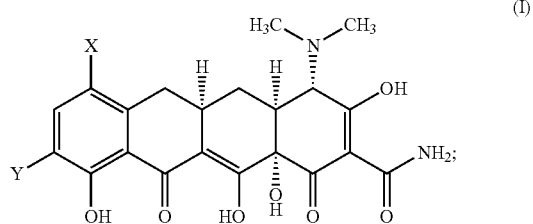

or a pharmaceutically acceptable salt thereof.

X is selected from $-CF_3$, $-CN$, $-OCF_3$ and $-OCH_3$.

Y is selected from hydrogen, $-(C_1-C_7)$alkyl, carbocyclyl, $-(C_1-C_4)$alkylene-$N(R^2)(R^3)$, $-(C_1-C_4)$alkylene-$N(R^F)-C(O)-[C(R^{5a})(R^{5b})]_{0-4}-N(R^2)(R^3)$, $-CH=N-OR^2$, $-C(O)-N(R^2)(R^4)$, $-NO_2$, $-COOH$, $-OH$, $-N=CH-N(R^2)(R^3)$, $-N(R^2)(R^3)$, $-N(R^F)-C(O)-[C(R^{5a})(R^{5b})]_{1-4}-N(R^2)(R^3)$, $-N(R^F)-C(O)-N(R^2)(R^3)$, $-N(R^F)-C(O)-(C_1-C_6)$alkyl, $-N(R^F)-C(O)$-heterocyclyl, $-N(R^F)-C(O)$-carbocyclyl, $-N(R^F)-S(O)_m-(C_1-C_4)$alkylene-$N(R^2)(R^3)$, $-N(R^F)-S(O)_m-N(R^2)(R^4)$, and $-N(R^F)-S(O)_m-(C_1-C_4)$alkylene-carbocyclyl.

Each $R^2$ and $R^3$ are independently selected from hydrogen, $(C_1-C_7)$alkyl, $-O-(C_1-C_7)$alkyl, $-(C_0-C_6)$ alkylene-carbocyclyl, $-(C_0-C_6)$alkylene-heterocyclyl, $-(C_1-C_6)$alkylene-O-carbocyclyl, $-(C_1-C_6)$alkylene-O-heterocyclyl, $-S(O)_m$, $-(C_1-C_6)$alkyl, $-(C_0-C_4)$alkylene-$S(O)_m$-carbocyclyl, and $-(C_0-C_4)$alkylene-$S(O)_m$-heterocyclyl.

Each $R^4$ is independently selected from hydrogen, $(C_1-C_6)$alkyl, $-O-(C_1-C_6)$alkyl, $-(C_0-C_6)$ alkylene-carbocyclyl and $-(C_0-C_6)$alkylene-heterocyclyl.

Each $R^{5a}$ and each $R^{5b}$ is independently selected from hydrogen, $(C_1-C_6)$alkyl, carbocyclyl, heterocyclyl, or a naturally occurring amino acid side chain moiety, or $R^{5a}$ and $R^{5b}$ taken together with the carbon atom to which they are bound form a 3-7 membered non-aromatic carbocyclyl or a 4-7 membered non-aromatic heterocyclyl, wherein the heterocyclyl formed by $R^{5a}$ and $R^{5b}$ optionally comprises one to two additional heteroatoms independently selected from N, S and O.

$R^F$ is selected from hydrogen, $(C_1-C_7)$alkyl, carbocyclyl or heteroaryl

Alternatively, $R^2$ and $R^3$, taken together with the nitrogen atom to which they are bound form a heterocyclyl, wherein the heterocyclyl optionally comprises 1 to 4 additional heteroatoms independently selected from N, S and O.

Each carbocyclyl or heterocyclyl described above (e.g., in the groups represented by Y, $R^2$, $R^3$, $R^4$, $R^{5a}$, $R^{5b}$, $-NR^2R^3$ or $R^{5a}$ and $R^{5b}$ taken together) is optionally and independently substituted with one or more substituents independently selected from halo (e.g., chloro or fluoro), $-(C_1-C_4)$ alkyl, $-OH$, $=O$, $-O-(C_1-C_4)$alkyl, $-(C_1-C_4)$alkylene-$O-(C_1-C_4)$alkyl, halo-substituted-$(C_1-C_4)$alkyl, halo-substituted-$O-(C_1-C_4)$alkyl, $-C(O)-(C_1-C_4)$alkyl, $-C(O)$-(fluoro-substituted-$(C_1-C_4)$alkyl), $-S(O)_m-(C_1-C_4)$alkyl, $-N(R^G)(R^G)$ and CN.

The heterocyclyl in $-N(R^F)-C(O)$-heterocyclyl represented by Y is optionally substituted with carbocyclyl or heterocyclyl in addition to the substituents described above, wherein the carbocyclyl or heterocyclyl is optionally substituted with one or more substituents independently selected from halo (e.g., chloro or fluoro), $(C_1-C_4)$alkyl, $-OH$, $=O$, $-O-(C_1-C_4)$alkyl, $-(C_1-C_4)$alkylene-O-$(C_1-C_4)$alkyl, halo-substituted-$(C_1-C_4)$alkyl, halo-substituted-$O-(C_1-C_4)$alkyl, $-C(O)-(C_1-C_4)$alkyl, $-C(O)$-(fluoro-substituted-$(C_1-C_4)$alkyl), $-S(O)_m-(C_1-C_4)$alkyl, $-N(R^G)(R^G)$ and CN.

Each alkyl described above (e.g., in the groups represented by Y, $R^2$, $R^3$, $R^4$, $R^{5a}$ or $R^{5b}$) is optionally and independently substituted with one or more substituents independently selected from halo (e.g., fluoro or chloro), $-(C_1-C_4)$alkyl, $-OH$, $-O-(C_1-C_4)$alkyl, $-(C_1-C_4)$alkylene-O-$(C_1-C_4)$alkyl, fluoro-substituted-$(C_1-C_4)$alkyl, $-S(O)_m-(C_1-C_4)$alkyl and $-N(R^G)(R^G)$.

Each $R^G$ is hydrogen or $(C_1-C_4)$alkyl, wherein each alkyl in the group represented by $R^G$ is optionally and independently substituted with one or more substituents independently selected from $-(C_1-C_4)$alkyl, $(C_3-C_6)$cycloalkyl, halo, $-OH$, $-O-(C_1-C_4)$alkyl, and $-(C_1-C_4)$alkylene-O-$(C_1-C_4)$alkyl.

Each m is 1 or 2.

Another embodiment of the present invention is directed to a pharmaceutical composition comprising a pharmaceutically acceptable carrier or diluent and a compound represented by Structural Formula (I) or a pharmaceutically acceptable salt thereof. The pharmaceutical composition is used in therapy, such as treating an infection (e.g., a bacterial infection) in a subject.

Another embodiment of the present invention is a method of treating an infection (e.g., a bacterial infection) in a subject comprising administering to the subject an effective amount of a compound represented by Structural Formula (I) or a pharmaceutically acceptable salt thereof.

Another embodiment of the present invention is a method of preventing an infection (e.g., a bacterial infection) in a subject comprising administering to the subject an effective amount of a compound represented by Structural Formula (I) or a pharmaceutically acceptable salt thereof.

Another embodiment of the present invention is the use of a compound represented by Structural Formula (I) or a pharmaceutically acceptable salt thereof for the manufacture of a medicament for treating an infection (e.g., a bacterial infection) in a subject.

Another embodiment of the present invention is the use of a compound represented by Structural Formula (I) or a pharmaceutically acceptable salt thereof for the manufacture of a medicament for preventing an infection (e.g., a bacterial infection) in a subject.

Another embodiment of the present invention is the use of a compound represented by Structural Formula (I) or a pharmaceutically acceptable salt thereof in therapy, such as treating or preventing an infection (e.g., a bacterial infection) in a subject.

DETAILED DESCRIPTION OF THE INVENTION

The present invention is directed to a compound represented by Structural Formula (I) or a pharmaceutically acceptable salt thereof. Values and alternative values for the variables in Structural Formula (I) and for each of the embodiments described herein are defined as the following:

X is selected from —CF$_3$, —CN, —OCF$_3$ and —OCH$_3$, Alternatively, X is —CF$_3$. In another alternative, X is —CN. In another alternative, X is —OCF$_3$. In another alternative, X is —OCH$_3$, Y is selected from hydrogen, —(C$_1$-C$_7$)alkyl, carbocyclyl, —(C$_1$-C$_4$)alkylene-N(R$^2$)(R$^3$), —(C$_1$-C$_4$)alkylene-N(R$^F$)—C(O)—[C(R$^{5a}$)(R$^{5b}$)]$_{0-4}$—N(R$^2$)(R$^3$), —CH=N—OR$^2$, —C(O)—N(R$^2$)(R$^4$), —NO$_2$, —COOH, —OH, —N=CH—N(R$^2$)(R$^3$), —N(R$^2$)(R$^3$), —N(R$^F$)—C(O)—[C(R$^{5a}$)(R$^{5b}$)]$_{1-4}$—N(R$^2$)(R$^3$), —N(R$^F$)—C(O)—N(R$^2$)(R$^3$), —N(R$^F$)—C(O)—(C$_1$-C$_6$)alkyl, —N(R$^F$)—C(O)-heterocyclyl, —N(R$^F$)—C(O)-carbocyclyl, —N(R$^F$)—S(O)$_m$—(C$_1$-C$_4$)alkylene-N(R$^2$)(R$^3$), —N(R$^F$)—S(O)$_m$—N(R$^2$)(R$^4$), and —N(R$^F$)—S(O)$_m$—(C$_1$-C$_4$)alkylene-carbocyclyl. In one embodiment, Y is selected from hydrogen, —(C$_1$-C$_4$)alkylene-N(R$^2$)(R$^3$), —C(O)—N(R$^2$)(R$^4$), —NO$_2$, —COOH, —OH, —N=CH—N(R$^2$)(R$^3$), —N(R$^2$)(R$^3$), —N(R$^F$)—C(O)—[C(R$^{5a}$)(R$^{5b}$)]$_{1-4}$—N(R$^2$)(R$^3$), —N(R$^F$)—C(O)—(C$_1$-C$_6$)alkyl, —N(R$^F$)—C(O)-heterocyclyl, —N(R$^F$)—C(O)-carbocyclyl, —N(R$^F$)—S(O)$_m$—(C$_1$-C$_4$) alkylene-N(R$^2$)(R$^3$), —N(R$^F$)—S(O)$_m$—N(R$^2$)(R$^4$), and —N(R$^F$)—S(O)$_m$—(C$_1$-C$_4$)alkylene-carbocyclyl, wherein R$^F$ in the groups represented by Y is hydrogen or (C$_1$-C$_3$)alkyl. Alternatively, Y is selected from hydrogen, —N(R$^2$)(R$^3$), —NH—C(O)—(CH$_2$)$_{1-4}$—N(R$^2$)(R$^3$), —NH—C(O)-heterocyclyl, —NH—C(O)-carbocyclyl, and —NH—S(O)$_2$—(C$_1$-C$_6$)alkyl. In another alternative, Y is selected from hydrogen, —NH$_2$, —NH—C(O)—CH$_2$—N(R$^2$)(R$^3$),

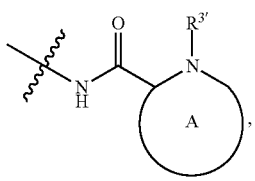

—NH—C(O)-phenyl, —NH—C(O)-thienyl and —NH—S(O)$_2$—(C$_1$-C$_6$)alkyl, wherein ring A represents a 4-7 membered saturated heterocyclyl and R$^{3'}$ is hydrogen, (C$_1$-C$_6$) alkyl, carbocyclyl or heterocyclyl, wherein the alkyl, carbocyclyl or heterocyclyl are optionally and independently substituted with one or more substituents independently selected from the group described above for Structural Formula (I). In another alternative, Y is selected from —NH—C(O)—CH$_2$—N(R$^2$)(R$^3$),

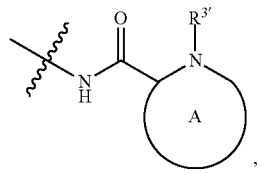

and —NH—S(O)$_2$—(C$_1$-C$_6$)alkyl, wherein ring A and R$^{3'}$ are as described above; and the alkyl group in —NH—S(O)$_2$—(C$_1$-C$_6$)alkyl is optionally substituted with fluoro. In another alternative, Y is selected from —NH$_2$, —NH—C(O)—CH$_2$—N(R$^2$)(R$^3$),

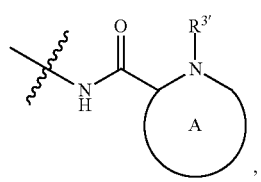

—NH—C(O)-phenyl and —NH—C(O)-thienyl, wherein ring A and R$^{3'}$ are as described above; and the phenyl in the —NH—C(O)-phenyl group is optionally substituted with —OCH$_3$ or —N(CH$_3$)$_2$. In another alternative, Y is selected from —NH$_2$, —NH—C(O)—CH$_2$—N(R$^2$)(R$^3$), and

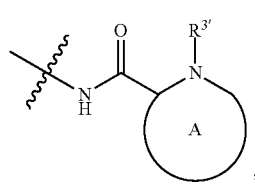

wherein ring A and R$^{3'}$ are as described above.

Each R$^2$ and R$^3$ are independently selected from hydrogen, (C$_1$-C$_7$)alkyl, —O—(C$_1$-C$_7$)alkyl, —(C$_0$-C$_6$) alkylene-carbocyclyl, —(C$_0$-C$_6$)alkylene-heterocyclyl, —(C$_1$-C$_6$) alkylene-O-carbocyclyl, —(C$_1$-C$_6$)alkylene-O-heterocyclyl, —S(O)$_m$—(C$_1$-C$_6$)alkyl, —(C$_0$-C$_4$)alkylene-S(O)$_m$-carbocyclyl, and —(C$_0$-C$_4$)alkylene-S(O)$_m$-heterocyclyl.

In one embodiment, each R$^2$ is independently selected from hydrogen, and (C$_1$-C$_3$)alkyl; and each R$^3$ is independently selected from hydrogen, (C$_1$-C$_6$)alkyl, —O—(C$_1$-C$_6$) alkyl, —(C$_0$-C$_6$) alkylene-carbocyclyl, —(C$_0$-C$_6$)alkylene-heterocyclyl, —S(O)$_m$—(C$_1$-C$_6$)alkyl, —S(O)$_m$-carbocyclyl and —S(O), heterocyclyl; or R$^2$ and R$^3$, taken together with the nitrogen atom to which they are bound form a heterocyclyl, wherein the heterocyclyl optionally comprises 1 to 4 additional heteroatoms independently selected from N, S and O.

Alternatively, each R$^2$ is independently selected from hydrogen and (C$_1$-C$_3$)alkyl; and each R$^3$ is independently selected from hydrogen, (C$_1$-C$_6$)alkyl, and —(C$_0$-C$_6$)alkylene-carbocyclyl; or R$^2$ and R$^3$ taken together with the nitrogen atom to which they are bound form a heterocyclyl, wherein the heterocyclyl optionally comprises 1 to 4 additional heteroatoms independently selected from N, S and O.

In another alternative, each R$^2$ is independently selected from hydrogen, and (C$_1$-C$_2$)alkyl; and each R$^3$ is independently selected from hydrogen, (C$_1$-C$_6$)alkyl, and —(C$_0$-C$_1$)

alkylene-cycloalkyl; or $R^2$ and $R^3$ taken together with the nitrogen atom to which they are bound form a saturated heterocyclyl.

In another alternative, each $R^2$ is independently selected from hydrogen and —$CH_3$; and each $R^3$ is independently selected from ($C_1$-$C_6$)alkyl, and —($C_0$-$C_1$)alkylene-carbocyclyl; or $R^2$ and $R^3$, taken together with the nitrogen atom to which they are bound form a saturated heterocyclyl optionally substituted with fluoro. In another alternative, each $R^2$ is independently selected from hydrogen and —$CH_3$; and each $R^3$ is independently selected from ($C_1$-$C_6$) alkyl optionally substituted with fluoro or —$OCH_3$, and —($C_0$-$C_1$)alkylene-carbocyclyl; or $R^2$ and $R^3$, taken together with the nitrogen atom to which they are bound form a saturated heterocyclyl optionally substituted with fluoro or —$OCH_3$.

Each $R^4$ is independently selected from hydrogen, ($C_1$-$C_6$)alkyl, —O—($C_1$-$C_6$)alkyl, —($C_0$-$C_6$) alkylene-carbocyclyl, and —($C_0$-$C_6$)alkylene-heterocyclyl.

Each $R^{5a}$ and each $R^{5b}$ is independently selected from hydrogen, ($C_1$-$C_6$)alkyl, carbocyclyl, heterocyclyl or a naturally occurring amino acid side chain moiety, or $R^{5a}$ and $R^{5b}$ taken together with the carbon atom to which they are bound form a 3-7 membered non-aromatic carbocyclyl or a 4-7 membered non-aromatic heterocyclyl, wherein the heterocyclyl formed by $R^{5a}$ and $R^{5b}$ optionally comprises one to two additional heteroatoms independently selected from N, S and O. In one embodiment, $R^{5a}$ and $R^{5b}$ taken together with the carbon atom to which they are bound form a 3-7 membered saturated carbocyclyl or a 4-7 membered saturated heterocyclyl, wherein the heterocyclyl formed by $R^{5a}$ and $R^{5b}$ optionally comprises one to two additional heteroatoms independently selected from N, S and O. In one embodiment, each $R^{5a}$ and each $R^{5b}$ is independently hydrogen, ($C_1$-$C_6$)alkyl or a naturally occurring amino acid side chain moiety. In another embodiment, $R^{5a}$ and $R^{5b}$ are both hydrogen.

Each carbocyclyl or heterocyclyl described above (e.g., in the groups represented by Y, $R^3$, $R^4$, $R^{5a}$, $R^{5b}$, —$NR^2R^3$ or $R^{5a}$ and $R^{5b}$ taken together) is optionally and independently substituted with one or more substituents independently selected from halo (e.g., chloro or fluoro), —($C_1$-$C_4$)alkyl, —OH, =O, —O—($C_1$-$C_4$)alkyl, —($C_1$-$C_4$)alkylene-O—($C_1$-$C_4$)alkyl, halo-substituted-($C_1$-$C_4$)alkyl, halo-substituted-O—($C_1$-$C_4$)alkyl, —C(O)—($C_1$-$C_4$)alkyl, —C(O)-(fluoro-substituted-($C_1$-$C_4$)alkyl), —S(O)$_m$—($C_1$-$C_4$)alkyl —N($R^G$)($R^G$) and CN. The heterocyclyl in —N($R^F$)—C(O)-heterocyclyl represented by Y is optionally substituted with carbocyclyl or heterocyclyl in addition to the substituents described above, wherein the carbocyclyl or heterocyclyl is optionally substituted with one or more substituents independently selected from chloro, fluoro, ($C_1$-$C_4$)alkyl, —OH, —O—($C_1$-$C_4$)alkyl, fluoro-substituted-($C_1$-$C_4$)alkyl, —C(O)—($C_1$-$C_4$)alkyl, —C(O)-(fluoro-substituted-($C_1$-$C_4$) alkyl), and —N($R^G$)($R^G$).

In one embodiment, each carbocyclyl, or heterocyclyl described above is optionally and independently substituted with one or more substituents independently selected from chloro, fluoro, ($C_1$-$C_4$)alkyl, —OH, —O—($C_1$-$C_4$)alkyl, fluoro-substituted-($C_1$-$C_4$)alkyl, —C(O)—($C_1$-$C_4$)alkyl, —C(O)-(fluoro-substituted-($C_1$-$C_4$)alkyl, and —N($R^2$)($R^2$).

Each alkyl described above (e.g., in the groups represented by Y, $R^2$, $R^3$, $R^4$, $R^{5a}$ or $R^{5b}$) is optionally and independently substituted with one or more substituents independently selected from halo (e.g., fluoro or chloro), —($C_1$-$C_4$)alkyl, —OH, —O—($C_1$-$C_4$)alkyl, —($C_1$-$C_4$)alkylene-O—($C_1$-$C_4$)alkyl, fluoro-substituted-($C_1$-$C_4$)alkyl, —S(O)$_m$—($C_1$-$C_4$)alkyl and —N($R^G$)($R^G$).

In one embodiment, each alkyl described above is optionally and independently substituted with one or more substituents independently selected from fluoro, chloro, —O—($C_1$-$C_4$)alkyl, and fluoro-substituted-($C_1$-$C_4$)alkyl.

Alternatively, each carbocyclyl (e.g., cycloalkyl or phenyl), or heterocyclyl described above is optionally and independently substituted with one or more substituents independently selected from fluoro, ($C_1$-$C_4$)alkyl, —O—($C_1$-$C_4$)alkyl, fluoro-substituted-($C_1$-$C_4$)alkyl, and —N($R^G$)($R^G$); and each alkyl described above is optionally and independently substituted with one or more substituents independently selected from fluoro, —O—($C_1$-$C_4$)alkyl, and fluoro-substituted-($C_1$-$C_4$)alkyl.

Alternatively, each carbocyclyl described above is ($C_3$-$C_6$)cycloalkyl or phenyl; each heterocyclyl described above is independently selected from azetidinyl, morphinyl, piperazinyl, piperidinyl, pyrrolidinyl, azepanyl and octahydrocyclopenta[c]pyrrolyl and thienyl; each of said carbocyclyl, cycloalkyl, heterocyclyl and phenyl is optionally substituted as described in the previous paragraph; and each said alkyl is optionally substituted as described in the previous paragraph.

Each $R^G$ is hydrogen or ($C_1$-$C_4$)alkyl, wherein each alkyl in the group represented by $R^G$ is optionally and independently substituted with one or more substituents independently selected from —($C_1$-$C_4$)alkyl, ($C_3$-$C_6$)cycloalkyl, halo, —OH, —O—($C_1$-$C_4$)alkyl, and —($C_1$-$C_4$)alkylene-O—($C_1$-$C_4$)alkyl.

Each m is 1 or 2. In one embodiment, m is 2.

In a first alternative embodiment, the compound of the present invention is represented by Structural Formula (I), or a pharmaceutically acceptable salt thereof, wherein:

X is selected from —$CF_3$, —CN, —$OCF_3$ and —$OCH_3$; and

Y is selected from hydrogen, —($C_1$-$C_4$)alkylene-N($R^2$)($R^3$), —CH=N—$OR^2$, —C(O)—N($R^2$)($R^4$), —$NO_2$, —COOH, —OH, —N=CH—N($R^2$)($R^3$), —N($R^2$)($R^3$), —N($R^F$)—C(O)—[C($R^{5a}$)($R^{5b}$)]$_{1-4}$—N($R^2$)($R^3$), —N($R^F$)—C(O)—($C_1$-$C_6$)alkyl, —N($R^F$)—C(O)-heterocyclyl, —N($R^F$)—C(O)-carbocyclyl, —N($R^F$)—S(O)$_m$—($C_1$-$C_4$)alkylene-N($R^2$)($R^3$), —N($R^F$)—S(O)$_m$—N($R^2$)($R^4$), and —N($R^F$)—S(O)$_m$—($C_1$-$C_4$)alkylene-carbocyclyl, wherein R' in the groups represented by Y is hydrogen or ($C_1$-$C_3$) alkyl.

each $R^2$ is independently selected from hydrogen, and ($C_1$-$C_3$)alkyl;

each $R^3$ is independently selected from hydrogen, ($C_1$-$C_6$)alkyl, —O—($C_1$-$C_6$)alkyl, —($C_0$-$C_6$) alkylene-carbocyclyl, —($C_0$-$C_6$)alkylene-heterocyclyl, —S(O)$_m$—($C_1$-$C_6$) alkyl, —S(O)$_m$-carbocyclyl, and —S(O)$_m$-heterocyclyl; or $R^2$ and $R^3$, taken together with the nitrogen atom to which they are bound form a heterocyclyl, wherein the heterocyclyl optionally comprises 1 to 4 additional heteroatoms independently selected from N, S and O.

each $R^4$ is independently selected from hydrogen, ($C_1$-$C_6$)alkyl, —O—($C_1$-$C_6$)alkyl, —($C_0$-$C_6$) alkylene-carbocyclyl, and —($C_0$-$C_6$)alkylene-heterocyclyl; or each $R^{5a}$ and each $R^{5b}$ is independently selected from hydrogen, ($C_1$-$C_6$)alkyl, carbocyclyl or heterocyclyl or a naturally occurring amino acid side chain moiety, or $R^{5a}$ and $R^{5b}$ taken together with the carbon atom to which they are bound form a 3-7 membered non-aromatic carbocyclyl or a 4-7 membered non-aromatic heterocyclyl, wherein the heterocyclyl formed by $R^{5a}$ and $R^{5b}$ optionally comprises one to two additional heteroatoms independently selected from N, S and O, $R^F$ is hydrogen or $(C_1-C_3)$alkyl; and each m is 1 or 2, wherein:

each carbocyclyl or heterocyclyl is optionally and independently substituted with one or more substituents independently selected from chloro, fluoro, $(C_1-C_4)$alkyl, —OH, —O—$(C_1-C_4)$alkyl, fluoro-substituted-$(C_1-C_4)$alkyl, —C(O)—$(C_1-C_4)$alkyl, —C(O)-(fluoro-substituted-$(C_1-C_4)$alkyl, and —N($R^G$)($R^G$);

each alkyl is optionally and independently substituted with one or more substituents independently selected from fluoro, chloro, —O—$(C_1-C_4)$alkyl, and fluoro-substituted-$(C_1-C_4)$alkyl; and each $R^G$ is hydrogen or $(C_1-C_3)$alkyl, wherein each alkyl group represented by $R^G$ is optionally and independently substituted with one or more substituents independently selected from fluoro, chloro, —O—$(C_1-C_4)$alkyl, and fluoro-substituted-$(C_1-C_4)$alkyl.

In a second alternative embodiment, the compound of the present invention is represented by Structural Formula (I), or a pharmaceutically acceptable salt thereof, wherein:

X is selected from —$CF_3$, —CN, —$OCF_3$ and —$OCH_3$.

Y is selected from hydrogen, —N($R^2$)($R^3$), —NH—C(O)—$(CH_2)_{1-4}$—N($R^2$)($R^3$), —NH—C(O)-heterocyclyl, —NH—C(O)-carbocyclyl, and —NH—S(O)$_2$—$(C_1-C_6)$alkyl, wherein:

each $R^2$ is independently selected from hydrogen, and $(C_1-C_3)$alkyl; and each $R^3$ is independently selected from hydrogen, $(C_1-C_6)$alkyl, and —$(C_0-C_6)$alkylene-carbocyclyl; or $R^2$ and $R^3$ taken together with the nitrogen atom to which they are bound form a heterocyclyl, wherein the heterocyclyl optionally comprises 1 to 4 additional heteroatoms independently selected from N, S and O;

each carbocyclyl or heterocyclyl is optionally and independently substituted with one or more substituents independently selected from fluoro, $(C_1-C_4)$alkyl, —O—$(C_1-C_4)$alkyl, fluoro-substituted-$(C_1-C_4)$alkyl, and —N($R^G$)($R^G$); and each alkyl is optionally and independently substituted with one or more substituents independently selected from fluoro, —O—$(C_1-C_4)$alkyl, and fluoro-substituted-$(C_1-C_4)$alkyl. The remainder of the variables are as described above in the first alternative embodiment.

In a third alternative embodiment, the compound of the present invention is represented by Structural Formula (I), or a pharmaceutically acceptable salt thereof, wherein:

X is selected from —$CF_3$, —CN, —$OCF_3$ and —$OCH_3$.

Y is selected from hydrogen, —$NH_2$, —NH—C(O)—$CH_2$—N($R^2$)($R^3$),

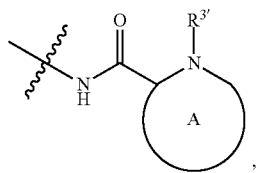

—NH—C(O)-phenyl, —NH—C(O)-thienyl and —NH—S(O)$_2$—$(C_1-C_6)$alkyl, wherein:

each $R^2$ is independently selected from hydrogen, and $(C_1-C_2)$alkyl; and each $R^3$ is independently selected from hydrogen, $(C_1-C_6)$alkyl, and —$(C_0-C_1)$alkylene-cycloalkyl; or $R^2$ and $R^3$ taken together with the nitrogen atom to which they are bound form a saturated heterocyclyl;

ring A represents a 4-7 membered saturated heterocyclyl;

$R^{3'}$ is hydrogen or methyl;

each cycloalkyl, phenyl or heterocyclyl is optionally and independently substituted with one or more substituents independently selected from fluoro, $(C_1-C_4)$alkyl, fluoro-substituted-$(C_1-C_4)$alkyl, and —N($R^G$)($R^G$); and each alkyl is optionally and independently substituted with one or more substituents independently selected from fluoro, —O—$(C_1-C_4)$alkyl, and fluoro-substituted-$(C_1-C_4)$alkyl. The remainder of the variables are as described above in the second alternative embodiment.

In a fourth alternative embodiment, the compound of Structural Formula (I) is represented by Structural Formula (II), (III), (IV) or (V):

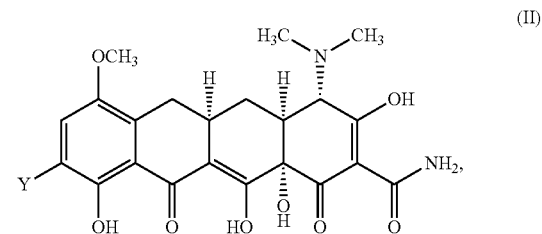

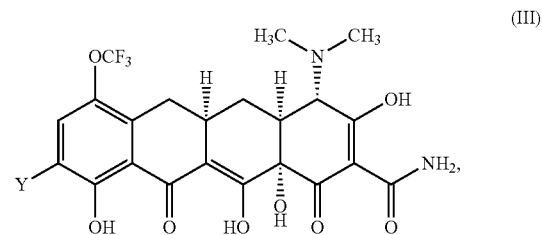

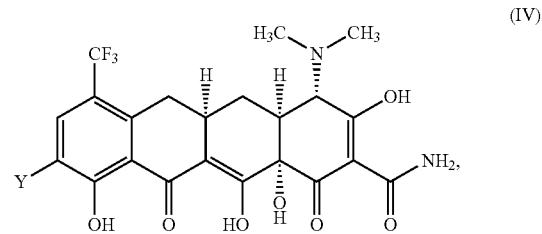

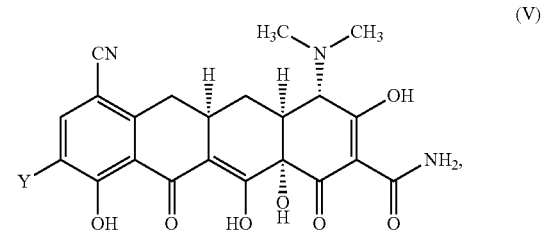

or pharmaceutically acceptable salt thereof, wherein:

Y is selected from —NH—C(O)—$CH_2$—N($R^2$)($R^3$), —NH—C(O)-heterocyclyl, —NH—C(O)-phenyl, and —NH—S(O)$_2$—$(C_1-C_6)$alkyl;

each $R^2$ is independently hydrogen or a $(C_1-C_3)$alkyl;

each $R^3$ is independently a $(C_1-C_6)$alkyl or a —$(C_0-C_1)$alkylene-carbocyclyl; or $R^2$ and $R^3$, taken together with the nitrogen atom to which they are bound form a saturated heterocyclyl. The saturated heterocyclyl (e.g., azetidinyl, morphinyl, piperazinyl, piperidinyl, pyrrolidinyl, azepanyl and octahydrocyclopenta[c]pyrrolyl) is optionally substituted with one or more substituents independently selected from fluoro, $(C_1\text{-}C_4)$alkyl, —O—$(C_1\text{-}C_4)$alkyl, fluoro-substituted-$(C_1\text{-}C_4)$alkyl, and —NN$_2$, —NH—$(C_1\text{-}C_3)$alkyl. The remainder of the variables are as described above for Structural Formula (I) in the second alternative embodiment.

In a fifth alternative embodiment, for compounds represented by Structural Formulas (II)-(V), Y is:

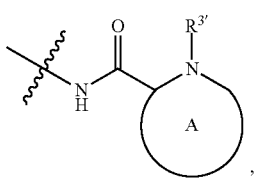

wherein ring A represents a 4-7 membered saturated heterocyclyl and $R^{3'}$ is hydrogen, $(C_1\text{-}C_6)$alkyl, carbocyclyl or heterocyclyl, wherein the alkyl, carbocyclyl or heterocyclyl are optionally substituted with one or more substituents independently selected from the groups described above for Structural Formula (I). The remainder of the variables are as described above in the fourth alternative embodiment. More specifically, $R^{3'}$ is hydrogen or $(C_1\text{-}C_6)$alkyl. Even more specifically, $R^{3'}$ is hydrogen or methyl. In another more specific embodiment, ring A is selected from the group consisting of azetidinyl, morphinyl, piperazinyl, piperidinyl, pyrrolidinyl, azepanyl and octahydrocyclopenta[c]pyrrolyl, each of which is optionally substituted with one or more substituents independently selected from $(C_1\text{-}C_3)$alkyl, —F, —O—$(C_1\text{-}C_4)$alkyl, and fluoro-substituted-$(C_1\text{-}C_4)$alkyl, such as —CF$_3$, —CH$_2$CF$_3$ or —CH$_2$CHF$_2$; and the remainder of the variables are as described above for the fifth alternative embodiment. Even more specifically, $R^{3'}$ is hydrogen or $(C_1\text{-}C_6)$alkyl (e.g. methyl).

In a sixth alternative embodiment, for compounds represented by Structural Formulas (II)-(V), Y is —NH—C(O)-heteroaryl, and the remainder of the variables are as described in the third alternative embodiment. More specifically, Y is —NH—C(O)-thienyl.

In a seventh alternative embodiment, for compounds represented by Structural Formulas (II)-(V), Y is —NH—C(O)—CH$_2$—N(R$^2$)(R$^3$), R$^3$ is a $(C_1\text{-}C_6)$alkyl or a —$(C_0\text{-}C_1)$alkylene-$(C_3\text{-}C_6)$cycloalkyl; and the remainder of the variables are as described in the fourth alternative embodiment.

In an eighth alternative embodiment, for compounds represented by Structural Formulas (II)-(V):
Y is —NH—C(O)—CH$_2$—N(R$^2$)(R$^3$);
R$^2$ is hydrogen or a $(C_1\text{-}C_3)$alkyl;
R$^3$ is a $(C_1\text{-}C_6)$alkyl or a —$(C_0\text{-}C_1)$alkylene-$(C_3\text{-}C_6)$cycloalkyl; or
R$^2$ and R$^3$, taken together with the nitrogen atom to which they are bound form a saturated heterocyclyl optionally substituted with one or more substituents independently selected from the group consisting of $(C_1\text{-}C_3)$alkyl, —F, —O—$(C_1\text{-}C_4)$alkyl, and fluoro-substituted-$(C_1\text{-}C_4)$alkyl, such as —CF$_3$, —CH$_2$CF$_3$ or —CH$_2$CHF$_2$.

Examples of the heterocyclyl include azetidinyl, piperidinyl, pyrrolidinyl, azepanyl and octahydrocyclopenta[c]pyrrolyl, each of the azetidinyl, piperidinyl, pyrrolidinyl, azepanyl and octahydrocyclopenta[c]pyrrolyl, each of which is optionally substituted with one or more substituents independently selected from the group consisting of $(C_1\text{-}C_3)$alkyl, —F, —O—$(C_1\text{-}C_4)$alkyl, and fluoro-substituted-$(C_1\text{-}C_4)$alkyl, such as —CF$_3$, —CH$_2$CF$_3$ or —CH$_2$CHF$_2$.

In a ninth alternative embodiment, the compounds of the present invention are represented by Structural Formula (II):

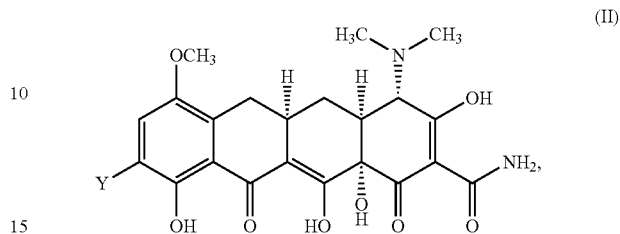

wherein:
Y is selected from —NH—C(O)—CH$_2$—N(R$^2$)(R$^3$),

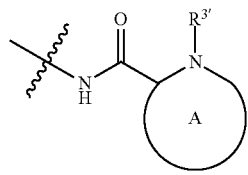

and —NH—S(O)$_2$—$(C_1\text{-}C_6)$alkyl, wherein the —NH—S(O)$_2$—$(C_1\text{-}C_6)$alkyl in the group represented by Y is optionally substituted with fluoro;
each R$^2$ is independently selected from hydrogen and —CH$_3$; and
each R$^3$ is independently selected from $(C_1\text{-}C_6)$alkyl, and —$(C_0\text{-}C_1)$alkylene-carbocyclyl; or
R$^2$ and R$^3$, taken together with the nitrogen atom to which they are bound form a saturated heterocyclyl optionally substituted with fluoro;
ring A represents a 4-7 membered saturated heterocyclyl;
R$^{3'}$ is hydrogen or methyl;
each carbocyclyl or heterocyclyl is optionally and independently substituted with one or more substituents independently selected from fluoro, $(C_1\text{-}C_4)$alkyl, —O—$(C_1\text{-}C_4)$alkyl, fluoro-substituted-$(C_1\text{-}C_4)$alkyl, and —N(R$^G$)(R$^G$);
each alkyl is optionally and independently substituted with one or more substituents independently selected from fluoro, —O—$(C_1\text{-}C_4)$alkyl, and fluoro-substituted-$(C_1\text{-}C_4)$alkyl; and
each R$^G$ is hydrogen or $(C_1\text{-}C_3)$alkyl, wherein each alkyl group represented by R$^G$ is optionally and independently substituted with one or more substituents independently selected from fluoro, chloro, —O—$(C_1\text{-}C_4)$alkyl, and fluoro-substituted-$(C_1\text{-}C_4)$alkyl.

Alternatively, for compounds of Structural Formula (II), the heterocyclyl represented by ring A or —NR$^2$R$^3$ is independently selected from the group consisting of azetidinyl, morphinyl, piperazinyl, piperidinyl, pyrrolidinyl, azepanyl and octahydrocyclopenta[c]pyrrolyl, each of which is optionally substituted with fluoro. The remainder of the variables are as described above for the ninth alternative embodiment.

Alternatively, for compounds of Structural Formula (II), the carbocyclyl in the group represented by R$^3$ is a $(C_3\text{-}C_6)$cycloalkyl and the remainder of the variables are as described in the ninth alternative embodiment.

In a tenth alternative embodiment, the compounds of the present invention are represented by Structural Formula (III):

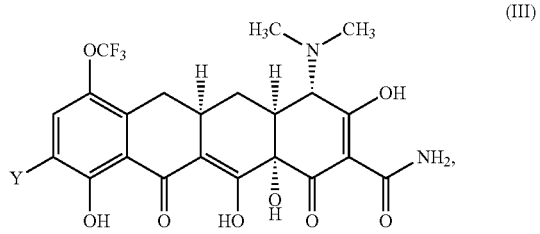

(III)

wherein:
Y is selected from —NH$_2$, —NH—C(O)—CH$_2$—N(R$^2$)(R$^3$),

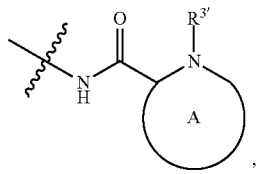

—NH—C(O)-phenyl, and —NH—C(O)-thienyl, wherein:
ring A represents a 4-7 membered saturated heterocyclyl;
R$^{3'}$ is hydrogen or methyl;
the phenyl in the group represented by Y is optionally substituted with —OCH$_3$ or —N(CH$_3$)$_2$;
each R$^2$ is independently selected from hydrogen and —CH$_3$; and
each R$^3$ is independently selected from (C$_1$-C$_6$)alkyl, and —(C$_0$-C$_1$)alkylene-carbocyclyl, wherein the (C$_1$-C$_6$)alkyl is optionally substituted with fluoro or —OCH$_3$; or
R$^2$ and R$^3$, taken together with the nitrogen atom to which they are bound form a saturated heterocyclyl optionally substituted with fluoro or —OCH$_3$;
each carbocyclyl or heterocyclyl is optionally and independently substituted with one or more substituents independently selected from fluoro, (C$_1$-C$_4$)alkyl, —O—(C$_1$-C$_4$)alkyl, fluoro-substituted-(C$_1$-C$_4$)alkyl, and —N(R$^G$)(R$^G$);
each alkyl is optionally and independently substituted with one or more substituents independently selected from fluoro, —O—(C$_1$-C$_4$)alkyl, and fluoro-substituted-(C$_1$-C$_4$)alkyl; and
each R$^G$ is hydrogen or (C$_1$-C$_3$)alkyl, wherein each alkyl group represented by R$^G$ is optionally and independently substituted with one or more substituents independently selected from fluoro, chloro, —O—(C$_1$-C$_4$)alkyl, and fluoro-substituted-(C$_1$-C$_4$)alkyl.

Alternatively, for compounds of Structural Formula (III) described in the tenth alternative embodiment, the heterocyclyl represented by ring A or —NR$^2$R$^3$ is independently selected from the group consisting of azetidinyl, piperazinyl, morpholinyl piperidinyl, pyrrolidinyl, azepanyl and octahydrocyclopenta[c]pyrrolyl, each of which is optionally substituted with fluoro or —OCH$_3$; and the remainder of the variables are as described in the tenth alternative embodiment.

In another embodiment, for compounds of Structural Formula (III) described in the tenth alternative embodiment, the carbocyclyl group represented by R$^3$ is a (C$_3$-C$_6$)cycloalkyl, and the remainder of the variables are as described in the tenth alternative embodiment.

In a eleventh alternative embodiment, the compounds of the present invention are represented by Structural Formula (IV):

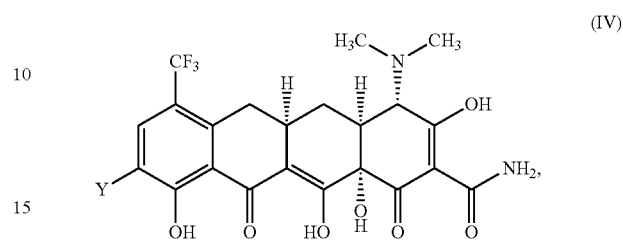

(IV)

wherein:
Y is selected from —NH$_2$, —NH—C(O)—CH$_2$—N(R$^2$)(R$^3$), and

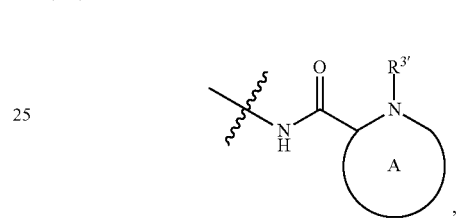

wherein ring A represents a 4-7 membered saturated heterocyclyl;
R$^{3'}$ is hydrogen or methyl;
each R$^2$ is independently selected from hydrogen and —CH$_3$; and
each R$^3$ is independently selected from (C$_1$-C$_6$) alkyl, and —(C$_0$-C$_1$)alkylene-carbocyclyl, wherein the (C$_1$-C$_6$) alkyl is optionally substituted with fluoro or —OCH$_3$; or
R$^2$ and R$^3$, taken together with the nitrogen atom to which they are bound form a saturated heterocyclyl optionally substituted with fluoro or —OCH$_3$;
each carbocyclyl or heterocyclyl is optionally and independently substituted with one or more substituents independently selected from fluoro, (C$_1$-C$_4$)alkyl, fluoro-substituted-(C$_1$-C$_4$)alkyl, and —N(R$^G$)(R$^G$);
each alkyl is optionally and independently substituted with one or more substituents independently selected from fluoro, —O—(C$_1$-C$_4$)alkyl, and fluoro-substituted-(C$_1$-C$_4$) alkyl; and
each R$^G$ is hydrogen or (C$_1$-C$_3$)alkyl, wherein each alkyl group represented by R$^G$ is optionally and independently substituted with one or more substituents independently selected from fluoro, chloro, —O—(C$_1$-C$_4$)alkyl, and fluoro-substituted-(C$_1$-C$_4$)alkyl.

In one embodiment, for compounds of Structural Formula (IV) described in the eleventh alternative embodiment, the heterocyclyl represented by ring A or —NR$^2$R$^3$ is independently selected from the group consisting of azetidinyl, piperidinyl, pyrrolidinyl, azepanyl and octahydrocyclopenta[c]pyrrolyl, each of which is optionally substituted with fluoro or —OCH$_3$. The remainder of the variables are as described above for the eleventh alternative embodiment.

In another embodiment, for compounds of Structural Formula (IV) described in the eleventh alternative embodiment, the carbocyclyl in the group represented by R$^3$ is a (C$_3$-C$_6$)cycloalkyl and the remainder of the variables are as described in the eleventh alternative embodiment.

In a twelfth alternative embodiment, the compounds of the present invention is represented by Structural Formula (V):

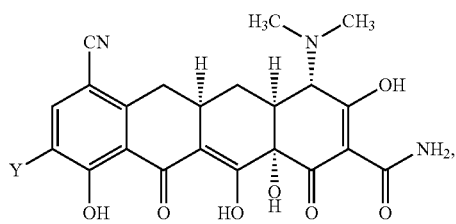

wherein:
Y is selected from hydrogen, —NH$_2$, —NH—C(O)—CH$_2$—N(R$^2$)(R$^3$), and

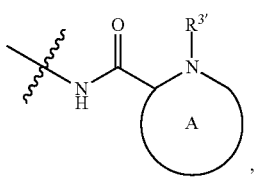

wherein ring A represents a 4-7 membered saturated heterocyclyl;
R$^{3'}$ is hydrogen or methyl;
each R$^2$ is independently selected from hydrogen and —CH$_3$; and
each R$^3$ is independently selected from (C$_1$-C$_6$) alkyl, and —(C$_0$-C$_1$)alkylene-carbocyclyl, wherein the (C$_1$-C$_6$) alkyl is optionally substituted with fluoro or —OCH$_3$; or
R$^2$ and R$^3$, taken together with the nitrogen atom to which they are bound form a saturated heterocyclyl optionally substituted with fluoro or —OCH$_3$;
each carbocyclyl or heterocyclyl is optionally and independently substituted with one or more substituents independently selected from fluoro, (C$_1$-C$_4$)alkyl, —O—(C$_1$-C$_4$) alkyl, fluoro-substituted-(C$_1$-C$_4$)alkyl, and —N(R$^G$)(R$^G$);
each alkyl is optionally and independently substituted with one or more substituents independently selected from fluoro, —O—(C$_1$-C$_4$)alkyl, and fluoro-substituted-(C$_1$-C$_4$) alkyl;
each R$^G$ is hydrogen or (C$_1$-C$_3$)alkyl, wherein each alkyl group represented by R$^G$ is optionally and independently substituted with one or more substituents independently selected from fluoro, chloro, —O—(C$_1$-C$_4$)alkyl, and fluoro-substituted-(C$_1$-C$_4$)alkyl.

In one embodiment, for compounds of Structural Formula (V) described in the twelfth alternative embodiment, the saturated heterocyclyl represented by ring A or —NR$^2$R$^3$ is independently is selected from the group consisting of azetidinyl, piperidinyl, pyrrolidinyl, azepanyl and octahydrocyclopenta[c]pyrrolyl. The remainder of the variables are as described above for the twelfth alternative embodiment.

In another embodiment, for compounds of Structural Formula (V) described in the twelfth alternative embodiment, the carbocyclyl in the group represented by R$^3$ is a (C$_3$-C$_6$)cycloalkyl and the remainder of the variables are as described in the twelfth alternative embodiment.

Exemplary compounds represented by Structural Formula (I) are shown in Tables 1-4 below:

TABLE 1

Exemplary Compounds of Formula II (X = OCH$_3$)

| Compound # | Y |
|---|---|
| 100 | H— |
| 101 | pyrrolidinyl-CH$_2$-C(O)-NH- |
| 102 | azetidinyl-CH$_2$-C(O)-NH- |
| 103 | piperidinyl-CH$_2$-C(O)-NH- |
| 104 | (H$_3$C-CH$_2$)(CH$_3$)N-CH$_2$-C(O)-NH- |
| 105 | (H$_3$C)(CH$_3$)N-CH$_2$-C(O)-NH- |
| 106 | (CH$_3$)$_2$CH-CH$_2$-NH-CH$_2$-C(O)-NH- |
| 107 | H$_3$C-CH(CH$_3$)-NH-CH$_2$-C(O)-NH- |
| 108 | cyclopropyl-NH-CH$_2$-C(O)-NH- |
| 109 | (H$_3$C)(H$_3$C)CH-NH-CH$_2$-C(O)-NH- |
| 110 | H$_2$N— |
| 111 | (H$_3$C)(H$_3$C)C(CH$_3$)-CH$_2$-C(O)-NH- |

TABLE 1-continued
Exemplary Compounds of Formula II (X = OCH₃)
| Compound # | Y |
|---|---|
| 112 | 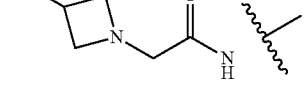 |
| 113 | 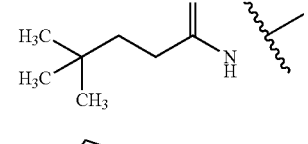 |
| 114 | 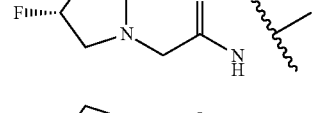 |
| 115 | 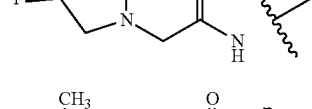 |
| 116 | 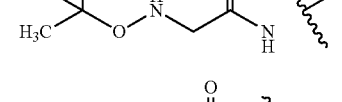 |
| 117 | 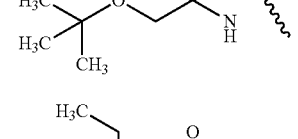 |
| 118 | 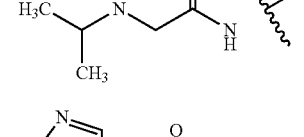 |
| 119 | 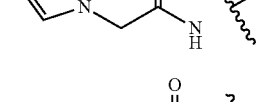 |
| 120 | 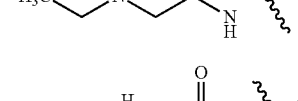 |
| 121 | 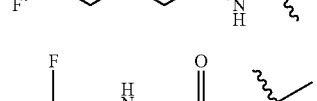 |
| 122 | 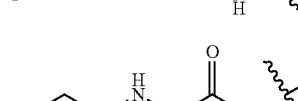 |
| 123 |  |
| 124 | 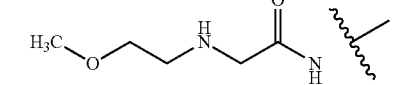 |
| 125 | 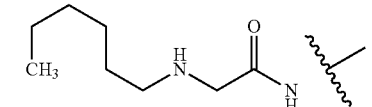 |
| 126 | 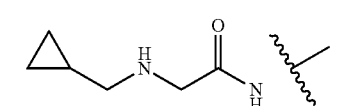 |
| 127 | 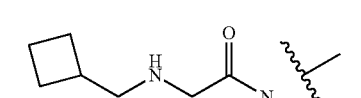 |
| 128 | 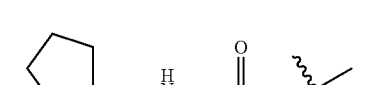 |
| 129 | 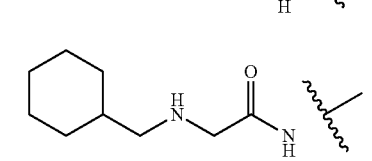 |
| 130 | 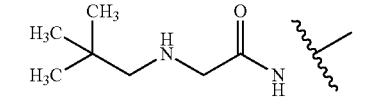 |
| 131 | 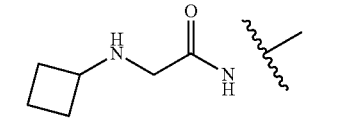 |
| 132 | 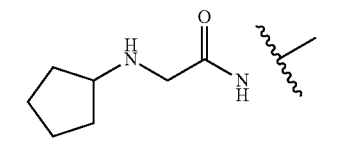 |
| 133 | 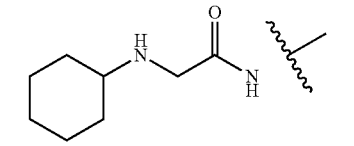 |
| 134 | 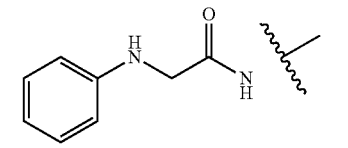 |

TABLE 1-continued

Exemplary Compounds of Formula II (X = OCH₃)

| Compound # | Y |
|---|---|
| 135 | (structure) |
| 136 | (structure) |
| 137 | (structure) |
| 138 | (structure) |
| 139 | (structure) |
| 140 | (structure) |
| 141 | (structure) |
| 142 | (structure) |
| 143 | (structure) |
| 144 | (structure) |
| 145 | (structure) |
| 146 | (structure) |
| 147 | (structure) |
| 148 | (structure) |
| 149 | (structure) |
| 150 | (structure) |
| 151 | (structure) |
| 152 | (structure) |
| 153 | (structure) |
| 154 | (structure) |

TABLE 1-continued
Exemplary Compounds of Formula II (X = OCH₃)
| Compound # | Y |
|---|---|
| 155 | 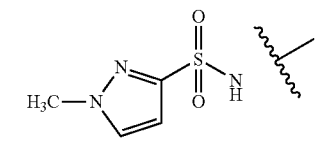 |
| 156 | 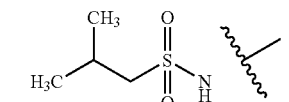 |
| 157 | |
| 158 | |
| 159 | |
| 160 | |
| 161 | |
| 162 | |
| 163 | |
| 164 | |
| 165 | |
| 166 | |
| 167 | |
| 168 | |
| 169 | |
| 170 | |
| 171 | |
| 172 | |
| 173 | |
| 174 | |
| 175 | |

TABLE 1-continued

Exemplary Compounds of Formula II (X = OCH₃)

| Compound # | Y |
|---|---|
| 176 | 3-(dimethylamino)benzenesulfonamide |
| 177 | pyridine-2-sulfonamide |
| 178 | piperidine-3-sulfonamide |
| 179 | 2-(pyrrolidin-1-yl)ethanesulfonamide |
| 180 | ethylamino |
| 181 | isopentylamino (3-methylbutylamino) |
| 182 | (2-methylbutyl)amino |
| 183 | (cyclopropylmethyl)amino |
| 184 | [(2S)-pyrrolidin-2-ylmethyl]amino |
| 185 | (3,3-dimethylbutyl)amino (neohexylamino) |
| 186 | [2-(tert-butylamino)ethyl]amino |
| 187 | N-(2,2-dimethylpropyl)amide (neopentylamide) |
| 188 | N-[2-(dimethylamino)ethyl]amide |
| 189 | carboxylic acid |
| 190 | methylaminomethyl |
| 191 | (isobutylamino)methyl |
| 192 | (neopentylamino)methyl |
| 193 | [isobutyl(methyl)amino]methyl |
| 194 | [neopentyl(methyl)amino]methyl |
| 195 | (dimethylamino)methyl |
| 196 | [(2-methylpropan-2-yl)amino]methyl (tert-butylaminomethyl) |
| 197 | (hydroxyimino)methyl |
| 198 | (methoxyimino)methyl |
| 199 | 3-(pyrrolidin-1-yl)propyl |

TABLE 1-continued

Exemplary Compounds of Formula II (X = OCH₃)

| Compound # | Y |
|---|---|
| 200 |  H₃C–NH– |
| 201 | F–CH₂–CH₂–NH– |
| 202 | CHF₂–CH₂–NH– |
| 203 | CF₃–CH₂–NH– |
| 204 | H₃C–N(CH₃)–CH₂CH₂CH₂– |
| 205 | azetidin-1-yl–CH₂CH₂CH₂– |
| 206 | HO– |

TABLE 2

Exemplary Compounds of Formula III (X = OCF₃).

| Compound # | Y |
|---|---|
| 207 | H– |
| 208 | O₂N– |
| 209 | H₂N– |
| 210 | azetidin-1-yl-CH₂-C(O)NH– |
| 211 | CHF₂CF₂... (2,2,2-trifluoroethyl)NH-CH₂-C(O)NH– |
| 212 | 3-fluoroazetidin-1-yl-CH₂-C(O)NH– |
| 213 | H₃C-CH₂-CH₂-NH-CH₂-C(O)NH– |
| 214 | H₃C-(CH₂)₃-NH-CH₂-C(O)NH– |
| 215 | CH₃-(CH₂)₄-NH-CH₂-C(O)NH– |
| 216 | (CH₃)₃C-CH₂-NH-CH₂-C(O)NH– |
| 217 | cyclopropyl-CH₂-NH-CH₂-C(O)NH– |
| 218 | H₃C-CH₂-N(CH₃)-CH₂-C(O)NH– |
| 219 | isoindolin-2-yl-CH₂-C(O)NH– |
| 220 | (CH₃)₂CH-NH-CH₂-C(O)NH– |
| 221 | 3-methoxyazetidin-1-yl-CH₂-C(O)NH– |
| 222 | F-CH₂-CH₂-NH-CH₂-C(O)NH– |
| 223 | cyclopentyl-CH₂-NH-CH₂-C(O)NH– |

TABLE 2-continued

Exemplary Compounds of Formula III (X = OCF₃).

| Compound # | Y |
|---|---|
| 224 | H₃C-NH-CH₂-C(=O)-NH-~ |
| 225 | (CH₃)(H₃C-CH₂-CH₂)N-CH₂-C(=O)-NH-~ |
| 226 | H₃C-O-CH₂-CH₂-NH-CH₂-C(=O)-NH-~ |
| 227 | (3S)-3-fluoropyrrolidin-1-yl-CH₂-C(=O)-NH-~ |
| 228 | pyridin-3-yl-NH-CH₂-C(=O)-NH-~ |
| 229 | pyridin-4-yl-NH-CH₂-C(=O)-NH-~ |
| 230 | H₃C-CH₂-CH₂-NH-CH₂-C(=O)-NH-~ |
| 231 | cyclohexyl-CH₂-NH-CH₂-C(=O)-NH-~ |
| 232 | (CH₃)₂CH-CH₂-NH-CH₂-C(=O)-NH-~ |
| 233 | piperidin-1-yl-CH₂-C(=O)-NH-~ |
| 234 | cyclobutyl-NH-CH₂-C(=O)-NH-~ |
| 235 | morpholin-4-yl-CH₂-C(=O)-NH-~ |
| 236 | (H₃C-CH₂)₂N-CH₂-C(=O)-NH-~ |
| 237 | cyclohexyl-NH-CH₂-C(=O)-NH-~ |
| 238 | phenyl-NH-CH₂-C(=O)-NH-~ |
| 239 | cyclopropyl-NH-CH₂-C(=O)-NH-~ |
| 240 | F₂CH-CH₂-NH-CH₂-C(=O)-NH-~ |
| 241 | (3R)-3-fluoropyrrolidin-1-yl-CH₂-C(=O)-NH-~ |
| 242 | octahydrocyclopenta[c]pyrrol-2-yl-CH₂-C(=O)-NH-~ |
| 243 | cyclobutyl-CH₂-NH-CH₂-C(=O)-NH-~ |
| 244 | (CH₃)₂N-CH₂-C(=O)-NH-~ |
| 245 | (CH₃)₃C-NH-CH₂-C(=O)-NH-~ |
| 246 | pyrrolidin-1-yl-CH₂-C(=O)-NH-~ |

TABLE 2-continued

Exemplary Compounds of Formula III (X = OCF$_3$).

| Compound # | Y |
|---|---|
| 247 | benzamide |
| 248 | 3-methoxybenzamide |
| 249 | 3-(trifluoromethyl)benzamide |
| 250 | thiophene-2-carboxamide |
| 251 | 4-(dimethylamino)benzamide |
| 252 | 3-(dimethylamino)benzamide |
| 253 | 2-(dimethylamino)benzamide |
| 254 | nicotinamide |
| 255 | isonicotinamide |
| 256 | picolinamide |
| 257 | piperidine-2-carboxamide |
| 258 | 1-methylazetidine-2-carboxamide |
| 259 | 1-methylpyrrolidine-2-carboxamide |
| 260 | azetidine-2-carboxamide |
| 261 | pyrrolidine-2-carboxamide |
| 262 | 2-hydroxy-2-methylpropanoyl |
| 263 | 2-(cyclopentylamino)acetamide |
| 264 | propylamino |
| 265 | (3-methylbutyl)amino |
| 266 | ethanesulfonamide |

TABLE 2-continued
Exemplary Compounds of Formula III (X = OCF₃).
| Compound # | Y |
|---|---|
| 267 | 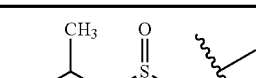 |
| 268 | 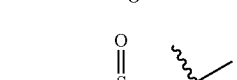 |
TABLE 3
Exemplary Compounds of Formula IV (X = CF₃).
| Compound # | Y |
|---|---|
| 269 | H— |
| 270 | H₂N— |
| 271 |  |
| 272 | 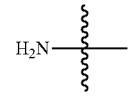 |
| 273 | 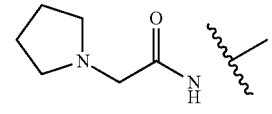 |
| 274 | 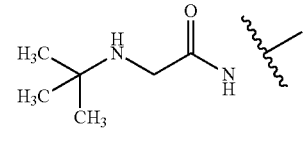 |
| 275 | 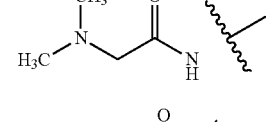 |
| 276 | 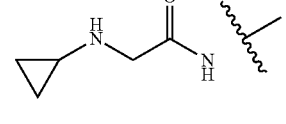 |
| 277 | 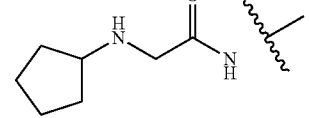 |
TABLE 3-continued
Exemplary Compounds of Formula IV (X = CF₃).
| Compound # | Y |
|---|---|
| 278 | 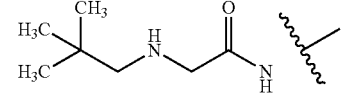 |
| 279 | |
| 280 | |
| 281 | |
| 282 | |
| 283 | |
| 284 | |
| 285 | |
| 286 | |
| 287 | |
| 288 | |
| 289 | 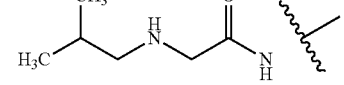 |

TABLE 3-continued

Exemplary Compounds of Formula IV (X = CF3).

| Compound # | Y |
|---|---|
| 290 | 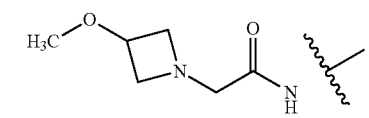 |
| 291 | 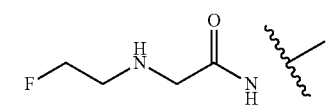 |
| 292 | H3C−NH−CH2−C(=O)−NH−⸾ |
| 293 | cyclobutyl−NH−CH2−C(=O)−NH−⸾ |
| 294 | H3C−O−CH2CH2−NH−CH2−C(=O)−NH−⸾ |
| 295 | H3C−CH2−N(CH3)−CH2−C(=O)−NH−⸾ |
| 296 | (H3C−CH2)2N−CH2−C(=O)−NH−⸾ |
| 297 | piperidinyl−CH2−C(=O)−NH−⸾ |
| 298 | isoindolinyl−CH2−C(=O)−NH−⸾ |
| 299 | H3C−CH2−NH−CH2−C(=O)−NH−⸾ |
| 300 | F2CH−CH2−NH−CH2−C(=O)−NH−⸾ |
| 301 | cyclobutyl−CH2−NH−CH2−C(=O)−NH−⸾ |
| 302 | H3C−O−azetidinyl−CH2−C(=O)−NH−⸾ |
| 303 | F−CH2CH2−NH−CH2−C(=O)−NH−⸾ |
| 304 | phenyl−NH−CH2−C(=O)−NH−⸾ |
| 305 | 3-F-phenyl−SO2−NH−⸾ |
| 306 | 1-methyl-pyrazol-3-yl−SO2−NH−⸾ |
| 307 | azetidin-2-yl−C(=O)−NH−⸾ |
| 308 | piperidin-2-yl−C(=O)−NH−⸾ |
| 309 | 1-methyl-azetidin-2-yl−C(=O)−NH−⸾ |
| 310 | pyrrolidin-2-yl−C(=O)−NH−⸾ |
| 311 | 1-methyl-pyrrolidin-2-yl−C(=O)−NH−⸾ |

TABLE 4

Exemplary Compounds of Formula V (X = CN).

| Compound # | Y |
|---|---|
| 312 | H– |
| 313 | H₂N– |
| 314 | pyrrolidinyl-CH₂-C(O)NH– |
| 315 | (CH₃)₃C-NH-CH₂-C(O)NH– |
| 316 | (CH₃)₂N-CH₂-C(O)NH– |
| 317 | (CH₃)₂CH-CH₂-NH-CH₂-C(O)NH– |
| 318 | cyclopropyl-NH-CH₂-C(O)NH– |
| 319 | CH₃CH₂-NH-CH₂-C(O)NH– |
| 320 | CH₃CH₂CH₂-NH-CH₂-C(O)NH– |
| 321 | cyclohexyl-CH₂-NH-CH₂-C(O)NH– |
| 322 | cyclobutyl-NH-CH₂-C(O)NH– |
| 323 | cyclopentyl-NH-CH₂-C(O)NH– |

TABLE 4-continued

Exemplary Compounds of Formula V (X = CN).

| Compound # | Y |
|---|---|
| 324 | cyclohexyl-NH-CH₂-C(O)NH– |
| 325 | N(CH₃)(CH₂CH₃)-CH₂-C(O)NH– |
| 326 | N(CH₂CH₃)₂-CH₂-C(O)NH– |
| 327 | N(CH₃)(CH₂CH₂CH₃)-CH₂-C(O)NH– |
| 328 | azetidinyl-CH₂-C(O)NH– |
| 329 | (CH₃)₂CH-NH-CH₂-C(O)NH– |
| 330 | (3-fluoropyrrolidinyl)-CH₂-C(O)NH– |
| 331 | isoindolinyl-CH₂-C(O)NH– |
| 332 | piperidinyl-CH₂-C(O)NH– |
| 333 | morpholinyl-CH₂-C(O)NH– |
| 334 | (1-methylazetidin-2-yl)-C(O)NH– |

TABLE 4-continued

Exemplary Compounds of Formula V (X = CN).

| Compound # | Y |
|---|---|
| 335 | [structure: H₃C-N-pyrrolidine-C(=O)-NH-] |

DEFINITIONS

"Alkyl" means a saturated aliphatic branched or straight-chain monovalent hydrocarbon radical having the specified number of carbon atoms. Thus, "($C_1$-$C_6$) alkyl" means a radical having from 1-6 carbon atoms in a linear or branched arrangement. "($C_1$-$C_6$)alkyl" includes methyl, ethyl, propyl, butyl, pentyl and hexyl.

"Alkylene" means a saturated aliphatic straight-chain divalent hydrocarbon radical having the specified number of carbon atoms. Thus, "($C_1$-$C_6$) alkylene" means a divalent saturated aliphatic radical having from 1-6 carbon atoms in a linear arrangement, e.g., —[$(CH_2)_n$]—, where n is an integer from 1 to 6. "($C_1$-$C_6$)alkylene" includes methylene, ethylene, propylene, butylene, pentylene and hexylene.

"Aryl" or "aromatic means an aromatic monocyclic or polycyclic (e.g. bicyclic or tricyclic) carbocyclic ring system. In one embodiment, "aryl" is a 6-12 membered monocyclic or bicyclic systems. Aryl systems include, but not limited to, phenyl, naphthalenyl, fluorenyl, indenyl, azulenyl, and anthracenyl.

"Carbocyclyl" means a cyclic group with only ring carbon atoms. "Carbocyclyl" includes 3-12 membered saturated or unsaturated aliphatic cyclic hydrocarbon ring or 6-12 membered aromatic ring. A carbocyclyl moiety can be monocyclic, fused bicyclic, bridged bicyclic, spiro bicyclic, or polycyclic.

Monocyclic carbocyclyls are saturated or unsaturated aliphatic cyclic hydrocarbon rings or aromatic hydrocarbon rings having the specified number of carbon atoms. Monocyclic carbocyclyls include cycloalkyl, cycloalkenyl, cycloalkynyl and phenyl.

A fused bicyclic carbocyclyl has two rings which have two adjacent ring atoms in common. The first ring is a monocyclic carbocyclyl and the second ring is a monocyclic carbocyclyl or a monocyclic heterocyclyl.

A spiro bicyclic carbocyclyl has two rings which have only one ring atom in common. The first ring is a monocyclic carbocyclyl and the second ring is a monocyclic carbocyclyl or a monocyclic heterocyclyl.

A bridged bicyclic carbocyclyl has two rings which have three or more adjacent ring atoms in common. The first ring is a monocyclic carbocyclyl and the second ring is a monocyclic carbocyclyl or a monocyclic heterocyclyl.

Polycyclic carbocyclyls have more than two rings (e.g., three rings resulting in a tricyclic ring system) and adjacent rings have at least one ring atom in common. The first ring is a monocyclic carbocyclyl and the remainder of the ring structures are monocyclic carbocyclyls or monocyclic heterocyclyls. Polycyclic ring systems include fused, bridged and spiro ring systems. A fused polycyclic ring system has at least two rings that have two adjacent ring atoms in common. A Spiro polycyclic ring system has at least two rings that have only one ring atom in common. A bridged polycyclic ring system has at least two rings that have three or more adjacent ring atoms in common.

"Cycloalkyl" means a saturated aliphatic cyclic hydrocarbon ring. Thus, "$C_3$-$C_7$ cycloalkyl" means a hydrocarbon radical of a (3-7 membered) saturated aliphatic cyclic hydrocarbon ring. A $C_3$-$C_7$ cycloalkyl includes, but is not limited to cyclopropyl, cyclobutyl, cyclopentyl, cyclohexyl and cycloheptyl.

"Cycloalkene" means an aliphatic cyclic hydrocarbon ring having one or more double bonds in the ring.

"Cycloalkyne" means an aliphatic cyclic hydrocarbon ring having one or more triple bonds in the ring.

"Heterocyclyl" means a cyclic 4-12 membered saturated or unsaturated aliphatic ring containing 1, 2, 3, 4 or 5 heteroatoms independently selected from N, O or S or a heteroaromatic ring. When one heteroatom is S, it can be optionally mono- or di-oxygenated (i.e. —S(O)— or —S(O)$_2$—). The heterocyclyl can be monocyclic, fused bicyclic, bridged bicyclic, spiro bicyclic or polycyclic.

"Saturated heterocyclyl" means an aliphatic heterocyclyl group without any degree of unsaturation (i.e., no double bond or triple bond). It can be monocyclic, fused bicyclic, bridged bicyclic, spiro bicyclic or polycyclic.

Examples of monocyclic saturated heterocyclyls include, but are not limited to, azetidine, pyrrolidine, piperidine, piperazine, azepane, hexahydropyrimidine, tetrahydrofuran, tetrahydropyran, morpholine, thiomorpholine, thiomorpholine 1,1-dioxide, tetrahydro-2H-1,2-thiazine, tetrahydro-2H-1,2-thiazine 1,1-dioxide, isothiazolidine, isothiazolidine 1,1-dioxide. Examples of heteroaromatic rings include, but are not limited to, furan, thiophene, pyrrole, imidazole, pyrazole, oxazole, isoxazole, thiazole, isothiazole, 1,2,3-triazole, 1,2,4-triazole, 1,3,4-oxadiazole, 1,2,5-thiadiazole, 1,2,5-thiadiazole 1-oxide, 1,2,5-thiadiazole 1,1-dioxide, 1,3,4-thiadiazole, pyridine, pyridine-N-oxide, pyrazine, pyrimidine, pyridazine, 1,2,4-triazine, 1,3,5-triazine, and tetrazole.

A fused bicyclic heterocyclyl has two rings which have two adjacent ring atoms in common. The first ring is a monocyclic heterocyclyl and the second ring is a monocyclic carbocycle (such as a cycloalkyl or phenyl) or a monocyclic heterocyclyl. For example, the second ring is a ($C_3$-$C_6$)cycloalkyl, such as cyclopropyl, cyclobutyl, cyclopentyl and cyclohexyl. Alternatively, the second ring is phenyl. Examples of fused bicyclic heterocyclyls include, but are not limited to, octahydrocyclopenta[c]pyrrolyl, indoline, isoindoline, 2,3-dihydro-1H-benzo[d]imidazole, 2,3-dihydrobenzo[d]oxazole, 2,3-dihydrobenzo[d]thiazole, octahydrobenzo[d]oxazole, octahydro-1H-benzo[d]imidazole, octahydrobenzo[d]thiazole, octahydrocyclopenta[c]pyrrole, 3-azabicyclo[3.1.0]hexane, 3-azabicyclo[3.2.0]heptane, indolizine, indole, isoindole, indazole, benzimidazole, benzthiazole, purine, quinoline, isoquinoline, cinnoline, phthalazine, quinazoline, quinoxaline, 1,8-naphthyridine, and pteridine.

A spiro bicyclic heterocyclyl has two rings which have only one ring atom in common. The first ring is a monocyclic heterocyclyl and the second ring is a monocyclic carbocycle (such as a cycloalkyl or phenyl) or a monocyclic heterocyclyl. For example, the second ring is a ($C_3$-$C_6$) cycloalkyl. Alternatively, the second ring is phenyl. Example of spiro bicyclic heterocyclyl includes, but are not limited to, azaspiro[4.4]nonane, 7-azaspiro[4.4]nonane, azaprio[4.5]decane, 8-azaspiro[4.5]decane, azaspiro[5.5]undecane, 3-azaspiro[5.5]undecane and 3,9-diazaspiro[5.5]undecane.

A bridged bicyclic heterocyclyl has two rings which have three or more adjacent ring atoms in common. The first ring is a monocyclic heterocyclyl and the other ring is a monocyclic carbocycle (such as a cycloalkyl or phenyl) or a monocyclic heterocyclyl. Examples of bridged bicyclic heterocyclyls include, but are not limited to, azabicyclo[3.3.1]nonane, 3-azabicyclo[3.3.1]nonane, azabicyclo[3.2.1]octane, 3-azabicyclo[3.2.1]octane, 6-azabicyclo[3.2.1]octane and azabicyclo[2.2.2]octane, 2-azabicyclo[2.2.2]octane.

Polycyclic heterocyclyls have more than two rings, one of which is a heterocyclyl (e.g., three rings resulting in a tricyclic ring system) and adjacent rings having at least one ring atom in common. Polycyclic ring systems include fused, bridged and spiro ring systems. A fused polycyclic ring system has at least two rings that have two adjacent ring atoms in common. A spiro polycyclic ring system has at least two rings that have only one ring atom in common A bridged polycyclic ring system has at least two rings that have three or more adjacent ring atoms in common.

Unless otherwise specified, a heterocyclyl or a carbocyclyl can be optionally substituted with one or more (such as two, three, four and five) substituents. Unless otherwise specified, suitable substituents include $(C_1-C_4)$alkyl, halo, —OH, $(C_1-C_4)$alkoxy, $(C_1-C_4)$alkylthio, $(C_1-C_4)$alkylsulfinyl, $(C_1-C_4)$alkylsulfonyl, $(C_1-C_4)$alkoxy$(C_1-C_4)$alkyl, —N($R^3$)($R^4$), —CN, halo$(C_1-C_4)$alkyl, and halo$(C_1-C_4)$alkoxy. Oxo (C=O) is also a suitable substituent and examples of heterocyclic rings with an oxo substituent include, but are not limited to, thiomorpholine 1-oxide, thiomorpholine 1,1-dioxide, tetrahydro-2H-1,2-thiazine 1,1-dioxide, and isothiazolidine 1,1-dioxide, pyrrolidin-2-one, piperidin-2-one, piperazin-2-one, and morpholin-2-one. When the heterocycle contains a ring nitrogen atom that is not connected to an adjacent ring atom by a double bond, substituents at such ring nitrogen atoms are also contemplated. Unless otherwise specified, suitable substituents for a ring nitrogen atoms include alkyl (such as -Me, or -Et) and acyl (e.g., —CHO, $CH_3CO$—, and $CH_3CH_2CO$—). In one embodiment, the substituents are independently selected from the group consisting of —Cl, —F, $(C_1-C_4)$alkyl, —OH, —O—$(C_1-C_4)$alkyl, fluoro-substituted-$(C_1-C_4)$alkyl, —C(O)—$(C_1-C_4$ alkyl), —C(O)-(fluoro-substituted-$C_1-C_4$ alkyl), and —N($R^2$)($R^2$).

"Heteroaryl" or "heteroaromatic ring" means a 5-12 membered monovalent heteroaromatic monocyclic or bicyclic ring radical. A heteroaryl contains 1, 2, 3 or 4 heteroatoms independently selected from N, O, and S. Heteroaryls include, but are not limited to pyrrole, imidazole, pyrazole, oxazole, isoxazole, thiazole, isothiazole, 1,2,3-triazole, 1,2,4-triazole, 1,3,4-oxadiazole, 1,2,5-thiadiazole, 1,2,5-thiadiazole 1-oxide, 1,2,5-thiadiazole 1,1-dioxide, 1,3,4-thiadiazole, pyridine, pyrazine, pyrimidine, pyridazine, 1,2,4-triazine, 1,3,5-triazine, and tetrazole. Bicyclic heteroaryl rings include, but are not limited to, bicyclo[4.4.0] and bicyclo[4.3.0] fused ring systems such as indolizine, indole, isoindole, indazole, benzimidazole, benzthiazole, purine, quinoline, isoquinoline, cinnoline, phthalazine, quinazoline, quinoxaline, 1,8-naphthyridine, and pteridine.

"Hetero" refers to the replacement of at least one carbon atom member in a ring system with at least one heteroatom selected from N, S, and O. "Hetero" also refers to the replacement of at least one carbon atom member in a acyclic system. A hetero ring system or a hetero acyclic system may have 1, 2, 3 or 4 carbon atom members replaced by a heteroatom.

"Halogen" used herein refers to fluorine, chlorine, bromine, or iodine.

"Alkoxy" means an alkyl radical attached through an oxygen linking atom. "$(C_1-C_6)$-alkoxy" includes methoxy, ethoxy, propoxy, butoxy, pentoxy and hexoxy.

Haloalkyl and halocycloalkyl include mono, poly, and perhaloalkyl groups where each halogen is independently selected from fluorine, chlorine, and bromine.

"Halogen" and "halo" are interchangeably used herein and each refers to fluorine, chlorine, bromine, or iodine.

"Fluoro" means —F.

As used herein, fluoro-substituted-$(C_1-C_4)$alkyl means a $(C_1-C_4)$alkyl substituted with one or more —F groups. Examples of fluoro-substituted-$(C_1-C_4)$alkyl include, but are not limited to, —$CF_3$, —$CH_2CF_3$, —$CH_2CF_2H$, —$CH_2CH_2F$ and —$CH_2CH_2CF_3$.

As used herein, "amino" include —$NH_2$, monoalkylamino and dialkylamino.

"Naturally occurring amino acid side chain moiety" refers to any amino acid side chain moiety present in a natural amino acid.

Unless otherwise specified, an alkyl group can be optionally substituted with one or more (such as two, three, four and five) substituents. Unless otherwise specified, the substituents are independently selected from the group consisting of halogen (—Cl, —F or —Br), alkyl, amino, —OH, alkoxy, haloalkyl, halocycloalkyl, cycloalkyl, aryl and heteroaryl. In one embodiment, the substituents are independently selected from the group consisting of —Cl, —F, $(C_1-C_4)$alkyl, —OH, —O—$(C_1-C_4)$alkyl, fluoro-substituted-$(C_1-C_4)$alkyl, —C(O)—$(C_1-C_4$ alkyl), —C(O)-(fluoro-substituted-$C_1-C_4$ alkyl), and —N($R^2$)($R^2$). In another embodiment, the substituents are independently selected from the group consisting of —F, —Cl, —O—$(C_1-C_4)$alkyl and fluoro-substituted-$(C_1-C_4)$alkyl.

Another embodiment of the present invention is a pharmaceutical composition comprising one or more pharmaceutically acceptable carrier and/or diluent and a compound disclosed herein or a pharmaceutically acceptable salt thereof.

"Pharmaceutically acceptable carrier" and "pharmaceutically acceptable diluent" means non-therapeutic components that are of sufficient purity and quality for use in the formulation of a composition of the invention that, when appropriately administered to an animal or human, typically do not produce an adverse reaction, and that are used as a vehicle for a drug substance (i.e. a compound of the present invention).

Pharmaceutically acceptable salts of the compounds of the present invention are also included. For example, an acid salt of a compound of the present invention containing an amine or other basic group can be obtained by reacting the compound with a suitable organic or inorganic acid, resulting in pharmaceutically acceptable anionic salt forms. Examples of anionic salts include the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate, and triethiodide salts.

Salts of the compounds of the present invention containing a carboxylic acid or other acidic functional group can be prepared by reacting with a suitable base. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N'-bisdehydroabietylamine, glutamine, N-methylglucamine, collidine, quinine, quinoline, and basic amino acids such as lysine and arginine.

The invention also includes various isomers and mixtures thereof. Certain of the compounds of the present invention may exist in various stereoisomeric forms. Stereoisomers are compounds which differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms. "R" and "S" represent the configuration of substituents around one or more chiral carbon atoms. When a chiral center is not defined as R or S, either a pure enantiomer or a mixture of both configurations is present.

"Racemate" or "racemic mixture" means a compound of equimolar quantities of two enantiomers, wherein such mixtures exhibit no optical activity; i.e., they do not rotate the plane of polarized light.

The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

When the stereochemistry of a disclosed compound is named or depicted by structure, the named or depicted stereoisomer is at least 60%, 70%, 80%, 90%, 99% or 99.9% by weight pure relative to the other stereoisomers. When a single enantiomer is named or depicted by structure, the depicted or named enantiomer is at least 60%, 70%, 80%, 90%, 99% or 99.9% by weight optically pure. Percent optical purity by weight is the ratio of the weight of the enantiomer that is present divided by the combined weight of the enantiomer that is present and the weight of its optical isomer.

The present invention also provides a method of treating or preventing a subject with a tetracycline-responsive disease or disorder comprising administering to the subject an effective amount of a compound of the present invention or a pharmaceutically acceptable salt thereof.

"Tetracycline-responsive disease or disorder" refers to a disease or disorder that can be treated, prevented, or otherwise ameliorated by the administration of a tetracycline compound of the present invention. Tetracycline-responsive disease or disorder includes infections, cancer, inflammatory disorders, autoimmune disease, arteriosclerosis, corneal ulceration, emphysema, arthritis, osteoporosis, osteoarthritis, multiple sclerosis, osteosarcoma, osteomyelitis, bronchiectasis, chronic pulmonary obstructive disease, skin and eye diseases, periodontitis, osteoporosis, rheumatoid arthritis, ulcerative colitis, prostatitis, tumor growth and invasion, metastasis, diabetes, diabetic proteinuria, panbronchiolitis; aortic or vascular aneurysms, skin tissue wounds, dry eye, bone, cartilage degradation, malaria, senescence, diabetes, vascular stroke, neurodegenerative disorders, cardiac disease, juvenile diabetes, acute and chronic bronchitis, sinusitis, and respiratory infections, including the common cold; Wegener's granulomatosis; neutrophilic dermatoses and other inflammatory diseases such as dermatitis herpetiformis, leukocytoclastic vasculitis, bullous lupus erythematosus, pustular psoriasis, erythema elevatum diutinum; vitiligo; discoid lupus erythematosus; pyoderma gangrenosum; pustular psoriasis; blepharitis, or meibomianitis; Alzheimer's disease; degenerative maculopathy; acute and chronic gastroenteritis and colitis; acute and chronic cystitis and urethritis; acute and chronic dermatitis; acute and chronic conjunctivitis; acute and chronic serositis; uremic pericarditis; acute and chronic cholecystis; cystic fibrosis, acute and chronic vaginitis; acute and chronic uveitis; drug reactions; insect bites; burns and sunburn, bone mass disorder, acute lung injury, chronic lung disorders, ischemia, stroke or ischemic stroke, skin wound, aortic or vascular aneurysm, diabetic retinopathy, hemorrhagic stroke, angiogenesis, and other states for which tetracycline compounds have been found to be active (see, for example, U.S. Pat. Nos. 5,789,395; 5,834,450; 6,277,061 and 5,532,227, each of which is expressly incorporated herein by reference).

In addition, a method to treat any disease or disease state that could benefit from modulating the expression and/or function of nitric oxide, metalloproteases, proinflammatory mediators and cytokines, reactive oxygen species, components of the immune response, including chemotaxis, lymphocyte transformation, delayed hypersensitivity, antibody production, phagocytosis, and oxidative metabolism of phagocytes. A method to treat any disease or disease state that could benefit from modulating the expression and/or function of C-reactive protein, signaling pathways (e.g., FAK signaling pathway), and/or augment the expression of COX-2 and $PGE_2$ production is covered. A method to treat any disease or disease state that could benefit from inhibition of neovascularization is covered.

Compounds of the invention can be used to prevent or treat important mammalian and veterinary diseases such as diarrhea, urinary tract infections, infections of skin and skin structure, ear, nose and throat infections, wound infection, mastitis and the like. In addition, methods for treating neoplasms using tetracycline compounds of the invention are also included (van der Bozert et al., Cancer Res., 48: 6686-6690 (1988)).

Infections that can be treated using compounds of the invention or a pharmaceutically acceptable salt thereof include, but are not limited to, skin infections, GI infections, urinary tract infections, genito-urinary infections, respiratory tract infections, sinuses infections, middle ear infections, systemic infections, cholera, influenza, bronchitis, acne, malaria, sexually transmitted disease including syphilis and gonorrhea, Legionnaires' disease, Lyme disease, Rocky Mountain spotted fever, Q fever, typhus, bubonic plague, gas gangrene, hospital acquired infections, leptospirosis, whooping cough, anthrax and infections caused by the agents responsible for lymphogranuloma venereum, inclusion conjunctivitis, or psittacosis. Infections can be bacterial, fungal, parasitic and viral infections (including those which are resistant to other tetracycline compounds).

In one embodiment, the infection can be caused bacteria. In another embodiment, the infection is caused by a Gram-positive bacteria. In a specific aspect of this embodiment, the infection is caused by a Gram-positive bacterium selected from *Staphylococcus* spp., *Streptococcus* spp., *Propionibacterium* spp., *Enterococcus* spp., *Bacillus* spp., *Corynebacterium* spp., *Nocardia* spp, *Clostridium* spp., *Actinobacteria* spp., and *Listeria* spp.

In another embodiment, the infection is caused by a Gram-negative bacterium. In one aspect of this embodiment, the infection is caused by a proteobacteria (e.g., Betaproteobacteria and Gammaproteobacteria), including *Escherichia coli, Salmonella, Shigella*, other Enterobacteriaceae, *Pseudomonas, Moraxella, Helicobacter, Stenotrophomonas, Bdellovibrio*, acetic acid bacteria, *Legionella* or alpha-proteobacteria such as *Wolbachia*. In another aspect, the infection is caused by a Gram-negative bacteria selected from cyanobacteria, spirochaetes, green sulfur or green non-sulfur bacteria. In a specific aspect of this embodiment, the infection is caused by a Gram-negative bacteria selected from Enterobactericeae (e.g., *E. coli, Klebsiella pneumonia* including those containing extended-spectrum β-lactamases and/or carbapenemases), Bacteroidaceae (e.g., *Bacteroides fragilis*), Vibrionaceae (*Vibrio cholerae*), Pasteurellae (e.g., *Haemophilus influenza*), Pseudomonadaceae (e.g., *Pseudomonas aeruginosa*), Neisseriaceae (e.g. *Neisseria meningitidis*), Rickettsiae, Moraxellaceae (e.g., *Moraxella catarrhalis*), any species of *Proteeae, Acinetobacter* spp., *Helicobacter* spp., and *Campylobacter* spp.

In a particular embodiment, the infection is caused by Gram-negative bacterium selected from the group consisting of Enterobactericeae (e.g., *E. coli, Klebsiella pneumoniae*), *Pseudomonas*, and *Acinetobacter* spp, In another embodiment, the infection is caused by an organism selected from the group consisting of *K. pneumoniae, Salmonella, E. hirae, A. baumanii, M. catarrhalis, H. influenzae, P. aeruginosa, E. faecium, E. coli, S. aureus*, and *E. faecalis*.

In another embodiment, the infection is caused by an organism selected from the group consisting of rickettsiae, chlamydiae, *Legionella* spp. and *Mycoplasma* spp. In another embodiment, the infection is caused by an organism resistant to tetracycline or any member of first and second generation of tetracycline antibiotics (e.g., doxycycline or minocycline).

In another embodiment, the infection is caused by an organism resistant to methicillin.

In another embodiment, the infection is caused by an organism resistant to vancomycin.

In another embodiment, the infection is caused by an organism resistant to a quinolone or fluoroquinolone.

In another embodiment, the infection is caused by an organism resistant to tigecycline.

In another embodiment, the infection is caused by a multidrug-resistant pathogen (having intermediate or full resistance to any two or more antibiotics). In another embodiment the infection is a *Bacillus anthracis* infection. "*Bacillus anthracis* infection" includes any state, diseases, or disorders caused or which result from exposure or alleged exposure to *Bacillus anthracis* or another member of the *Bacillus cereus* group of bacteria. In another embodiment, the infection is caused by *Bacillus anthracia* (anthrax), *Yersinia pestis* (plague), or *Francisella tularensis* (tularemia).

In yet another embodiment, the infection can be caused by more than one organism described above. Examples of such infections include, but are not limited to, intra-abdominal infections (often a mixture of a gram-negative species like *E. coli* and an anaerobe like *B. fragilis*), diabetic foot (various combinations of *Streptococcus, Serratia, Staphylococcus* and *Enterococcus* spp., anaerobes (S. E. Dowd, et al., PloS one 2008; 3:e3326) and respiratory disease (especially in patients that have chronic infections like cystic fibrosis— e.g., *S. aureus* plus *P. aeruginosa* or *H. influenza*, atypical pathogens), wounds and abscesses (various gram-negative and gram-positive bacteria, notably MSSA/MRSA, coagulase-negative staphylococci, enterococci, *Acinetobacter, P. aeruginosa, E. coli, B. fragilis*), and bloodstream infections (13% were polymicrobial (H. Wisplinghoff, et al., Clin. Infect. Dis. 2004; 39:311-317)).

In a further embodiment, the tetracycline responsive disease or disorder is not a bacterial infection. In another embodiment, the tetracycline compounds of the invention are essentially non-antibacterial. For example, non-antibacterial compounds of the invention may have MIC values greater than about 4 µg/ml (as measured by assays known in the art and/or the assay given in Example 14. In another embodiment, the tetracycline compounds of the invention have both antibacterial and non-antibacterial effects.

Tetracycline responsive disease or disorder also includes diseases or disorders associated with inflammatory process associated states (IPAS). The teen "inflammatory process associated state" includes states in which inflammation or inflammatory factors (e.g., matrix metalloproteinases (MMPs), nitric oxide (NO), TNF, interleukins, plasma proteins, cellular defense systems, cytokines, lipid metabolites, proteases, toxic radicals, adhesion molecules, etc.) are involved or are present in an area in aberrant amounts, e.g., in amounts which may be advantageous to alter, e.g., to benefit the subject. The inflammatory process is the response of living tissue to damage. The cause of inflammation may be due to physical damage, chemical substances, microorganisms, tissue necrosis, cancer or other agents. Acute inflammation is short-lasting, lasting only a few days. If it is longer lasting however, then it may be referred to as chronic inflammation.

IPASs include inflammatory disorders. Inflammatory disorders are generally characterized by heat, redness, swelling, pain and loss of function. Examples of causes of inflammatory disorders include, but are not limited to, microbial infections (e.g., bacterial and fungal infections), physical agents (e.g., burns, radiation, and trauma), chemical agents (e.g., toxins and caustic substances), tissue necrosis and various types of immunologic reactions.

Examples of inflammatory disorders can be treated using the compounds of the invention or a pharmaceutically acceptable salt thereof include, but are not limited to, osteoarthritis, rheumatoid arthritis, acute and chronic infections (bacterial and fungal, including diphtheria and pertussis); acute and chronic bronchitis, sinusitis, and upper respiratory infections, including the common cold; acute and chronic gastroenteritis and colitis; inflammatory bowel disorder; acute and chronic cystitis and urethritis; vasculitis; sepsis; nephritis; pancreatitis; hepatitis; lupus; inflammatory skin disorders including, for example, eczema, dermatitis, psoriasis, pyoderma gangrenosum, acne rosacea, and acute and chronic dermatitis; acute and chronic conjunctivitis; acute and chronic serositis (pericarditis, peritonitis, synovitis, pleuritis and tendinitis); uremic pericarditis; acute and chronic cholecystis; acute and chronic vaginitis; acute and chronic uveitis; drug reactions; insect bites; burns (thermal, chemical, and electrical); and sunburn.

IPASs also include matrix metalloproteinase associated states (MMPAS). MMPAS include states characterized by aberrant amounts of MMPs or MMP activity. Examples of matrix metalloproteinase associated states ("MMPAS's") can be treated using compounds of the invention or a pharmaceutically acceptable salt thereof, include, but are not limited to, arteriosclerosis, corneal ulceration, emphysema, osteoarthritis, multiple sclerosis (Liedtke et al., Ann. Neural. 1998, 44: 35-46; Chandler et al., J. Neuroimmunol. 1997, 72: 155-71), osteosarcoma, osteomyelitis, bronchiectasis, chronic pulmonary obstructive disease, skin and eye diseases, periodontitis, osteoporosis, rheumatoid arthritis, ulcerative colitis, inflammatory disorders, tumor growth and invasion (Stetler-Stevenson et al., Annu. Rev. Cell Biol. 1993, 9: 541-73; Tryggvason et al., Biochim. Biophys. Acta 1987, 907: 191-217; Li et al., Mol. Carcillog. 1998, 22: 84-89)), metastasis, acute lung injury, stroke, ischemia, diabetes, aortic or vascular aneurysms, skin tissue wounds, dry eye, bone and cartilage degradation (Greenwald et al., Bone 1998, 22: 33-38; Ryan et al., Curr. Op. Rheumatol. 1996, 8: 238-247). Other MMPAS include those described in U.S. Pat. Nos. 5,459,135; 5,321,017; 5,308,839; 5,258,371; 4,935,412; 4,704,383, 4,666,897, and RE 34,656, incorporated herein by reference in their entirety.

In a further embodiment, the IPAS includes disorders described in U.S. Pat. Nos. 5,929,055; and 5,532,227, incorporated herein by reference in their entirety.

Tetracycline responsive disease or disorder also includes diseases or disorders associated with NO associated states. The term "NO associated states" includes states which involve or are associated with nitric oxide (NO) or inducible nitric oxide synthase (iNOS). NO associated state includes states which are characterized by aberrant amounts of NO and/or iNOS. Preferably, the NO associated state can be treated by administering tetracycline compounds of the invention. The disorders, diseases and states described in U.S. Pat. Nos. 6,231,894; 6,015,804; 5,919,774; and 5,789,395 are also included as NO associated states. The entire contents of each of these patents are hereby incorporated herein by reference.

Examples of diseases or disorders associated with NO associated states can be treated using the compounds of the present invention or a pharmaceutically acceptable salt thereof include, but are not limited to, malaria, senescence, diabetes, vascular stroke, neurodegenerative disorders (Alzheimer's disease and Huntington's disease), cardiac disease (reperfusion-associated injury following infarction), juvenile diabetes, inflammatory disorders, osteoarthritis, rheumatoid arthritis, acute, recurrent and chronic infections (bacterial, viral and fungal); acute and chronic bronchitis, sinusitis, and respiratory infections, including the common cold; acute and chronic gastroenteritis and colitis; acute and chronic cystitis and urethritis; acute and chronic dermatitis; acute and chronic conjunctivitis; acute and chronic serositis (pericarditis, peritonitis, synovitis, pleuritis and tendonitis); uremic pericarditis; acute and chronic cholecystis; cystic fibrosis, acute and chronic vaginitis; acute and chronic uveitis; drug reactions; insect bites; burns (thermal, chemical, and electrical); and sunburn.

In another embodiment, the tetracycline responsive disease or disorder is cancer. Examples of cancers that can be treated using the compounds of the invention or a pharmaceutically acceptable salt thereof include all solid tumors, i.e., carcinomas e.g., adenocarcinomas, and sarcomas. Adenocarcinomas are carcinomas derived from glandular tissue or in which the tumor cells form recognizable glandular structures. Sarcomas broadly include tumors whose cells are embedded in a fibrillar or homogeneous substance like embryonic connective tissue, Examples of carcinomas which may be treated using the methods of the invention include, but are not limited to, carcinomas of the prostate, breast, ovary, testis, lung, colon, and breast. The methods of the invention are not limited to the treatment of these tumor types, but extend to any solid tumor derived from any organ system. Examples of treatable cancers include, but are not limited to, colon cancer, bladder cancer, breast cancer, melanoma, ovarian carcinoma, prostate carcinoma, lung cancer, and a variety of other cancers as well. The methods of the invention also cause the inhibition of cancer growth in adenocarcinomas, such as, for example, those of the prostate, breast, kidney, ovary, testes, and colon. In one embodiment, the cancers treated by methods of the invention include those described in U.S. Pat. Nos. 6,100,248; 5,843,925; 5,837,696; or 5,668,122, incorporated herein by reference in their entirety.

Alternatively, the tetracycline compounds may be useful for preventing or reducing the likelihood of cancer recurrence, for example, to treat residual cancer following surgical resection or radiation therapy. The tetracycline compounds useful according to the invention are especially advantageous as they are substantially non-toxic compared to other cancer treatments.

In a further embodiment, the compounds of the invention are administered in combination with standard cancer therapy, such as, but not limited to, chemotherapy.

Examples of tetracycline responsive states can be treated using the compounds of the invention or a pharmaceutically acceptable salt thereof also include neurological disorders which include both neuropsychiatric and neurodegenerative disorders, but are not limited to, such as Alzheimer's disease, dementias related to Alzheimer's disease (such as Pick's disease), Parkinson's and other Lewy diffuse body diseases, senile dementia, Huntington's disease, Gilles de la Tourette's syndrome, multiple sclerosis, amyotrophic lateral sclerosis (ALS), progressive supranuclear palsy, epilepsy, and Creutzfeldt-Jakob disease; autonomic function disorders such as hypertension and sleep disorders, and neuropsychiatric disorders, such as depression, schizophrenia, schizoaffective disorder, Korsakoff's psychosis, mania, anxiety disorders, or phobic disorders; learning or memory disorders, e.g., amnesia or age-related memory loss, attention deficit disorder, dysthymic disorder, major depressive disorder, mania, obsessive-compulsive disorder, psychoactive substance use disorders, anxiety, phobias, panic disorder, as well as bipolar affective disorder, e.g., severe bipolar affective (mood) disorder (BP-1), bipolar affective neurological disorders, e.g., migraine and obesity.

Further neurological disorders include, for example, those listed in the American Psychiatric Association's Diagnostic and Statistical manual of Mental Disorders (DSM), the most current version of which is incorporated herein by reference in its entirety.

In another embodiment, the tetracycline responsive disease or disorder is diabetes. Diabetes that can be treated using the compounds of the invention or a pharmaceutically acceptable salt thereof include, but are not limited to, juvenile diabetes, diabetes mellitus, diabetes type I, or diabetes type II. In a further embodiment, protein glycosylation is not affected by the administration of the tetracycline compounds of the invention. In another embodiment, the tetracycline compound of the invention is administered in combination with standard diabetic therapies, such as, but not limited to insulin therapy.

In another embodiment, the tetracycline responsive disease or disorder is a bone mass disorder. Bone mass disorders that can be treated using the compounds of the invention or a pharmaceutically acceptable salt thereof include disorders where a subjects bones are disorders and states where the formation, repair or remodeling of bone is advantageous. For examples bone mass disorders include osteoporosis (e.g., a decrease in bone strength and density), bone fractures, bone formation associated with surgical procedures (e.g., facial reconstruction), osteogenesis imperfecta (brittle bone disease), hypophosphatasia, Paget's disease, fibrous dysplasia, osteopetrosis, myeloma bone disease, and the depletion of calcium in bone, such as that which is related to primary hyperparathyroidism. Bone mass disorders include all states in which the formation, repair or remodeling of bone is advantageous to the subject as well as all other disorders associated with the bones or skeletal system of a subject which can be treated with the tetracycline compounds of the invention. In a further embodiment, the bone mass disorders include those described in U.S. Pat. Nos. 5,459,135; 5,231,017; 5,998,390; 5,770,588; RE 34,656; 5,308,839; 4,925,833; 3,304,227; and 4,666,897, each of which is hereby incorporated herein by reference in its entirety.

In another embodiment, the tetracycline responsive disease or disorder is acute lung injury. Acute lung injuries that can be treated using the compounds of the invention or a pharmaceutically acceptable salt thereof include adult respiratory distress syndrome (ARDS), post-pump syndrome (PPS), and trauma. Trauma includes any injury to living tissue caused by an extrinsic agent or event. Examples of trauma include, but are not limited to, crush injuries, contact with a hard surface, or cutting or other damage to the lungs.

The tetracycline responsive disease or disorders of the invention also include chronic lung disorders. Examples of chronic lung disorders that can be treated using the compounds of the invention or a pharmaceutically acceptable salt thereof include, but are not limited, to asthma, cystic fibrosis, chronic obstructive pulmonary disease (COPD), and emphysema. In a further embodiment, the acute and/or chronic lung disorders that can be treated using the compounds of the invention or a pharmaceutically acceptable salt thereof include those described in U.S. Pat. Nos. 5,977,091; 6,043,231; 5,523,297; and 5,773,430, each of which is hereby incorporated herein by reference in its entirety.

In yet another embodiment, the tetracycline responsive disease or disorder is ischemia, stroke, or ischemic stroke.

In a further embodiment, the tetracycline compounds of the invention or a pharmaceutically acceptable salt thereof can be used to treat such disorders as described above and in U.S. Pat. Nos. 6,231,894; 5,773,430; 5,919,775 and 5,789,395, incorporated herein by reference.

In still a further embodiment, the tetracycline compounds of the invention or a pharmaceutically acceptable salt thereof can be used to treat pain, for example, inflammatory, nociceptive or neuropathic pain. The pain can be either acute or chronic.

In another embodiment, the tetracycline responsive disease or disorder is a skin wound. The invention also provides a method for improving the healing response of the epithelialized tissue (e.g., skin, mucosae) to acute traumatic injury (e.g., cut, burn, scrape, etc.). The method includes using a tetracycline compound of the invention or a pharmaceutically acceptable salt thereof to improve the capacity of the epithelialized tissue to heal acute wounds. The method may increase the rate of collagen accumulation of the healing tissue. The method may also decrease the proteolytic activity in the epithelialized tissue by decreasing the collagenolytic and/or gellatinolytic activity of MMPs. In a further embodiment, the tetracycline compound of the invention or a pharmaceutically acceptable salt thereof is administered to the surface of the skin (e.g., topically). In a further embodiment, the tetracycline compound of the invention or a pharmaceutically acceptable salt thereof is used to treat a skin wound, and other such disorders as described in, for example, U.S. Pat. Nos. 5,827,840; 4,704,383; 4,935,412; 5,258,371; 5,308,839, 5,459,135; 5,532,227; and 6,015,804; each of which is incorporated herein by reference in its entirety.

In yet another embodiment, the tetracycline responsive disease or disorder is an aortic or vascular aneurysm in vascular tissue of a subject (e.g., a subject having or at risk of having an aortic or vascular aneurysm, etc.). The tetracycline compound or a pharmaceutically acceptable salt thereof may be effective to reduce the size of the vascular aneurysm or it may be administered to the subject prior to the onset of the vascular aneurysm such that the aneurysm is prevented. In one embodiment, the vascular tissue is an artery, e.g., the aorta, e.g., the abdominal aorta. In a further embodiment, the tetracycline compounds of the invention are used to treat disorders described in U.S. Pat. Nos. 6,043,225 and 5,834,449, incorporated herein by reference in their entirety.

The compounds of the invention or a pharmaceutically acceptable salt thereof can be used alone or in combination with one or more therapeutic agent in the methods of the invention disclosed herein.

The language "in combination with" another therapeutic agent or treatment includes co-administration of the tetracycline compound and with the other therapeutic agent or treatment as either a single combination dosage form or as multiple, separate dosage forms, administration of the tetracycline compound first, followed by the other therapeutic agent or treatment and administration of the other therapeutic agent or treatment first, followed by the tetracycline compound.

The other therapeutic agent may be any agent that is known in the art to treat, prevent, or reduce the symptoms of a tetracycline-responsive disease or disorder. The choice of additional therapeutic agent(s) is based upon the particular tetracycline-responsive disease or disorder being treated. Such choice is within the knowledge of a treating physician. Furthermore, the other therapeutic agent may be any agent of benefit to the patient when administered in combination with the administration of a tetracycline compound.

As used herein, the term "subject" means a mammal in need of treatment or prevention, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of the specified treatment.

As used herein, the term "treating" or 'treatment" refers to obtaining desired pharmacological and/or physiological effect. The effect can include achieving, partially or substantially, one or more of the following results: partially or totally reducing the extent of the disease, disorder or syndrome; ameliorating or improving a clinical symptom or indicator associated with the disorder; delaying, inhibiting or decreasing the likelihood of the progression of the disease, disorder or syndrome.

As used herein, "preventing" or "prevention" refers to reducing the likelihood of the onset or development of disease, disorder or syndrome.

"Effective amount" means that amount of active compound agent that elicits the desired biological response in a subject. In one embodiment, the effective amount of a compound of the invention is from about 0.01 mg/kg/day to about 1000 mg/kg/day, from about 0.1 mg/kg/day to about 100 mg/kg/day, or from about 0.5 mg/kg/day to about 50 mg/kg/day.

The invention further includes the process for making the composition comprising mixing one or more of the present compounds and an optional pharmaceutically acceptable carrier; and includes those compositions resulting from such a process, which process includes conventional pharmaceutical techniques.

The compositions of the invention include ocular, oral, nasal, transdermal, topical with or without occlusion, intravenous (both bolus and infusion), inhalable, and injection (intraperitoneally, subcutaneously, intramuscularly, intratumorally, or parenterally) formulations. The composition may be in a dosage unit such as a tablet, pill, capsule, powder, granule, liposome, ion exchange resin, sterile ocular solution, or ocular delivery device (such as a contact lens or the like facilitating immediate release, timed release, or sustained release), parenteral solution or suspension, metered aerosol or liquid spray, drop, ampoule, auto-injector device, or suppository; for administration ocularly, orally, intranasally, sublingually, parenterally, or rectally, or by inhalation or insufflation.

Compositions of the invention suitable for oral administration include solid forms such as pills, tablets, caplets, capsules (each including immediate release, timed release, and sustained release formulations), granules and powders; and, liquid forms such as solutions, syrups, elixirs, emulsions, and suspensions. Forms useful for ocular administration include sterile solutions or ocular delivery devices. Forms useful for parenteral administration include sterile solutions, emulsions, and suspensions.

The compositions of the invention may be administered in a form suitable for once-weekly or once-monthly administration. For example, an insoluble salt of the active compound may be adapted to provide a depot preparation for intramuscular injection (e.g., a decanoate salt) or to provide a solution for ophthalmic administration.

The dosage form containing the composition of the invention contains an effective amount of the active ingredient necessary to provide a therapeutic effect. The composition may contain from about 5,000 mg to about 0.5 mg (preferably, from about 1,000 mg to about 0.5 mg) of a compound of the invention or salt form thereof and may be constituted into any form suitable for the selected mode of administration. The composition may be administered about 1 to about 5 times per day. Daily administration or post-periodic dosing may be employed.

For oral administration, the composition is preferably in the form of a tablet or capsule containing, e.g., 500 to 0.5 milligrams of the active compound. Dosages will vary depending on factors associated with the particular patient being treated (e.g., age, weight, diet, and time of administration), the severity of the condition being treated, the compound being employed, the mode of administration, and the strength of the preparation.

The oral composition is preferably formulated as a homogeneous composition, wherein the active ingredient is dispersed evenly throughout the mixture, which may be readily subdivided into dosage units containing equal amounts of a compound of the invention. Preferably, the compositions are prepared by mixing a compound of the invention (or pharmaceutically acceptable salt thereof) with one or more optionally present pharmaceutical carriers (such as a starch, sugar, diluent, granulating agent, lubricant, glidant, binding agent, and disintegrating agent), one or more optionally present inert pharmaceutical excipients (such as water, glycols, oils, alcohols, flavoring agents, preservatives, coloring agents, and syrup), one or more optionally present conventional tableting ingredients (such as corn starch, lactose, sucrose, sorbitol, talc, stearic acid, magnesium stearate, dicalcium phosphate, and any of a variety of gums), and an optional diluent (such as water).

Binder agents include starch, gelatin, natural sugars (e.g., glucose and beta-lactose), corn sweeteners and natural and synthetic gums (e.g., acacia and tragacanth). Disintegrating agents include starch, methyl cellulose, agar, and bentonite.

Tablets and capsules represent an advantageous oral dosage unit form. Tablets may be sugarcoated or filmcoated using standard techniques. Tablets may also be coated or otherwise compounded to provide a prolonged, control-release therapeutic effect. The dosage form may comprise an inner dosage and an outer dosage component, wherein the outer component is in the form of an envelope over the inner component. The two components may further be separated by a layer which resists disintegration in the stomach (such as an enteric layer) and permits the inner component to pass intact into the duodenum or a layer which delays or sustains release. A variety of enteric and non-enteric layer or coating materials (such as polymeric acids, shellacs, acetyl alcohol, and cellulose acetate or combinations thereof) may be used.

Compounds of the invention may also be administered via a slow release composition; wherein the composition includes a compound of the invention and a biodegradable slow release carrier (e.g., a polymeric carrier) or a pharmaceutically acceptable non-biodegradable slow release carrier (e.g., an ion exchange carrier).

Biodegradable and non-biodegradable slow release carriers are well known in the art. Biodegradable carriers are used to form particles or matrices which retain an active agent(s) and which slowly degrade/dissolve in a suitable environment (e.g., aqueous, acidic, basic and the like) to release the agent. Such particles degrade/dissolve in body fluids to release the active compound(s) therein. The particles are preferably nanoparticles or nanoemulsions (e.g., in the range of about 1 to 500 nm in diameter, preferably about 50-200 nm in diameter, and most preferably about 100 nm in diameter). In a process for preparing a slow release composition, a slow release carrier and a compound of the invention are first dissolved or dispersed in an organic solvent. The resulting mixture is added into an aqueous solution containing an optional surface-active agent(s) to produce an emulsion. The organic solvent is then evaporated from the emulsion to provide a colloidal suspension of particles containing the slow release carrier and the compound of the invention.

The compound disclosed herein may be incorporated for administration orally or by injection in a liquid form such as aqueous solutions, suitably flavored syrups, aqueous or oil suspensions, flavored emulsions with edible oils such as cottonseed oil, sesame oil, coconut oil or peanut oil and the like, or in elixirs or similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone, and gelatin. The liquid forms in suitably flavored suspending or dispersing agents may also include synthetic and natural gums. For parenteral administration, sterile suspensions and solutions are desired. Isotonic preparations, which generally contain suitable preservatives, are employed when intravenous administration is desired.

The compounds may be administered parenterally via injection. A parenteral formulation may consist of the active ingredient dissolved in or mixed with an appropriate inert liquid carrier. Acceptable liquid carriers usually comprise aqueous solvents and other optional ingredients for aiding solubility or preservation. Such aqueous solvents include sterile water, Ringer's solution, or an isotonic aqueous saline solution. Other optional ingredients include vegetable oils (such as peanut oil, cottonseed oil, and sesame oil), and organic solvents (such as solketal, glycerol, and formyl). A sterile, non-volatile oil may be employed as a solvent or suspending agent. The parenteral formulation is prepared by dissolving or suspending the active ingredient in the liquid carrier whereby the final dosage unit contains from 0.005 to 10% by weight of the active ingredient. Other additives include preservatives, isotonizers, solubilizers, stabilizers, and pain-soothing agents. Injectable suspensions may also be prepared, in which case appropriate liquid carriers, suspending agents and the like may be employed.

Compounds of the invention may be administered intranasally using a suitable intranasal vehicle.

In another embodiment, the compounds of this invention may be administered directly to the lungs by inhalation.

Compounds of the invention may also be administered topically or enhanced by using a suitable topical transdermal vehicle or a transdermal patch.

For ocular administration, the composition is preferably in the form of an ophthalmic composition. The ophthalmic compositions are preferably formulated as eye-drop formulations and filled in appropriate containers to facilitate administration to the eye, for example a dropper fitted with a suitable pipette. Preferably, the compositions are sterile and aqueous based, using purified water. In addition to the compound of the invention, an ophthalmic composition may contain one or more of: a) a surfactant such as a polyoxyethylene fatty acid ester; b) a thickening agents such as cellulose, cellulose derivatives, carboxyvinyl polymers, polyvinyl polymers, and polyvinylpyrrolidones, typically at a concentration n the range of about 0.05 to about 5.0% (wt/vol); c) (as an alternative to or in addition to storing the composition in a container containing nitrogen and optionally including a free oxygen absorber such as Fe), an anti-oxidant such as butylated hydroxyanisol, ascorbic acid, sodium thiosulfate, or butylated hydroxytoluene at a concentration of about 0.00005 to about 0.1% (wt/vol); d) ethanol at a concentration of about 0.01 to 0.5% (wt/vol); and e) other excipients such as an isotonic agent, buffer, preservative, and/or pH-controlling agent. The pH of the ophthalmic composition is desirably within the range of 4 to 8.

In certain embodiments, the composition of this invention includes one or more additional agents. The other therapeutic agent may be any agent that is capable of treating, preventing or reducing the symptoms of a tetracycline-responsive disease or disorder. Alternatively, the other therapeutic agent may be any agent of benefit to a patient when administered in combination with the tetracycline compound in this invention.

While this invention has been particularly shown and described with references to example embodiments thereof, it will be understood by those skilled in the art that various changes in form and details may be made therein without departing from the scope of the invention encompassed by the appended claims.

EXEMPLIFICATION

The following abbreviations are used in throughout the application.
Ac acetyl
AIBN 2,2'-azobis(2-methylpropionitrile)
aq aqueous
Bn benzyl
Boc tert-butoxycarbonyl
Bu butyl
Cbz benzyloxycarbonyl
Cy tricyclohexylphosphine
dba dibenzylideneacetone
DIBAL-H diisobutylaluminum hydride
DIEA N N-diisopropylethylamine
DMAP 4-(dimethylamino)pyridine
DME 1,2-dimethoxyethane
DMF N,N-dimethylformamide
DMPU 1,3-dimethyl-3,4-5,6-tetrahydro-2(1H)-pyrimidone
DMSO dimethyl sulfoxide
EDC N-(3-dimethylaminopropyl)-N'-ethylcarbodiimide
ESI electrospray ionization
Et ethyl
EtOAc ethyl acetate
HPLC high performance liquid chromatography
HOBt 1-hydroxybenzotriazole
i iso
IBX 2-iodoxybenzoic acid
LDA lithium diisopropylamide
LHMDS lithium bis(trimethylsilyl)amide
LTMP lithium 2,2,6,6-tetramethylpiperidide
MeOH methanol
Ms methanesulfonyl
MS mass spectrometry
MTBE methyl tert-butyl ether
MW molecular weight
NBS N-bromosuccinimide
NCS N-chlorosuccinimide
NMR nuclear magnetic resonance spectrometry
Ph phenyl
Pr propyl
secondary
t tertiary
TMEDA N,N,N'N'-tetramethylethylenediamine
TBS tert-butyldimethylsilyl
TEA triethylamine
Tf trifluoromathanesulfonyl
TFA trifluoroacetic acid
TFAA trifluoroacetic anhydride
THF tetrahydrofuran
TLC thin layer chromatography
Ts para-toluenesulfonyl
TsOH para-toluenesulfonic acid
Xantphos 4,5-bis(diphenylphosphino)-9,9-dimethylxanthene

EXAMPLE 1

Synthesis of Compound 100. Compound 100 was prepared according to Scheme 1, below.

Scheme 1:

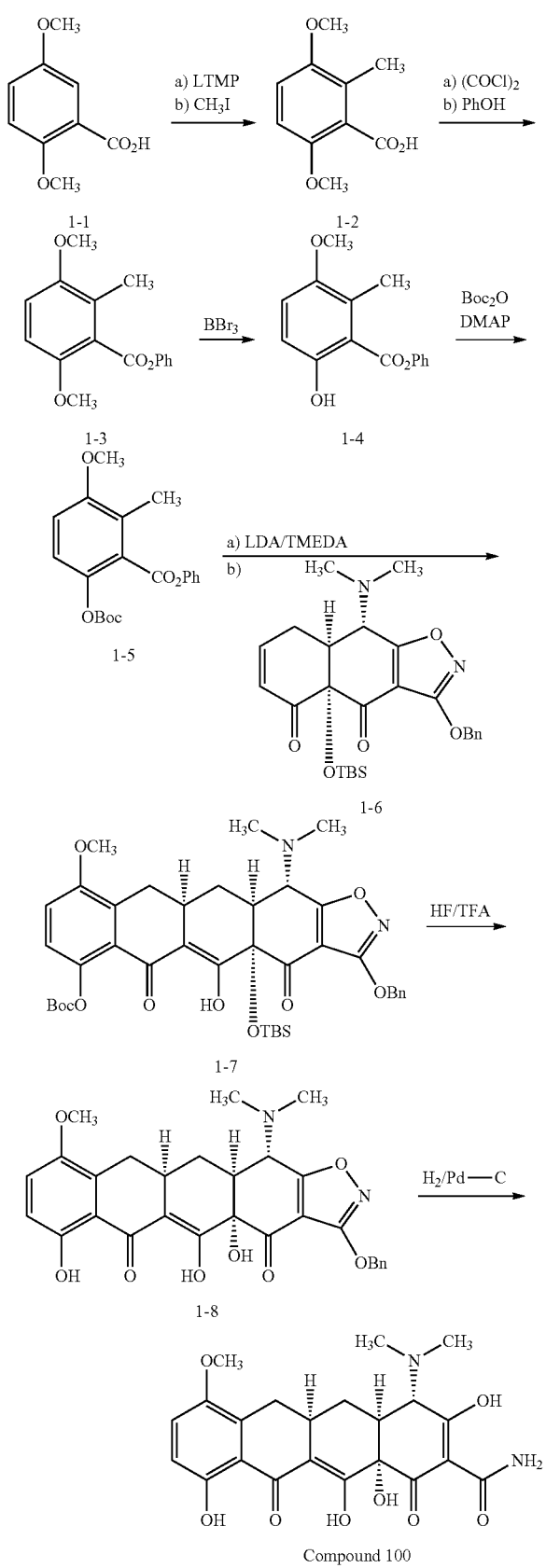

3,6-dimethoxy-2-methylbenzoic acid (1-2)

nBuLi (8.6 mL, 13.7 mmol, 5.0 equiv) was added to a THF solution (5 mL) of tetramethylpiperidine (2.3 mL, 13.7 mmol, 5.0 equiv) at 0° C. The reaction was stirred at 0° C. for 30 min. To the resulting solution was added a THF solution of 2,5-dimothoxybenzoic acid (1-1, 500 mg, 2.75 mmol) at 0° C. The reaction was stirred at 0° C. for 2.5 h. MeI (1.0 mL, 16.5 mmol, 6.0 equiv) was added to the reaction mixture dropwise. The reaction was allowed to warm to 25° C. over 1 h and stirred at 25° C. for 1 h. NaOH (6 N, 20 mL) was added. The resulting mixture was extracted with t-butylmethyl ether (20 mL×2). The aqueous layer was acidified with HCl (6 N) to pH 1 and extracted with EtOAc (20 mL×4). The combined EtOAc extracts were dried ($Na_2SO_4$) and concentrated to give 350 mg of crude product 1-2.

Phenyl 3,6-dimethoxy-2-methylbenzoate (1-3)

Oxalyl chloride (0.61 mL, 7.1 mmol, 4.0 equiv) was added to $CH_2Cl_2$ solution (15 mL, anhydrous) of crude 1-2 (350 mg, 1.79 mmol). DMF (0.1 mL) was added to the resulting mixture. The reaction was stirred at 25° C. for 1 h and concentrated. The resulting solid was re-dissolved in 15 mL of anhydrous $CH_2Cl_2$. Phenol (337 mg, 3.58 mmol, 2.0 equiv), DMAP (437 mg, 3.58 mmol, 2.0 equiv), and triethylamine (1.20 mL, 8.95 mmol, 5.0 equiv) were added to the reaction mixture. The reaction was stirred at 25° C. for 12 h and concentrated. EtOAc and $H_2O$ were added to the residue. The organic layer was washed with NaOH (1 N), $H_2O$, and brine, dried ($Na_2SO_4$), and concentrated. Flash chromatography on silica gel (20:1 hexanes/EtOAc) yielded 291 mg of compound 1-3 (39% for 2 steps).

Phenyl 6-hydroxy-3-methoxy-2-methylbenzoate (1-4)

$BBr_3$ (1.9 mL, 1.0 M, 1.9 mmol, 0.9 equiv) was added to a $CH_2Cl_2$ solution (10 mL) of 1-3 (582 mg, 2.14 mmol) at −78° C. The reaction was stirred from −78° C. to 25° C. for 1.5 h, quenched with saturated $NaHCO_3$ and concentrated. EtOAc and $H_2O$ were added to the reaction mixture. The aqueous layer was extracted with EtOAc. The combined EtOAc extracts were dried ($Na_2SO_4$) and concentrated to yield 480 mg of crude 1-4.

Phenyl 6-(tert-butoxycarbonyloxy)-3-methoxy-2-methylbenzoate (1-5)

$Boc_2O$ (487 mg, 2.23 mmol, 1.2 equiv) and DMAP (20 mg, 0.16 mmol, 0.1 equiv) were added to a $CH_2Cl_2$ solution of crude 1-4 (480 mg). The reaction was stirred at 25° C. for 1.5 h and concentrated. Flash chromatography on silica gel (15:1 hexanes/EtOAc) yielded 530 mg of compound 1-5 (80% for 2 steps).

(4aS,11aR,12aS,13S)-3-(benzyloxy)-4a-(tert-butyldimethylsilyloxy)-13-(dimethylamino)-5-hydroxy-10-methoxy-4,6-dioxo-4,4a,6,11,11a,12,12a,13-octahydrotetraceno[2,3-d]isoxazol-7-yl tert-butyl carbonate (1-7)

A THF solution (8 mL) of 1-5 (520 mg, 1.45 mmol, 2.5 equiv) was added to a THF solution (8 mL) of LDA (6.50 mL, 10% wt, 4.36 mmol, 7.5 equiv) and TMEDA (1.0 mL, 7.3 mmol, 12.5 equiv) at −78° C. The reaction was stirred at −78° C. for 5 min. A THF solution (8 mL) of enone 1-6 (280 mg, 0.58 mmol, 1.0 equiv) was added to the reaction mixture dropwise. The enone 1-6 was prepared as described in PCT publication WO 2005/112945 and WO 2007/117639. The reaction was stirred from −78° C. to 25° C. for 1 h, quenched with saturated NH₄Cl, and extracted with EtOAc. The combined EtOAc extracts were dried (Na₂SO₄) and concentrated to yield the crude product. Preparative reverse phase HPLC purification on a Waters Autopurification system using a Sunfire Prep C18 OBD column [5 μm, 19×50 mm; flow rate, 20 mL/min; Solvent A: H₂O with 0.1% HCO₂H; Solvent B: CH₃CN with 0.1% HCO₂H; injection volume: 4.0 mL (CH₃CN); gradient: 80→100% B over 15 min; mass-directed fraction collection]. Fractions with the desired MW were collected and concentrated on a RotaVap at 25° C. to remove most of the acetonitrile. The resulting mostly aqueous solution was extracted with EtOAc. The combined EtOAc extracts were dried (Na₂SO₄) and concentrated to give 290 mg of pure 1-7 (67%).

(4aS,11aR,12aS,13S)-3-(benzyloxy)-13-(dimethyl-amino)-4a,5,7-trihydroxy-10-methoxy-11a,12,12a,13-tetrahydrotetraceno[2,3-d]isoxazole-4,6(4aH,11H)-dione (1-8)

Aqueous HF (2.4 mL, 48%) and TFA (0.1 mL) were added to a CH₃CN solution (9 mL) of 1-7 (210 mg, 0.29 mmol) in a polypropylene tube at 25° C. The reaction was stirred at 25° C. for 18 h. The resulting mixture was poured into an aqueous solution of K₂HPO₄ (21 g, dissolved in 150 mL water). The mixture was extracted with EtOAc. The combined EtOAc extracts were dried (Na₂SO₄) and concentrated to yield 86 mg of crude 1-8.

Compound 100.

Palladium on carbon (10 mg, 10 wt %) was added to a MeOH/dioxane solution (4 mL/4 mL) of crude 1-8 (86 mg). The reaction was purged with hydrogen and stirred under H₂ (balloon) at 25° C. for 1 h. The reaction mixture was filtered through a small Celite plug. The filtrate was concentrated to yield the crude product. Preparative reverse phase HPLC purification on a Waters Autopurification system using a Phenomenex Polymerx™ 10μ RP-1 100 A column [10 μm, 150×21.20 mm; flow rate, 20 mL/min; Solvent A: 0.05 N HCl/water; Solvent B: CH₃CN; injection volume: 4.0 mL (0.05 N HCl/water); gradient: 0→100% B over 15 min; mass-directed fraction collection]. Fractions with the desired MW were collected and freeze-dried to yield 47 mg of Compound 100 (81% for 2 steps): $^1$H NMR (400 MHz, CD₃OD) δ 7.21 (d, J=8.2 Hz, 1H), 6.78 (d, J=8.2 Hz, 1H), 4.05 (s, 1H), 3.78 (s, 3H), 3.08-2.90 (m, 3H), 3.01 (s, 3H), 2.94 (s, 3H), 2.20-2.11 (m, 2H), 1.67-1.56 (m, 1H); MS (ESI) m/z 445.23 (M+H).

EXAMPLE 2

Synthesis of Compounds of Formula II, Wherein Y is —NH—C(O)—CH₂—N(R²)(R³)

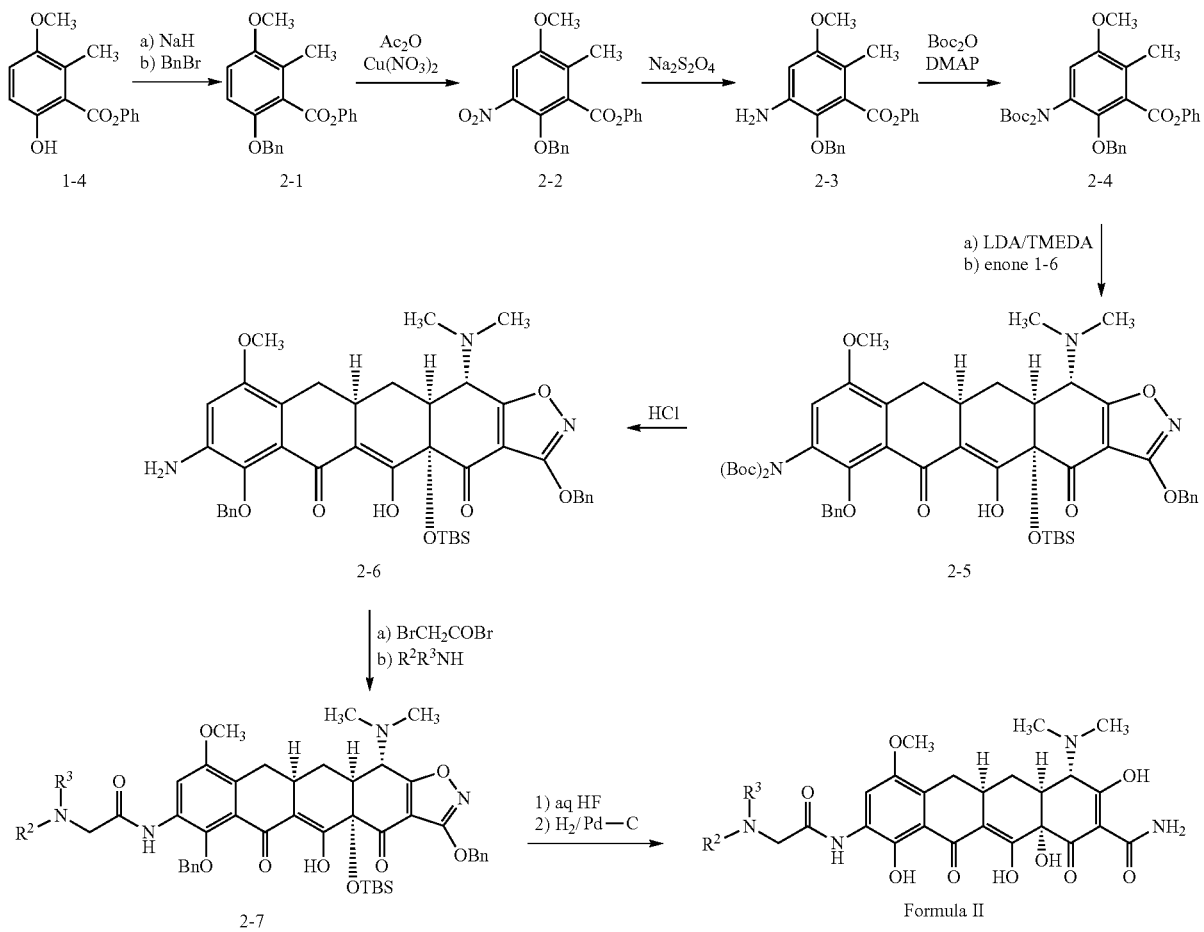

Phenyl 6-(benzyloxy)-3-methoxy-2-methylbenzoate (2-1)

Phenol 1-4 (4.58 g, 17.7 mmol) was dissolved in anhydrous DMF (71 mL) and NaH (1.42 g, 35.5 g, 2 eq) was added. The mixture was stirred at rt for 30 min. Benzylbromide (4.2 mL, 35.5 mmol, 2 eq) was then added. After stirring for an overnight at rt, the mixture was partitioned between EtOAc and $H_2O$. The organic layer was further washed with additional $H_2O$ three times and brine once. The organic phase was dried over $Na_2SO_4$, filtered and concentrated with rotavapor. Purification of the residue by flash chromatography (silica gel, 97:3 hexanes/EtOAc) gave 2-1 (4.09 g) as white solid: $^1H$ NMR (400 MHz, $CDCl_3$) δ7.45-7.22 (m, 8H), 7.13 (m, 2H), 6.82 (m, 2H), 5.11 (s, 2H), 3.81 (s, 3H), 2.32 (s, 3H); MS (ESI) m/z 371.2 (M+Na), calcd for $C_{22}H_{20}NaO_4$ 371.14.

Phenyl 2-(benzyloxy)-5-methoxy-6-methyl-3-nitrobenzoate (2-2)

Solid $Cu(NO_3)_2.xH_2O$ (3.006 g, 12.9 mmol, 1.1 eq) was added to a stirred solution of the compound 2-1 (4.09 g, 11.8 mmol) in acetic anhydride (47 mL) at 0° C. The reaction mixture was stirred at 0° C. for 1 h and rt for 2 h, then poured into 100 mL ice-water. Stirring was continued for another 1 h. The resulting yellow precipitate was collected by filtration. Further purification with flash chromatography (silica gel, 95:5 hexanes/EtOAc) yielded compound 2-2 as light yellow solid (3.58 g): $^1H$ NMR (400 MHz, $CDCl_3$) δ7.50 (s, 1H), 7.47-7.25 (m, 8H), 7.02-7.00 (m, 2H), 5.11 (s, 2H), 3.92 (s, 3H), 2.36 (s, 3H); MS (ESI) m/z 392.2 (M−H), calcd for $C_{22}H_{18}NO_6$ 392.12.

Phenyl 2-(benzyloxy)-5-methoxy-6-methyl-3-aminobenzoate (2-3)

A mixture of nitro 2-2 (3.58 g, 9.11 mmol), $Na_2S_2O_4$ (9.33 g, 45.5 mmol, 5 equiv), 136 mL THF, and 87 mL $H_2O$ was stirred at rt for an overnight. After removing most of THF with rotavapor, the aqueous solution was extracted with EtOAc three times. The combined organic layers were washed with brine, dried over $Na_2SO_4$, filtered and concentrated. The crude product 2-3 was used directly in the next step.

Phenyl 2-(benzyloxy)-3-(bis(tert-butoxycarbonyl)amino)-5-methoxy-6-methylbenzoate (2-4)

Di-tert-butyl dicarbonate (5.04 g, 23.1 mmol, 2.5 eq) and DMAP (56 mg, 0.46 mmol, 0.05 eq) were added to the solution of 2-3 (3.36 g, 9.24 mmol) in anhydrous DMF (92 mL). The resulting mixture was stirred at rt for 5 h, and then diluted with EtOAc. The solution was washed with $H_2O$ three times, brine, dried over $Na_2SO_4$, filtered and concentrated. Further purification with flash chromatography (silica gel, 9:1 hexanes/EtOAc) yielded compound 2-4 as white solid (4.20 g): $^1H$ NMR (400 MHz, $CDCl_3$) δ7.34-7.14 (m, 8H), 6.96 (d, J=7.8 Hz, 2H), 6.65 (s, 1H), 4.86 (s, 2H), 3.76 (s, 3H), 2.24 (s, 3H), 1.33 (s, 18H); MS (ESI) m/z 586.2 (M+Na), calcd for $C_{32}H_{37}NNaO_8$ 586.25.

Intermediate 2-5.

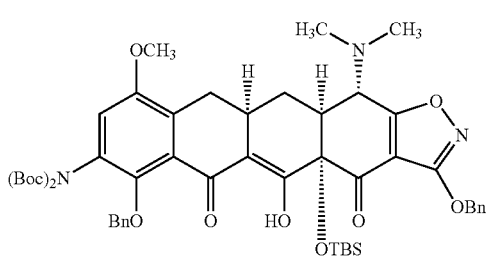

A solution of nBuLi in hexanes (1.60 M, 5.70 mL, 9.13 mmol, 1.1 eq) was added dropwise to a solution of $^iPr_2NH$ (1.29 mL, 9.13 mmol, 1.1 eq) and TMEDA (1.49 mL, 9.96 mmol, 1.2 eq) in THF (23 mL) at −78° C. The resulting solution was stirred at −78° C. for 1 h whereupon a solution of compound 2-4 (4.68 g, 8.30 mmol, 1 eq) in THF (30 mL) was added dropwise via cannula (colorless to dark orange-red). After completion of addition, the mixture was stirred for another 30 min at −78° C., and then cooled to −100° C. Pre-cooled to −78° C. solution of enone 1-6 (2.0 g, 4.15 mmol, 0.5 eq) in THF (30 mL) was added dropwise via cannula. The resulting red color mixture was allowed to warm to −20° C. in 2 h. The reaction was quenched with sat. aq. $NH_4Cl$, then extracted with EtOAc three times. The combined EtOAc extracts were washed with brine, dried ($Na_2SO_4$), and concentrated. Purification of the residue by flash chromatography (silica gel, 95:5 to 85:15 hexanes/EtOAc) gave desired product 2-5 (3.589 g) as a light yellow foam: $^1H$ NMR (400 MHz, $CDCl_3$) δ16.05 (s, 1H), 7.52-7.26 (m, 10H), 6.85 (s, 1H), 5.35 (s, 2H), 4.97 (d, J=9.8 Hz, 1H), 4.73 (d, J=9.8 Hz, 1H), 3.99 (d, J=10.4 Hz, 1H), 3.80 (s, 3H), 3.36 (dd, J=16.5, 4.9 Hz, 1H), 2.98-2.92 (m, 1H), 2.60-2.40 (m, 8H), 2.36-2.28 (m, 1H), 2.16-2.13 (m, 1H), 1.38 (s, 18H), 0.80 (s, 9H), 0.24 (s, 3H), 0.13 (s, 3H); MS (ESI) m/z 952.59 (M+H), calcd for $C_{52}H_{66}N_3O_{12}Si$ 952.43.

(4aS,11aR,12aS,13S)-8-amino-3,7-bis(benzyloxy)-4a-(tert-butyldimethylsilyloxy)-13-(dimethylamino)-5-hydroxy-10-methoxy-11a,12,12a,13-tetrahydrotetraceno[2,3-d]isoxazole-4,6(4aH,11H)-dione (2-6)

To a solution of compound 2-5 (468 mg, 0.49 mmol) in anhydrous dioxane (9 mL) was added solution of HCl in dioxane (4M, 9 mL) at rt. The resulting mixture was stirred at rt and the reaction was monitored by LC-MS. The volatiles were evaporated after SM was completely consumed. The residue was suspended in EtOAc, and washed with sat. $NaHCO_3$, brine, dried ($Na_2SO_4$), and concentrated. Purification of the residue by flash chromatography (silica gel, 80:20 hexanes/EtOAc) gave desired product 2-6 (422 mg) as a light yellow foam: $^1H$ NMR (400 MHz, $CDCl_3$) δ16.14 (s, 1H), 7.52-7.26 (m, 10H), 6.48 (s, 1H), 5.35 (s, 2H), 4.88 (d, J=9.8 Hz, 1H), 4.81 (d, J=9.8 Hz, 1H), 3.84 (br s, 1H), 3.74 (s, 3H), 3.22 (dd, J=16.5, 4.9 Hz, 1H), 2.98-2.88 (m, 1H), 2.60-2.40 (m, 8H), 2.31-2.20 (m, 1H), 2.16-2.10 (m, 1H), 0.82 (s, 9H), 0.27 (s, 3H), 0.13 (s, 3H); MS (ESI) m/z 752.3 (M+H), calcd for $C_{42}H_{53}N_3O_8Si$ 752.33.

The choice of amine $NHR^2R^3$ used to convert 2-6 to 2-7 varied depending upon the desired final product.

Compound 101.

2-6 (29 mg, 0.039 mmol) was dissolved in THF (1.5 mL). bromoacetyl bromide (4.0 µL, 0.046 mmol) was added.

After stirred at rt for 30 min, pyrrolidine (16.0 μL, 0.19 mmol) was added. Stirring was continued at rt. The reaction mixture was poured into brine after SM was completely consumed and extracted with EtOAc three times. The combined EtOAc layers were dried with $Na_2SO_4$ and concentrated to give a crude 2-7 wherein $R^2$ and $R^3$ are taken together to from pyrrolidine, which was used directly for the next step without purification. In a plastic vial, 2-7 was dissolved in $CH_3CN$ (1 mL). Aqueous HF (48%, 0.25 mL) was added. After stirred at rt for 16 h, the reaction mixture was poured into aqueous solution (12.5 mL) of $K_2HPO_4$ (1.75 g). The resulting mixture was extracted three times with EtOAc. The combined organic phases were washed with brine, dried, concentrated to give crude product. The above crude was dissolved in 0.5 N HCl in MeOH (155 μL, 2 eq). The excess volatiles were evaporated. The pre-formed HCl salt was re-dissolved in MeOH (2.0 mL) and to the resulting solution was added palladium on carbon (10% wt, 9.0 mg, 30% w/w). The reaction flask was briefly evacuated and re-filled with hydrogen. The reaction mixture was stirred at rt and monitored by LC-MS. After SM was consumed, the mixture was filtered through a small pad of Celite. The filtrate was concentrated to give crude, which was purified by HPLC on a Waters Autopurification system using a Phenomenex Polymerx™ 10μ RP-γ 100 R column [30×21.20 mm, 10 micron; flow rate, 20 mL/min; Solvent A: 0.05 N HCl/water; Solvent B: $CH_3CN$; injection volume: 4.0 mL (0.05 N HCl/water); gradient: 10→50% B over 10 min; mass-directed fraction collection]. Fractions with the desired MW, eluting at 5.14-5.60 min, were collected and freeze-dried to give Compound 101 as a yellow solid: $^1$H NMR (400 MHz, $CD_3OD$) δ 8.11 (s, 1H), 4.32 (s, 2H), 4.09 (s, 1H), 3.81-3.75 (m, 5H), 3.30-3.15 (m, 3H), 110-2.90 (m, 8H), 2.25-2.00 (m, 6H), 1.68-1.54 (m, 1H); MS (ESI) m/z 571.2 (M+H), calcd for $C_{28}H_{35}N_4O_9$ 571.23.

Compound 102.

Compound 102 was obtained by the procedure of Compound 101 employing azetidine as $NR^2R^3$. Crude product was purified by HPLC on a Waters Autopurification system using a Phenomenex Polymerx™ 10μ RP-γ 100 R column [30×21.20 mm, 10 micron; flow rate, 20 mL/min; Solvent A: 0.05 N HCl/water; Solvent B: $CH_3CN$; injection volume: 4.0 mL (0.05 N HCl/water); gradient: 10→40% B over 10 min; mass-directed fraction collection]. Fractions with the desired MW, eluting at 5.36-5.80 min, were collected and freeze-dried to give Compound 102 as a yellow solid: $^1$H NMR (400 MHz, $CD_3OD$) δ 8.08 (s, 1H), 4.42-4.34 (m, 4H), 4.25-4.18 (m, 2H), 4.10 (s, 1H), 3.77 (s, 3H), 3.28-3.20 (m, 1H), 3.08-2.92 (m, 8H), 2.70-2.62 (m, 1H), 2.56-2.44 (m, 1H), 2.22-2.06 (m, 2H), 1.65-1.56 (m, 1H); MS (ESI) m/z 557.2 (M+H), calcd for $C_{27}H_{33}N_4O_9$ 557.22.

Compound 103.

Compound 103 was obtained by the procedure of Compound 101 employing piperidine as $NR^2R^3$. Crude product was purified by HPLC on a Waters Autopurification system using a Phenomenex Polymerx™ 10μ RP-γ 100 R column [30×21.20 mm, 10 micron; flow rate, 20 mL/min; Solvent A: 0.05 N HCl/water; Solvent B: $CH_3CN$; injection volume: 4.0 mL (0.05 N HCl/water); gradient: 10→30% B over 10 min; mass-directed fraction collection]. Fractions with the desired MW, eluting at 7.12-7.80 min, were collected and freeze-dried to give Compound 103 as a yellow solid: $^1$H NMR (400 MHz, $CD_3OD$) δ8.11 (s, 1H), 4.19 (s, 2H), 4.09 (s, 1H), 3.79 (s, 3H), 3.65-3.62 (m, 2H), 3.28-3.20 (m, 1H), 3.18-2.90 (m, 10H), 2.25-2.08 (m, 2H), 2.00-1.80 (m, 6H), 1.65-1.56 (m, 1H); MS (ESI) m/z 585.2 (M+H), calcd for $C_{29}H_{37}N_4O_9$ 585.25.

Compound 104.

Compound 104 was obtained by the procedure of Compound 101 employing N-ethyl methylamine as $NR^2R^3$. Crude product was purified by HPLC on a Waters Autopurification system using a Phenomenex Polymerx™ 10μ RP-γ 100 R column [30×21.20 mm, 10 micron; flow rate, 20 mL/min; Solvent A: 0.05 N HCl/water; Solvent B: $CH_3CN$; injection volume: 4.0 mL (0.05 N HCl/water); gradient: 10→30% B over 10 min; mass-directed fraction collection]. Fractions with the desired MW, eluting at 5.80-6.30 min, were collected and freeze-dried to give Compound 104 as a yellow solid: $^1$H NMR (400 MHz, $CD_3OD$) δ8.12 (s, 1H), 4.30 (d, J=16.0 Hz, 1H), 4.19 (d, J=16.0 Hz, 1H), 4.10 (s, 1H), 3.80 (s, 3H), 3.45-3.20 (m, 3H), 3.10-2.90 (m, 11H), 2.25-2.08 (m, 2H), 1.65-1.56 (m, 1H), 1.40 (t, J=7.3 Hz, 3H); MS (ESI) m/z 559.2 (M+H), calcd for $C_{27}H_{35}N_4O_9$ 559.23.

Compound 105.

Compound 105 was obtained by the procedure of Compound 101 employing dimethylamine as $NR^2R^3$. Crude product was purified by HPLC on a Waters Autopurification system using a Phenomenex Polymerx™ 10μ RP-γ 100 R column [30×21.20 mm, 10 micron; flow rate, 20 mL/min; Solvent A: 0.05 N HCl/water; Solvent B: $CH_3CN$; injection volume: 4.0 mL (0.05 N HCl/water); gradient: 10→30% B over 10 min; mass-directed fraction collection]. Fractions with the desired MW, eluting at 5.76-6.22 min, were collected and freeze-dried to give Compound 105 as a yellow solid: $^1$H NMR (400 MHz, $CD_3OD$) δ8.12 (s, 1H), 4.24 (s, 2H), 4.09 (s, 1H), 3.80 (s, 3H), 3.30-3.25 (m, 1H), 3.10-2.90 (m, 14H), 2.25-2.08 (m, 2H), 1.65-1.56 (m, 1H); MS (ESI) m/z 545.2 (M+H), calcd for $C_{26}H_{33}N_4O_9$ 545.22.

Compound 106.

Compound 106 was obtained by the procedure of Compound 101 employing isobutylamine as $NR^2R^3$. Crude product was purified by HPLC on a Waters Autopurification system using a Phenomenex Polymerx™ 10μ RP-γ 100 R column [30×21.20 mm, 10 micron; flow rate, 20 mL/min; Solvent A: 0.05 N HCl/water; Solvent B: $CH_3CN$; injection volume: 4.0 mL (0.05 N HCl/water); gradient: 10→30% B over 10 min; mass-directed fraction collection]. Fractions with the desired MW, eluting at 7.36-8.05 min, were collected and freeze-dried to give Compound 106 as a yellow solid: $^1$H NMR (400 MHz, $CD_3OD$) δ 8.13 (s, 1H), 4.09 (s, 3H), 3.79 (s, 3H), 3.30-3.25 (m, 1H), 3.10-2.90 (m, 10H), 2.25-2.05 (m, 3H), 1.65-1.56 (m, 1H), 1.07 (d, J=6.9 Hz, 6H); MS (ESI) m/z 573.3 (M+H), calcd for $C_{28}H_{37}N_4O_9$ 573.25.

Compound 107.

Compound 107 was obtained by the procedure of Compound 101 employing isopropylamine as $NR^2R^3$. Crude product was purified by HPLC on a Waters Autopurification system using a Phenomenex Polymerx™ 10μ RP-γ 100 R column [30×21.20 mm, 10 micron; flow rate, 20 mL/min; Solvent A: 0.05 N HCl/water; Solvent B: $CH_3CN$; injection volume: 4.0 mL (0.05 N HCl/water); gradient: 10→30% B over 10 min; mass-directed fraction collection]. Fractions with the desired MW, eluting at 6.10-6.54 min, were collected and freeze-dried to give Compound 107 as a yellow solid: $^1$H NMR (400 MHz, $CD_3OD$) δ8.13 (s, 1H), 4.09 (s, 3H), 3.79 (s, 3H), 3.45-3.55 (m, 1H), 3.30-3.25 (m, 1H), 3.10-2.90 (m, 8H), 2.25-2.10 (m, 2H), 1.65-1.56 (m, 1H), 1.38 (d, J=6.4 Hz, 6H); MS (ESI) m/z 559.3 (M+H), calcd for $C_{27}H_{35}N_4O_9$ 559.23.

Compound 108.

Compound 108 was obtained by the procedure of Compound 101 employing cyclopropylamine as $NR^2R^3$. Crude product was purified by HPLC on a Waters Autopurification system using a Phenomenex Polymerx™ 10μ RP-γ 100 R column [30×21.20 mm, 10 micron; flow rate, 20 mL/min; Solvent A: 0.05 N HCl/water; Solvent B: $CH_3CN$; injection volume: 4.0 mL (0.05 N HCl/water); gradient: 10→30% B over 10 min; mass-directed fraction collection]. Fractions with the desired MW, eluting at 5.82-6.50 min, were collected and freeze-dried to give Compound 108 as a yellow solid: $^1H$ NMR (400 MHz, $CD_3OD$) δ 8.13 (s, 1H), 4.09 (s, 3H), 3.79 (s, 3H), 3.45-3.55 (m, 1H), 3.30-3.25 (m, 1H), 3.10-2.90 (m, 8H), 2.25-2.10 (m, 2H), 1.65-1.56 (m, 1H), 1.38 (d, J=6.4 Hz, 6H); MS (ESI) m/z 557.3 (M+H), calcd for $C_{27}H_{33}N_4O_9$ 557.22.

Compound 109.

Compound 109 was obtained by the procedure of Compound 101 employing tert-butylamine as $NR^2R^3$. Crude product was purified by HPLC on a Waters Autopurification system using a Phenomenex Polymerx™ 10μ RP-γ 100 R column [30×21.20 mm, 10 micron; flow rate, 20 mL/min; Solvent A: 0.05 N HCl/water; Solvent B: $CH_3CN$; injection volume: 4.0 mL (0.05 N HCl/water); gradient: 10→30% B over 10 min; mass-directed fraction collection]. Fractions with the desired MW, eluting at 6.46-6.92 min, were collected and freeze-dried to give Compound 109 as a yellow solid: $^1H$ NMR (400 MHz, $CD_3OD$) δ 8.14 (s, 1H), 4.08 (s, 3H), 3.78 (s, 3H), 3.30-3.25 (m, 1H), 3.10-2.90 (m, 8H), 2.25-2.10 (m, 2H), 1.65-1.56 (m, 1H), 1.42 (s, 9H); MS (ESI) m/z 573.2 (M+H), calcd for $C_{28}H_{37}N_4O_9$ 573.25.

Compound 110.

Compound 110 was obtained from 2-5 by HF treatment and hydrogenation according to procedures used in the preparation of Compound 101. Crude product was purified by HPLC on a Waters Autopurification system using a Phenomenex Polymerx™ 10μ RP-γ 100 R column [30×21.20 mm, 10 micron; flow rate, 20 mL/min; Solvent A: 0.05 N HCl/water; Solvent B: $CH_3CN$; injection volume: 4.0 mL (0.05 N HCl/water); gradient: 10→30% B over 10 min; mass-directed fraction collection]. Fractions with the desired MW, eluting at 4.88-5.78 min, were collected and freeze-dried to give Compound 110 as a yellow solid: $^1H$ NMR (400 MHz, $CD_3OD$) δ 7.27 (s, 1H), 4.09 (s, 1H), 3.83 (s, 3H), 3.30-3.25 (m, 1H), 3.10-2.90 (m, 8H), 2.25-2.10 (m, 2H), 1.65-1.56 (m, 1H); MS (ESI) m/z 460.2 (M+H), calcd for $C_{22}H_{26}N_3O_8$ 460.16.

Compound 111.

Compound 111 was obtained by the procedure of Compound 101, substituting bromoacetyl bromide and pyrrolidine with 3,3,-dimethylbutyryl chloride. Crude product was purified by HPLC on a Waters Autopurification system using a Phenomenex Polymerx™ 10μ RP-γ 100 R column [30×21.20 mm, 10 micron; flow rate, 20 mL/min; Solvent A: 0.05 N HCl/water; Solvent B: $CH_3CN$; injection volume: 4.0 mL (0.05 N HCl/water); gradient: 10→30% B over 10 min; mass-directed fraction collection]. Fractions with the desired MW, eluting at 12.40-13.97 min, were collected and freeze-dried to give Compound 111 as a yellow solid: $^1H$ NMR (400 MHz, $CD_3OD$) δ 7.99 (s, 1H), 4.07 (s, 1H), 3.79 (s, 3H), 3.30-3.25 (m, 1H), 3.10-2.90 (m, 8H), 2.34 (s, 2H), 2.25-2.10 (m, 2H), 1.65-1.56 (m, 1H), 1.10 (s, 9H); MS (ESI) m/z 558.0 (M+H), calcd for $C_{28}H_{36}N_3O_9$ 558.24.

Compound 112.

Compound 112 was obtained by the procedure of Compound 101 employing 3-fluoroazetidine as $NR^2R^3$. Crude product was purified by HPLC on a Waters Autopurification system using a Phenomenex Polymerx™ 10μ RP-γ 100 R column [30×21.20 mm, 10 micron; flow rate, 20 mL/min; Solvent A: 0.05 N TFA/water; Solvent B: $CH_3CN$; injection volume: 4.0 mL (0.05 N HCl/water); gradient: 10→30% B over 20 min; mass-directed fraction collection]. Fractions with the desired MW, eluting at 12.35-13.50 min, were collected and freeze-dried to give Compound 112 as a yellow solid: $^1H$ NMR (400 MHz, $CD_3OD$) δ8.10 (s, 1H), 5.51-5.37 (m, 1H), 4.70-4.39 (m, 6H), 4.05 (s, 1H), 3.79 (s, 3H), 3.30-3.25 (m, 1H), 3.10-2.90 (m, 8H), 2.25-2.10 (m, 2H), 1.65-1.56 (m, 1H); MS (ESI) m/z 575.2 (M+H), calcd for $C_{27}H_{32}FN_4O_9$ 575.21.

Compound 113.

Compound 113 was obtained by the procedure of Compound 101, substituting bromoacetyl bromide and pyrrolidine with 4,4,-dimethylpentyryl chloride. Crude product was purified by HPLC on a Waters Autopurification system using a Phenomenex Polymerx™ 10μ RP-γ 100 R column [30×21.20 mm, 10 micron; flow rate, 20 mL/min; Solvent A: 0.05 N HCl/water; Solvent B: $CH_3CN$; injection volume: 4.0 mL (0.05 N HCl/water); gradient: 15→60% B over 10 min; mass-directed fraction collection]. Fractions with the desired MW, eluting at 9.06-9.74 min, were collected and freeze-dried to give Compound 113 as a yellow solid: $^1H$ NMR (400 MHz, $CD_3OD$) δ8.02 (s, 1H), 4.07 (s, 1H), 3.78 (s, 3H), 3.30-3.25 (m, 1H), 3.10-2.90 (m, 8H), 2.48-2.44 (m, 2H), 2.25-2.10 (m, 2H), 1.65-1.56 (m, 3H), 0.96 (s, 9H); MS (ESI) m/z 572.4 (M+H), calcd for $C_{29}H_{38}N_3O_9$ 572.25.

Compound 114.

Compound 114 was obtained by the procedure of Compound 101 employing (R)-3-fluoropyrrolidine as $NR^2R^3$. Crude product was purified by HPLC on a Waters Autopurification system using a Phenomenex Polymerx™ 10μ RP-γ 100 R column [30×21.20 mm, 10 micron; flow rate, 20 mL/min; Solvent A: 0.05 N HCl/water; Solvent B: $CH_3CN$; injection volume: 4.0 mL (0.05 N HCl/water); gradient: 5→25% B over 12 min; mass-directed fraction collection]. Fractions with the desired MW, eluting at 9.05-11.05 min, were collected and freeze-dried to give Compound 114 as a yellow solid: $^1H$ NMR (400 MHz, $CD_3OD$) δ8.13 (s, 1H), 5.55-5.42 (m, 1H), 4.45-4.41 (m, 2H), 4.15-3.95 (m, 3H), 3.79 (s, 3H), 3.50-3.40 (m, 2H), 3.30-3.25 (m, 1H), 3.10-2.90 (m, 8H), 2.50-2.35 (m, 2H), 2.25-2.10 (m, 2H), 1.65-1.56 (m, 1H); MS (ESI) m/z 589.3 (M+H), calcd for $C_{29}H_{34}FN_4O_9$ 589.22.

Compound 115.

Compound 115 was obtained by the procedure of Compound 101 employing (S)-3-fluoropyrrolidine as $NR^2R^3$. Crude product was purified by HPLC on a Waters Autopurification system using a Phenomenex Polymerx™ 10μ RP-γ 100 R column [30×21.20 mm, 10 micron; flow rate, 20 mL/min; Solvent A: 0.05 N HCl/water; Solvent B: $CH_3CN$; injection volume: 4.0 mL (0.05 N HCl/water); gradient: 5→30% B over 12 min; mass-directed fraction collection]. Fractions with the desired MW, eluting at 8.05-9.85 min, were collected and freeze-dried to give Compound 115 as a yellow solid: $^1H$ NMR (400 MHz, $CD_3OD$) δ8.12 (s, 1H), 5.55-5.42 (m, 1H), 4.46-4.42 (m, 2H), 4.15-3.95 (m, 3H), 3.79 (s, 3H), 3.50-3.40 (m, 2H), 3.30-3.25 (m, 1H), 3.10-2.90 (m, 8H), 2.55-2.40 (m, 2H), 2.25-2.10 (m, 2H), 1.65-1.56 (m, 1H); MS (ESI) m/z 589.3 (M+H), calcd for $C_{29}H_{34}FN_4O_9$ 589.22.

Compound 116.

Compound 116 was obtained by the procedure of Compound 101 employing O-tert-butyl hydroxylamine as $NR^2R^3$. $^1H$ NMR (400 MHz, $CD_3OD$) δ 8.12 (s, 1H), 4.34 (s, 2H), 4.15 (s, 1H), 3.80 (s, 3H), 2.85-3.50 (m, 3H), 3.07 (s, 3H), 2.99 (s, 3H), 2.22-2.28 (m, 1H), 2.07-2.16 (m, 1H), 1.55-1.65 (m, 1H), 1.47 (s, 9H); MS (ESI) m/z 589.1 (M+H), calcd for $C_{28}H_{37}N_4O_{10}$ 589.25.

Compound 117.

Compound 117 was obtained by the procedure of Compound 101 substituting bromoacetyl bromide and an amine with tert-butoxyacetyl chloride. $^1$H NMR (400 MHz, CD$_3$OD) δ8.31 (s, 1H), 4.08 (s, 1H), 4.07 (s, 2H), 3.80 (s, 3H), 3.24 (dd, J=7.3, 16.0 Hz, 1H), 2.90-3.10 (m, 2H), 3.05 (s, 3H), 2.97 (s, 3H), 2.15-2.22 (m, 1H), 2.05-2.21 (m, 1H), 1.55-1.65 (m, 1H), 1.32 (s, 9H); MS (ESI) m/z 574.2 (M+H), calcd for C$_{28}$H$_{37}$N$_3$O$_{10}$ 574.24.

Compound 118.

Compound 118 was prepared similarly to Compound 101 using ethylisopropylamine as NR$^2$R$^3$. $^1$H NMR (400 MHz, CD$_3$OD) δ8.13 (s, 1H), 4.32 (s, J=17.5 Hz, 1H), 4.08 (s, 1H), 4.06 (d, J=17.5 Hz, 1H), 3.78 (s, 3H), 3.75-3.85 (m, 2H), 2.80-3.50 (m, 10H), 2.10-2.22 (m, 2H), 1.50-1.70 (m, 1H), 1.35-1.45 (m, 9H); MS (ESI) m/z 587.1 (M+H), calcd for C$_{29}$H$_{39}$N$_4$O$_9$ 587.27.

Compound 119.

Compound 119 was prepared similarly to Compound 101 using imidazole as NR$^2$R$^3$. $^1$H NMR (400 MHz, CD$_3$OD) δ9.02 (s, 1H), 8.07 (s, 1H), 7.68 (s, 1H), 7.63 (s, 1H), 5.34 (s, 2H), 4.07 (s, 1H), 3.76 (s, 3H), 2.80-3.50 (m, 9H), 2.10-2.22 (m, 2H), 1.55-1.70 (m, 1H); MS (ESI) m/z 568.1 (M+H), calcd for C$_{27}$H$_{33}$N$_5$O$_9$ 568.21.

EXAMPLE 3

Synthesis of Certain Compounds of Formula II, wherein Y is —NH—C(O)—CH$_2$—NH(R$^3$), or —NH—C(O)-heterocyclyl. Scheme 3 depicts the synthesis of compounds of Formula II, wherein Y is —NH—C(O)-heterocyclyl or —NH—C(O)—CH$_2$—NH(R$^3$) where R$^3$ is not hydrogen.

(51 mg, 0.48 mmol, 6.0 equiv) were added into the reaction mixture and stirred at it for 1 hr. Ethylamine (0.80 mmol, 10.0 equiv) was added into the reaction mixture and stirred for 1 h. HCl/MeOH (1.1 mL 4 N) was added at 0° C. and the solution was stirred for 5 min, concentrated in vacuo, and purified by reverse phase preparative HPLC to yield the desired Compound 120 as a yellow solid: $^1$H NMR (400 MHz, CD$_3$OD) δ 8.11 (s 1H), 4.10-4.09 (m, 3 IA), 3.79 (s, 3H), 3.23-2.95 (m, 11H), 2.25-2.10 (m, 2H), 1.69-1.53 (m, 1H), 1.37 (t, J=7.2 Hz, 3H); MS (ESI) m/z 545.2 (M+H).

Compound 121.

Compound 121 was prepared similarly to Compound 120, substituting ethylamine with 2-fluoroethylamine: $^1$H NMR (400 MHz, CD$_3$OD) δ 8.08 (s 1H), 4.68 (t, J=4.4 Hz, 1H), 4.11 (s, 2H), 4.01 (s, 1H), 3.74 (s, 3H), 3.49 (t, J=4.8 Hz, 1H), 3.42 (t, J=4.8 Hz, 1H), 3.25-2.87 (m, 10H), 2.15-2.03 (m, 2H), 1.61-1.49 (m, 1H); MS (ESI) m/z 563.2 (M+H).

Compound 122.

Compound 122 was prepared similarly to Compound 120, substituting ethylamine with 2,2-difluoroethylamine: $^1$H NMR (400 MHz, CD$_3$OD) δ 8.15 (s 1H), 6.36 (t, J=44 Hz, 1H), 4.21 (s, 2H), 4.09 (s, 1H), 3.80 (s, 3H), 3.73-3.65 (m, 2H), 3.13-2.95 (m, 9H), 2.23-2.09 (m, 2H), 1.69-1.57 (m, 1H); MS (ESI) m/z 581.1 (M+H).

Compound 123.

Compound 123 was prepared similarly to Compound 120, substituting ethylamine with n-propylamine: $^1$H NMR (400 MHz, CD$_3$OD) δ 8.14 (s 1H), 4.09 (s, 3H), 3.81 (s, 3H), 3.30-3.25 (m, 2H), 3.10-2.95 (m, 9H), 2.23-2.08 (m, 2H), 1.83-1.73 (m, 2H), 1.68-1.57 (m, 1H), 1.08 (t, J=7.2 Hz, 3H); MS (ESI) m/z 559.2 (M+H).

Scheme 3:

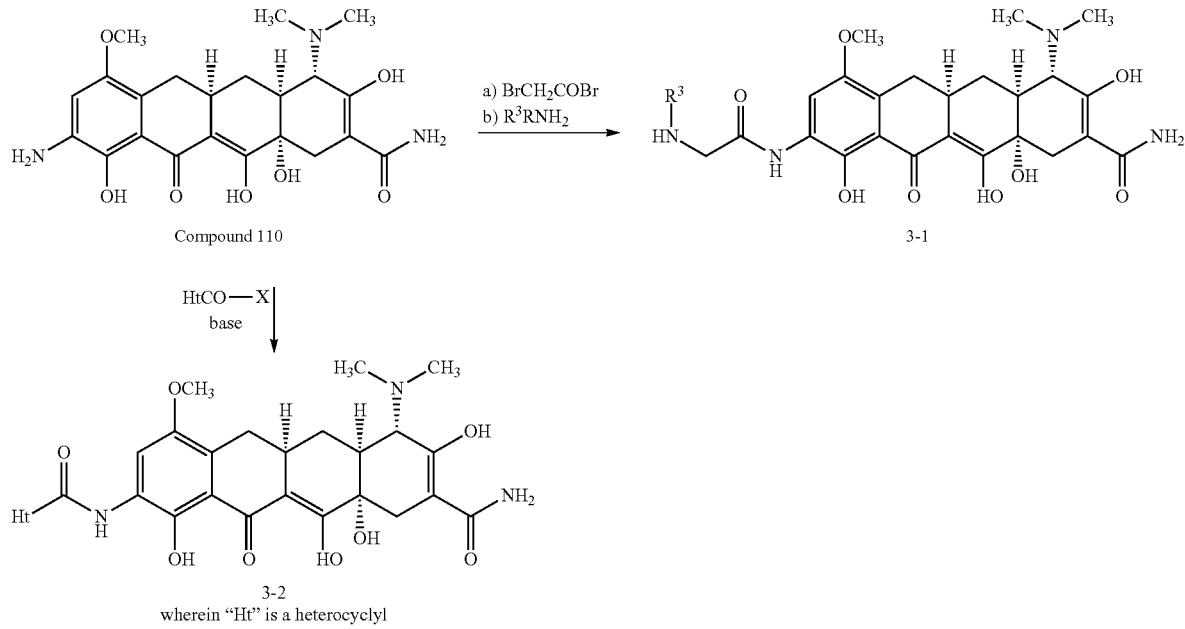

Compound 120.

Compound 110 (40 mg crude, ~0.08 mmol, 1 equiv) was dissolved in CH$_3$CN and 3 drops of DMPU. Then bromoacetyl bromide (24 mg, 0.12 mmol, 1.5 equiv) and Na$_2$CO$_3$ Compound 124.

Compound 124 was prepared similarly to Compound 120, substituting ethylamine with 2-methoxyethylamine: $^1$H NMR (400 MHz, CD$_3$OD) δ 8.13 (s, 1H), 4.13 (s, 2H), 4.05-3.93 (m, 1H), 3.80 (s, 3H), 3.75-3.65 (m, 2H), 3.44 (s, 3H), 3.36-3.23 (m, 3H), 3.10-2.90 (m, 8H), 2.25-2.05 (m, 2H), 1.68-1.59 (m, 1H); MS (ESI) m/z 575.2 (M+H).

Compound 125.

Compound 125 was prepared similarly to Compound 120, substituting ethylamine with n-hexylamine: $^1$H NMR (400 MHz, CD$_3$OD) δ 8.12 (s 1H), 4.06 (s, 3H), 3.80 (s, 3H), 3.12-2.91 (m, 11H), 2.19-2.08 (m, 2H), 1.75-1.55 (m, 3H), 1.45-1.32 (m, 6H), 0.92 (t, J=7.2 Hz, 3H); MS (ESI) m/z 601.3 (M+H).

Compound 126.

Compound 126 was prepared similarly to Compound 120, substituting ethylamine with cyclopropylmethylamine: $^1$H NMR (400 MHz, CD$_3$OD) δ 8.13 (s, 1H), 4.13 (s, 2H), 4.10 (s, 1H), 3.80 (s, 3H), 3.05-2.91 (m, 11H), 2.25-2.10 (m, 2H), 1.68-1.56 (m, 1H), 1.19-1.10 (m, 1H), 0.78-0.73 (m, 2H), 0.48-0.43 (m, 2H); MS (ESI) m/z 571.2 (M+H).

Compound 127.

Compound 127 was prepared similarly to Compound 120, substituting ethylamine with cyclobutylmethylamine: $^1$H NMR (400 MHz, CD$_3$OD) δ 8.33 (s, 1H), 4.28 (s, 1H), 4.25 (s, 2H), 3.99 (s, 3H), 3.37-3.14 (m, 11H), 2.97-2.86 (m, 1H), 2.45-2.06 (m, 8H), 1.87-1.75 (m, 1H); MS (ESI) m/z 585.3 (M+H).

Compound 128.

Compound 128 was prepared similarly to Compound 120, substituting ethylamine with cyclopentylmethylamine $^1$H NMR (400 MHz, CD$_3$OD) δ 8.34 (s, 1H), 4.29 (s, 3H), 4.07 (s, 3H), 3.30-3.10 (m, 11H), 2.50-2.30 (m, 3H), 2.18-2.10 (m, 2H), 1.95-1.78 (m, 4H), 1.55-1.46 (m, 3H); MS (ESI) m/z 599.3 (M+H).

Compound 129.

Compound 129 was prepared similarly to Compound 120, substituting ethylamine with cyclohexylmethylamine: $^1$H NMR (400 MHz, CD$_3$OD) δ 8.14 (s, 1H), 4.09 (s, 3H), 3.80 (s, 3H), 3.05-2.95 (m, 11H), 2.23-2.08 (m, 2H), 1.88-1.55 (m, 8H), 1.40-1.21 (m, 4H); MS (ESI) m/z 613.3 (M+H).

Compound 130.

Compound 130 was prepared similarly to Compound 120, substituting ethylamine with neopentylamine: $^1$H NMR (400 MHz, CD$_3$OD) δ 8.13 (s 1H), 4.11-4.10 (m, 3H), 3.80 (s, 3H), 3.26-3.20 (m, 1H), 3.08-2.95 (m, 10H), 2.25-2.06 (m, 2H), 1.66-1.54 (m, 1H), 1.12 (s, 9H); MS (ESI) m/z 587.3 (M+H).

Compound 131.

Compound 131 was prepared similarly to Compound 120, substituting ethylamine with cyclobutylamine: $^1$H NMR (400 MHz, CD$_3$OD) δ 8.11 (s 1H), 4.07 (s, 1H), 3.95 (s, 2H), 3.88-3.80 (m, 1H), 3.77 (s, 3H), 3.25-3.20 (m, 1H), 3.06-2.92 (m, 8H), 2.38-2.06 (m, 6H), 1.95-1.84 (m, 2H), 1.63-1.54 (m, 1H); MS (ESI) m/z 571.2 (M+H).

Compound 132.

Compound 132 was prepared similarly to Compound 120, substituting ethylamine with cyclopentylamine: $^1$H NMR (400 MHz, CD$_3$OD) δ 8.15 (s 1H), 4.10 (s, 3H), 3.84 (s, 3H), 3.68-3.64 (m, 1H), 3.26-3.22 (m, 1H), 3.08-2.95 (m, 8H), 2.25-2.10 (m, 4H), 1.92-1.60 (m, 7H); MS (ESI) m/z 585.3 (M+H).

Compound 133.

Compound 133 was prepared similarly to Compound 120, substituting ethylamine with cyclohexylamine: $^1$H NMR (400 MHz, CD$_3$OD) δ 8.12 (s 1H), 4.08 (s, 2H), 4.07 (s, 1H), 3.86 (s, 3H), 3.22-2.90 (m, 10H), 2.22-2.08 (m, 4H), 1.95-1.85 (m, 2H), 1.68-1.55 (m, 2H), 1.46-1.30 (m, 5H); MS (ESI) m/z 599.3 (M+H).

Compound 134.

Compound 134 was prepared similarly to Compound 120, substituting ethylamine with aniline: $^1$H NMR (400 MHz, CD$_3$OD) δ 8.22 (s 1H), 7.56-7.30 (m, 5H), 4.34 (s, 2H), 4.09 (s, 1H), 3.86 (s, 3H), 3.14-2.95 (m, 9H), 2.25-2.10 (m, 2H), 1.68-1.58 (m, 1H); MS (ESI) m/z 593.2 (M+H).

Compound 135.

Compound 135 was prepared similarly to Compound 120, substituting ethylamine with N-methylpropylamine: $^1$H NMR (400 MHz, CD$_3$OD) δ 8.11 (s 1H), 4.32 (d, J=16.0 Hz, 1H), 4.20 (d, J=16.0 Hz, 1H), 4.10 (s, 1H), 3.80 (s, 3H), 3.27-2.90 (m, 14H), 125-2.10 (m, 2H), 1.88-1.79 (m, 2H), 1.67-1.57 (m, 1H), 1.05 (t, J=7.2 Hz, 3H); MS (ESI) m/z 573.3 (M+H).

Compound 136.

Compound 136 was prepared similarly to Compound 120, substituting ethylamine with diethylamine: $^1$H NMR (400 MHz, CD$_3$OD) δ 8.10 (s 1H), 4.22 (s, 2H), 4.05 (s, 1H), 3.79 (s, 3H), 3.46-3.22 (m, 5H), 3.07-2.90 (m, 8H), 2.20-2.07 (m, 2H), 1.66-1.57 (m, 1H), 1.38 (t, J=7.2 Hz, 6H); MS (ESI) m/z 573.2 (M+H).

Compound 137.

Compound 137 was prepared similarly to Compound 120, substituting ethylamine with 3-azabicyclo[3,3,0]octane: $^1$H NMR (400 MHz, CD$_3$OD) δ 8.07 (d, J=9.2 Hz, 1H), 4.25-4.16 (m, 2H), 4.15-4.05 (m, 1H), 4.02 (s, 1H), 3.95-3.80 (m, 1H), 3.74 (s, 3H), 3.63-3.54 (m, 1H), 3.43-3.35 (m, 1H), 3.07-2.85 (m, 9H), 2.75-2.60 (m, 2H), 2.15-2.02 (m, 2H), 1.65-1.50 (m, 7H); MS (ESI) m/z 611.3 (M+H).

Compound 138.

Compound 138 was prepared similarly to Compound 120, substituting ethylamine with isoindoline: $^1$H NMR (400 MHz, CD$_3$OD) δ 8.16 (s 1H), 7.42 (s, 4H), 5.10-5.00 (m, 2H), 4.73-4.62 (m, 2H), 4.55 (s, 2H), 4.07 (s, 1H), 3.79 (s, 3H), 3.25-3.17 (m, 1H), 3.07-2.90 (m, 8H), 2.22-2.08 (m, 2H), 1.67-1.55 (m, 1H); MS (ESI) m/z 619.2 (M+H).

Compound 139.

Compound 139 was prepared similarly to Compound 120, substituting bromoacetyl bromide/amine with 3-dimethylaminobenzoyl chloride: $^1$H NMR (400 MHz, CD$_3$OD) δ 8.16 (s 1H), 8.02 (d, J=8.0 Hz, 1H), 7.91 (s, 1H), 7.85-7.82 (m, 1H), 7.71-7.67 (m, 1H), 4.01 (s, 1H), 3.73 (s, 3H), 3.28 (s, 6H), 3.20-3.16 (m, 1H), 3.01-2.85 (m, 8H), 2.20-1.98 (m, 2H), 1.57-1.48 (m, 1H), MS (ESI) m/z 607.1 (M+H).

Compound 140.

Compound 140 was prepared similarly to Compound 120, substituting bromoacetyl bromide/amine with nicotinyl chloride: $^1$H NMR (400 MHz, CD$_3$OD) δ 9.41 (s 1H), 9.14 (d, J=8.4 Hz, 1H), 9.06 (d, J=5.6 Hz, 1H), 8.23 (d, J=2.0 Hz, 1H), 8.04 (s, 1H), 4.01 (s, 1H), 3.84 (s, 3H), 3.20-3.16 (m, 1H), 3.08-2.95 (m, 8H), 2.25-2.12 (m, 2H); 1.70-1.58 (m, 1H), MS (ESI) m/z 565.1 (M+H).

EXAMPLE 4

Synthesis of Certain Compounds of Formula II, wherein Y is —NH—C(O)-(saturated heterocyclyl). Scheme 4 depicts the synthesis of other compounds of Formula II, wherein Y is —NH—C(O)-(saturated heterocyclyl).

Scheme 4:

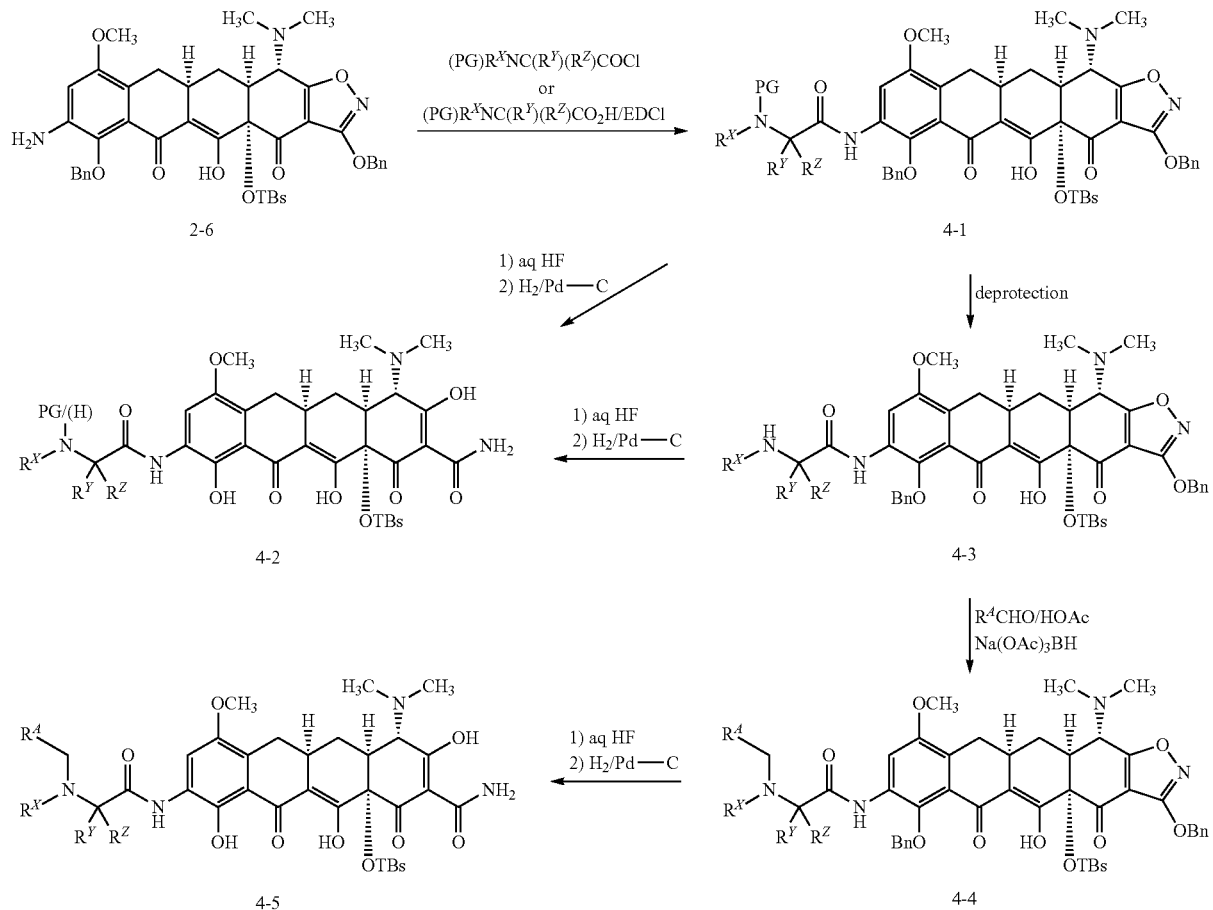

In Scheme 4, "PG" represents a protecting group and $R^A$ represents hydrogen, $(C_1-C_5)$alkyl, —$(C_0-C_5)$ alkylene-carbocyclyl, or —$(C_0-C_5)$alkylene-heterocyclyl. For all of the compounds made by Scheme 4 and described below, $R^Z$ is hydrogen and $R^X$ and $R^Y$ are taken together with the carbon and nitrogen atoms to which they are respectively bound to form an optionally substituted 4-7 membered saturated heterocyclyl. It will be readily apparent to those of skill in the art, however, that this Scheme 4 will also be useful to synthesize compounds where $R^X$, $R^Y$ and $R^Z$ are $R^2$, $R^{5b}$ and $R^{5b}$, respectively, as defined in structural formula (I).

Compound 141

4-1-1

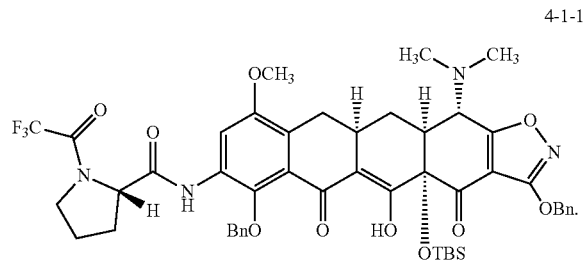

A solution of (S)-(−)—N-(trifluoroacetyl)prolyl chloride in DCM (0.1 M, 383 µL, 0.038 mmol, 1.2 equiv) was added to a solution of aniline 2-6 (24 mg, 0.032 mmol, 1.0 equiv) in THF (2 mL). The resulting light orange solution was stirred at rt for 5 min, diluted with brine (10 mL). The resulting mixture was extracted with EtOAc (2×15 mL). The combined organic extracts were dried ($Na_2SO_4$), filtered and concentrated to yield the crude product 4-1-1: MS (ESI) m/z 945.38 (M+H). Aqueous HF (48-50%, 0.2 mL) was added to a solution of the above crude product 4-1-1 in acetonitrile (0.5 mL) in a polypropylene reaction vessel at 23° C. The resulting mixture was stirred vigorously at 23° C. overnight and poured into aqueous $K_2HPO_4$ (2.5 g dissolved in 20 mL water). The resulting mixture was extracted with EtOAc (30 mL, then 2×10 mL). The combined organic extracts were dried over anhydrous sodium sulfate, filtered, and concentrated. The residue was used directly in the next step without further purification.

The above crude product was dissolved in MeOH (2 mL) and dioxane (1 mL). Pd—C (10 wt %, 6 mg) was added in one portion at 23° C. The reaction vessel was sealed and purged with hydrogen by briefly evacuating the flask followed by flushing with hydrogen gas (1 atm). After stirring at 23° C. for 4 hrs, more Pd—C (10 wt %, 5 mg) was added. The resulting mixture was stirred for 2 h and filtered through a small Celite pad. The filtrate was concentrated. The residue was purified by a preparative reverse phase HPLC on a Waters Autopurification system using a Phenomenex Polymerx™ 10µ RP-γ 100 A column [10 µm, 150×21.20 mm; flow rate, 20 mL/min; Solvent A: 0.05 N HCl/water; Solvent B: CH₃CN; injection volume: 3.0 mL (0.05 N HCl/water and MeCN, 1:1); gradient: 15→60% B over 10 min; mass-directed fraction collection]. Fractions containing the desired product, eluting at 7.3-8.0 min, were collected and freeze-dried to yield Compound 141 (11.9 mg). The product was re-purified by a preparative reverse phase HPLC on a Waters Autopurification system using a Phenomenex Polymerx™ 10μ RP-γ 100 A column [10 μm, 150×21.20 mm; flow rate, 20 mL/min; Solvent A: 0.05 N HCl/water; Solvent B: CH₃CN; injection volume: 3.0 mL (0.05 N HCl/water and MeCN, 1:1); gradient: 15→60% B over 20 min; mass-directed fraction collection]. Fractions containing the desired product, eluting at 11.4-11.8 min, were collected and freeze-dried to yield Compound 141 (8.4 mg, 38% over 3 steps): ¹H NMR (400 MHz, CD₃OD) δ 8.03 (s, 1H), 4.81-4.78 (m, 1H), 4.07 (s, 1H), 3.85 (t, J=6.4 Hz, 2H), 3.78 (s, 3H), 3.27-3.21 (m, 1H), 3.03-2.92 (m, 8H), 2.40-2.32 (m, 1H), 2.20-2.03 (m, 5H), 1.66-1.56 (m, 1H); MS (ESI) m/z 653.31 (M+H).

Compound 142

4-3-1

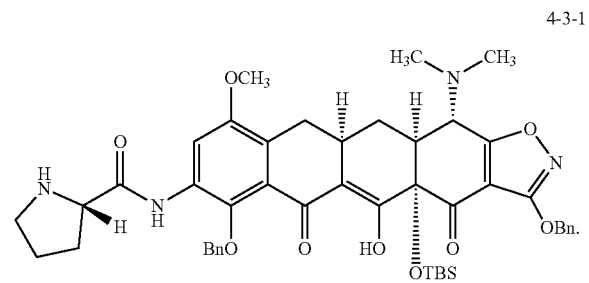

K₂CO₃ (14.7 mg, 0.106 mmol, 1.6 equiv) was added in one portion to a solution of crude product 4-1-1 (0.067 mmol, 1.0 equiv) in a mixture of MeOH (2 mL), THF (0.5 mL) and water (0.3 mL) The resulting orange reaction mixture was stirred at rt overnight. More K₂CO₃ (9 mg, 0.065 mmol, 0.98 equiv), and the reaction mixture was stirred at rt overnight. The reaction mixture was then diluted with brine (20 mL) and extracted with EtOAc (50 mL, then 20 mL). The combined organic extracts were dried over anhydrous sodium sulfate, filtered, and concentrated. The residue was purified by a Preparative reverse phase HPLC on a Waters Autopurification system using a Sunfire Prep C18 OBD column [5 μm, 19×50 mm; flow rate, 20 mL/min; Solvent A: H₂O with 0.1% HCO₂H; Solvent B: CH₃CN with 0.1% HCO₂H; injection volume: 4.0 mL (CH₃CN); gradient: 10→100% B over 10 min; mass-directed fraction collection]. Fractions with the desired MW, were collected and concentrated on a RotaVap at rt to remove most of the acetonitrile. The resulting mostly aqueous solution was neutralized with pH 7 buffer and extracted with EtOAc. The combined EtOAc extracts were dried (Na₂SO₄) and concentrated to the desired product 4-3-1 (19.3 mg, 34% over 2 steps): ¹H NMR (400 MHz, CDCl₃) δ 15.63 (br s, 1H), 11.94 (br s, 1H), 8.67 (s, 1H), 7.51-7.48 (m, 2H), 7.42-7.32 (m, 3H), 7.28-7.22 (m, 3H), 7.18-7.16 (m, 2H), 5.38 (s, 2H), 5.22, 4.52 (ABq, J=11.6 Hz, 2H), 4.60 (d, J=6.7 Hz, 1H), 4.01 (d, 9.8 Hz, 1H), 3.55 (s, 3H), 3.51-3.23 (m, 3H), 2.95-2.88 (m, 1H), 2.64-2.43 (m, 8H), 2.24-1.89 (m, 5H), 1.59-1.51 (m, 1H), 0.80 (s, 9H), 0.24 (s, 3H), 0.14 (s, 3H); MS (ESI) m/z 849.36 (M+H).

Aqueous HF (48-50%, 0.2 mL) was added to a solution of Compound 4-3-1 (9 mg, 0.011 mmol, 1.0 equiv) in acetonitrile (0.5 mL) in a polypropylene reaction vessel at 23° C. The resulting mixture was stirred vigorously at 23° C. overnight and poured into aqueous K₂HPO₄ (2.5 g dissolved in 20 mL water). The resulting mixture was extracted with EtOAc (30 mL, then 20 mL) The combined organic extracts were dried over anhydrous sodium sulfate, filtered, and concentrated. The residue was used directly in the next step without further purification.

The above crude product was dissolved in MeOH (2 mL) and dioxane (0.5 mL) Pd—C (10 wt %, 5 mg) was added in one portion at 23° C. The reaction vessel was sealed and purged with hydrogen by briefly evacuating the flask followed by flushing with hydrogen gas (1 atm). After stirring at 23° C. for 25 min, the resulting mixture was filtered through a small Celite pad. The filtrate was concentrated. The residue was purified by a preparative reverse phase HPLC on a Waters Autopurification system using a Phenomenex Polymerx™ 10μ RP-γ 100 A column [10 μm, 150×21.20 mm; flow rate, 20 mL/min; Solvent A: 0.05 N HCl/water; Solvent B: CH₃CN; injection volume: 3.0 mL (0.05 N HCl/water and MeCN, 1:1); gradient: 0→30% B over 10 min; mass-directed fraction collection]. Fractions containing the desired product, eluting at 7.5-8.7 min, were collected and freeze-dried to yield Compound 142 (1.73 mg, some product was spilled during the purification): ¹H NMR (400 MHz, CD₃OD) δ 8.03 (s, 1H), 4.56 (t, J=6.8 Hz, 1H), 4.07 (s, 1H), 3.79 (s, 3H), 3.49-3.24 (m, 3H), 3.03-2.93 (m, 8H), 2.60-2.53 (m, 1H), 2.19-2.08 (m, 5H), 1.67-1.57 (m, 1H); MS (ESI) m/z 557.27 (M+H).

Compound 145

4-4-1

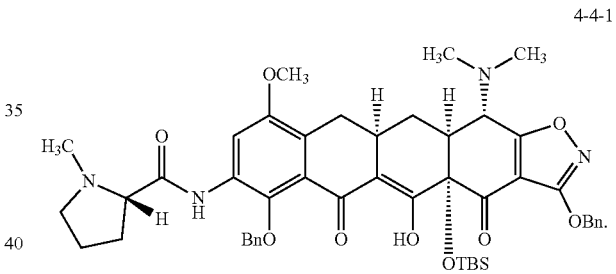

K₂CO₃ (43.9 mg, 0.318 mmol, 3.0 equiv) was added in one portion to a solution of crude product 4-1-1 (0.106 mmol, 1.0 equiv) in a mixture of MeOH (2 mL), THF (0.5 mL) and water (0.3 mL). The resulting brownish reaction mixture was stirred at rt for 3 h, and diluted with saturated aqueous ammonium chloride and pH 7 phosphate buffer (1:1, 30 mL) and extracted with EtOAc (2×50 mL). The combined organic extracts were dried over anhydrous sodium sulfate, filtered, and concentrated. The crude product 4-3-1 was used directly in the next reaction. HCHO (47 μL, 0.636 mmol, 6.0 equiv), acetic acid (18 μL, 0.318 mmol, 3.0 equiv) and sodium triacetoxyborohydride (45 mg, 0.212 mmol, 2.0 equiv) were added sequentially to a solution of the above crude product 4-3-1 in 1,2-dichloroethane (3 mL) at 23° C. After stirring for 35 min, the reaction mixture was quenched by the addition of saturated aqueous sodium bicarbonate and pH 7 phosphate buffer (1:1, mL) and extracted with EtOAc (2×50 mL). The combined organic extracts were dried over anhydrous sodium sulfate, filtered, and concentrated. The residue was purified by a Preparative reverse phase HPLC on a Waters Autopurification system using a Sunfire Prep C18 OBD column [5 μm, 19×50 mm; flow rate, 20 mL/min; Solvent A: H₂O with 0.1% HCO₂H; Solvent B: CH₃CN with 0.1% HCO₂H; injection volume: 4.0 mL (CH₃CN); gradient: 20→75% B over 20 min; mass-directed fraction collection]. Fractions with the desired MW, eluting at 12.7-13.6 min, were collected and concentrated on a RotaVap at rt to remove most of the acetonitrile. The resulting mostly aqueous solution was neutralized with pH 7 phosphate buffer and extracted with EtOAc. The combined EtOAc extracts were dried ($Na_2SO_4$) and concentrated to the desired product 4-4-1 (44.5 mg, 48% over 3 steps): $^1$H NMR (400 MHz, $CDCl_3$) δ 16.02 (br s, 1H), 10.09 (br s, 1H), 8.45 (s, 1H), 7.50-7.48 (m, 4H), 7.40-7.30 (m, 6H), 5.35 (s, 2H), 4.91, 4.80 (ABq, J=10.4 Hz, 2H), 3.99 (d, J=10.4 Hz, 1H), 3.87 (s, 3H), 3.32 (dd, J=4.9, 15.9 Hz, 1H), 3.05-2.91 (m, 3H), 2.56-2.41 (m, 8H), 2.36-2.23 (m, 5H), 2.14 (d, J=14.6 Hz, 1H), 1.95-1.89 (m, 1H), 1.78-1.68 (m, 1H), 1.62-1.53 (m, 1H), 1.39-1.33 (m, 1H), 0.81 (s, 9H), 0.26 (s, 3H), 0.12 (s, 3H); MS (ESI) m/z 863.56 (M+H).

Aqueous HF (48-50%, 0.3 mL) was added to a solution of Compound 4-4-1 (44.5 mg, 0.051 mmol, 1.0 equiv) in acetonitrile (0.8 mL) in a polypropylene reaction vessel at 23° C. The resulting mixture was stirred vigorously at 23° C. overnight and poured into aqueous $K_2HPO_4$ (3.6 g dissolved in 30 mL water). The resulting mixture was extracted with EtOAc (2×25 mL). The combined organic extracts were dried over anhydrous sodium sulfate, filtered, and concentrated. The residue was used directly in the next step without further purification.

The above crude product was dissolved in MeOH (2 mL) and EtOAc (1 mL). Pd—C (10 wt %, 22 mg) was added in one portion at 23° C. The reaction vessel was sealed and purged with hydrogen by briefly evacuating the flask followed by flushing with hydrogen gas (1 atm). After stirring at 23° C. for 1 h 20 min, more Pd—C (10 wt %, 10 mg) was added. The resulting mixture was stirred under hydrogen for 2 h. Then s solution of HCl in MeOH (0.5 N, 204 µL, 2.0 equiv) was added. The resulting reaction mixture was stirred under hydrogen for 45 min, and filtered through a small Celite pad. The filtrate was concentrated. The residue was purified by a preparative reverse phase HPLC on a Waters Autopurification system using a Phenomenex Polymerx™ 10µ RP-γ 100 A column [10 µm, 150×21.20 mm; flow rate, 20 mL/min; Solvent A: 0.05 N HCl/water; Solvent B: $CH_3CN$; injection volume: 3.0 mL (0.05 N HCl/water and MeCN, 1:1); gradient: 0→35% B over 10 min; mass-directed fraction collection]. Fractions containing the desired product, eluting at 7.3-8.2 min, were collected and freeze-dried to yield Compound 145 (15.0 mg, 46% yield over 2 steps): $^1$H NMR (400 MHz, $CD_3OD$) δ 8.02 (s, 1H), 4.36 (t, J=7.8 Hz, 1H), 4.07 (s, 1H), 3.79 (s, 3H), 3.78-3.75 (m, 1H), 3.28-3.24 (m, 2H), 3.03-2.93 (m, 11H), 2.73-2.67 (m, 1H), 2.30-2.10 (m, 5H), 1.67-1.57 (m, 1H); MS (ESI) m/z 571.36 (M+H).

(9 mg, 0.066 mmol, 1.0 equiv). The resulting red solution was stirred at rt overnight, and purified by a Preparative reverse phase HPLC on a Waters Autopurification system using a Sunfire Prep C18 OBD column [5 µm, 19×50 mm; flow rate, 20 mL/min; Solvent A: $H_2O$ with 0.1% $HCO_2H$; Solvent B: $CH_3CN$ with 0.1% $HCO_2H$; injection volume: 4.0 mL ($CH_3CN$); gradient: 10→100% B over 10 min; mass-directed fraction collection]. Fractions with the desired MW, eluting at 5.8-7.2 min, were collected and freeze-dried to give the desired product 4-1-3 as a mixture of diastereomers (25.9 mg, 45%): $^1$H NMR (400 MHz, $CDCl_3$) δ 15.92 (s, 0.33H), 15.89 (s, 0.66H), 8.00 (s, 0.33H), 7.84 (s, 0.66 H), 7.50-7.48 (m, 2H), 7.41-7.29 (m, 8H), 5.36-5.34 (m, 2H), 4.90-4.73 (m, 2H), 4.00-3.97 (m, 1H), 3.85 (s, 1H), 3.72 (s, 2H), 3.52-3.23 (m, 3H), 2.95-2.82 (m, 2H), 2.61-2.43 (m, 8H), 2.34-2.12 (m, 3H), 1.88-1.38 (m, 5H), 0.83-0.80 (m, 9H), 0.26-0.24 (m, 3H), 0.15-0.13 (m, 3H); MS (ESI) m/z 863.47 (M+H).

Aqueous HF (48-50%, 0.2 mL) was added to a solution of the above product 4-1-3 (13 mg, 0.015 mmol, 1.0 equiv) in acetonitrile (0.5 mL) in a polypropylene reaction vessel at 23° C. The resulting mixture was stirred vigorously at 23° C. overnight and poured into aqueous $K_2HPO_4$ (2.5 g dissolved in 20 mL water). The resulting mixture was extracted with EtOAc (40 mL, then 2×15 mL). The combined organic extracts were dried over anhydrous sodium sulfate, filtered, and concentrated. The residue was used directly in the next step without further purification.

The above crude product was dissolved in MeOH (2 mL) and dioxane (0.5 mL) Pd—C (10 wt %, 5 mg) was added in one portion at 23° C. The reaction vessel was sealed and purged with hydrogen by briefly evacuating the flask followed by flushing with hydrogen gas (1 atm). After stirring at 23° C. for 1 h 30 min, the reaction mixture was filtered through a small Celite pad. The filtrate was concentrated. The residue was purified by a preparative reverse phase HPLC on a Waters Autopurification system using a Phenomenex Polymerx™ 10µ RP-γ 100 A column [10 µm, 150×21.20 mm; flow rate, 20 mL/min; Solvent A: 0.05 N HCl/water; Solvent B: $CH_3CN$; injection volume: 3.0 mL (0.05 N HCl/water and MeCN, 1:1); gradient: 0→35% B over 10 min; mass-directed fraction collection]. Fractions containing the desired product, eluting at 8.5-9.3 min, were collected and freeze-dried to yield Compound 143 (2.3 mg, 24% yield over 2 steps): $^1$H NMR (400 MHz, $CD_3OD$) δ 8.03 (s, 1H), 4.11-4.06 (m, 1H), 4.08 (s, 1H), 3.79 (s, 3H), 3.48-3.43 (m, 1H), 3.28-3.24 (m, 1H), 3.08-2.94 (m, 9H), 2.37-2.33 (m, 1H), 2.20-2.10 (m, 2H), 2.03-1.69 (m, 5H), 1.67-1.57 (m, 1H); MS (ESI) m/z 571.25 (M+H).

Compound 143

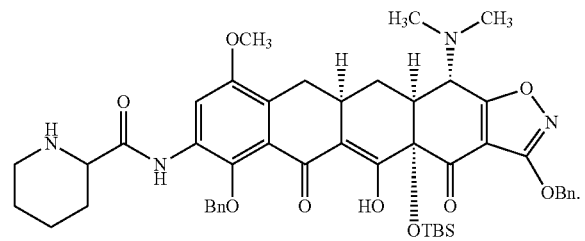

4-1-3

Compound 146

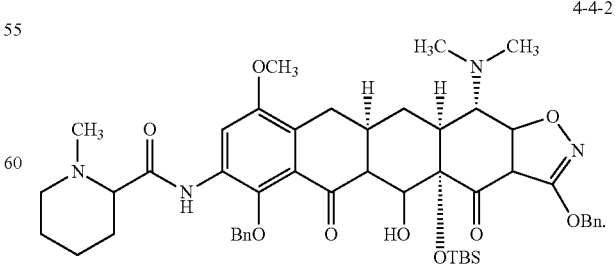

4-4-2

DMF (0.5 mL) was added to a mixture of 2-6 (50 mg, 0.066 mmol, 1.0 equiv), pipecolinic acid (22 mg, 0.13 mmol, 2.0 equiv), EDCI (25 mg, 0.13 mmol, 2.0 equiv) and HOBt HCHO (6.7 µL, 0.09 mmol, 6.0 equiv), acetic acid (5.2 µL, 0.09 mmol, 6.0 equiv) and sodium triacetoxyborohydride (9.5 mg, 0.045 mmol, 3.0 equiv) were added sequentially to a solution of Compound 4-1-3 in 1,2-dichloroethane (1 mL) at 23° C. After stirring for 2 h, the reaction mixture was quenched by the addition of saturated aqueous sodium bicarbonate and brine (1:1, 10 mL) and extracted with DCM (20 mL, then 10 mL). The combined organic extracts were dried over anhydrous sodium sulfate, filtered, and concentrated. The residue was purified by a Preparative reverse phase HPLC on a Waters Autopurification system using a Sunfire Prep C18 OBD column [5 μm, 19×50 mm; flow rate, 20 mL/min; Solvent A: $H_2O$ with 0.1% $HCO_2H$; Solvent B: $CH_3CN$ with 0.1% $HCO_2H$; injection volume: 4.0 mL ($CH_3CN$); gradient: 10→100% B over 10 min; mass-directed fraction collection]. Fractions with the desired MW, eluting at 7.1-7.6 min, were collected and freeze-dried to afford the desired product 4-4-2 (6.8 mg, 51%): $^1$H NMR (400 MHz, $CDCl_3$) δ 15.83 (s, 1H), 8.11-7.84 (m, 1H), 7.43-7.18 (m, 10H), 5.30 (s, 2H), 5.00-4.67 (m, 2H), 3.95-3.94 (m, 1H), 3.78-3.71 (m, 4H), 3.51-3.47 (m, 1H), 3.27-3.08 (m, 2H), 2.91-2.88 (m, 2H), 2.71-2.39 (m, 12H), 2.27-1.37 (m, 9H), 0.75 (s, 9H), 0.19 (m, 3H), 0.07-0.05 (m, 3H); MS (ESI) m/z 877.44 (M+H). Aqueous HF (48-50%, 0.2 mL) was added to a solution of the above product 4-4-2 (6.8 mg, 0.0078 mmol, 1.0 equiv) in acetonitrile (0.5 mL) in a polypropylene reaction vessel at 23° C. The resulting mixture was stirred vigorously at 23° C. overnight and poured into aqueous $K_2HPO_4$ (2.5 g dissolved in 20 mL water). The resulting mixture was extracted with EtOAc (30 mL, then 20 mL) The combined organic extracts were dried over anhydrous sodium sulfate, filtered, and concentrated. The residue was used directly in the next step without further purification.

The above crude product was dissolved in MeOH (2 mL) and dioxane (0.5 mL). Pd—C (10 wt %, 2 mg) was added in one portion at 23° C. The reaction vessel was sealed and purged with hydrogen by briefly evacuating the flask followed by flushing with hydrogen gas (1 atm). After stirring at 23° C. for 2 h, the reaction mixture was filtered through a small Celite pad. The filtrate was concentrated. The residue was purified by a preparative reverse phase HPLC on a Waters Autopurification system using a Phenomenex Polymerx™ 10μ RP-γ 100 A column [10 μm, 150×21.20 mm; flow rate, 20 mL/min; Solvent A: 0.05 N HCl/water; Solvent B: $CH_3CN$; injection volume: 3.0 mL (0.05 N HCl/water and MeCN, 1:1); gradient: 0→35% B over 10 min; mass-directed fraction collection]. Fractions containing the desired product, eluting at 8.2-8.6 min, were collected and freeze-dried to yield Compound 146 (0.98 mg, 1:1 diastereomers): $^1$H NMR (400 MHz, $CD_3OD$) δ 8.03 (s, 0.5H), 8.01 (s, 0.5H), 4.08 (s, 1H), 4.08-4.03 (m, 1H), 3.80 (s, 3H), 3.58-3.55 (m, 1H), 3.26-3.24 (m, 1H), 3.20-3.12 (m, 1H), 3.03-2.92 (m, 11H), 2.34-2.31 (m, 1H), 2.20-2.10 (m, 2H), 2.03-1.1.97 (m, 2H), 1.92-1.81 (m, 2H), 1.67-1.61 (m, 2H); Fractions containing the desired product, eluting at 8.6-9.1 min, were collected and freeze-dried to yield Compound 4-5-2 (1.16 mg, single enantiomer): $^1$H NMR (400 MHz, $CD_3OD$) δ 8.01 (s, 1H), 4.08 (s, 1H), 4.08-4.04 (m, 1H), 3.80 (s, 3H), 3.58-3.55 (m, 1H), 3.28-3.24 (m, 1H), 3.20-3.12 (m, 1H), 3.03-2.92 (m, 11H), 2.35-2.32 (m, 1H), 2.21-2.10 (m, 2H), 2.00-1.1.97 (m, 2H), 1.92-1.82 (m, 2H), 1.67-1.61 (m, 2H); MS (ESI) m/z 585.27 (M+H).

Compounds 147 and 148 were prepared similarly to Compound 146 using enantiomerically pure pipecolinic acids.

Compound 147.

$^1$H NMR (400 MHz, $CD_3OD$) δ 8.01 (s, 1H), 4.10 (s, 1H), 4.12-4.08 (m, 1H), 3.80 (s, 3H), 3.58-3.55 (m, 1H), 3.29-3.24 (m, 1H), 3.22-3.15 (m, 1H), 3.04-2.93 (m, 11H), 2.34-2.31 (m, 1H), 2.23-2.18 (m, 1H), 2.12 (dd, J=13.7, 16.0 Hz, 1H), 1.99-1.97 (m, 2H), 1.92-1.78 (m, 2H), 1.72-1.56 (m, 2H); MS (ESI) m/z 585.52 (M+H).

Compound 148.

$^1$H NMR (400 MHz, $CD_3OD$) δ 8.00 (s, 1H), 4.09 (s, 1, H), 4.09-4.06 (m, 1H), 3.80 (s, 3H), 3.58-3.55 (m, 1H), 3.29-3.24 (m, 1H), 3.22-3.15 (m, 1H), 3.04-2.92 (m, 11H), 2.35-2.32 (m, 1H), 2.23-2.17 (m, 1H), 2.13 (dd, J=13.7, 16.0 Hz, 1H), 2.00-1.96 (m, 2H), 1.92-1.78 (m, 2H), 1.72-1.57 (m, 2H); MS (ESI) m/z 585.56 (M+H).

Compound 144

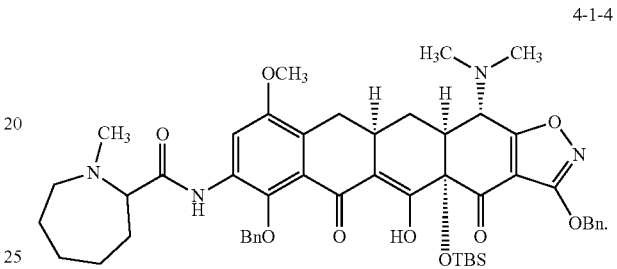

4-1-4

A solution of 1-methylazepane-2-carbonyl chloride (HCl salt) in DCM (0.4 M, 120 μL, 0.048 mmol, 1.2 equiv) was added to a solution of aniline 2-6 (30 mg, 0.040 mmol, 1.0 equiv) in THF (1 mL). The resulting light orange solution was stirred at rt for 10 min, and more acid chloride (0.4 M/DCM, 120 μL, 0.048 mmol, 1.2 equiv) was added. The resulting mixture was stirred for 30 min and diluted with brine and pH 7 phosphate buffer (1:1, 20 mL). The resulting mixture was extracted with EtOAc (50 mL). The organic phase was separated, dried ($Na_2SO_4$), filtered and concentrated. The residue was purified by a Preparative reverse phase HPLC on a Waters Autopurification system using a Sunfire Prep C18 OBD column [5 μm, 19×50 mm; flow rate, 20 mL/min; Solvent A: $H_2O$ with 0.1% $HCO_2H$; Solvent B: $CH_3CN$ with 0.1% $HCO_2H$; injection volume: 4.0 mL ($CH_3CN$); gradient: 20→100% B over 8 min; mass-directed fraction collection]. Fractions with the desired MW, eluting at 6.3-9.0 min, were collected and freeze-dried to afford the desired product 4-1-4 (20 mg, 84%): $^1$H NMR (400 MHz, $CDCl_3$) δ 15.96 (s, 1H), 8.44 (s, 1H), 7.50-7.44 (m, 3H), 7.39-7.29 (m, 7H), 5.35 (s, 2H), 4.89, 4.80 (ABq, J=10.4 Hz, 2H), 3.98-4.80 (d, J=10.4 Hz, 1H), 3.86 (s, 3H), 3.32 (dd, J=4.9, 16.5 Hz, 1H), 3.09 (br s, 1H), 2.99-2.92 (m, 1H), 2.80-2.70 (m, 2H), 2.57-2.41 (m, 8H), 2.35-2.13 (m, 5H), 2.02-1.85 (m, 2H), 1.63-1.41 (m, 6H), 0.81 (s, 9H), 0.27 (s, 3H), 0.12 (s, 3H); MS (ESI) m/z 891.74 (M+H).

Aqueous HF (48-50%, 0.3 mL) was added to a solution of the above product 4-1-4 (20 mg, 0.022 mmol, 1.0 equiv) in acetonitrile (0.6 mL) in a polypropylene reaction vessel at 23° C. The resulting mixture was stirred vigorously at 23° C. overnight and poured into aqueous $K_2HPO_4$ (3.6 g dissolved in 25 mL water). The resulting mixture was extracted with EtOAc (30 mL, then 20 mL). The combined organic extracts were dried over anhydrous sodium sulfate, filtered, and concentrated. The residue was used directly in the next step without further purification.

The above crude product was dissolved in MeOH (1 mL) and HCl/MeOH (0.5 N, 88 μL, 2.0 equiv). Pd—C (10 wt %, 8 mg) was added in one portion at 23° C. The reaction vessel was sealed and purged with hydrogen by briefly evacuating the flask followed by flushing with hydrogen gas (1 atm). After stirring at 23° C. for 2 h 25 min, the reaction mixture was filtered through a small Celite pad. The filtrate was concentrated. The residue was purified by a preparative reverse phase HPLC on a Waters Autopurification system using a Phenomenex Polymerx™ 10μ RP-γ 100 A column [10 μm, 150×21.20 mm; flow rate, 20 mL/min; Solvent A: 0.05 N HCl/water; Solvent B: CH$_3$CN; injection volume: 3.0 mL (0.05 N HCl/water and MeCN, 1:1); gradient: 5→35% B over 10 min; mass-directed fraction collection]. Fractions containing the desired product, eluting at 8.0-8.4 min, were collected and freeze-dried to yield Compound 144 (2.52 mg, 17% over 2 steps): $^1$H NMR (400 MHz, CD$_3$OD) δ 7.95 (s, 1H), 4.28 (dd, J=3.7, 6.4 Hz, 1H), 4.08 (s, 1H), 3.80 (s, 3H), 3.50 (t, J=5.0 Hz, 2H), 3.29-3.24 (m, 1H), 3.08-2.94 (m, 11H), 2.29-2.10 (m, 4H), 2.02-1.98 (m, 2H), 1.86-1.82 (m, 2H), 1.74-1.70 (m, 2H), 1.67-1.57 (m, 1H); MS (ESI) m/z 599.48 (M+H).

EXAMPLE 5

Synthesis of Certain Compounds of Formula II, wherein Y is —NH—C(O)-(saturated heterocyclyl). Scheme 5 depicts the synthesis of still other compounds of Formula II, wherein Y is —NH—C(O)-(saturated heterocyclyl).

Compound 149

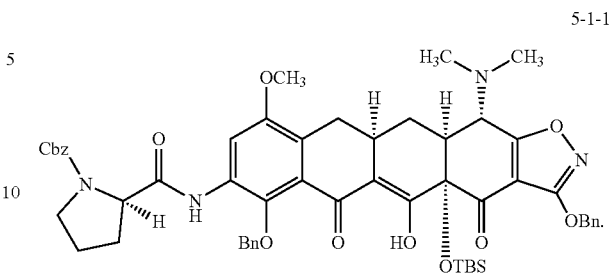

5-1-1

A solution of (R)—N-(carbobenzoxy)prolyl chloride in DCM (1.0 M, 69 μL, 0.069 mmol, 1.2 equiv) was added to a solution of aniline 2-6 (43.5 mg, 0.058 mmol, 1.0 equiv) in THF (1 mL). The resulting light orange solution was stirred at rt for 3 h, diluted with brine (20 mL) The resulting mixture was extracted with DCM (2×25 mL). The combined organic extracts were dried (Na$_2$SO$_4$), filtered and concentrated to yield the crude product 5-1-1: MS (ESI) m/z 983.58 (M+H).

Aqueous HF (48-50%, 0.2 mL) was added to a solution of the above crude product 5-1-1 in acetonitrile (0.5 mL) in a

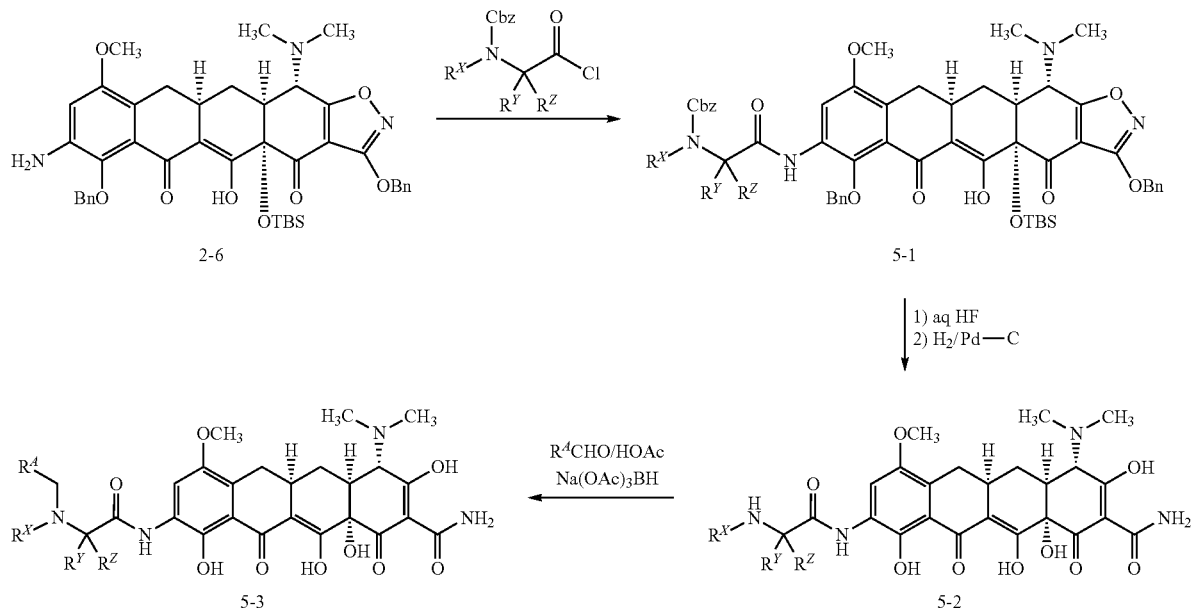

Scheme 5:

In Scheme 5, R$^A$ represents hydrogen, (C$_1$-C$_5$)alkyl, —(C$_0$-C$_5$) alkylene-carbocyclyl, or —(C$_0$-C$_5$)alkylene-heterocyclyl. For all of the compounds made by Scheme 5 and described below, R$^Z$ is hydrogen and R$^X$ and R$^Y$ are taken together with the carbon and nitrogen atoms to which they are respectively bound to form an optionally substituted 4-7 membered saturated heterocyclyl. It will be readily apparent to those of skill in the art, however, that this Scheme 5 will also be useful to synthesize compounds where R$^X$, R$^Y$ and R$^Z$ are R$^2$, R$^{5a}$ and R$^{5b}$, respectively, as defined in structural formula (I).

polypropylene reaction vessel at 23° C. The resulting mixture was stirred vigorously at 23° C. overnight and poured into aqueous K$_2$HPO$_4$ (3.6 g dissolved in 30 mL water). The resulting mixture was extracted with EtOAc (40 mL, then 2×15 mL). The combined organic extracts were dried over anhydrous sodium sulfate, filtered, and concentrated. The residue was used directly in the next step without further purification.

The above crude product was dissolved in MeOH (2 mL) and dioxane (0.4 mL) Pd—C (10 wt %, 20 mg) was added in one portion at 23° C. The reaction vessel was sealed and purged with hydrogen by briefly evacuating the flask followed by flushing with hydrogen gas (1 atm). After stirring at 23° C. for 3 h, the resulting reaction mixture was filtered through a small Celite pad. The filtrate was concentrated. The residue was purified by a preparative reverse phase HPLC on a Waters Autopurification system using a Phenomenex Polymerx™ 10μ RP-γ 100 A column [10 μm, 150×21.20 mm; flow rate, 20 mL/min; Solvent A: 0.05 N HCl/water; Solvent B: CH$_3$CN; injection volume: 3.0 mL (0.05 N HCl/water and MeCN, 1:1); gradient: 0→35% B over 10 min; mass-directed fraction collection]. Fractions containing the desired product, eluting at 7.5-8.4 min, were collected and freeze-dried to yield Compound 149 (7.9 mg, 49% yield over 3 steps): $^1$H NMR (400 MHz, CD$_3$OD) δ 8.03 (s, 1H), 4.58 (dd, J=6.9, 8.7 Hz, 1H), 4.10 (s, 1H), 3.79 (s, 3H), 3.50-3.39 (m, 2H), 3.28-3.23 (m, 1H), 3.04-2.95 (m, 8H), 2.62-2.53 (m, 1H), 2.23-2.03 (m, 5H), 1.67-1.57 (m, 1H); MS (ESI) m/z 557.33 (M+H).

Compound 151.

HCHO (14.4 μL, 0.052 mmol, 6.0 equiv), TEA (6.1 μL, 0.044 mmol, 3.0 equiv) and sodium triacetoxyborohydride (9.2 mg, 0.044 mmol, 3.0 equiv) were added sequentially to a solution of Compound 149 (9.1 mg, 0.014 mmol, 1.0 equiv) in DMF (0.3 mL) at 23° C. After stirring for 15 min, the reaction mixture was diluted with 0.05 N HCl/water, and purified by a preparative reverse phase HPLC on a Waters Autopurification system using a Phenomenex Polymerx™ 10μ RP-γ 100 A column [10 μm, 150×21.20 mm; flow rate, 20 mL/min; Solvent A: 0.05 N HCl/water; Solvent B: CH$_3$CN; injection volume: 3.0 mL (0.05 N HCl/water and MeCN, 1:1); gradient: 0→35% B over 10 min; mass-directed fraction collection]. Fractions containing the desired product, eluting at 8.0-8.8 min, were collected and freeze-dried to yield Compound 5-3-1 mixed with a byproduct (MS (ESI) m/z 601.35 (M+H)). The product was dissolved in MeOH (0.5 mL). Then conc. HCl (0.5 mL) was added. The resulting mixture was stirred at rt for 40 min, and concentrated. The residue was diluted with MeCN (1 mL) and freeze-dried. The residue was re-purified by a prepara-tive reverse phase HPLC on a Waters Autopurification system using a Phenomenex Polymerx™ 10μ RP-γ 100 A column (same method as before) to afford the desired product Compound 151(2.69 mg, 29% yield): $^1$H NMR (400 MHz, CD$_3$OD) δ 8.03 (s, 1H), 4.37 (t, 7.8 Hz, 1H), 4.08 (s, 1H), 3.80 (s, 3H), 3.78-3.76 (m, 1H), 3.28-3.24 (m, 2H), 3.03-2.94 (m, 11H), 2.75-2.68 (m, 1H), 2.30-2.07 (m, 5H), 1.67-1.57 (m, 1H); MS (ESI) m/z 571.55 (M+H).

Compound 150.

Compound 150 was prepared similarly to Compound 149. $^1$H NMR (400 MHz, CD$_3$OD) δ 8.12 (s, 1H), 5.28 (dd, J=7.3, 9.2 Hz, 1H), 4.21-4.14 (m, 1H), 4.09 (s, 1H), 4.07-4.00 (m, 1H), 3.81 (s, 3H), 3.28-3.24 (m, 1H), 3.04-2.90 (m, 9H), 2.71-2.62 (m, 1H), 2.23-2.09 (m, 2H), 1.66-1.57 (m, 1H); MS (ESI) m/z 543.23 (M+H).

Compound 152.

Compound 152 was prepared similarly to Compound 151. $^1$H NMR (400 MHz, CD$_3$OD) δ 8.10 (s, 1H), 5.18 (t, J=9.2 Hz, 1H), 4.21-4.04 (m, 3H), 3.80 (s, 3H), 3.26-3.25 (m, 1H), 3.05-2.87 (m, 12H), 2.69-2.59 (m, 1H), 2.22-2.10 (m, 2H), 1.68-1.57 (m, 1H); MS (ESI) m/z 557.35 (M+H).

EXAMPLE 6

Synthesis of Certain Compounds of Formula II, wherein Y is —NH—S(O)$_m$—(C$_1$-C$_6$ alkyl), —NH—S(O)$_m$—(C$_1$-C$_4$ alkylene)-N(R$^2$)(R$^3$), —NH—S(O)$_m$—N(R$^2$)(R$^4$), —NH—S(O)$_m$-heterocyclyl, —NH—S(O)$_m$-carbocyclyl, and —NH—S(O)$_m$—(C$_1$-C$_4$)alkylene-carbocyclyl

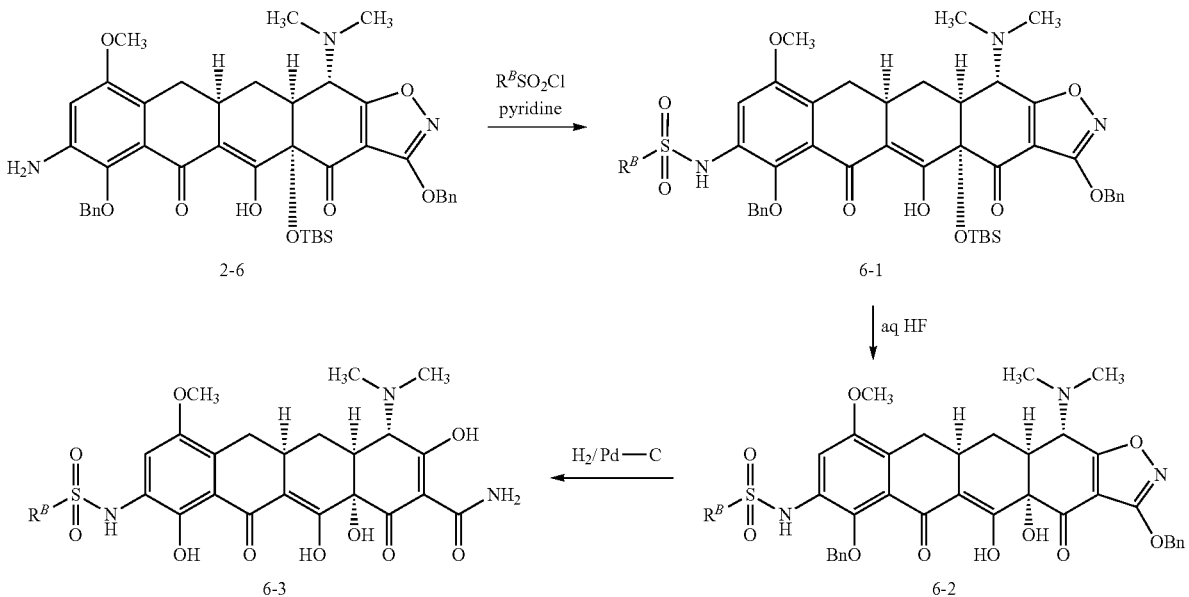

Scheme 6:

In Scheme 6, R$^B$ represents —(C$_1$-C$_6$ alkyl), —(C$_1$-C$_4$ alkylene)-N(R$^2$)(R$^3$), —N(R$^2$)(R$^4$), -heterocyclyl, -carbocyclyl, or —(C$_1$-C$_4$) alkylene-carbocyclyl.

Compound 153.

Compound 2-6 (28 mg, 0.038 mmol) was dissolved in CH$_2$Cl$_2$ (0.2 mL). Benzenesulfonyl chloride (14.4 μL, 0.11 mmol, 3 eq) and pyridine (15.3 μL, 0.19 mmol, 5 eq) were added. The resulting mixture was stirred at rt and the reaction was monitored by LC-MS. The reaction mixture was diluted with EtOAc after SM was completely consumed. The organic solution was washed with water, 1N HCl and brine, dried with $Na_2SO_4$ and concentrated to give crude 6-1, where R is benzene (6-1-1). Preparative reverse phase HPLC purification on a Waters Autopurification system using a Sunfire Prep C18 OBD column [5 μm, 19×50 mm; flow rate, 20 mL/min; Solvent A: $H_2O$ with 0.1% $HCO_2H$; Solvent B: $CH_3CN$ with 0.1% $HCO_2H$; injection volume: 4.0 mL ($CH_3CN$); gradient: 80→100% B over 15 min; mass-directed fraction collection]. Fractions with the desired MW, eluting at 7.50-8.95 min, were collected and concentrated on a RotaVap at rt to remove most of the acetonitrile. The resulting mostly aqueous solution was extracted with EtOAc. The combined EtOAc extracts were dried ($Na_2SO_4$) and concentrated to give pure 6-1-1.

In a plastic vial, 6-1-1 was dissolved in $CH_3CN$ (1 mL). Aqueous HF (48%, 0.25 mL) was added. After stirred at rt for 16 h, the reaction mixture was poured into aqueous solution (12.5 mL) of $K_2HPO_4$ (1.75 g). The resulting mixture was extracted three times with EtOAc. The combined organic phases were washed with brine, dried, concentrated to give crude product 6-2-1.

The crude 6-2-1 was dissolved in 0.5 N HCl in MeOH (155 μL, 2 eq). The excess volatiles were evaporated. The pre-formed HCl salt was re-dissolved in MeOH (2.0 mL) and to the resulting solution was added palladium on carbon (10% wt, 9.0 mg, 30% w/w). The reaction flask was briefly evacuated and re-filled with hydrogen. The reaction mixture was stirred at rt and monitored by LC-MS. After SM was consumed, the mixture was filtered through a small pad of Celite. The filtrate was concentrated to give crude Compound 153, which was purified by HPLC on a Waters Autopurification system using a Phenomenex Polymerx™ 10μ RP-γ 100 R column [30×21.20 mm, 10 micron; flow rate, 20 mL/min; Solvent A: 0.05 N HCl/water; Solvent B: $CH_3CN$; injection volume: 4.0 mL (0.05 N HCl/water); gradient: 15→60% B over 15 min; mass-directed fraction collection]. Fractions with the desired MW, eluting at 13.50-14.65 min, were collected and freeze-dried to give product as a yellow solid: $^1$H NMR (400 MHz, $CD_3OD$) δ7.78 (d, J=7.8 Hz, 2H), 7.56 (t, J=7.8 Hz, 1H), 7.45 (t, J=7.8 Hz, 2H), 7.38 (s, 1H), 4.02 (s, 1H), 3.76 (s, 3H), 3.30-3.15 (m, 1H), 3.10-2.90 (m, 8H), 2.18-2.01 (m, 2H), 1.62-1.52 (m, 1H); MS (ESI) m/z 600.2 (M+H), calcd for $C_{28}H_{30}N_3O_{10}S$ 600.16.

Compound 154.

Compound 154 was obtained by the procedure of Compound 153 employing methanesulfonyl chloride. Crude product was purified by HPLC on a Waters Autopurification system using a Phenomenex Polymerx™ 10μ RP-γ 100 R column [30×21.20 mm, 10 micron; flow rate, 20 mL/min; Solvent A: 0.05 N HCl/water; Solvent B: $CH_3CN$; injection volume: 4.0 mL (0.05 N HCl/water); gradient: 15→60% B over 15 min; mass-directed fraction collection]. Fractions with the desired MW, eluting at 8.24-9.25 min, were collected and freeze-dried to give product as a yellow solid: $^1$H NMR (400 MHz, $CD_3OD$) δ7.38 (s, 1H), 4.08 (s, 1H), 3.79 (s, 3H), 3.30-3.15 (m, 1H), 3.10-2.90 (m, 11H), 2.20-2.05 (m, 2H), 1.66-1.55 (m, 1H); MS (ESI) m/z 538.5 (M+H), calcd for $C_{23}H_{28}N_3O_{10}S$ 538.14.

Compound 155.

Compound 155 was obtained by the procedure of Compound 153 employing trifluoromethanesulfonic anhydride. Crude product was purified by HPLC on a Waters Autopurification system using a Phenomenex Polymerx™ 10μ RP-γ 100 R column [30×21.20 mm, 10 micron; flow rate, 20 mL/min; Solvent A: 0.05 N HCl/water; Solvent B: $CH_3CN$; injection volume: 4.0 mL (0.05 N HCl/water); gradient: 20→70% B over 15 min; mass-directed fraction collection]. Fractions with the desired MW, eluting at 7.70-8.58 min, were collected and freeze-dried to give product as a yellow solid: $^1$H NMR (400 MHz, $CD_3OD$) δ7.28 (s, 1H), 4.08 (s, 1H), 3.79 (s, 3H), 3.30-3.15 (m, 1H), 3.10-2.90 (m, 8H), 2.20-2.10 (m, 2H), 1.66-1.55 (m, 1H); MS (ESI) m/z 592.4 (M+H), calcd for $C_{23}H_{25}F_3N_3O_{10}S$ 592.11.

Compound 156.

Compound 156 was obtained by the procedure of Compound 153 employing 3-methoxybenzenesulfonyl chloride. Crude product was purified by HPLC on a Waters Autopurification system using a Phenomenex Polymerx™ 10μ RP-γ 100 R column [30×21.20 mm, 10 micron; flow rate, 20 mL/min; Solvent A: 0.05 N HCl/water; Solvent B: $CH_3CN$; injection volume: 4.0 mL (0.05 N HCl/water); gradient: 15→60% B over 15 min; mass-directed fraction collection]. Fractions with the desired MW, eluting at 11.85-12.95 min, were collected and freeze-dried to give product as a yellow solid: $^1$H NMR (400 MHz, $CD_3OD$) δ7.40-7.30 (m, 4H), 7.10 (br s, 1H), 4.08 (s, 1H), 3.76 (s, 6H), 3.25-3.10 (m, 1H), 3.00-2.85 (m, 8H), 2.18-2.00 (m, 2H), 1.66-1.55 (m, 1H); MS (ESI) m/z 630.4 (M+H), calcd for $C_{29}H_{32}N_3O_{11}S$ 630.17.

Compound 157.

Compound 157 was obtained by the procedure of Compound 153 employing 2-fluorobenzenesulfonyl chloride. Crude product was purified by HPLC on a Waters Autopurification system using a Phenomenex Polymerx™ 10μ RP-γ 100 R column [30×21.20 mm, 10 micron; flow rate, 20 mL/min; Solvent A: 0.05 N HCl/water; Solvent B: $CH_3CN$; injection volume: 4.0 mL (0.05 N HCl/water); gradient: 15→60% B over 15 min; mass-directed fraction collection]. Fractions with the desired MW, eluting at 11.84-12.74 min, were collected and freeze-dried to give product as a yellow solid: $^1$H NMR (400 MHz, $CD_3OD$) δ7.77 (t, J=7.3 Hz, 1H), 7.65-7.56 (m 1H), 7.33 (s, 1H), 7.26-7.20 (m, 2H), 4.06 (s, 1H), 3.74 (s, 3H), 3.22-3.12 (m, 1H), 3.06-2.85 (m, 8H), 2.20-2.00 (m, 2H), 1.66-1.55 (m, 1H); MS (ESI) m/z 618.4 (M+H), calcd for $C_{28}H_{29}FN_3O_{10}S$ 618.15.

Compound 158.

Compound 158 was obtained by the procedure of Compound 153 employing p-nitrobenzenesulfonyl chloride. Crude product was purified by HPLC on a Waters Autopurification system using a Phenomenex Polymerx™ 10μ RP-γ 100 R column [30×21.20 mm, 10 micron; flow rate, 20 mL/min; Solvent A: 0.05 N HCl/water; Solvent B: $CH_3CN$; injection volume: 4.0 mL (0.05 N HCl/water); gradient: 15→60% B over 15 min; mass-directed fraction collection]. Fractions with the desired MW, eluting at 11.15-12.05 mM, were collected and freeze-dried to give product as a yellow solid: $^1$H NMR (400 MHz, $CD_3OD$) δ7.88 (d, J=7.8 Hz, 2H), 7.44-7.39 (m 3H), 4.09 (s, 1H), 3.79 (s, 3H), 3.22-3.12 (m, 1H), 3.06-2.85 (m, 8H), 2.20-2.00 (m, 2H), 1.66-1.55 (m, 1H); MS (ESI) m/z 615.4 (M+H), calcd for $C_{28}H_{31}N_4O_{10}S$ 615.17.

Compound 159.

Compound 159 was obtained by the procedure of Compound 153 employing 3-fluorobenzenesulfonyl chloride. Crude product was purified by HPLC on a Waters Autopurification system using a Phenomenex Polymerx™ 10μ RP-γ 100 R column [30×21.20 mm, 10 micron; flow rate, 20 mL/min; Solvent A: 0.05 N HCl/water; Solvent B: $CH_3CN$; injection volume: 4.0 mL (0.05 N HCl/water); gradient: 15→60% B over 15 min; mass-directed fraction collection]. Fractions with the desired MW, eluting at 14.00-15.10 min, were collected and freeze-dried to give product as a yellow solid: $^1$H NMR (400 MHz, $CD_3OD$) δ7.60-7.43 (m, 3H), 7.37 (s, 1H), 7.32 (t, J=7.8 Hz, 1H), 4.07 (s, 1H), 3.78 (s, 3H), 3.22-3.12 (m, 1H), 3.08-2.88 (m, 8H), 2.20-2.00 (m, 2H), 1.62-1.52 (m, 1H); MS (ESI) m/z 618.4 (M+H), calcd for $C_{28}H_{29}FN_3O_{10}S$ 618.15.

Compound 160.

Compound 160 was obtained by the procedure of Compound 153 employing 4-methylbenzenesulfonyl chloride. Crude product was purified by HPLC on a Waters Autopurification system using a Phenomenex Polymerx™ 10μ RP-γ 100 R column [30×21.20 mm, 10 micron; flow rate, 20 mL/min; Solvent A: 0.05 N HCl/water; Solvent B: CH$_3$CN; injection volume: 4.0 mL (0.05 N HCl/water); gradient: 15→60% B over 15 min; mass-directed fraction collection]. Fractions with the desired MW, eluting at 13.80-15.30 min, were collected and freeze-dried to give product as a yellow solid: $^1$H NMR (400 MHz, CD$_3$OD) δ7.63 (d, J=7.8 Hz, 2H), 7.35 (s, 1H), 7.23 (d, J=7.8 Hz, 2H), 4.06 (s, 1H), 3.74 (s, 3H), 3.25-3.10 (m, 1H), 3.06-2.85 (m, 8H), 2.34 (s, 3H), 2.18-2.00 (m, 2H), 1.60-1.50 (m, 1H); MS (ESI) m/z 614.5 (M+H), calcd for C$_{29}$H$_{32}$N$_3$O$_{10}$S 614.17.

Compound 161.

Compound 161 was obtained by the procedure of Compound 153 employing 4-methoxybenzenesulfonyl chloride. Crude product was purified by HPLC on a Waters Autopurification system using a Phenomenex Polymerx™ 10μ RP-γ 100 R column [30×21.20 mm, 10 micron; flow rate, 20 mL/min; Solvent A; 0.05 N HCl/water; Solvent B: CH$_3$CN; injection volume: 4.0 mL (0.05 N HCl/water); gradient: 15→60% B over 15 min; mass-directed fraction collection]. Fractions with the desired MW, eluting at 13.20-15.00 min, were collected and freeze-dried to give product as a yellow solid: $^1$H NMR (400 MHz, CD$_3$OD) δ7.69 (d, J=7.8 Hz, 2H), 7.36 (s, 1H), 6.93 (d, J=7.8 Hz, 2H), 4.07 (s, 1H), 3.80 (s, 3H), 3.76 (s, 3H), 3.25-3.12 (m, 1H), 3.08-2.85 (m, 8H), 2.18-2.00 (m, 2H), 1.61-1.52 (m, 1H); MS (ESI) m/z 630.4 (M+H), calcd for C$_{29}$H$_{32}$N$_3$O$_{11}$S 630.17.

Compound 162.

Compound 162 was obtained by the procedure of Compound 153 employing 2-nitrobenzenesulfonyl chloride. Crude product was purified by HPLC on a Waters Autopurification system using a Phenomenex Polymerx™ 10μ RP-γ 100 R column [30×21.20 mm, 10 micron; flow rate, 20 mL/min; Solvent A: 0.05 N HCl/water; Solvent B: CH$_3$CN; injection volume: 4.0 mL (0.05 N HCl/water); gradient: 15→60% B over 15 min; mass-directed fraction collection]. Fractions with the desired MW, eluting at 13.00-14.50 min, were collected and freeze-dried to give product as a yellow solid: $^1$H NMR (400 MHz, CD$_3$OD) δ7.62 (d, J=7.8 Hz, 1H), 7.55 (t, J=7.8 Hz, 1H), 7.31 (m, 2H), 7.14 (t, J=7.8 Hz, 1H), 4.08 (s, 1H), 3.78 (s, 3H), 3.22-3.12 (m, 1H), 3.06-2.85 (m, 8H), 2.22-2.00 (m, 2H), 1.61-1.51 (m, 1H); MS (ESI) m/z 615.4 (M+H), calcd for C$_{28}$H$_{31}$N$_4$O$_{10}$S 615.17.

Compound 163.

Compound 163 was obtained by the procedure of Compound 153 employing 3-nitrobenzenesulfonyl chloride. Crude product was purified by HPLC on a Waters Autopurification system using a Phenomenex Polymerx™ 10μ RP-γ 100 R column [30×21.20 mm, 10 micron; flow rate, 20 mL/min; Solvent A: 0.05 N HCl/water; Solvent B: CH$_3$CN; injection volume: 4.0 mL (0.05 N HCl/water); gradient: 15→60% B over 15 min; mass-directed fraction collection]. Fractions with the desired MW, eluting at 9.60-11.00 min, were collected and freeze-dried to give product as a yellow solid: $^1$H NMR (400 MHz, CD$_3$OD) δ7.90 (d, J=7.8 Hz, 1H), 7.83 (s, 1H), 7.67-7.60 (m, 2H), 7.40 (s, 1H), 4.09 (s, 1H), 3.80 (s, 3H), 3.22-3.12 (m, 1H), 3.06-2.85 (m, 8H), 2.22-2.00 (m, 2H), 1.61-1.51 (m, 1H); MS (ESI) m/z 615.4 (M+H), calcd for C$_{28}$H$_{31}$N$_4$O$_{10}$S 615.17.

Compound 164.

Compound 164 was obtained by the procedure of Compound 153 employing 1-methylimidazole-4-sulfonyl chloride. Crude product was purified by HPLC on a Waters Autopurification system using a Phenomenex Polymerx™ 10μ RP-γ 100 R column [30×21.20 mm, 10 micron; flow rate, 20 mL/min; Solvent A: 0.05 N HCl/water; Solvent B: CH$_3$CN; injection volume: 4.0 mL (0.05 N HCl/water); gradient: 15→50% B over 15 min; mass-directed fraction collection]. Fractions with the desired MW, eluting at 9.85-11.00 min, were collected and freeze-dried to give product as a yellow solid: $^1$H NMR (400 MHz, CD$_3$OD) δ8.77 (s, 1H), 7.99 (s, 1H), 7.36 (s, 1H), 4.08 (s, 1H), 3.88 (s, 3H), 3.81 (s, 3H), 3.30-3.22 (m, 1H), 3.06-2.85 (m, 8H), 2.22-2.00 (m, 2H), 1.61-1.51 (m, 1H); MS (ESI) m/z 604.4 (M+H), calcd for C$_{26}$H$_{30}$N$_5$O$_{10}$S 604.16.

Compound 165.

Compound 165 was obtained by the procedure of Compound 153 employing 1-methyl-1H-pyrazole-3-sulfonyl chloride. Crude product was purified by HPLC on a Waters Autopurification system using a Phenomenex Polymerx™ 10μ RP-γ 100 R column [30×21.20 mm, 10 micron; flow rate, 20 mL/min; Solvent A: 0.05 N HCl/water; Solvent B: CH$_3$CN; injection volume: 4.0 mL (0.05 N HCl/water); gradient: 15→50% B over 15 min; mass-directed fraction collection]. Fractions with the desired MW, eluting at 11.85-13.00 min, were collected and freeze-dried to give product as a yellow solid: $^1$H NMR (400 MHz, CD$_3$OD) δ7.64 (d, J=2.3 Hz, 1H), 7.45 (s, 1H), 6.62 (d, J=2.3 Hz, 1H), 4.07 (s, 1H), 3.88 (s, 3H), 3.77 (s, 3H), 3.22-3.14 (m, 1H), 3.06-2.85 (m, 8H), 2.22-2.00 (m, 2H), 1.63-1.53 (m, 1H); MS (ESI) m/z 604.4 (M+H), calcd for C$_{26}$H$_{30}$N$_5$O$_{10}$S 604.16.

Compound 166.

Compound 166 was obtained by the procedure of Compound 153 employing isobutanesulfonyl chloride. Crude product was purified by HPLC on a Waters Autopurification system using a Phenomenex Polymerx™ 10μ RP-γ 100 R column [30×21.20 mm, 10 micron; flow rate, 20 mL/min; Solvent A: 0.05 N HCl/water; Solvent B: CH$_3$CN; injection volume: 4.0 mL (0.05 N HCl/water); gradient: 15→60% B over 15 min; mass-directed fraction collection]. Fractions with the desired MW, eluting at 12.80-14.00 min, were collected and freeze-dried to give product as a yellow solid: $^1$H NMR (400 MHz, CD$_3$OD) δ7.35 (s, 1H), 4.08 (s, 1H), 3.78 (s, 3H), 3.30-3.20 (m, 1H), 3.08-2.90 (m, 10H), 2.30-2.10 (m, 3H), 1.66-1.55 (m, 1H), 1.05 (d, J=6.8 Hz, 6H); MS (ESI) m/z 580.5 (M+H), calcd for C$_{26}$H$_{34}$N$_3$O$_{10}$S 580.19.

Compound 167.

Compound 167 was obtained by the procedure of Compound 153 employing furan-2-sulfonyl chloride. Crude product was purified by HPLC on a Waters Autopurification system using a Phenomenex Polymerx™ 10μ RP-γ 100 R column [30×21.20 mm, 10 micron; flow rate, 20 mL/min; Solvent A: 0.05 N HCl/water; Solvent B: CH$_3$CN; injection volume: 4.0 mL (0.05 N HCl/water); gradient: 15→60% B over 15 min; mass-directed fraction collection]. Fractions with the desired MW, eluting at 12.55-13.60 min, were collected and freeze-dried to give product as a yellow solid: $^1$H NMR (400 MHz, CD$_3$OD) δ7.69 (s, 1H), 7.33 (s, 1H), 6.96 (d, J=3.6 Hz, 1H), 6.51 (t, J=1.8 Hz, 1H), 4.06 (s, 1H), 3.77 (s, 3H), 3.25-3.12 (m, 1H), 3.08-2.85 (m, 8H), 2.18-2.00 (m, 2H), 1.61-1.52 (m, 1H); MS (ESI) m/z 590.4 (M+H), calcd for C$_{26}$H$_{28}$N$_3$O$_{11}$S 590.14.

Compound 168.

Compound 168 was obtained by the procedure of Compound 153 employing phenylmethanesulfonyl chloride. Crude product was purified by HPLC on a Waters Autopurification system using a Phenomenex Polymerx™ 10μ RP-γ 100 R column [30×21.20 mm, 10 micron; flow rate, 20 mL/min; Solvent A: 0.05 N HCl/water; Solvent B: CH$_3$CN; injection volume: 4.0 mL (0.05 N HCl/water); gradient: 15→60% B over 15 min; mass-directed fraction collection]. Fractions with the desired MW, eluting at 13.90-15.50 min, were collected and freeze-dried to give product as a yellow solid: $^1$H NMR (400 MHz, CD$_3$OD) δ7.38-7.34 (m, 2H), 7.28-7.26 (m, 3H), 7.13 (s, 1H), 4.45 (s, 2H), 4.07 (s, 1H), 3.68 (s, 3H), 3.25-3.12 (m, 1H), 3.08-2.85 (m, 8H), 2.18-2.00 (m, 2H), 1.61-1.52 (m, 1H); MS (ESI) m/z 614.5 (M+H), calcd for $C_{29}H_{32}N_3O_{10}S$ 614.17.

Compound 169.

Compound 169 was obtained by the procedure of Compound 153 employing ethanesulfonyl chloride. Crude product was purified by HPLC on a Waters Autopurification system using a Phenomenex Polymerx™ 10µ RP-γ 100 R column [30×21.20 mm, 10 micron; flow rate, 20 mL/min; Solvent A: 0.05 N HCl/water; Solvent B: $CH_3CN$; injection volume: 4.0 mL (0.05 N HCl/water); gradient: 15→50% B over 15 min; mass-directed fraction collection]. Fractions with the desired MW, eluting at 12.05-13.20 min, were collected and freeze-dried to give product as a yellow solid: $^1$H NMR (400 MHz, $CD_3OD$) δ7.36 (s, 1H), 4.08 (s, 1H), 3.78 (s, 3H), 3.30-3.20 (m, 1H), 3.10-2.85 (m, 10H), 2.22-2.05 (m, 2H), 1.65-1.55 (m, 1H), 1.36 (t, J=7.3 Hz, 3H); MS (ESI) m/z 552.4 (M+H), calcd for $C_{24}H_{30}N_3O_{10}S$ 552.16.

Compound 170.

Compound 170 was obtained by the procedure of Compound 153 employing 1-propanesulfonyl chloride. Crude product was purified by HPLC on a Waters Autopurification system using a Phenomenex Polymerx™ 10µ RP-γ 100 R column [30×21.20 mm, 10 micron; flow rate, 20 mL/min; Solvent A: 0.05 N HCl/water; Solvent B: $CH_3CN$; injection volume: 4.0 mL (0.05 N HCl/water); gradient: 15→60% B over 15 min; mass-directed fraction collection]. Fractions with the desired MW, eluting at 11.75-12.80 min, were collected and freeze-dried to give product as a yellow solid: $^1$H NMR (400 MHz, $CD_3OD$) δ7.35 (s, 1H), 4.08 (s, 1H), 3.78 (s, 3H), 3.30-3.20 (m, 1H), 3.10-2.85 (m, 10H), 2.22-2.05 (m, 2H), 1.88-1.82 (m, 2H), 1.65-1.55 (m, 1H), 1.00 (t, J=7.3 Hz, 3H); MS (ESI) m/z 566.5 (M+H), calcd for $C_{25}H_{32}N_3O_{10}S$ 566.17.

Compound 171.

Compound 171 was obtained by the procedure of Compound 153 employing 1-butanesulfonyl chloride. Crude product was purified by HPLC on a Waters Autopurification system using a Phenomenex Polymerx™ 10 RP-γ 100 R column [30×21.20 mm, 10 micron; flow rate, 20 mL/min; Solvent A: 0.05 N HCl/water; Solvent B; $CH_3CN$; injection volume: 4.0 mL (0.05 N HCl/water); gradient: 15→60% B over 15 min; mass-directed fraction collection]. Fractions with the desired MW, eluting at 13.05-13.95 min, were collected and freeze-dried to give product as a yellow solid: $^1$H NMR (400 MHz, $CD_3OD$) δ7.36 (s, 1H), 4.07 (s, 1H), 3.78 (s, 3H), 3.30-3.20 (m, 1H), 3.10-2.85 (m, 10H), 2.22-2.05 (m, 2H), 1.83-1.78 (m, 2H), 1.65-1.55 (m, 1H), 1.44-1.38 (m, 2H), 0.90 (t, J=7.3 Hz, 3H); MS (ESI) m/z 580.5 (M+H), calcd for $C_{26}H_{34}N_3O_{10}S$ 580.19.

Compound 172.

Compound 172 was obtained by the procedure of Compound 153 employing 1-hexanesulfonyl chloride. Crude product was purified by HPLC on a Waters Autopurification system using a Phenomenex Polymerx™ 10µ RP-γ 100 R column [30×21.20 mm, 10 micron; flow rate, 20 mL/min; Solvent A: 0.05 N HCl/water; Solvent B: $CH_3CN$; injection volume: 4.0 mL (0.05 N HCl/water); gradient: 15→65% B over 15 min; mass-directed fraction collection]. Fractions with the desired MW, eluting at 14.85-15.30 min, were collected and freeze-dried to give product as a yellow solid: $^1$H NMR (400 MHz, $CD_3OD$) δ7.37 (s, 1H), 4.08 (s, 1H), 3.79 (s, 3H), 3.30-3.20 (m, 1H), 3.10-2.85 (m, 10H), 2.22-2.05 (m, 2H), 1.85-1.78 (m, 2H), 1.65-1.55 (m, 1H), 1.44-1.25 (m, 6H), 0.88 (t, 7.3 Hz, 3H); MS (ESI) m/z 608.5 (M+H), calcd for $C_{28}H_{38}N_3O_{10}S$ 608.22.

Compound 173.

Compound 173 was obtained by the procedure of Compound 153 employing 2,2,2-trifluoroethanesulfonyl chloride. Crude product was purified by HPLC on a Waters Autopurification system using a Phenomenex Polymerx™ 10µ RP-γ 100 R column [30×21.20 mm, 10 micron; flow rate, 20 mL/min; Solvent A: 0.05 N HCl/water; Solvent B: $CH_3CN$; injection volume: 4.0 mL (0.05 N HCl/water); gradient: 15→50% B over 15 min; mass-directed fraction collection]. Fractions with the desired MW, eluting at 14.10-15.20 min, were collected and freeze-dried to give product as a yellow solid: $^1$H NMR (400 MHz, $CD_3OD$) δ7.29 (s, 1H), 4.18 (q, J=9.6 Hz, 2H), 4.08 (s, 1H), 3.79 (s, 3H), 3.30-3.20 (m, 1H), 3.10-2.85 (m, 8H), 2.22-2.05 (m, 2H), 1.65-1.55 (m, 1H); MS (ESI) m/z 606.4 (M+H), calcd for $C_{24}H_{27}F_3N_3O_{10}S$ 606.13.

Compound 174.

Compound 174 was obtained by the procedure of Compound 153 employing dimethylsulfamoyl chloride. Crude product was purified by HPLC on a Waters Autopurification system using a Phenomenex Polymerx™ 10µ RP-γ 100 R column [30×21.20 mm, 10 micron; flow rate, 20 mL/min; Solvent A: 0.05 N HCl/water; Solvent B: $CH_3CN$; injection volume: 4.0 mL (0.05 N HCl/water); gradient: 20→60% B over 15 min; mass-directed fraction collection]. Fractions with the desired MW, eluting at 10.00-11.10 min, were collected and freeze-dried to give product as a yellow solid: $^1$H NMR (400 MHz, $CD_3OD$) δ7.41 (s, 1H), 4.07 (s, 1H), 3.78 (s, 3H), 3.30-3.20 (m, 1H), 3.10-2.85 (m, 8H), 2.77 (s, 6H), 2.22-2.05 (m, 2H), 1.65-1.55 (m, 1H); MS (ESI) m/z 567.4 (M+H), calcd for $C_{24}H_{31}N_4O_{10}S$ 567.17.

Compound 175.

Compound 175 was obtained by the procedure of Compound 153 employing DMF as solvent. Crude product was purified by HPLC on a Waters Autopurification system using a Phenomenex Polymerx™ 10µ RP-γ 100 R column [30×21.20 mm, 10 micron; flow rate, 20 mL/min; Solvent A: 0.05 N HCl/water; Solvent B: $CH_3CN$; injection volume: 4.0 mL (0.05 N HCl/water); gradient: 5→30% B over 15 min; mass-directed fraction collection]. Fractions with the desired MW, eluting at 11.90-13.05 min, were collected and freeze-dried to give product as a yellow solid: $^1$H NMR (400 MHz, $CD_3OD$) δ 8.53 (s, 1H), 7.35 (s, 1H), 4.10 (s, 1H), 3.85 (s, 3H), 3.43 (s, 3H), 3.32 (s, 3H), 3.30-3.20 (m, 1H), 3.10-2.85 (m, 8H), 2.26-2.10 (m, 2H), 1.65-1.55 (m, 1H); MS (ESI) m/z 515.4 (M+H), calcd for $C_{25}H_{31}N_4O_8$ 515.21.

Compound 176.

Compound 176 (9.0 mg, 0.0015 mmol) was dissolved in MeOH (2.0 mL) and to the resulting solution was added palladium on carbon (10% wt, 5.0 mg). The reaction flask was briefly evacuated and re-filled with hydrogen. Formaldehyde (0.1 mL, 1.34 mmol) was then added. The reaction mixture was stirred at rt and monitored by LC-MS. After SM was consumed, the mixture was filtered through a small pad of Celite. The filtrate was concentrated to give the crude product, which was purified by HPLC on a Waters Autopurification system using a Phenomenex Polymerx™ 10µ RP-γ 100 R column [30×21.20 mm, 10 micron; flow rate, 20 mL/min; Solvent A: 0.05 N HCl/water; Solvent B: $CH_3CN$; injection volume: 4.0 mL (0.05 N HCl/water); gradient: 15→60% B over 15 min; mass-directed fraction collection]. Fractions with the desired MW, eluting at 12.60-13.25 min, were collected and freeze-dried to give product 6-3-24 as a yellow solid: $^1$H NMR (400 MHz, $CD_3OD$) δ7.66 (s, 1H), 7.58-7.45 (m, 3H), 7.40 (s, 1H), 4.06 (s, 1H), 3.79 (s, 3H), 3.25-3.15 (m, 1H), 3.12 (s, 6H), 3.06-2.90 (m, 8H), 2.26-2.10 (m, 2H), 1.65-1.55 (m, 1H) MS (ESI) m/z 643.5 (M+H), calcd for $C_{30}H_{35}N_4O_8S$ 643.20.

Compound 177.

Compound 177 was obtained by the procedure of Compound 153 employing pyridine-2-sulfonyl chloride: $^1$H NMR (400 MHz, $CD_3OD$) δ8.60 (d, J=4.6 Hz, 1H), 7.95-8.10 (m, 2H), 7.65-7.75 (m, 1H), 7.48 (s, 1H), 4.04 (s, 1H), 3.79 (s, 3H), 2.75-3.50 (m, 9H), 2.00-2.20 (m, 2H), 1.52-1.70 (m, 1H); MS (ESI) m/z 601.1 (M+H), calcd for C$_{27}$H$_{29}$N$_4$O$_{10}$S 601.16.

Compound 178.

Compound 178 was obtained by the procedure of Compound 153 employing pyridine-3-sulfonyl chloride: $^1$H NMR (400 MHz, CD$_3$OD) δ7.35 (s, 1H), 4.08 (s, 1H), 3.80 (s, 3H), 2.80-3.90 (m, 14H), 1.90-2.40 (m, 5H), 1.55-1.80 (m, 2H); MS (ESI) m/z 607.3 (M+H), calcd for C$_{27}$H$_{35}$N$_4$O$_{10}$S 607.21.

Compound 179

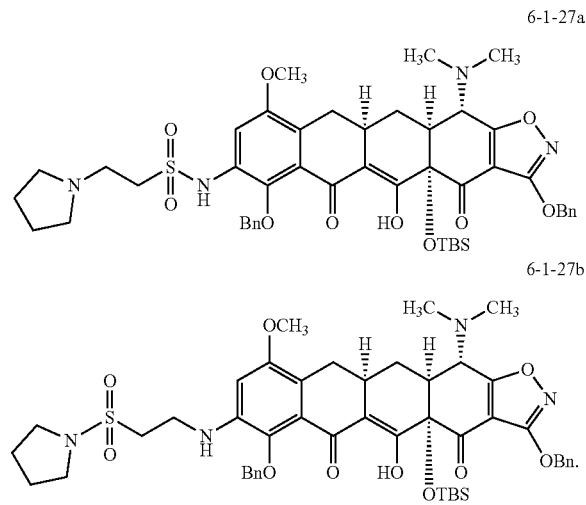

To a solution of 2-6 (38 mg, 0.05 mmol) in dichloroethane (1 mL) was added pyridine (6.1 μL, 0.075 mmol, 1.5 equiv) and 2-chloroethanesulfonyl chloride (6.9 μL, 0.65 mmol, 1.3 equiv). After 18 h, the solution was heated to 45° C. for 2 h, and then was cooled to ambient temperature. Additional pyridine (12.2 μL, 0.15 mmol, 3 equiv) and 2-chloroethanesulfonyl chloride (15.7 μL, 0.15 mmol, 3 equiv) were added and the reaction was heated to 45° C. for 21 h. Pyrrolidine (41 μL, 0.500 mmol, 10 equiv) was added to the reaction mixture, and the reaction was heated to 45° C. After four hours, the reaction was cooled, additional pyrrolidine was added (82 μL, 1.00 mmol, 20 equiv), and the reaction was heated to 45° C. for 24 h. The reaction mixture was poured into aqueous pH 7 phosphate buffer (3 mL) and brine (2 mL), and the mixture was extracted with EtOAc (2×10 mL) The combined organic extracts were dried (Na$_2$SO$_4$), filtered, and concentrated to yield an oil. Preparative reverse phase HPLC purification of this crude mixture was performed on a Waters Autopurification system using a Sunfire Prep C18 OBD column [5 μm, 19×50 mm; flow rate, 20 mL/min; Solvent A: H$_2$O with 0.1% HCO$_2$H; Solvent B: CH$_3$CN with 0.1% HCO$_2$H; injection volume: 4×3.6-4.2 mL (CH$_3$CN); gradient: 88→100% B over 12 min; mass-directed fraction collection]. Fractions with the desired MW, eluting at 3.0-3.4 and 12.6-13.2 min, were collected and lyophilized to give 5.3 mg of 6-1-27a (12%) and 2.8 mg of 6-1-27b (6%), respectively. 6-1-27a: $^1$H NMR (400 MHz, CDCl$_3$) δ 15.9 (s, 1H), 8.18 (s, 1H), 7.52-7.30 (m, 11H), 5.41-5.31 (m, 2H), 4.95 (d, J=10.4 Hz, 1H), 4.82 (d, J=10.4 Hz, 1H), 3.92 (d, J=10.4 Hz, 1H), 3.86 (s, 3H), 3.37-3.30 (m, 3H), 3.21-3.09 (m, 2H), 3.05-2.94 (m, 1H), 2.88-2.74 (m, 4H), 2.62-2.52 (m, 1H), 2.55-2.42 (m, 6H), 2.38-2.30 (m, 1H), 2.20-2.14 (m, 1H), 1.91-1.78 (m, 4H), 0.84 (s, 9H), 0.30 (s, 3H), 0.15 (s, 3H); MS (ESI) m/z 913.69 (M+H).

To a solution of 6-1-27a (5.3 mg, 0.0058 mmol, 1 equiv) in a plastic vial in acetonitrile (1.0 mL) was added an aqueous solution of hydrogen fluoride (50%, 250 μl). After 20 h, the reaction solution was diluted with an aqueous solution of K$_2$HPO$_4$ (3.2 g in 30 mL) and extracted with EtOAc (2×30 mL). The combined organic layers were dried (Na$_2$SO$_4$), filtered, and concentrated to yield the crude product. Palladium on carbon (10%, 7 mg) was added to a solution of this crude oil in dioxane:methanol (1:1, 1 mL). The flask was fitted with a septum and evacuated and back-filled three times with hydrogen gas. Hydrogen gas was bubbled through the reaction solution for three minutes, and the reaction mixture was stirred under an atmosphere (balloon) of hydrogen gas for 2 h. The reaction mixture was filtered through Celite to remove the palladium catalyst and concentrated under reduced pressure. Preparative reverse phase HPLC purification of the resulting oil was performed on a Waters Autopurification system using a Polymerx™ 10μ RP-γ 100 R column [30×21.20 mm, 10 micron, solvent A: 0.05N HCl in water, solvent B: CH$_3$CN; injection volume: 4.8 mL (0.05N HCl in water); gradient elution with 20→80% B over 15 min, then held at 100% for 5 min; mass-directed fraction collection], Fractions with the desired MW, eluting at 7.45-8.5 min, were collected and freeze-dried to yield 0.65 mg of Compound 179 (18%): $^1$H NMR (400 MHz, CD$_3$OD) δ 7.31 (s, 1H), 4.09 (s, 1H), 3.81-3.65 (m, 6H), 3.60-3.55 (m, 1H), 3.21-2.90 (m, 14H), 2.25-2.00 (m, 5H), 1.72-1.55 (m, 1H); MS (ESI) m/z 621.38 (M+H).

EXAMPLE 7

Synthesis of Compounds of Formula II, wherein Y is —NH(R$^3$), and R$^3$ is selected from —(C$_1$-C$_6$) alkyl, —(C$_1$-C$_6$) alkylene-carbocyclyl, and —(C$_1$-C$_6$)alkylene-heterocyclyl Scheme 7:

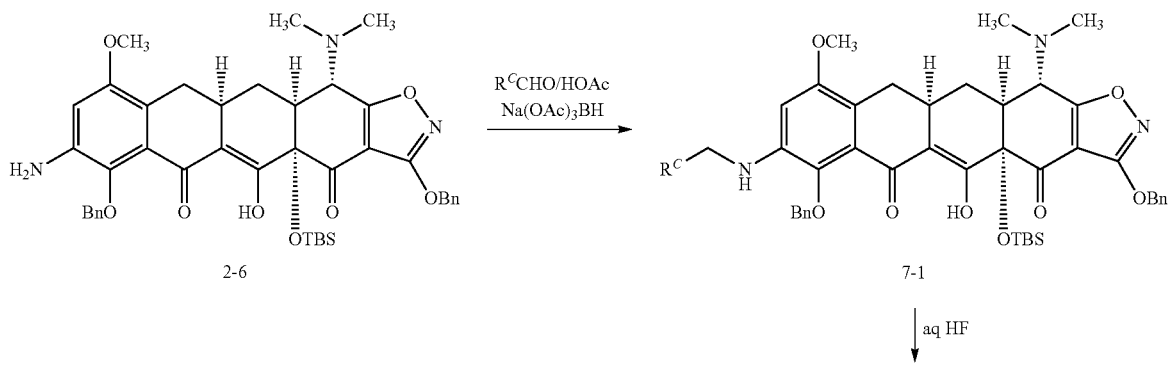

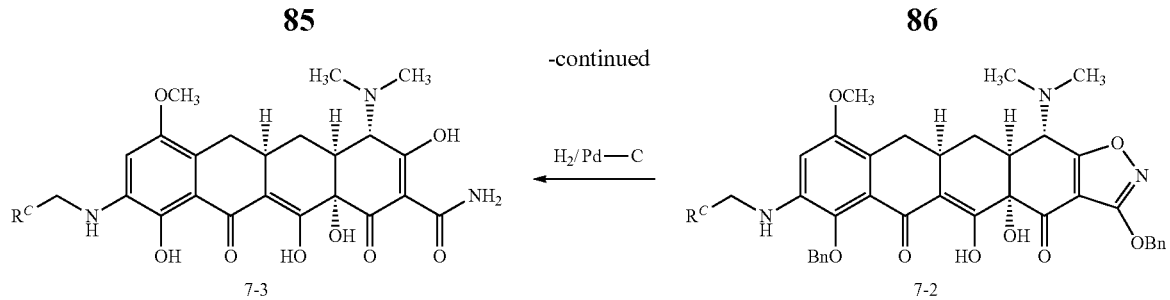

In Scheme 7, —CH$_2$—R$^C$ represents R$^3$.

Compound 180.

Compound 2-6 (20 mg, 0.026 mmol) was dissolved in 1,2-dichloroethane (1.0 mL). Propionaldehyde (2.9 μL, 0.040 mmol, 1.5 eq) was added, followed by acetic acid (7.6 μL, 0.13 mmol, 5 eq). After stirred at rt for 1 h, sodium triacetoxyborohydride (16.9 mg, 0.080 mmol, 3 eq) was added. Stirring was continued for another 2 h. The reaction mixture was poured into pH=7 buffer and sat. NaHCO$_3$ solution, extracted three times with EtOAc. The combined organic extracts were washed with brine, dried over Na$_2$SO$_4$, and concentrated to give crude 7-1, wherein —CH$_2$—R$^A$ is n-propyl (7-1-1), which was used directly for the next step without purification.

In a plastic vial, 7-1-1 was dissolved in CH$_3$CN (1 mL). Aqueous HF (48%, 0.25 mL) was added. After stirred at rt for 16 h, the reaction mixture was poured into aqueous solution (12.5 mL) of K$_2$HPO$_4$ (1.75 g). The resulting mixture was extracted three times with CH$_2$Cl$_2$. The combined organic phases were washed with brine, dried, concentrated to give crude 7-2, wherein —CH$_2$—R$^A$ is n-propyl (7-2-1). The crude 7-2-1 was dissolved in 0.5 N HCl in MeOH (105 μL, 2 eq). The excess volatiles were evaporated. The pre-formed HCl salt was re-dissolved in MeOH (2.0 mL) and to the resulting solution was added palladium on carbon (10% wt, 7.0 mg, 30% w/w). The reaction flask was briefly evacuated and re-filled with hydrogen. The reaction mixture was stirred at rt and monitored by LC-MS. After SM was consumed, the mixture was filtered through a small pad of Celite. The filtrate was concentrated to give the crude product, which was purified by HPLC on a Waters Autopurification system using a Phenomenex Polymerx™ 10μ RP-γ 100 R column [30×21.20 mm, 10 micron; flow rate, 20 mL/min; Solvent A: 0.05 N HCl/water; Solvent B: CH$_3$CN; injection volume: 4.0 mL (0.05 N HCl/water); gradient: 15→60% B over 15 min; mass-directed fraction collection]. Fractions with the desired MW, eluting at 6.80-7.70 min, were collected and freeze-dried to give Compound 180 as a yellow solid: $^1$H NMR (400 MHz, CD$_3$OD) δ7.30 (s, 1H), 4.10 (s, 1H), 3.86 (s, 3H), 3.40-3.25 (m, 3H), 3.10-2.90 (m, 8H), 2.26-2.16 (m, 2H), 1.85-1.75 (m, 2H), 1.62-1.52 (m, 1H), 1.06 (t, J=7.3 Hz, 3H); MS (ESI) m/z 502.4 (M+H), calcd for C$_{25}$H$_{32}$N$_3$O$_8$ 502.21.

Compound 181.

Compound 181 was obtained by the procedure of Compound 180 employing isovaleraldehyde. Crude product was purified by HPLC on a Waters Autopurification system using a Phenomenex Polymerx™ 10μ RP-γ 100 R column [30×21.20 mm, 10 micron; flow rate, 20 mL/min; Solvent A: 0.05 N HCl/water; Solvent B: CH$_3$CN; injection volume: 4.0 mL (0.05 N HCl/water); gradient: 15→50% B over 15 min; mass-directed fraction collection]. Fractions with the desired MW, eluting at 10.40-11.75 min, were collected and freeze-dried to give product as a yellow solid: $^1$H NMR (400 MHz, CD$_3$OD) δ7.38 (s, 1H), 4.10 (s, 1H), 3.87 (s, 3H), 3.50-3.40 (m, 2H), 3.35-3.30 (m, 1H), 3.10-2.90 (m, 8H), 2.26-2.16 (m, 2H), 1.80-1.58 (m, 4H), 0.98 (d, J=6.4 Hz, 6H); MS (ESI) m/z 530.4 (M+H), calcd for C$_{27}$H$_{36}$N$_3$O$_8$ 530.24.

Compound 182.

Compound 182 was obtained by the procedure of Compound 180 employing 2-methylbutyraldehyde. Crude product was purified by HPLC on a Waters Autopurification system using a Phenomenex Polymerx™ 10μ RP-γ 100 R column [30×21.20 mm, 10 micron; flow rate, 20 mL/min; Solvent A: 0.05 N HCl/water; Solvent B: CH$_3$CN; injection volume: 4.0 mL (0.05 N HCl/water); gradient: 15→50% B over 15 m; mass-directed fraction collection]. Fractions with the desired MW, eluting at 11.80-12.90 min, were collected and freeze-dried to give product as a yellow solid: $^1$H NMR (400 MHz, CD$_3$OD) δ7.37 (s, 1H), 4.10 (s, 1H), 3.86 (s, 3H), 3.40-3.20 (m, 3H), 3.10-2.90 (m, 8H), 2.26-2.16 (m, 2H), 1.95-1.85 (m, 1H), 1.70-1.55 (m, 2H), 1.40-1.30 (m, 1H), 1.12 (d, J=6.4 Hz, 3H), 0.98 (t, J=7.3 Hz, 3H); MS (ESI) m/z 530.4 (M+H), calcd for C$_{27}$H$_{36}$N$_3$O$_8$ 530.24.

Compound 183.

Compound 183 was obtained by the procedure of Compound 180 employing cyclopropanecarboxaldehyde. Crude product was purified by HPLC on a Waters Autopurification system using a Phenomenex Polymerx™ 10μ RP-γ 100 R column [30×21.20 mm, 10 micron; flow rate, 20 mL/min; Solvent A: 0.05 N HCl/water; Solvent B: CH$_3$CN; injection volume: 4.0 mL (0.05 N HCl/water); gradient: 15→50% B over 15 min; mass-directed fraction collection]. Fractions with the desired MW, eluting at 10.40-11.75 min, were collected and freeze-dried to give product as a yellow solid: $^1$H NMR (400 MHz, CD$_3$OD) δ7.37 (s, 1H), 4.10 (s, 1H), 3.87 (s, 3H), 3.35-3.30 (m, 3H), 3.10-2.90 (m, 8H), 2.26-2.16 (m, 2H), 1.70-1.58 (m, 1H), 1.25-1.16 (m, 1H), 0.76-0.70 (m, 2H), 0.46-0.42 (m, 2H); MS (ESI) m/z 514.4 (M+H), calcd for C$_{26}$H$_{32}$N$_3$O$_8$ 514.21.

Compound 184.

Compound 2-6 (32 mg, 0.042 mmol) was dissolved in 1,2-dichloroethane (1.0 mL). N-(tert-butoxycarbonyl)-L-prolinal (12 μL, 0.064 mmol, 1.5 eq) was added, followed by acetic acid (12 μL, 0.21 mmol, 5 eq). After stirred at rt for 1 h, sodium triacetoxyborohydride (27 mg, 0.13 mmol, 3 eq) was added. Stirring was continued for another 2 h. The reaction mixture was poured into pH=7 buffer and sat. NaHCO$_3$ solution, extracted three times with EtOAc. The combined organic extracts were washed with brine, dried over Na$_2$SO$_4$, and concentrated to give crude 7-1, wherein R$^A$ is pyrrolidin-2-yl (7-1-5), which was used directly for the next step without purification.

Compound 7-1-5 obtained above was dissolved in anhydrous dioxane (1 mL). Solution of HCl in dioxane (4M, 1 mL) was added at rt. The resulting mixture was stirred at rt and the reaction was monitored by LC-MS. The volatiles were evaporated after SM was completely consumed. The residue was suspended in EtOAc, and washed with sat. NaHCO$_3$, brine, dried (Na$_2$SO$_4$), and concentrated. Preparative reverse phase HPLC purification on a Waters Autopurification system using a Sunfire Prep C18 OBD column [5 μm, 19×50 mm; flow rate, 20 mL/min; Solvent A: H$_2$O with 0.1% HCO$_2$H; Solvent B: CH$_3$CN with 0.1% HCO$_2$H; injection volume: 4.0 mL (CH$_3$CN); gradient: 0→100% B over 10 min; mass-directed fraction collection]. Fractions with the desired MW, eluting at 7.08-8.00 min, were collected and concentrated on a RotaVap at rt to remove most of the acetonitrile. The resulting mostly aqueous solution was extracted with EtOAc. The combined EtOAc extracts were dried (Na$_2$SO$_4$) and concentrated.

The residue was dissolved in CH$_3$CN (1 mL) in a plastic vial. Aqueous HF (48%, 0.25 mL) was added. After stirred at rt for 16 h, the reaction mixture was poured into aqueous solution (12.5 mL) of K$_2$HPO$_4$ (1.75 g). The resulting mixture was extracted three times with EtOAc. The combined organic phases were washed with brine, dried, concentrated to give crude product 7-2, wherein R$^A$ is pyrrolidin-2-yl (7-2-5).

The crude 7-2-5 was dissolved in 0.5 N HCl in MeOH (105 μL, 3 eq). The excess volatiles were evaporated. The pre-formed HCl salt was re-dissolved in MeOH (2.0 mL) and to the resulting solution was added palladium on carbon (10% wt, 7.0 mg, 30% w/w). The reaction flask was briefly evacuated and re-filled with hydrogen. The reaction mixture was stirred at rt and monitored by LC-MS. After SM was consumed, the mixture was filtered through a small pad of Celite. The filtrate was concentrated to give crude Compound 184, which was purified by HPLC on a Waters Autopurification system using a Phenomenex Polymerx™ 10 RP-γ 100 R column [30×21.20 mm, 10 micron; flow rate, 20 mL/min; Solvent A: 0.05 N HCl/water; Solvent B: CH$_3$CN; injection volume: 4.0 mL (0.05 N HCl/water); gradient: 10→40% B over 15 min; mass-directed fraction collection]. Fractions with the desired MW, eluting at 9.95-10.05 min, were collected and freeze-dried to give product as a yellow solid: $^1$H NMR (400 MHz, CD$_3$OD) δ7.30 (s, 1H), 4.10 (s, 1H), 3.86 (s, 3H), 3.40-3.25 (m, 3H), 3.10-2.90 (m, 8H), 2.26-2.16 (m, 2H), 1.85-1.75 (m, 2H), 1.62-1.52 (m, 1H), 1.06 (t, J=7.3 Hz, 3H); MS (ESI) m/z 543.4 (M+H), calcd for C$_{27}$H$_{35}$N$_4$O$_8$ 543.24.

Compound 185.

Compound 185 was obtained by the procedure of Compound 180 employing 3,3-dimethylbutyraldehyde. $^1$H NMR (400 MHz, CD$_3$OD) δ7.24 (s, 1H), 4.09 (s, 1H), 3.85 (s, 3H), 3.35-3.45 (m, 2H), 2.95-3.10 (m, 9H), 2.12-2.25 (m, 2H), 1.65-1.72 (m, 3H), 0.98 (s, 9H); MS (ESI) m/z 544.4 (M+H), calcd for C$_{28}$H$_{38}$N$_3$O$_8$ 544.23.

Compound 186.

Compound 186 was obtained by the procedure of Compound 180 employing tert-butyl-N(Cbz)CH$_2$CHO. $^1$H NMR (400 MHz, CD$_3$OD) δ6.95 (s, 1H), 4.07 (s, 1H), 3.81 (s, 3H), 3.64 (t, J=6.5 Hz, 2H), 3.20 (dd, J=3.9, 14.2 Hz, 1H), 3.03 (s, 3H), 2.95 (s, 3H), 2.90-3.10 (m, 4H), 2.15-2.20 (m, 1H), 2.01-2.13 (m, 1H), 1.55-1.65 (m, 1H), 1.41 (s, 9H); MS (ESI) m/z 5592 (M+H), calcd for C$_{28}$H$_{39}$N$_4$O$_8$ 559.28.

EXAMPLE 8

Synthesis of Compounds of Formula II, wherein Y is —(C$_1$-C$_4$)alkylene-N(R$^2$)(R$^3$), —CH=N—OR$^2$, or —C(O)—N(R$^2$)(R$^4$)

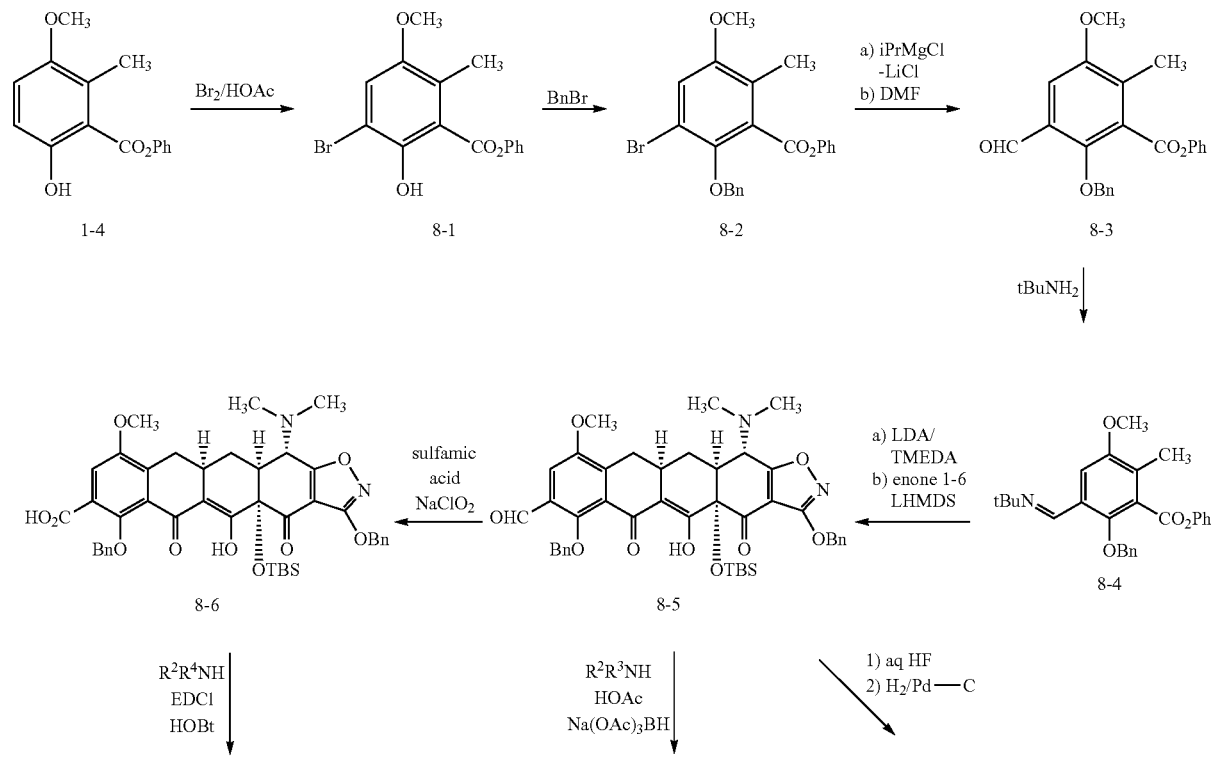

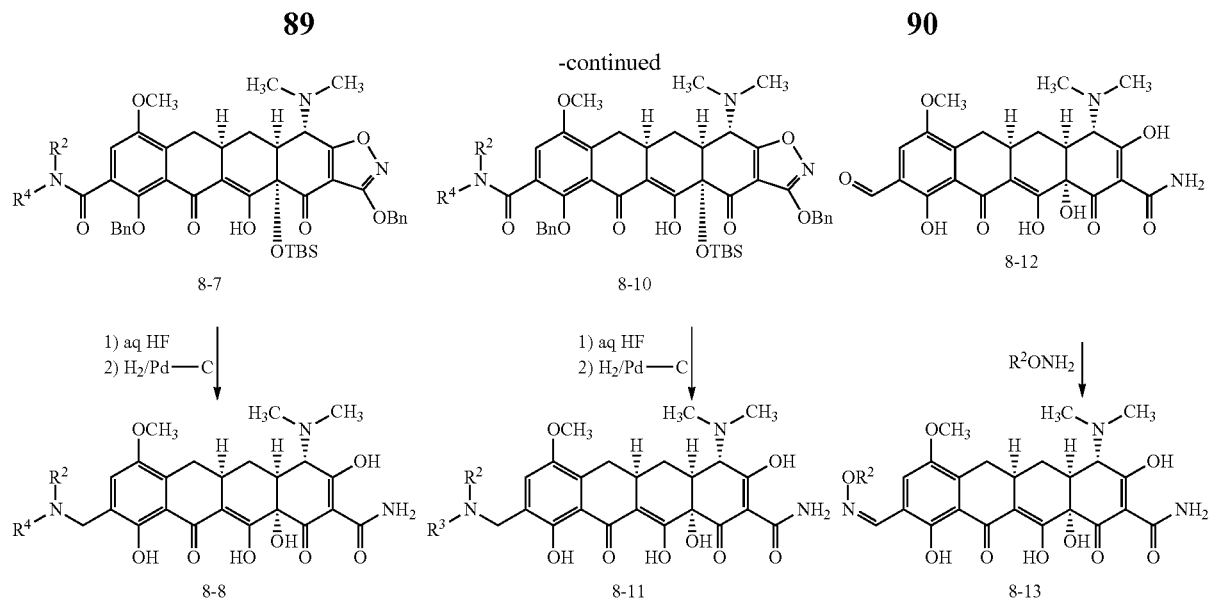

Phenyl 2-(benzyloxy)-3-bromo-5-methoxy-6-methylbenzoate (8-2)

A solution of Br$_2$ (0.328 mL, 6.4 mmol, 1.1 equiv) in HOAc (2 mL) was added to a solution of phenol 1-4 (1.50 g, 5.8 mmol, 1.0 equiv) in HOAc (10 mL) dropwise at 10° C. The resulting red solution was then stirred at rt for 50 min, and more Br$_2$ (30 µL, 0.58 mmol, 0.1 equiv) in HOAc (0.2 mL) was added. After stirring at rt for 1 h, the reaction mixture was poured onto ice-water (80 mL), diluted with EtOAc (150 mL). The organic phase was separated, washed with water (4×75 mL). The resulting organic phase was dried over magnesium sulfate, filtered, and concentrated to afford a brownish solid. The crude product was used directly for the next reaction. K$_2$CO$_3$ (1.60 g, 11.6 mmol, 2.0 equip) was added to a solution of the above product in acetone (30 mL). Then BnBr (1.03 mL, 8.7 mmol, 1.5 equiv) was added. The resulting reaction mixture was stirred at rt for 20 h and heated at 50° C. for 45 min. The reaction was then cooled to rt and filtered. The filtrate was concentrated, and the residue was diluted with EtOAc and water. The organic phase was separated, washed with brine. The resulting organic phase was dried over magnesium sulfate, filtered, and concentrated. The residue was purified by flash chromatography (2-4% EtOAc/Hexanes) to give 8-2 (1.79 g, 72% over 2 steps): $^1$H NMR (400 MHz, CDCl$_3$) δ 7.51-7.49 (m, 2H), 7.39-7.33 (m, 5H), 7.26-7.22 (m, 1H), 7.10 (s, 1H), 7.07-7.05 (m, 2H), 5.08 (s, 2H), 3.85 (s, 3H), 2.26 (s, 3H); MS (ESI) m/z 425.26, 427.32 (M−H).

Phenyl 2-(benzyloxy)-3-formyl-5-methoxy-6-methylbenzoate (8-3)

To a solution of 8-2 (76 mg, 0.178 mmol, 1.0 equiv) in anhydrous THF (1 mL) was added a solution of i-PrMgCl. LiCl in THF (1.2 M, 252 µL, 0.303 mmol, 1.7 equiv) dropwise at 0° C. under a N$_2$ atmosphere. The resulting reaction mixture was stirred at rt for 1 h 20 min. DMF (47 µL, 0.606 mmol, 3.0 equiv) was then added. The reaction was stirred for 5 min at rt, and quenched by saturated aqueous NH$_4$Cl. The resulting mixture was extracted twice with EtOAc (30 mL). The organic phase was separated, dried over sodium sulfate, filtered, and concentrated. The residue was purified by flash chromatography (2-5% EtOAc/Hexanes) to give 8-3 (55.5 mg, 83%): $^1$H NMR (400 MHz, CDCl$_3$) δ 10.14 (s, 1H), 7.41-7.34 (m, 7H), 7.33 (s, 1H), 7.28-7.25 (m, 1H), 7.13-7.11 (m, 2H), 5.12 (s, 2H), 3.89 (s, 3H), 2.39 (s, 3H); MS (ESI) m/z 375.33 (M−H).

Phenyl 2-(benzyloxy)-3-((tert-butylimino)methyl)-5-methoxy-6-methylbenzoate (8-4)

Tert-butyl amine (78 µL, 0.738 mmol, 5.0 equiv) was added to a solution of 8-3 (55.5 mg, 0.147 mmol, 1.0 equiv) in toluene (1 mL) The resulting reaction mixture was stirred at rt overnight, and then diluted with toluene (5 mL), concentrated, and dried under high vacuum. The crude product 8-4 was used directly for the next reaction. $^1$H NMR (400 MHz, CDCl$_3$) δ 8.63 (s, 1H), 7.64 (s, 1H), 7.50-7.44 (m, 7H), 7.38-7.34 (m, 1H), 7.24-7.22 (m, 2H), 5.09 (s, 2H), 4.02 (s, 3H), 2.45 (s, 3H), 1.34 (s, 9H); MS (ESI) m/z 432.39 (M+H).

(4aS,11aR,12aS,13S)-3,7-bis(benzyloxy)-4a-(tert-butyldimethylsilyloxy)-13-(dimethylamino)-5-hydroxy-10-methoxy-4,6-dioxo-4,4a,6,11,11a,12,12a,13-octahydrotetraceno[2,3-d]isoxazole-8-carbaldehyde (8-5)

A solution of the above crude imine 8-4 in THF (1.5 mL) was added to a solution of LDA (1.8 M, 90 µL, 0.162 mmol, 1.1 equiv) and TMEDA (24 µL, 0.162 mmol, 1.1 equiv) in THF (1 mL) dropwise via a cannula at −78° C. The resulting red solution was stirred at that temperature for 5 min. A solution of enone 1-6 (57 mg, 0.118 mmol, 0.8 equiv) in THF (2 mL) was added very slowly. The resulting light yellow solution was stirred at −78° C. for 5 min. A solution of LHMDS in THF (1.0 M, 147 µL, 0.147 mmol, 1.0 equiv) was added. The resulting reaction mixture was then allowed to warm up to −20° C. over 40 min. Saturated aqueous NH$_4$Cl was added. The resulting mixture was stirred at rt for 5 min, and extracted with EtOAc (30 mL). The organic phase was separated, dried over sodium sulfate, filtered, and concentrated. The residue was purified by a Preparative reverse phase HPLC on a Waters Autopurification system using a Sunfire Prep C18 OBD column [5 µm, 19×50 mm;

flow rate, 20 mL/min; Solvent A: H₂O with 0.1% HCO₂H; Solvent B: CH₃CN with 0.1% HCO₂H; injection volume: 4.0 mL (CH₃CN); gradient: 10→100% B over 10 min; mass-directed fraction collection]. Fractions with the desired MW of the imine product and aldehyde product were collected, allowed to stand in the hood overnight, and concentrated to afford the desired aldehyde product 8-5 (62.4 mg, 69%): ¹H NMR (400 MHz, CDCl₃) δ 15.86 (br s, 1H), 10.12 (s, 1H), 7.50-7.48 (m, 2H), 7.39-7.29 (m, 9H), 5.36 (s, 2H), 5.02, 4.93 (ABq, J=11.0 Hz, 2H), 3.97 (d, J=11.0 Hz, 1H), 3.88 (s, 3H), 3.42 (dd, J=4.9, 16.5 Hz, 1H), 3.04-2.96 (m, 1H), 2.59-2.56 (m, 1H), 2.52-2.44 (m, 7H), 2.37 (t, J=15.9 Hz, 1H), 2.18 (d, J=14.6 Hz, 1H), 0.82 (s, 9H), 0.28 (s, 3H), 0.14 (s, 3H); MS (ESI) m/z 765.52 (M+H).

Compound 190.

A solution of methylamine in THF (2.0 M, 122 μL, 0.24 mmol, 6.0 equiv), acetic acid (14 μL, 0.24 mmol, 6.0 equiv) and sodium triacetoxyborohydride (17 mg, 0.08 mmol, 2.0 equiv) were added sequentially to a solution of compound 8-5 (31 mg, 0.040 mmol, 1.0 equiv) in 1,2-dichloroethane (1 mL) at 23° C. After stirring for 3 h, the reaction mixture was quenched by the addition of saturated aqueous sodium bicarbonate (2 mL) and pH 7 phosphate buffer (10 mL) and extracted with dichloromethane (2×25 mL). The combined organic extracts were dried over anhydrous sodium sulfate, filtered, and concentrated. The residue was used directly in the next reaction.

Aqueous HF (48-50%, 0.3 mL) was added to a solution of the above crude product in acetonitrile (0.6 mL) in a polypropylene reaction vessel at 23° C. The resulting mixture was stirred vigorously at 23° C. overnight and poured into aqueous K₂HPO₄ (3.6 g dissolved in 25 mL water). The resulting mixture was extracted with EtOAc (30 mL, then 20 mL). The combined organic extracts were dried over anhydrous sodium sulfate, filtered, and concentrated. The residue was used directly in the next step without further purification.

The above crude product was dissolved in MeOH (1 mL) and HCl/MeOH (0.5 N, 80 μL, 2.0 equiv). Pd—C (10 wt %, 10 mg) was added in one portion at 23° C. The reaction vessel was sealed and purged with hydrogen by briefly evacuating the flask followed by flushing with hydrogen gas (1 atm). After stirring at 23° C. for 40 min, the reaction mixture was filtered through a small Celite pad. The filtrate was concentrated. The residue was purified by a preparative reverse phase HPLC on a Waters Autopurification system using a Phenomenex Polymerx™ 10μ RP-γ 100 A column [10 μm, 150×21.20 mm; flow rate, 20 mL/min; Solvent A: 0.05 N HCl/water; Solvent B: CH₃CN; injection volume: 3.0 mL (0.05 N HCl/water and MeCN, 1:1); gradient: 15→35% B over 15 min; mass-directed fraction collection]. Fractions containing the desired product, eluting at 5.2-7.1 min, were collected and freeze-dried to yield Compound 190 (11.6 mg, 52% over 3 steps): ¹H NMR (400 MHz, CD₃OD) δ 7.39 (s, 1H), 4.25 (s, 2H), 4.11 (s, 1H), 3.84 (s, 3H), 3.32-3.27 (m, 1H), 3.04-2.96 (m, 8H), 2.73 (s, 3H), 2.24-2.20 (m, 1H), 2.14 (dd, J=13.7, 16.0 Hz, 1H), 1.66-1.57 (m, 1H); MS (ESI) m/z 488.35 (M+H).

The following compounds were prepared similarly to Compound 190 coupling the appropriate amine NHR²R³ to 8-5.

Compound 191.

¹H NMR (400 MHz, CD₃OD) δ 7.43 (s, 1H), 4.28 (s, 2H), 4.11 (s, 1H), 3.85 (s, 3H), 3.33-3.28 (m, 1H), 3.05-2.97 (m, 8H), 2.92 (d, J=7.3 Hz, 2H), 2.25-2.06 (m, 3H), 1.67-1.58 (m, 1H), 1.05 (d, J=6.4 Hz, 6H); MS (ESI) m/z 530.31 (M+H).

Compound 192

¹H NMR (400 MHz, CD₃OD) δ 7.42 (s, 1H), 4.33 (s, 2H), 4.10 (s, 1H), 3.85 (s, 3H), 3.34-3.29 (m, 1H), 3.04-2.96 (m, 8H), 2.87 (s, 2H), 2.24-2.13 (m, 2H), 1.68-1.58 (m, 1H), 1.05 (s, 9H); MS (ESI) m/z 544.55 (M+H).

Compound 193.

¹H NMR (400 MHz, CD₃OD) δ 7.46 (s, 1H), 4.64-4.60 (m, 1H), 4.18 (d, J=12.8 Hz, 1H), 4.12 (s, 1H), 3.86 (s, 3H), 3.33-3.30 (m, 1H), 3.16-2.97 (m, 10H), 2.84 (s, 3H), 2.30-2.12 (m, 3H), 1.67-1.58 (m, 1H), 1.12-1.05 (m, 6H); MS (ESI) m/z 544.34 (M+H).

Compound 194.

¹H NMR (400 MHz, CD₃OD) δ 7.54 (s, 1H), 4.63-4.58 (m, 1H), 4.30 (d, J=12.8 Hz, 1H), 4.11 (s, 1H), 3.86 (s, 3H), 3.34-3.27 (m, 1H), 3.11 (dd, J=1.8, 13.7 Hz, 1H), 3.04-2.96 (m, 12H), 2.24-2.11 (m, 2H), 1.67-1.58 (m, 1H), 1.07 (d, J=5.5 Hz, 9H); MS (ESI) m/z 558.35 (M+H).

Compound 195.

¹H NMR (400 MHz, CD₃OD) δ 7.43 (s, 1H), 4.37 (s, 2H), 4.11 (s, 1H), 3.85 (s, 3H), 3.33-3.28 (m, 1H), 3.04-2.96 (m, 8H), 2.90 (s, 3H), 2.89 (s, 3H), 2.24-2.21 (m, 1H), 2.14 (dd, J=14.2, 16.5 Hz, 1H), 1.66-1.56 (m, 1H); MS (ESI) m/z 502.37 (M+H).

Compound 196.

¹H NMR (400 MHz, CD₃OD) δ 7.42 (s, 1H), 4.18-4.27 (m, 2H), 4.09 (s, 1H), 3.86 (s, 3H), 3.78-3.90 (m, 2H), 2.95-3.40 (m, 7H), 2.10-125 (m, 2H), 1.55-1.70 (m, 1H), 1.48 (s, 9H); MS (ESI) m/z 530.3 (M+H).

Compound 197

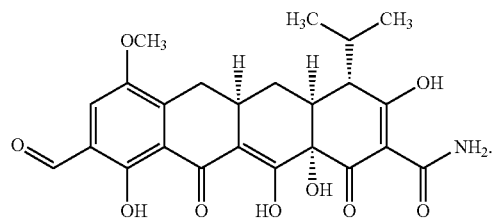

8-12

Aqueous HF (48-50%, 0.2 mL) was added to a solution of aldehyde 8-5 (24 mg, 0.031 mmol, 1.0 equiv) in acetonitrile (0.5 mL) in a polypropylene reaction vessel at 23° C. The resulting mixture was stirred vigorously at 23° C. overnight and poured into aqueous K₂HPO₄ (3.6 g dissolved in 25 mL water). The resulting mixture was extracted with EtOAc (30 mL, then 20 mL). The combined organic extracts were dried over anhydrous sodium sulfate, filtered, and concentrated. The residue was used directly in the next step without further purification.

The above crude product was dissolved in MeOH (1 mL) and HCl/MeOH (0.5 N, 61 μL, 1.0 equiv). Pd—C (10 wt %, 5 mg) was added in one portion at 23° C. The reaction vessel was sealed and purged with hydrogen by briefly evacuating the flask followed by flushing with hydrogen gas (1 atm). After stirring at 23° C. for 30 min, the reaction mixture was filtered through a small Celite pad. The filtrate was concentrated. The residue was purified by a preparative reverse phase HPLC on a Waters Autopurification system using a Phenomenex Polymerx™ 10μ RP-γ 100 A column [10 μm, 150×21.20 mm; flow rate, 20 mL/min; Solvent A: 0.05 N HCl/water; Solvent B: CH₃CN; injection volume: 3.0 mL (0.05 N HCl/water and MeCN, 1:1); gradient: 20→50% B over 15 min; mass-directed fraction collection]. Fractions containing the desired product, eluting at 11.0-12.1 min, were collected and freeze-dried to yield compound 8-12 (4.3 mg, 29% over 2 steps): $^1$H NMR (400 MHz, CD$_3$OD) δ 7.38 (s, 1H), 5.66 (s, 1H), 4.07 (s, 1H), 3.79 (s, 3H), 3.32-3.29 (m, 1H), 3.03-2.93 (m, 8H), 2.20-2.10 (m, 2H), 1.66-1.57 (m, 1H); MS (ESI) m/z 473.29 (M+H).
Compound 197.

NH$_2$OH.HCl (1.3 mg, 0.018 mmol, 1.0 equiv) was added to a solution of aldehyde 8-12 (4.3 mg, 0.009 mmol, 1.0 equiv) in MeOH (0.5 mL). The resulting reaction mixture was stirred at rt for 1 h 30 min, and concentrated. The residue was purified by a preparative reverse phase HPLC on a Waters Autopurification system using a Phenomenex Polymerx™ 10μ RP-γ 100 A column [10 μm, 150×21.20 mm; flow rate, 20 mL/min; Solvent A: 0.05 N HCl/water; Solvent B: CH$_3$CN; injection volume: 3.0 mL (0.05 N HCl/water and MeCN, 1:1); gradient: 20→50% B over 15 min; mass-directed fraction collection]. Fractions containing the desired product, eluting at 9.5-10.8 min, were collected and freeze-dried to yield Compound 197 (2.0 mg, 45%): $^1$H NMR (400 MHz, CD$_3$OD) δ $^1$H NMR (400 MHz, CD$_3$OD) δ 8.41 (s, 1H), 7.60 (s, 1H), 4.07 (s, 1H), 3.81 (s, 3H), 3.32-3.30 (m, 1H), 3.03-2.93 (m, 8H), 2.20-2.11 (m, 2H), 1.67-1.57 (m, 1H); MS (ESI) m/z 488.29 (M+H).
Compound 198.

Compound 198 was prepared similarly to compound 197: $^1$H NMR (400 MHz, CD$_3$OD) δ 8.40 (s, 1H), 7.59 (s, 1H), 4.08 (s, 1H), 3.94 (s, 3H), 3.81 (s, 3H), 3.32-3.26 (m, 1H), 3.04-2.93 (m, 8H), 2.23-2.10 (m, 2H), 1.67-1.57 (m, 1H); MS (ESI) m/z 502.34 (M+H).

1H), 2.61-2.58 (m, 1H), 2.53-2.45 (m, 7H), 2.37 (t, J=16.5 Hz, 1H), 2.19 (d, J=14.6 Hz, 1H), 0.82 (s, 9H), 0.28 (s, 3H), 0.14 (s, 3H); MS (ESI) m/z 781.51 (M+H).
Compound 189.

Aqueous HF (48-50%, 0.2 mL) was added to a solution of aldehyde 8-6 (18 mg, 0.023 mmol, 1.0 equiv) in acetonitrile (0.5 mL) in a polypropylene reaction vessel at 23° C. The resulting mixture was stirred vigorously at 23° C. overnight and poured into aqueous K$_2$HPO$_4$ (2.4 g dissolved in 25 mL water). The resulting mixture was extracted with EtOAc (40 mL). The organic phase was dried over anhydrous sodium sulfate, filtered, and concentrated. The residue was used directly in the next step without further purification. The above crude product was dissolved in MeOH (2 mL) and dioxane (2 mL). Pd—C (10 wt %, 8 mg) was added in one portion at 23° C. The reaction vessel was sealed and purged with hydrogen by briefly evacuating the flask followed by flushing with hydrogen gas (1 atm). After stirring at 23° C. for 40 min, the reaction mixture was filtered through a small Celite pad. The filtrate was concentrated. The residue was purified by a preparative reverse phase HPLC on a Waters Autopurification system using a Phenomenex Polymerx™ 10μ RP-γ 100 A column [10 μm, 150×21.20 mm; flow rate, 20 mL/min; Solvent A: 0.05 N HCl/water; Solvent B: CH$_3$CN; injection volume: 3.0 mL (0.05 N HCl/water); gradient: 20→60% B over 15 min; mass-directed fraction collection]. Fractions containing the desired product, eluting at 6.6-8.0 min, were collected and freeze-dried to yield Compound 189 (6.5 mg, 58% over 2 steps): $^1$H NMR (400 MHz, CD$_3$OD) δ 7.67 (s, 1H), 4.07 (s, 1H), 3.83 (s, 3H), 3.33-3.30 (m, 1H), 3.03-2.92 (m, 8H), 2.20-2.10 (m, 2H), 1.65-1.55 (m, 1H); MS (ESI) m/z 489.28 (M+H).

Compound 189

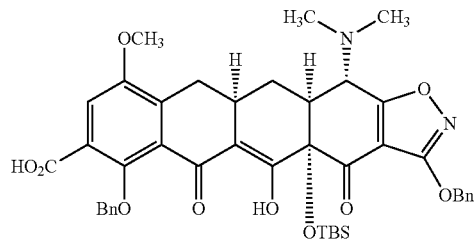

8-6

Compound 187

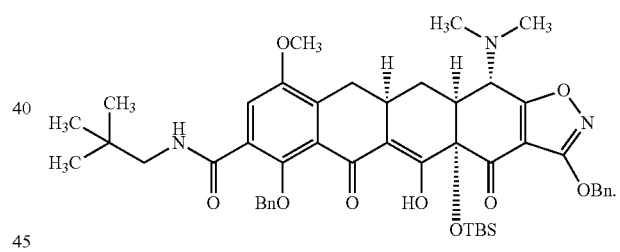

8-7-1

A solution of sulfamic acid (11 mg, 0.113 mmol, 1.4 equiv) in water (0.35 mL) was added dropwise to a solution of aldehyde 8-5 (61.8 mg, 0.081 mmol, 1.0 equiv) in MeCN (7 mL) at 0° C. Then a solution of NaOClO in water (0.35 mL, 0.113 mmol, 1.4 equiv) was added dropwise. The resulting reaction mixture was stirred at 0° C. for 15 min, and diluted with water (5 mL). The resulting mixture was stirred at rt for 5 min and extracted with EtOAc (50 mL). The organic phase was separated, dried over sodium sulfate, filtered and concentrated. The residue was purified by a Preparative reverse phase HPLC on a Waters Autopurification system using a Sunfire Prep C18 OBD column [5 μm, 19×50 mm; flow rate, 20 mL/min; Solvent A: H$_2$O with 0.1% HCO$_2$H; Solvent B: CH$_3$CN with 0.1% HCO$_2$H; injection volume: 4.0 mL (CH$_3$CN); gradient: 50→100% B over 10 min; mass-directed fraction collection]. Fractions with the desired MW, eluting at 9.0-10.6 min, were collected and concentrated to give the desired product 8-6 (36.9 mg, 58%): $^1$H NMR (400 MHz, CDCl$_3$) δ 15.83 (s, 1H), 7.72 (s, 1H), 7.51-7.49 (m, 2H), 7.40-7.33 (m, 8H), 5.36 (s, 2H), 5.05, 4.95 (ABq, J=9.8 Hz, 2H), 3.96 (d, J=11.0 Hz, 1H), 3.90 (s, 3H), 3.42 (dd, J=4.9, 17.1 Hz, 1H), 3.04-2.97 (m, Neopentyl amine (9.2 μL, 0.039 mmol, 2.0 equiv) was added to a solution of 8-6 (15.3 mg, 0.020 mmol, 1.0 equiv), EDCI (7.5 mg, 0.039 mmol, 2.0 equiv) and HOBt (1.3 mg, 0.010 mmol, 0.5 equiv) in DMF (0.5 mL). The resulting reaction mixture was stirred at rt overnight, and purified by a Preparative reverse phase HPLC on a Waters Autopurification system using a Sunfire Prep C18 OBD column [5 μm, 19×50 mm; flow rate, 20 mL/min; Solvent A: H$_2$O with 0.1% HCO$_2$H; Solvent B: CH$_3$CN with 0.1% HCO$_2$H; injection volume: 4.0 mL (CH$_3$CN); gradient: 90→100% B over 10 min; mass-directed fraction collection]. Fractions with the desired MW, eluting at 5.4-6.6 min, were collected and concentrated to give the desired amide 8-7-1 (11 mg, 66%): $^1$H NMR (400 MHz, CDCl$_3$) δ 16.01 (s, 1H), 9.53 (t, J=6.1 Hz, 1H), 7.83 (s, 1H), 7.50-7.48 (m, 2H), 7.40-7.32 (m, 8H), 5.35 (s, 2H), 4.87 (s, 2H), 3.97 (d, J=11.0 Hz, 1H), 3.90 (s, 3H), 3.39 (dd, J=4.9, 17.1 Hz, 1H), 3.13-3.04 (m, 2H), 3.00-2.93 (m, 1H), 2.58-2.54 (m, 1H), 2.49 (s, 6H), 2.47-2.42 (m, 1H), 2.36 (t, J=16.5 Hz, 1H), 2.17 (d, J=14.6 Hz, 1H), 0.81 (s, 9H), 0.73 (s, 9H), 0.27 (s, 3H), 0.12 (s, 3H); MS (ESI) m/z 850.72 (M+H). Aqueous HF (48-50%, 0.2 mL) was added to a solution of amide (11 mg, 0.013 mmol, 1.0 equiv) in acetonitrile (0.5 mL) in a polypropylene reaction vessel at 23° C. The resulting mixture was stirred vigorously at 23° C. overnight and poured into aqueous K₂HPO₄ (2.4 g dissolved in 25 mL water). The resulting mixture was extracted with EtOAc (50 mL). The organic phase was dried over anhydrous sodium sulfate, filtered, and concentrated. The residue was used directly in the next step without further purification.

The above crude product was dissolved in MeOH (1.5 mL) and HCl/MeOH (0.5 N, 26 µL, 1.0 equiv). Pd—C (10 wt %, 3.5 mg) was added in one portion at 23° C. The reaction vessel was sealed and purged with hydrogen by briefly evacuating the flask followed by flushing with hydrogen gas (1 atm). After stirring at 23° C. for 30 min, the reaction mixture was filtered through a small Celite pad. The filtrate was concentrated. The residue was purified by a preparative reverse phase HPLC on a Waters Autopurification system using a Phenomenex Polymerx™ 10µ RP-γ 100 A column [10 µm, 150×21.20 mm; flow rate, 20 mL/min; Solvent A: 0.05 N HCl/water; Solvent B: CH₃CN; injection volume: 3.0 mL (0.05 N HCl/water); gradient: 25→60% B over 15 min; mass-directed fraction collection]. Fractions containing the desired product, eluting at 11.0-12.6 min, were collected and freeze-dried to yield Compound 187 (3.0 mg, 39% over 2 steps): $^1$H NMR (400 MHz, CD₃OD) δ 7.86 (s, 1H), 4.09 (s, 1H), 3.84 (s, 3H), 3.35-3.30 (m, 1H), 3.03-2.96 (m, 8H), 2.23-2.15 (m, 2H), 1.68-1.58 (m, 1H), 0.99 (s, 9H); MS (ESI) m/z 558.38 (M+H).

Compound 188.

Compound 188 was prepared Compound 187 using dimethylaminoethylamine in place of neopentyl amine. $^1$H NMR (400 MHz, CDCl₃) δ 7.89 (s, 1H), 4.11 (s, 1H), 3.85 (s, 3H), 3.85-3.82 (m, 2H), 3.41 (t, J=6.0 Hz, 2H), 337-332 (m, 1H), 3.04-2.96 (m, 14H), 2.23-2.15 (m, 2H), 1.68-1.58 (m, 1H); MS (ESI) m/z 559.44 (M+H).

EXAMPLE 9

Compounds of Formula II wherein Y is —(CH₂)₃—N(R²)(R³)

Scheme 9:

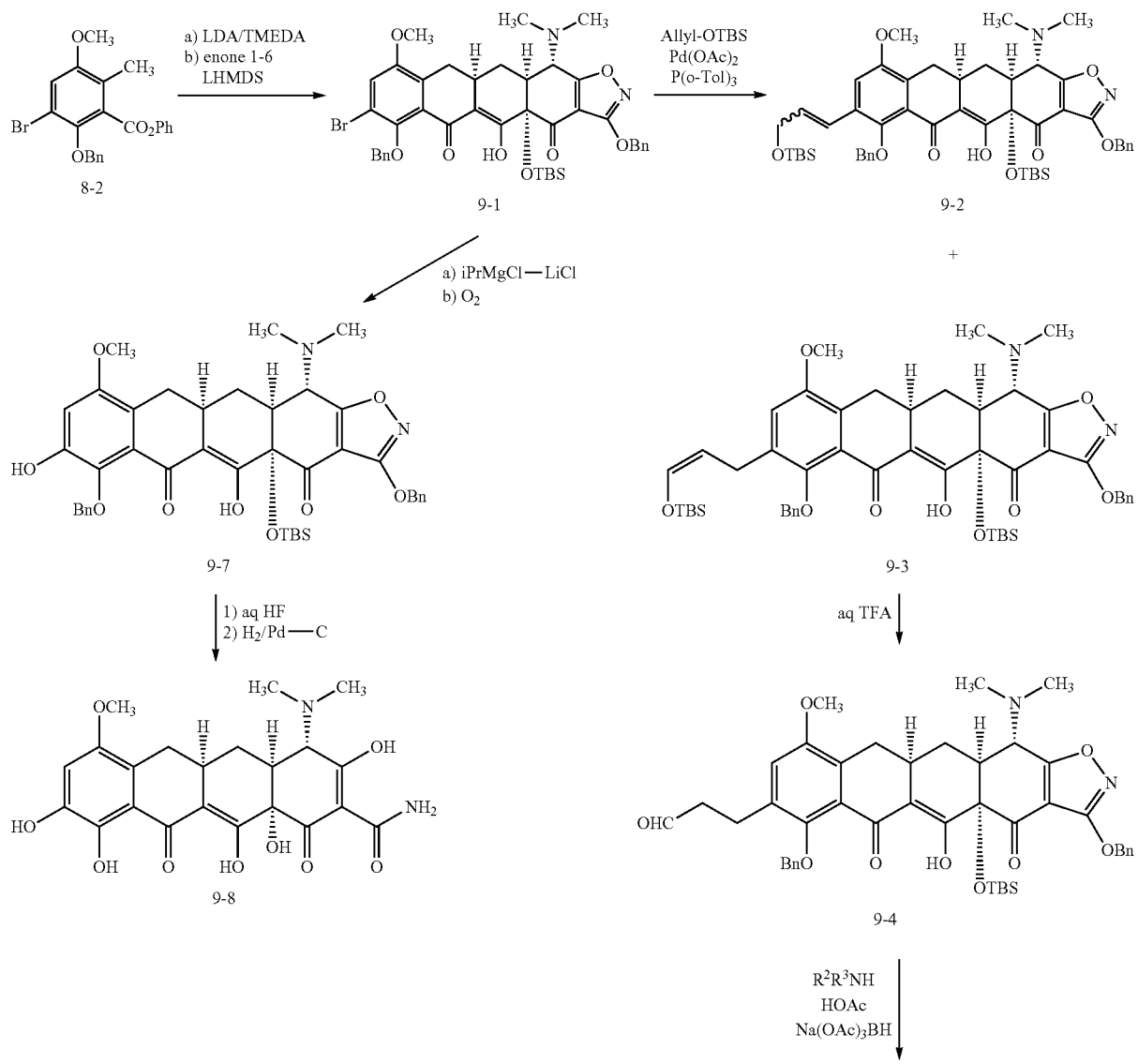

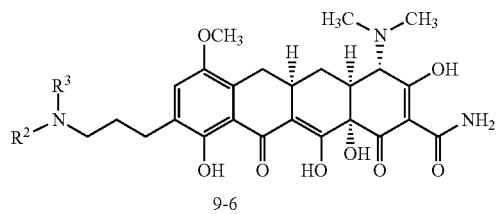

9-6

1) aq HF
2) H₂/Pd—C

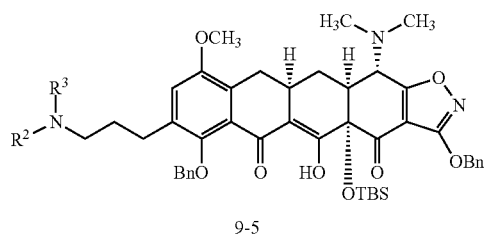

9-5

(4aS,11aR,12aS,13S)-3,7-bis(benzyloxy)-8-bromo-4a-(tert-butyldimethylsilyloxy)-13-(dimethylamino)-5-hydroxy-10-methoxy-11a,12,12a,13-tetrahydrotetraceno[2,3-d]isoxazole-4,6(4aH,11H)-dione (9-1)

n-BuLi (5.24 mL, 1.6 M/hexanes, 8.38 mmol, 2.0 equiv) was added dropwise to a solution of diisopropylamine (1.18 mL, 8.38 mmol, 2.0 equiv) and TMEDA (1.26 mL, 8.38 mmol, 2.0 equiv) in THF (40 mL) at −78° C. The reaction solution was stirred at −78° C. for 30 min. A solution of ester 8-2 (1.79 g, 4 A9 mmol, 1.0 equiv) in THF (20 mL) was added via a cannula over 20 min. The resulting deep red solution was stirred at −78° C. for 20 min and was then cooled to −100° C. A solution of enone 1-6 (1.62 g, 3.35 mmol, 0.8 equiv) in THF (20 mL) was added to the reaction mixture via a cannula. The reaction mixture was allowed to warm to −30° C. over 1 h 30 min, quenched by a mixture of saturated aqueous NH₄Cl (100 mL). The resulting mixture was extracted with EtOAc (200 mL, then 50 mL) The combined EtOAc extracts were dried (sodium sulfate), filtered and concentrated. The residue was purified by flash chromatography (9:1:1 Hexanes/EtOAc/DCM) to give compound 9-1 (1.27 g, 46%): ¹H NMR (400 MHz, CDCl₃) δ 16.00 (s, 1H), 7.59-7.57 (m, 2H), 7.52-7.50 (m, 2H), 7.41-7.32 (m, 6H), 7.26 (s, 1H), 5.37 (s, 2H), 5.00, 4.92 (ABq, J=9.2 Hz, 2H), 3.98 (d, J=10.4 Hz, 1H), 3.85 (s, 3H), 3.32 (dd, J=4.9, 15.9 Hz, 1H), 2.98-2.91 (m, 1H), 2.58-2.43 (m, 8H), 2.29 (t, J=15.9 Hz, 1H), 2.15 (d, J=14.0 Hz, 1H), 0.82 (s, 9H), 0.28 (s, 3H), 0.14 (s, 3H); MS (ESI) m/z 815.59, 817.59 (M+H).

(4aS,11aR,12aS,13S)-3,7-bis(benzyloxy)-4a-(tert-butyldimethylsilyloxy)-8-((Z)-3-(tert-butyldimethylsilyloxy)allyl)-13-(dimethylamino)-5-hydroxy-10-methoxy-11a,12,12a,13-tetrahydrotetraceno[2,3-d]isoxazole-4,6(4aH,11H)-dione (9-3)

A reaction vessel charged with bromide 9-1 (321 mg, 0.394 mmol, 1.0 equiv), Pd(OAc)₂ (17.7 mg, 0.079 mmol, 0.2 equiv) and P(o-Tol)₃ (36 mg, 0.118 mmol, 0.3 eq) was vacuumed/back flushed with N₂ several times. Then DMF (2 mL), TEA (275 μL, 1.97 mmol, 5.0 equiv) and allyl dimethyl-tert-butylsilyl ether (168 μL, 0.789 mmol, 2.0 equiv) were added under N₂. The reaction was then sealed and heated at 80° C. for 6 h. The reaction mixture was cooled to rt, diluted with MeCN, and purified by a Preparative reverse phase HPLC on a Waters Autopurification system using a Sunfire Prep C18 OBD column [5 μm, 19×50 mm; flow rate, 20 mL/min; Solvent A: H₂O with 0.1% HCO₂H; Solvent B: CH₃CN with 0.1% HCO₂H; injection volume: 4.0 mL (CH₃CN); gradient: 90→100% B over 7 min; mass-directed fraction collection]. Fractions with the desired MW were collected and concentrated to afford the desired products 9-3 (containing small amount of the isomer) (212.9 mg, 60%): ¹H NMR (400 MHz, CDCl₃) δ 16.07 (s, 1H), 7.42-7.34 (m, 4H), 7.31-7.22 (m, 7H), 6.87 (s, 1H), 6.23 (d, J=6.1 Hz, 1H), 5.27 (s, 2H), 4.75, 4.69 (ABq, J=10.0 Hz, 2H), 3.92 (d, J=10.4 Hz, 1H), 3.72 (s, 3H), 3.44-3.14 (m, 3H), 2.89-2.82 (m, 1H), 2.48-2.18 (m, 9H), 2.05 (d, J=14.6 Hz, 1H), 0.83 (s, 9H), 0.73 (s, 9H), 0.19 (s, 3H), 0.05 (s, 6H), 0.04 (s, 3H); MS (ESI) m/z 907.87 (M+H).

3-((4aS,11aR,12aS,13S)-3,7-bis(benzyloxy)-4a-(tert-butyldimethylsilyloxy)-13-(dimethylamino)-5-hydroxy-10-methoxy-4,6-dioxo-4,4a,6,11,11a,12,12a,13-octahydrotetraceno[2,3-d]isoxazol-8-yl)propanal (9-4)

Water (0.5 mL) was added to a solution of 9-3 (162.4 mg, 0.179 mmol, 1.0 equiv). Then TFA (0.5 mL) was added dropwise at 0° C. The resulting reaction mixture was then stirred at rt for 2 h and cooled to 0° C. Saturated sodium bicarbonate (8 mL) was added slowly. The resulting mixture was then extracted with EtOAc (40 mL, then 10 mL). The combined organic phase was dried over anhydrous sodium sulfate, filtered and concentrated. The crude product 9-4 was used directly for the next step.

Compound 199

9-5-1

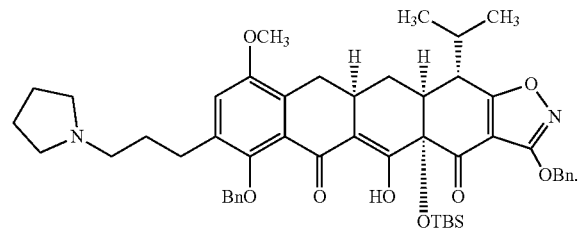

Pyrrolidine (19 μL, 0.22 mmol, 5.0 equiv), acetic acid (13 μL, 0.22 mmol, 5.0 equiv) and sodium triacetoxyborohydride (28 mg, 0.13 mmol, 3.0 equiv) were added sequentially to one fourth of the above product 9-4 (0.045 mmol, 1.0 equiv) in 1,2-dichloroethane (1 mL) at 23° C. After stirring for overnight, the reaction mixture was quenched by the addition of saturated aqueous sodium bicarbonate (5 mL) and pH 7 phosphate buffer (10 mL) and extracted with dichloromethane (3×15 mL). The combined organic extracts were dried over anhydrous sodium sulfate, filtered, and concentrated. The residue was purified by a Preparative reverse phase HPLC on a Waters Autopurification system using a Sunfire Prep C18 OBD column [5 μm, 19×50 mm; flow rate, 20 mL/min; Solvent A: H₂O with 0.1% HCO₂H; Solvent B: CH₃CN with 0.1% HCO₂H; injection volume: 4.0 mL (CH₃CN); gradient: 10→100% B over 10 min; mass-directed fraction collection]. Fractions with the desired MW, eluting at 6.0-7.7 min, were collected and freeze-dried to afford the desired products 9-5-1 (16 mg, 42% for 2 steps): ¹H NMR (400 MHz, CD₃OD) δ 16.12 (br s, 1H), 7.50-7.48 (m, 2H), 7.44-7.42 (m, 2H), 7.39-7.30 (m, 6H), 6.90 (s, 1H), 5.35 (s, 2H), 4.80, 4.77 (ABq, J=10.4 Hz, 2H), 3.99 (d, J=10.4 Hz, 1H), 182 (s, 3H), 3.31 (dd, J=4.9, 15.9 Hz, 1H), 2.99-2.92 (m, 1H), 2.70-2.42 (m, 16H), 2.31 (t, J=15.3 Hz, 1H), 2.14 (d, J=14.6 Hz, 1H), 1.88-1.77 (m, 6H), 0.81 (s, 9H), 0.27 (s, 3H), 0.12 (s, 3H); MS (ESI) m/z 848.69 (M+H).

Aqueous HF (48-50%, 0.3 mL) was added to a solution of amine 9-5-1 (16 mg, 0.019 mmol, 1.0 equiv) in acetonitrile (0.6 mL) in a polypropylene reaction vessel at 23° C. The resulting mixture was stirred vigorously at 23° C. overnight and poured into aqueous $K_2HPO_4$ (3.6 g dissolved in 25 mL water). The resulting mixture was extracted with EtOAc (3×15 mL). The combined organic phase was dried over anhydrous sodium sulfate, filtered, and concentrated. The residue was used directly in the next step without further purification.

The above crude product was dissolved in MeOH (1.5 mL) and HCl/MeOH (0.5 N, 76 µL, 2.0 equiv). Pd—C (10 wt %, 4.3 mg) was added in one portion at 23° C. The reaction vessel was sealed and purged with hydrogen, by briefly evacuating the flask followed by flushing with hydrogen gas (1 atm). After stirring at 23° C. for 1 h, the reaction mixture was filtered through a small Celite pad. The filtrate was concentrated. The residue was purified by a preparative reverse phase HPLC on a Waters Autopurification system using a Phenomenex Polymerx™ 10µ RP-γ 100 A column [10 µm, 150×21.20 mm; flow rate, 20 mL/min; Solvent A: 0.05 N HCl/water; Solvent B: $CH_3CN$; injection volume: 3.0 mL (0.05 N HCl/water); gradient: 10→35% B over 15 min; mass-directed fraction collection]. Fractions containing the desired product, eluting at 11.6-13.5 min, were collected and freeze-dried to yield Compound 199 (4.8 mg, 40% over 2 steps): $^1$H NMR (400 MHz, $CD_3OD$) δ 7.19 (s, 1H), 4.08 (s, 1H), 3.80 (s, 3H), 3.69-3.63 (m, 2H), 3.28-3.21 (m, 3H), 3.08-2.93 (m, 10H), 2.77 (t, J=7.8 Hz, 2H), 2.22-2.00 (m, 8H), 1.65-1.55 (m, 1H); MS (ESI) m/z 556.51 (M+H).

Compounds 200-205 were prepared similarly to Compound 199, using the appropriate amine $NR^2R^3$.

Compound 200.
$^1$H NMR (400 MHz, $CD_3OD$) δ 7.18 (s, 1H), 4.08 (s, 1H), 3.80 (s, 3H), 3.28-3.24 (m, 1H), 3.09-2.90 (m, 12H), 2.78 (t, J=7.3 Hz, 2H), 2.21-1.97 (m, 4H), 1.66-1.56 (m, 1H), 1.31 (t, J=7.3 Hz, 3H); MS (ESI) m/z 530.42 (M+H).

Compound 201.
$^1$H NMR (400 MHz, $CD_3OD$) δ 7.18 (s, 1H), 4.73 (dt, J=4.6, 47.2 Hz, 2H), 4.08 (s, 1H), 3.80 (s, 3H), 3.39 (dt, J=4.6, 26.6 Hz, 2H), 3.28-3.23 (m, 1H), 3.12-2.93 (m, 10H), 2.78 (t, J=7.8 Hz, 2H), 2.21-2.01 (m, 4H), 1.66-1.55 (m, 1H); MS (ESI) m/z 548.47 (M+H).

Compound 202.
$^1$H NMR (400 MHz, $CD_3OD$) δ 7.18 (s, 1H), 6.30 (tt, J=2.8, 54.0 Hz, 1H), 4.08 (s, 1H), 3.80 (s, 3H), 3.56 (dt, J=3.2, 15.6 Hz, 2H), 3.28-3.23 (m, 1H), 3.17-3.13 (m, 2H), 3.04-2.93 (m, 8H), 2.78 (t, J=7.3 Hz, 2H), 2.22-2.02 (m, 4H), 1.65-1.55 (m, 1H); MS (ESI) m/z 566.49 (M+H).

Compound 203.
$^1$H NMR (400 MHz, $CD_3OD$) δ 7.18 (s, 1H), 4.08 (s, 1H), 4.04 (q, J=9.2 Hz, 1H), 3.80 (s, 3H), 3.28-3.23 (m, 1H), 3.21-3.17 (m, 2H), 3.04-2.93 (m, 8H), 2.78 (t, J=7.3 Hz, 2H), 2.20-2.05 (m, 4H), 1.65-1.55 (m, 1H); MS (ESI) m/z 584.48 (M+H).

Compound 204.
$^1$H NMR (400 MHz, $CD_3OD$) δ 7.19 (s, 1H), 4.07 (s, 1H), 3.79 (s, 3H), 3.27-3.08 (m, 5H), 3.03-2.84 (m, 8H), 2.84 (s, 3H), 2.76 (t, J=7.3 Hz, 2H), 2.20-2.05 (m, 4H), 1.65-1.55 (m, 1H), 1.32 (t, J=7.3 Hz, 3H); MS (ESI) m/z 544.42 (M+H).

Compound 205.
$^1$H NMR (400 MHz, $CD_3OD$) δ 7.18 (s, 1H), 4.26-4.20 (m, 2H), 4.08-4.03 (m, 3H), 3.80 (s, 3H), 3.28-3.20 (m, 3H), 3.04-2.93 (m, 8H), 2.73 (t, J=7.3 Hz, 2H), 2.62-2.55 (m, 1H), 2.44-2.40 (m, 1H), 2.21-2.18 (m, 1H), 2.13-2.06 (m, 1H), 1.92-1.85 (m, 2H), 1.65-1.55 (m, 1H); MS (ESI) m/z 542.44 (M+H).

(4aS,11aR,12aS,13S)-3,7-bis(benzyloxy)-4a-(tert-butyldimethylsilyloxy)-13-(dimethylamino)-5,8-dihydroxy-10-methoxy-11a,12,12a,13-tetrahydrotetraceno[2,3-d]isoxazole-4,6(4aH,11H)-dione (9-7)

9-1 (46 mg, 0.056 mmol, 1.0 equiv) was dissolved in tetrahydrofurane (2 mL). Turbo Grignard reagent (isopropylmagnesium chloride with lithium chloride, 1.2 M, 113 µL, 0.135 mmol) was added dropwise at −78° C. The mixture was warmed up to −20° C. and stirred for 1 h. Oxygen was then passed through the reaction mixture slowly for 30 min. The reaction was then quenched by adding 5 mL ammonium chloride solution following addition of ethyl acetate. The mixture was washed with $H_2O$ (10 mL) and concentrated to give crude 9-7, which was purified by HPLC on a Sunfire column to yield 4.0 mg yellow solid.

Compound 206.
Aqueous HF (0.3 mL, 48-50%) was added to a $CH_3CN$ solution (1.0 mL) of 9-7 in a plastic vial at 25° C. The reaction was stirred at 25° C. for 18 hrs. The resulting mixture was poured into an aqueous solution (10 mL) of $K_2HPO_4$ (2 g). The solution was extracted with EtOAc (3×15 mL). The combined EtOAc extracts were dried over sodium sulfate and concentrated to give the crude intermediate.

10% Pd—C (20 mg) was added to a dioxane/MeOH solution (2 mL, 1:1) of the above crude intermediate. The reaction mixture was stirred under $H_2$ (balloon) at 25° C. for 2 hrs and filtered through a pad of Celite. The filtrate was concentrated to give the crude product 144 mg. The crude product was purified by HPLC on a Polymerx™ 10µ RP-γ 100 R column [30×21.20 mm, 10 micron, solvent A: 0.05 N HCl, solvent B: $CH_3CN$, sample in 2.0 mL (0.05 N HCl), gradient elution with 0-70% B over 15 min, mass-directed fraction collection] to yield Compound 206 as a yellow solid (1.64 mg, 6.3%, 3 steps): $^1$H NMR (400 MHz, $CD_3OD$) δ 6.82 (s, 1H), 4.05 (s, 1H), 3.74 (s, 3H), 3.17 (dd, J=15.6, 4.6 Hz, 1H), 3.02 (s, 3H), 2.96 (s, 3H), 3.01-2.89 (m, 2H), 2.19-2.11 (m, 1H), 2.09-2.00 (m, 1H), 1.65-1.53 (m, 1H); MS (ESI) m/z 461.22 (M+H).

EXAMPLE 10

Synthesis of Compounds of Formula III, wherein Y is —NH—C(O)—$CH_2$—$NR^2R^3$, —NH—C(O)—($C_1$-$C_6$)alkyl, —NH—C(O)-heterocyclyl, or —NH—C(O)-carbocyclyl Scheme 10:

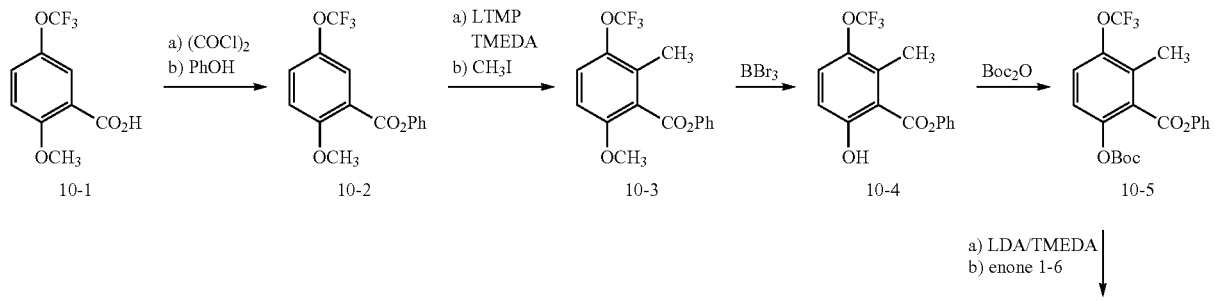

a) LDA/TMEDA
b) enone 1-6

101

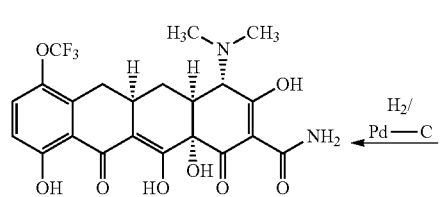

Compound 207

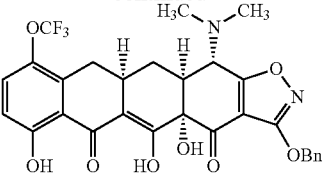

10-7

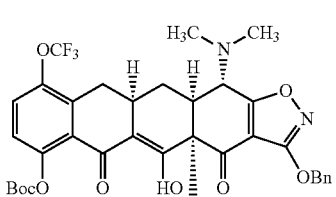

10-6

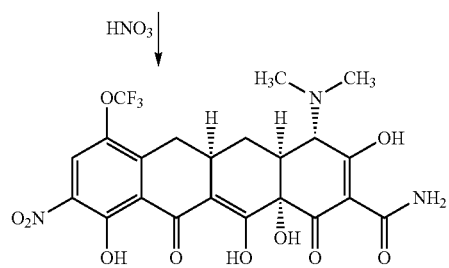

Compound 208

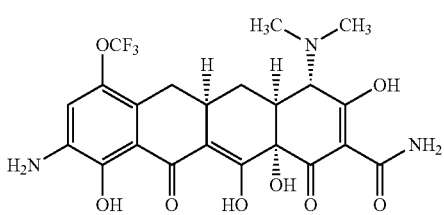

Compound 209

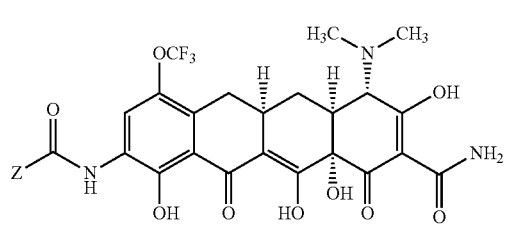

10-11

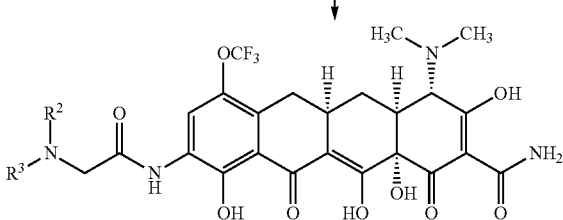

10-12

In Scheme 10, Z represents —($C_1$-$C_6$)alkyl, -heterocyclyl, or -carbocyclyl. Compounds 207-209 are compounds of the invention, as well as being used as intermediates to produce additional compounds of the invention.

Phenyl 2-methoxy-5-(trifluoromethoxy) benzoate (10-2)

To commerically available 2-methoxy-5-(trifluoromethoxy)benzoic acid (10-1) (4.73 g, 18.91 mmol, 1 equiv) in dry DCM at room temperature was added anhydrous DMF (5 drops) and oxalyl chloride (4.87 mL, 56.71 mmol, 3.0 equiv) dropwise. The reaction was stirred at room temperature for 1 hr (until gas evolution ceased). The reaction solution was concentrated in vacuo to yield the crude acid chloride as a yellow oil, which was re-dissolved in dry DCM, and added with PhOH (2.67 g, 28.37 mmol, 1.5 equiv), DIEA (9.88 mL, 56.72 mmol, 3.0 equiv) and DMAP (0.23 g, 1.88 mmol, 0.1 equiv). The reaction was stirred at room temperature for overnight, quenched with saturated sodium bicarbonate aqueous solution (100 mL), and extracted with DCM (100 mL×3). The combined DCM extracts were dried over sodium sulfate and concentrated in vacuo. Flash column chromatography with 0% and 5% EtOAc/hexanes gave the desired phenyl ester 10-2 as a pale oil (6.09 g, quantitative): $R_f$ 0.20 (10% EtOAc/hexanes); $^1$H NMR (400 MHz, CDCl$_3$) δ 7.87 (d, J=2.4 Hz, 1H), 7.36-7.43 (m, 3H), 7.17-7.30 (m, 3H), 7.02 (d, J=9.2 Hz, 1H), 3.94 (s, 3H).

Phenyl 6-methoxy-2-methyl-3-(trifluoromethoxy)benzoate (10-3). 2,2,6,6-Tetramethylpiperidine (TMP) (3.97 mL, 23.38 mmol, 1.2 equiv) was dissolved in anhydrous THF (50 mL) and cooled to −78° C. nBuLi (9.35 mL, 2.5 M in hexane, 23.38 mmol, 1.2 equiv) was added dropwise. The yellow solution was stirred at 0° C. for 10 min and cooled to −78° C. Anhydrous N,N,N',N'-tetramethylethylenediamine (TMEDA) (4.38 mL, 29.22 mmol, 1.5 equiv) was added, followed by dropwise addition of phenyl ester 10$^{-2}$ (6.09 g, 19.50 mmol, in 50 mL anhydrous THF, 1.0 equiv) over a period of 15 min. The resulting deep yellow-brown solution was stirred at −78° C. for 30 min. Methyl iodide (1.82 mL, 29.23 mmol, 1.5 equiv) was added. The deep-brown solution was stirred from −78° C. to room temperature for 2 hrs and at room temperature for 1 hr. HOAc (6 mL) and water (100 mL) were added sequentially to quench the reaction. The bright orange solution was concentrated in vacuo and extracted with EtOAc (200 mL×1). The EtOAc extract was washed with 1 N aqueous HCl (50 mL×2) and brine (50 mL×1), dried over sodium sulfate, and concentrated in vacuo. Flash column chromatography with 0% and 5% EtOAc/hexanes gave the desired phenyl ester 10$^{-3}$ as a pale solid (2.92 g, 46%): $R_f$ 0.30 (10% EtOAc/hexanes); $^1$H NMR (400 MHz, CDCl$_3$) δ 7.40-7.45 (m, 2H), 7.20-7.30 (m, 4H), 6.81 (d, J=8.5 Hz, 1H), 3.88 (s, 3H), 2.37 (s, 3H).

Phenyl 6-hydroxy-2-methyl-3-(trifluoromethoxy)benzoate (10-4)

Methyl ether 10-3 (500 mg, 1.53 mmol, 1 equiv) was dissolved in anhydrous DCM (10 mL) and cooled to −78° C. BBr$_3$ (1.60 mL, 1.0 M/DCM, 1.60 mmol, 1.02 equiv) was added dropwise. The deep-orange solution was stirred from −78° C. to −10° C. for 4 hrs. The reaction was quenched with saturated sodium bicarbonate aqueous solution (100 mL) and extracted with DCM (50 mL×3). The combined DCM extracts were dried over sodium sulfate and concentrated in vacuo to yield the crude phenol 10-4 as a yellow oil (410 mg, 86%): R$_f$ 0.55 (10% EtOAc/hexanes); $^1$H NMR (400 MHz, CDCl$_3$) δ 10.86 (s, 1H), 7.42-7.50 (m, 2H), 7.30-7.40 (m, 2H), 7.19 (d, J=7.9 Hz, 2H), 6.91 (d, J=9.2 Hz, 1H), 2.64 (s, 3H).

Phenyl 6-(tert-butoxycarbonyloxy)-2-methyl-3-(trifluoromethoxy)benzoate (10-5)

Crude phenol 10-4 (410 mg, 1.31 mmol, 1 equiv) was dissolved in anhydrous DCM (10 mL). (Boc)$_2$O (430 mg, 1.97 mmol, 1.5 equiv), DIEA (0.46 mL, 2.64 mmol, 2 equiv), and DMAP (16 mg, 0.13 mmol, 0.1 equiv) were added sequentially at room temperature. The reaction was stirred at room temperature for 1 hr, quenched with saturated aqueous sodium bicarbonate (50 mL), and extracted with DCM (50 mL×3). The combined DCM extracts were dried over sodium sulfate and concentrated in vacuo. Flash column chromatography with 0% and 2% EtOAc/hexanes gave the desired product 10-5 as a white solid (540 mg, quantitative): R$_f$ 0.60 (10% EtOAc/hexanes); $^1$H NMR (400 MHz, CDCl$_3$) δ 7.41-7.48 (m, 2H), 7.38 (d, J=10.3 Hz, 1H), 7.22-7.32 (m, 3H), 7.18 (d, J=9.2 Hz, 1H), 2.45 (s, 3H), 1.45 (s, 9H).

(4aS,11aR,12aS,13S)-3-(benzyloxy)-4a-(tert-butyldimethylsilyloxy)-13-(dimethylamino)-5-hydroxy-4,6-dioxo-10-(trifluoromethoxy)-4,4a,6,11,11a,12,12a,13-octahydrotetraceno[2,3-d]isoxazol-7-yl tert-butyl carbonate (10-6)

To diisopropylamine (0.062 mL, 0.44 mmol, 2.2 equiv) in THF (5 mL) at −78° C. was added with nBuLi dropwise (0.27 mL, 1.6 M/hexane, 0.44 mmol, 2.2 equiv). The pale solution was brought to 0° C., stirred at that temperature for 10 min, and cooled to −78° C. TMEDA (0.075 mL, 0.50 mmol, 2.5 equiv) was added, followed by dropwise addition of compound 10-5 (91 mg, 0.22 mmol, 1.1 equiv, in 5 mL THF) over a period of 10 min. The resulting deep-red solution was stirred at −78° C. for 15 min. Enone 1-6 (97 mg, 0.20 mmol, 1 equiv, in 5 mL THF) was added dropwise over a period of 2 min. The resulting yellow solution was stirred from −78° C. to −10° C. over a period of 1 hr, quenched with aqueous saturated ammonium chloride (50 mL), and extracted with EtOAc (50 mL×3). The extracts were combined, dried over sodium sulfate, and concentrated in vacuo. Preparative HPLC purification on a C-18 column (mobile phase: A-0.1% formic acid/water, B-0.1% formic acid/acetonitrile; gradient: 80% B to 100% B over 10 min) yielded the desired product 10-6-1 as a yellow solid (90 mg, 56%): R$_f$ 0.40 (10% EtOAc/hexane); $^1$H NMR (400 MHz, CDCl$_3$) δ 15.48 (s, 1H), 7.36 (d, J=7.2 Hz, 2H), 7.29-7.20 (m, 4H), 6.94 (d, J=7.2 Hz, 1H), 5.22 (s, 2H), 3.81 (d, J=10.8 Hz, 1H), 3.15 (dd, J=16.0, 4.8 Hz, 1H), 2.94-2.85 (m, 1H), 2.44-2.31 (m, 9H), 2.03 (d, J=14.4 Hz, 1H), 1.42 (s, 9H), 0.78 (s, 9H), 0.15 (s, 3H), 0.08 (s, 3H); MS (ESI) m/z 801.3 (M+H).

(4aS,11aR,12aS,13S)-tert-butyl 3-(benzyloxy)-4a-(tert-butyldimethylsilyloxy)-13-(dimethylamino)-5,7-dihydroxy-4,6-dioxo-10-(trifluoromethoxy)-4,4a,6,11,11a,12,12a,13-octahydrotetraceno[2,3-d]isoxazole-8-carboxylate (10-6-2)

The title compound (10-6-2) was also isolated from the preparation of 10-6-1: MS (ESI) m/z 801.3 (M+H).

(4aS,11aR,12aS,13S)-3-(benzyloxy)-13-(dimethylamino)-4a,5,7-trihydroxy-10-(trifluoromethoxy)-11a,12,12a,13-tetrahydrotetraceno[2,3-d]isoxazole-4,6(4aH,11H)-dione (10-7)

10-6 (90 mg, 0.11 mmol) was dissolved in acetonitrile (2 mL). HF (1 mL, 40% in water) was added. The yellow solution was stirred at rt for overnight. The reaction solution was then slowly added into K$_2$HPO$_4$ (4.3 g) in water (20 mL) with rapid stirring. The mixture was extracted with DCM (10 mL×3). The combined extracts were dried over sodium sulfate and concentrated in vacuo to yield the crude product 10-7 as a yellow solid (76 mg),

(4S,4aS,5aR,12aS)-4-(dimethylamino)-3,10,12,12a-tetrahydroxy-1,11-dioxo-7-(trifluoromethoxy)-1,4,4a,5,5a,6,11,12a-octahydrotetracene-2-carboxamide (Compound 207)

10-7 (crude, 0.11 mmol, 1 equiv) was dissolved 1,4-dioxane/methanol (5 mL, 1:4 v/v). 10% Pd—C (47 mg, 0.022 mmol Pd, 0.2 equiv) was added. The mixture was purged by bubbling hydrogen through for 5 min and rapidly stirred under 1 atm hydrogen atmosphere at rt for 1 hr. The catalyst was filtered off with a small Celite pad and washed with more methanol (2 mL×3). The filtrate was concentrated in vacuo. Preparative HPLC purification on a Polymerx™ column yielded the desired product Compound 207 as a yellow solid (72 mg, quantitative): $^1$H NMR (400 MHz, CD$_3$OD) δ 7.45 (dd, J=9.2, 0.9 Hz, 1H), 6.91 (d, J=9.2 Hz, 1H), 4.11 (s, 1H), 3.19-2.96 (m, 9H), 2.36-2.30 (m, 1H), 2.25-2.20 (m, 1H), 1.69-1.63 (m, 1H); MS (ESI) m/z 499.4 (M+H).

(4S,4aS,5aR,12aS)-4-(dimethylamino)-3,10,12,12a-tetrahydroxy-9-nitro-1,11-dioxo-7-(trifluoromethoxy)-1,4,4a,5,5a,6,11,12a-octahydrotetracene-2-carboxamide (Compound 208)

Compound 207 (70 mg, 0.14 mmol, 1 equiv) was dissolved in cold (0°) sulfuric acid (4 mL). A solution of HNO$_3$ in H$_2$SO$_4$ (0.42 mL, 0.5 M, 0.21 mmol, prepared prior to use by mixing 70% aqueous nitric acid with concentrated sulfuric acid) was added dropwise at 0° C. The deep-red solution was stirred at 0° C. for 1 hr. The resulting yellow solution was added dropwise into diethyl ether (200 mL) with rapid stirring. The yellow solid was collected, washed with more diethyl ether (5 mL×4), and dried in vacuo to yield the crude product Compound 208 as a yellow solid, which was used directly in the next step.

(4S,4aS,5aR,12aS)-9-amino-4-(dimethylamino)-3,10,12,12a-tetrahydroxy-1,11-dioxo-7-(trifluoromethoxy)-1,4,4a,5,5a,6,11,12a-octahydrotetracene-2-carboxamide (Compound 209)

Compound 208 (0.10 mmol, crude) was dissolved in 0.1 N HCl/methanol (5 mL). 10% Pd—C (54 mg, 0.02 mmol Pd, 0.2 equiv) was added. The mixture was purged by bubbling hydrogen through for 5 min and rapidly stirred under 1 atm hydrogen atmosphere at rt for 1 hr. The catalyst was filtered off with a small Celite pad and washed with more methanol (5 mL×4). The filtrate was concentrated in vacuo. Preparative HPLC purification on a Polymerx™ column yielded the desired aniline Compound 209 as a brown solid (13 mg, 22%): $^1$H NMR (400 MHz, CD$_3$OD) δ 7.60 (s, 1H), 4.12 (s, 1H), 3.21-2.93 (m, 9H), 2.38-2.32 (m, 1H), 2.25-2.22 (m, 1H), 1.69-1.59 (m, 1H); MS (ESI) m/z 514.1 (M+H).

Compound 210.

Compound 209 (4 mg, 0.0068 mmol, 1 equiv) was dissolved in acetonitrile/DMPU (1 mL, 1:3 v/v). Sodium carbonate (4 mg, 0.04 mmol, 6 equiv) and bromoacetyl bromide/acetonitrile (0.041 mL, 0.2 M, 0.0082 mmol, 1.2 equiv, prepared prior to use by dissolving bromoacetyl bromide in anhydrous acetonitrile) was added at rt. The reaction was stirred at rt for 10 min. LC/MS analysis indicated complete consumption of the starting aniline 6. Azetidine (0.0092 mL, 0.14 mmol, 20 equiv) was added. The reaction was stirred at rt for 1 hr. LC/MS analysis indicated complete consumption of the intermediate bromide. The reaction mixture was then added dropwise into 5 mM HCl/diethyl ether (50 mL) with rapid stirring. The solid was collected on a small Celite pad, washed with more 5 mM HCl/diethyl ether (5 mL×4), and eluted with 0.1 N HCl/water (4 mL). The yellow eluent was then directly injected into a preparative HPLC system equipped with a Polymerx™ column for purification. The desired product Compound 210 was obtained as a yellow solid after freeze-drying (3.2 mg, 2 HCl, 69%): $^1$H NMR (400 MHz, CD$_3$OD) δ 8.40 (s, 1H), 4.30-4.40 (m, 4H), 4.10-4.23 (m, 2H), 4.09 (s, 1H), 2.90-3.50 (m, 3H), 3.03 (s, 3H), 2.94 (s, 3H), 2.58-2.70 (m, 1H), 2.42-2.52 (m, 1H), 2.28-2.36 (m, 1H), 2.18-2.25 (m, 1H), 1.58-1.70 (m, 1H); MS (ESI) m/z 611.3 (M+H).

The following compounds were prepared similarly to Compound 210 substituting the appropriate amine (NHR$^2$R$^3$).

Compound 211.
$^1$H NMR (400 MHz, CD$_3$OD): δ 8.45 (s, 1H), 4.23 (s, 2H), 4.11-4.09 (m, 3H), 3.19-2.93 (m, 9H), 2.35-2.26 (m, 1H), 2.25-2.17 (m, 1H), 1.68-157 (m, 1H); MS (ESI) m/z 653.1 (M+H).

Compound 212.
$^1$H NMR (400 MHz, CD$_3$OD): δ 8.39 (s, 1H), 5.53-5.35 (m, 1H), 4.58-4.42 (m, 6H), 4.10 (s, 1H), 3.15-2.93 (m, 9H), 2.35-2.25 (m, 1H), 2.23-2.18 (m, 1H), 1.37-158 (m, 1H); MS (ESI) m/z 629.1 (M+H).

Compound 213.
$^1$H NMR (400 MHz, CD$_3$OD) δ 8.43 (s, 1H), 4.11-4.10 (m, 3H), 3.18-2.96 (m, 11H), 2.36-2.21 (m, 2H), 1.75-1.63 (m, 3H), 1.49-1.43 (m, 2H), 1.02 (t, J=7.2 Hz, 3H); MS (ESI) m/z 627.2 (M+H).

Compound 214.
$^1$H NMR (400 MHz, CD$_3$OD) δ 8.47 (s, 1H, 4.14 (s, 3H), 3.22-3.00 (m, 11H), 2.39-2.26 (m, 2H), 1.79-1.77 (m, 2H), 1.69-1.67 (m, 1H), 1.46-1.45 (m, 4H), 1.02 (t, J=7.2 Hz, 3H); MS (ESI) m/z 641.2 (M+H).

Compound 215.
$^1$H NMR (400 MHz, CD$_3$OD) δ 8.46 (s, 1H), 4.12 (s, 3H), 3.21-2.98 (m, 11H), 2.38-2.31 (m, 2H), 1.79-1.75 (m, 2H), 1.69-1.66 (m, 1H), 1.48-1.39 (m, 6H), 0.98 (t, J=7.2 Hz, 3H); MS (ESI) m/z 655.2 (M+H).

Compound 216.
$^1$H NMR (400 MHz, CD$_3$OD) δ 8.43 (s, 1H), 4.10 (s, 2H), 4.08 (s, 1H), 3.17-2.94 (m, 11H), 2.35-2.27 (m, 1H), 2.25-2.18 (m, 1H), 1.64-1.61 (m, 1H), 1.10 (m, 9H); MS (ESI) m/z 641.1 (M+H).

Compound 217.
$^1$H NMR (400 MHz, CD$_3$OD) δ 8.34 (s, 1H), 4.04 (s, 2H), 4.01 (s, 1H), 3.11-2.87 (m, 11H), 2.26-2.13 (m, 2H), 1.60-1.53 (m, 1H), 1.18-1.05 (m, 1H), 0.67-0.63 (m, 2H), 0.37-0.33 (m, 2H); MS (ESI) m/z 625.2 (M+H).

Compound 218.
$^1$H NMR (400 MHz, CD$_3$OD) δ 8.44 (s, 1H), 4.35-4.20 (m, 2H), 4.13 (s, 1H), 3.43-3.33 (q, J=7.2 Hz, 2H), 3.22-2.98 (m, 12H), 2.37-2.24 (m, 2H), 2.22-2.09 (m, 1H), 1.45-1.42 (t, J=7.2 Hz, 3H); MS (ESI) m/z 613.2 (M+H).

Compound 219.
$^1$H NMR (400 MHz, CD$_3$OD) δ 8.49 (s, 1H), 7.44 (s, 4H), 5.06 (brs, 2H), 4.73 (brs, 2H), 4.63 (s, 2H), 4.14 (s, 1H), 3.21-2.98 (m, 9H), 2.38-2.27 (m, 2H), 1.70-1.67 (m, 1H); MS (ESI) m/z 673.2 (M+H).

Compound 220.
$^1$H NMR (400 MHz, CD$_3$OD) δ 8.44 (s, 1H), 4.10 (s, 3H), 3.50-3.47 (m, 1H), 3.18-2.96 (m, 9H), 2.36-2.22 (m, 2H), 1.65-1.63 (m, 1H), 1.38 (t, J=6.8 Hz, 6H); MS (ESI) m/z 613.2 (M+H).

Compound 221.
$^1$H NMR (400 MHz, CD$_3$OD) δ 8.44 (s, 1H), 4.73-4.68 (m, 1H), 4.45-4.37 (m, 5H), 4.1.5 (s, 1H), 4.14-4.10 (m, 1H), 3.40 (s, 3H), 3.22-2.92 (m, 9H), 2.40-2.32 (m, 2H), 1.70-1.67 (m, 1H); MS (ESI) m/z 641.3 (M+H).

Compound 222
$^1$H NMR (400 MHz, CD$_3$OD) δ 8.35 (s, 1H), 4.81 (t, J=4.4 Hz, 1H), 4.64 (t, J=4.4 Hz, 1H), 4.09 (s, 2H), 4.00 (s, 1H), 3.45 (t, J=4.4 Hz, 1H), 3.39 (t, J=4.4 Hz, 1H), 3.09-2.79 (m, 9H), 2.27-2.09 (m, 2H), 1.62-1.58 (m, 1H); MS (ESI) m/z 617.2 (M+H).

Compound 223.
$^1$H NMR (400 MHz, CD$_3$OD) δ 8.46 (s, 1H), 4.12 (s, 3H), 3.32-2.97 (m, 11H), 2.38-2.27 (m, 2H), 1.99-1.90 (s, 3 PI), 1.74-1.64 (m, 5H), 1.33 (m, 2H); MS (ESI) m/z 653.1 (M+H).

Compound 224.
$^1$H NMR (400 MHz, CD$_3$OD) δ 8.34 (s, 1H), 4.02 (s, 1H), 4.00 (s, 2H), 3.10 (q, J=7.2 Hz, 2H), 3.10-2.87 (m, 9H), 2.28-2.15 (m, 2H),1.57-1.46 (m, 1H), 1.27 (t, J=7.2 Hz, 3H); MS (ESI) m/z 599.1 (M+H).

Compound 225
$^1$H NMR (400 MHz, CD$_3$OD) δ 8.43 (s, 1H), 4.35-4.20 (m, 2H), 4.11 (s, 1H), 3.38-2.94 (m, 14H), 2.35-2.21 (m, 2H), 1.89-1.79 (m, 2H), 1.68-1.63 (m, 1H), 1.09 (t, J=7.2 Hz, 3H); MS (ESI) m/z 627.1 (M+H).

Compound 226.
$^1$H NMR (400 MHz, CD$_3$OD) δ 8.35 (s, 1H), 4.04 (s, 2H), 4.00 (s, 1H), 3.61 (t, J=4.8 Hz, 2H), 3.38 (s, 3H), 3.21 (t, J=4.8 Hz, 2H), 3.15-2.86 (m, 9H), 2.18-2.09 (m, 2H), 1.61-1.52 (m, 1H); MS (ESI) m/z 629.1 (M+H).

Compound 227.
$^1$H NMR (400 MHz, CD$_3$OD) δ 8.34 (s, 1H), 5.47-5.32 (m, 1H), 4.34 (s, 2H), 4.02 (s, 1H), 3.98-3.82 (m, 2H), 3.3.48-3.32 (m, 2H), 3.11-2.87 (m, 9H), 2.47-2.36 (m, 2H), 2.34-2.19 (m, 2H), 1.58-1.50 (m, 1H); MS (ESI) m/z 643.1 (M+H).

Compound 228.
$^1$H NMR (400 MHz, CD$_3$OD) δ 8.30 (s, 1H), 8.06 (s, 1H), 7.94 (d, J=4.8 Hz, 1H), 7.73-7.67 (m, 2H), 4.17 (s, 2H), 4.02 (s, 1H), 3.24-2.86 (m, 9H), 2.25-2.12 (m, 2H), 1.59-1.49 (m, 1H); MS (ESI) m/z 648.1 (M+H).

Compound 229.
$^1$H NMR (400 MHz, CD$_3$OD) δ 8.35 (s, 1H), 8.02 (d, J=7.2 Hz, 2H), 6.84 (d, J=7.2 Hz, 2H), 5.17 (s, 2H),4.09 (s, 1H), 3.28-2.936 (m, 9H), 2.32-2.19 (m, 2H), 1.66-1.56 (m, 1H); MS (ESI) m/z 648.1 (M+H).

Compound 230.
$^1$H NMR (400 MHz, CD$_3$OD) δ 8.43 (s, 1H), 4.07 (s, 3H), 3.20-2.94 (m, 11H), 2.35-2.29 (m, 1H), 2.25-2.17 (m, 1H), 1.93-1.79 (m, 2H), 1.78-1.58 (m, 1H), 1.05 (t, J=7.2 Hz, 3H); MS (ESI) m/z 613.2 (M+H).

Compound 231.
$^1$H NMR (400 MHz, CD$_3$OD) δ 8.42 (s, 1H), 4.12 (s, 3H), 3.19-2.87 (m, 11H), 2.38-2.19 (m, 2H), 1.90-1.61 (m, 6H), 1.38-1.19 (m, 4H), 1.15-1.01 (m, 2H); MS (ESI) m/z 667.2 (M+H).

Compound 232.
$^1$H NMR (400 MHz, CD$_3$OD) δ 8.35 (s, 1H), 4.01 (s, 3H), 3.14-2.73 (m, 11H), 2.26-2.13 (m, 2H), 2.03-2.01 (m, 1H), 1.60-1.51 (m, 1H), 0.99-0.92 (t, J=6.8 Hz, 6H); MS (ESI) m/z 627.2 (M+H).

Compound 233.
$^1$H NMR (400 MHz, CD$_3$OD) δ 8.34 (s, 1H), 4.12 (s, 2H), 4.01 (s, 1H), 3.56-3.53 (m, 2H), 3.11-2.73 (m, 11H), 2.27-2.13 (m, 2H), 1.89-1.76 (m, 5H), 1.60-1.57 (m, 2H); MS (ESI) m/z 639.2 (M+H).

Compound 234.
$^1$H NMR (400 MHz, CD$_3$OD) δ 8.35 (s, 1H), 4.09 (s, 1H), 4.02 (s, 2H), 3.89-3.70 (m, 1H), 3.11-2.86 (m, 9H), 2.27-2.02 (m, 6H), 1.91-1.71 (m, 2H), 1.60-1.40 (m, 1H); MS (ESI) m/z 625.3 (M+H).

Compound 235.
$^1$H NMR (400 MHz, CD$_3$OD) δ 8.44 (s, 1H), 4.31 (s, 2H), 4.12 (s, 1H), 4.12-3.78 (m, 4H), 3.78-3.44 (m, 4H), 3.22-2.90 (m, 9H), 2.38-2.23 (m, 2H), 1.71-1.61 (m, 1H); MS (ESI) m/z 641.1 (M+H).

Compound 236.
$^1$H NMR (400 MHz, CD$_3$OD) δ 8.42 (s, 1H), 4.27 (s, 2H), 4.11 (s, 1H), 3.40-3.31 (m, 4H), 3.21-2.96 (m, 9H), 2.36-2.23 (m, 2H), 1.69-1.60 (m, 1H), 1.40 (t, J=7.2 Hz, 6H); MS (ESI) m/z 627.2 (M+H).

Compound 237.
$^1$H NMR (400 MHz, CD$_3$OD) δ 8.46 (s, 1H), 4.11 (s, 3H), 3.31-2.94 (m, 10H), 2.40-2.20 (m, 2H), 2.20-2.00 (m, 2H), 1.94-1.82 (m, 2H), 1.68-1.56 (m, 1H), 1.48-1.32 (m, 4H), 1.28-1.16 (m, 2H); MS (ESI) m/z 653.3 (M+H).

Compound 238.
$^1$H NMR (400 MHz, CD$_3$OD) δ 8.41 (s, 1H), 7.46-7.26 (m, 2H), 7.25-7.11 (m, 3H), 4.16 (s, 2H), 4.01 (s, 1H), 3.15-2.78 (m, 9H), 2.26-2.11 (m, 2H), 1.58-1.49 (m, 1H); MS (ESI) m/z 647.0 (M+H).

Compound 239.
$^1$H NMR (400 MHz, CD$_3$OD) δ 8.43 (s, 1H), 4.21 (s, 2H), 4.11 (s, 1H), 3.18-2.84 (m, 9H), 2.90-2.84 (m, 1H), 2.35-2.22 (m, 2H), 1.69-1.59 (m, 1H), 0.95-0.93 (m, 4H); MS (ESI) m/z 611.4 (M+H).

Compound 240.
$^1$H NMR (400 MHz, CD$_3$OD) δ 8.43 (s, 1H), 6.38 (tt, J=60, 1.6 Hz, 1H), 4.21 (s, 2H), 4.12 (s, 1H), 3.68 (td, J=7.2, 1.6 Hz, 2H), 3.18-2.90 (m, 9H), 2.36-2.18 (m, 2H), 1.69-1.58 (m, 1H); MS (ESI) m/z 635.1 (M+H).

Compound 241.
$^1$H NMR (400 MHz, CD$_3$OD) δ 8.46 (s, 1H), 5.56-5.43 (m, 1H), 4.45 (s, 2H), 4.12 (s, 1H), 4.13-3.90 (m, 2H), 3.58-3.41 (m, 2H), 3.20-2.90 (m, 9H), 2.38-2.23 (m, 4H), 1.71-1.61 (m, 1H); MS (ESI) m/z 643.2 (M+H).

Compound 242.
$^1$H NMR (400 MHz, CD$_3$OD) δ 8.35-8.33 (m, 1H), 4.22-4.18 (m, 2H), 4.02 (s, 1H), 3.92-3.87 (m, 1H), 3.39-3.28 (m, 1H), 3.09-2.86 (m, 11H), 2.74-2.60 (m, 2H), 2.27-2.12 (m, 2H), 1.71-1.45 (m, 7H); MS (ESI) m/z 665.2 (M+H).

Compound 243.
$^1$H NMR (400 MHz, CD$_3$OD) δ 8.44 (s, 1H), 4.12 (s, 1H), 4.08 (s, 2H), 3.18-2.90 (m, 11H), 2.78-2.66 (m, 1H), 2.38-2.15 (m, 4H), 2.08-1.80 (m, 3H), 1.71-1.54 (m, 1H); MS (ESI) m/z 639.2 (M+H).

Compound 244.
$^1$H NMR (400 MHz, CD$_3$OD) δ 8.38 (s, 1H), 4.20 (s, 2H), 4.02 (s, 1H), 3.18-2.82 (m, 15H), 2.32-2.11 (m, 2H), 1.66-1.52 (m, 1H); MS (ESI) m/z 599.1 (M+H).

Compound 245.
$^1$H NMR (400 MHz, CD$_3$OD) δ 8.46 (s, 1H), 4.09 (s, 3H), 2.90-3.30 (m, 3H), 3.03 (s, 3H), 2.94 (s, 3H), 2.29-2.37 (m, 1H), 2.18-2.25 (m, 1H), 1.58-1.70 (m, 1H), 1.41 (s, 9H); MS (ESI) m/z 627.4 (M+H).

Compound 246.
$^1$H NMR (400 MHz, CD$_3$OD) δ 8.44 (s, 1H), 4.33 (s, 2H), 4.10 (s, 1H), 3.75-3.85 (m, 2H), 2.90-3.50 (m, 7H), 3.03 (s, 3H), 2.94 (s, 3H), 2.28-2.37 (m, 1H), 2.00-2.25 (m, 5H), 1.58-1.70 (m, 1H); MS (ESI) m/z 625.1 (M+H).

Compound 263.
$^1$H NMR (400 MHz, CD$_3$OD) δ 8.46 (s, 1H), 4.12 (s, 1H), 4.11 (s, 2H), 3.70-3.61 (m, 1H), 3.22-2.93 (m, 9H), 2.38-2.10 (m, 4H), 1.92-1.80 (m, 2H), 1.76-1.56 (m, 5H); MS (ESI) m/z 639.2 (M+H).

The following compounds were prepared similarly to Compound 210 substituting bromoacetyl bromide and an amine (NHR$^2$R$^3$) with an acid chloride (appropriately protected if needed) or a carboxylic acid (appropriately protected if needed) and a coupling reagent such as HATU.

Compound 247.
$^1$H NMR (400 MHz, CD$_3$OD) δ 8.34 (s, 1H), 7.88 (d, J=7.6 Hz, 2H), 7.55-7.45 (m, 3H), 4.03 (s, 1H), 3.13-2.88 (m, 9H), 2.33-2.28 (m, 1H), 2.19-2.13 (m, 1H), 1.64-1.53 (m, 1H); MS (ESI) m/z 611.4 (M+H).

Compound 248.
$^1$H NMR (400 MHz, CD$_3$OD) δ 8.37 (s, 1H), 7.50-7.41 (m, 3H), 7.16 (dd, J=8.0 Hz, 1.6 Hz, 1H), 4.09 (s, 1H), 3.86 (s, 3H), 3.18-2.97 (m, 9H), 2.37-2.29 (m, 1H), 2.24-2.20 (m, 1H), 1.69-1.62 (m, 1H); MS (ESI) m/z 648.2 (M+H).

Compound 249.
$^1$H NMR (400 MHz, CD$_3$OD) δ 8.24 (s, 1H), 8.16 (s, 1H), 8.12 (d, J=8.0 Hz, 1H), 7.83 (d, J=8.0 Hz, 1H), 7.66 (t, J=8.0 Hz, 1H), 4.01 (s, 1H), 3.12-2.73 (m, 9H), 2.26 (m, 1H), 2.16-2.12 (m, 1H), 1.63-1.52 (m, 1H); MS (ESI) m/z 686.1 (M+H).

Compound 250.
$^1$H NMR (400 MHz, CD$_3$OD) δ 8.29 (s, 1H), 7.88 (d, J=3.6 Hz, 1H), 7.77 (d, J=4.8 Hz, 1H), 7.21 (t, J=4.4 Hz, 1H), 4.10 (s, 1H), 3.19-2.96 (m, 9H), 2.38-2.30 (m, 1H), 2.28-2.20 (m, 1H), 1.70-1.60 (m, 1H); MS (ESI) m/z 624.1 (M+H).

Compound 251.
$^1$H NMR (400 MHz, CD$_3$OD) δ 8.29 (s, 1H), 7.98 (d, J=8.4 Hz, 2H), 7.44 (d, J=8.8 Hz, 2H), 4.03 (s, 1H), 3.18 (s, 6H), 3.11-2.87 (m, 9H), 2.25-2.20 (m, 1H), 2.16-2.13 (m, 1H), 1.58-1.55 (m, 1H); MS (ESI) m/z 661.1 (M+H).

Compound 252.
$^1$H NMR (400 MHz, CD$_3$OD) δ 8.25 (s, 1H), 8.17 (s, 1H), 8.04 (d, J=7.6 Hz, 1H), 7.85 (dd, J=7.2 Hz, 1.6 Hz, 1H), 7.70 (t, J=8.0 Hz, 1H), 4.04 (s, 1H), 3.20 (s, 6H), 3.12-2.88 (m, 9H), 2.26 (m, 1H), 2.18-2.15 (m, 1H), 1.58-1.55 (m, 1H); MS (ESI) m/z 661.1 (M+H).

Compound 253.
$^1$H NMR (400 MHz, CD$_3$OD) δ 8.26 (s, 1H), 8.10 (d, J=7.6 Hz, 1H), 7.95 (d, J=8.0 Hz, 1H), 7.80 (t, J=7.6 Hz, 1H), 7.65 (t, J=7.6 Hz, 1H), 4.03 (s, 1H), 3.26 (s, 6H), 3.14-2.87 (m, 9H), 2.29-2.25 (m, 1H), 2.13-2.10 (m, 1H), 1.63-1.56 (m, 1H); MS (ESI) m/z 661.1 (M+H).

Compound 254.
$^1$H NMR (400 MHz, CD$_3$OD) δ 9.38 (s, 1H), 9.08-9.04 (m, 2H), 8.37 (s, 1H), 8.22 (t, J=7.6 Hz, 1H), 4.13 (s, 1H), 3.22-2.98 (m, 9H), 2.36 (m, 1H), 2.13-2.10 (m, 1H), 1.70-1.63 (m, 1H); MS (ESI) m/z 619.0 (M+H).

Compound 255.

$^1$H NMR (400 MHz, CD$_3$OD) δ 9.07 (d, J=5.6 Hz, 2H), 8.49 (d, J=5.6 Hz, 2H), 8.37 (s, 1H), 4.12 (s, 1H), 3.22-2.97 (m, 9H), 2.37 (m, 1H), 2.29-2.23 (m, 1H), 1.70-1.63 (m, 1H); MS (ESI) m/z 619.0(M+H).

Compound 256.

$^1$H NMR (400 MHz, CD$_3$OD) δ 8.72-8.70 (m, 2H), 8.23 (d, J=7.2 Hz, 1H), 8.06 (t, J=7.6 Hz, 1H), 7.65 (dd, J=10.8, 6.8 Hz, 1H), 4.12 (s, 1H), 3.19-2.97 (m, 9H), 2.32-2.25 (m, 1H), 2.26-2.23 (m, 1H), 1.67-1.64 (m, 1H); MS (ESI) m/z 619.0(M+H).

Compound 257.

$^1$H NMR (400 MHz, CD$_3$OD) δ 8.33 (s, 1H), 4.09-4.08 (m, 2H), 3.45-3.42 (m, 1H), 3.16-2.93 (m, 10H), 2.34-2.18 (m, 3H), 1.95-1.88 (m, 2H), 1.88-1.60 (m, 4H); MS (ESI) m/z 625.1 (M+H)

Compound 258. $^1$H NMR (400 MHz, CD$_3$OD) δ 8.44 (s, 1H), 5.20 (t, J=9.2 Hz, 1H), 4.19-4.07 (m, 3H), 3.19-2.92 (m, 12H), 2.66-2.61 (m, 2H), 2.33 (m, 1H), 2.22-2.03 (m, 1H),1.66-1.63 (m, 1H); MS (ESI) m/z 611.1 (M+H)

Compound 259.

$^1$H NMR (400 MHz, CD$_3$OD) δ 8.34 (s, 1H), 4.39 (t, J=7.6 Hz, 1H), 4.10 (s, 1H), 3.76-3.74 (m, 1H), 3.27-2.93 (m, 12H), 2.70-2.63 (m, 1H), 2.34-2.15 (m, 6H), 1.63-1.60 (m, 1H); MS (ESI) m/z 625.1 (M+H).

Compound 260.

$^1$H NMR (400 MHz, CD$_3$OD) δ 8.36 (s, 1H), 5.20 (t, J=8.0 Hz, 1H), 4.09-4.07 (m, 1H), 4.02 (s, 1H), 3.96-3.73 (m, 1H), 3.21-2.72 (m, 11H), 2.59-2.13 (m, 2H), 1.56-1.54 (m, 1H); MS (ESI) m/z 597.1 (M+H).

Compound 261.

$^1$H NMR (400 MHz, CD$_3$OD) δ 8.33 (s, 1H), 4.57 (t, J=7.6 Hz, 1H), 4.09 (s, 1H), 3.47-3.36 (m, 2H), 3.18-2.93 (m, 9H), 2.54-2.52 (m, 1H), 2.34-2.31 (m, 1H), 227-2.07 (m, 4H),1.63-1.58 (m, 1H); MS (ESI) m/z 611.1 (M+H).

Compound 262.

Compound 262 was prepared from 10-6-2 via aqueous HF treatment followed by hydrogenation similarly to Compound 210: $^1$H NMR (400 MHz, CD$_3$OD) δ 8.00 (s, 1H), 4.09 (s, 1H), 2.80-3.50 (m, 9H), 232-2.42 (m, 1H), 2.19-2.27 (m, 1H), 1.58-1.70 (m, 1H); MS (ESI) m/z 543.3 (M+H).

EXAMPLE 11

Synthesis of Compounds of Formula III, wherein Y is —NR$^2$R$^3$

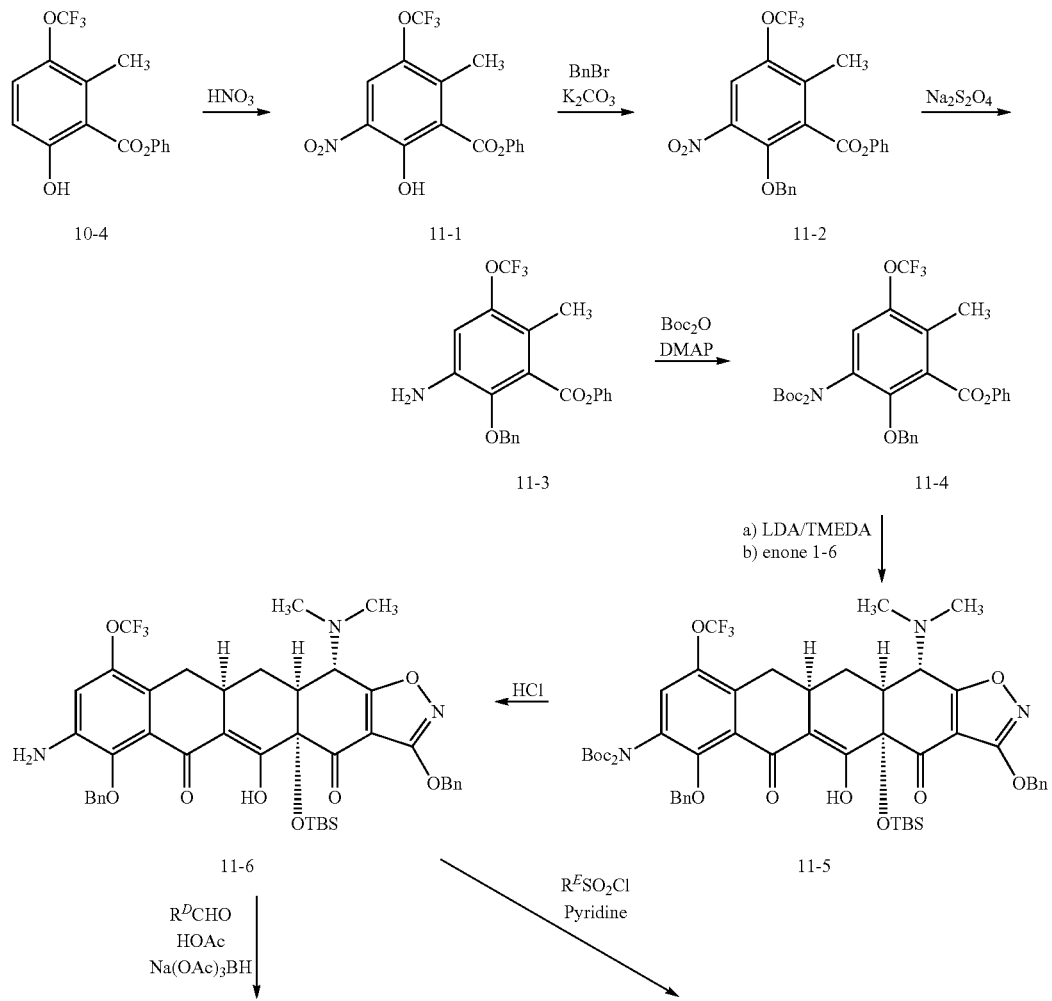

Scheme 11:

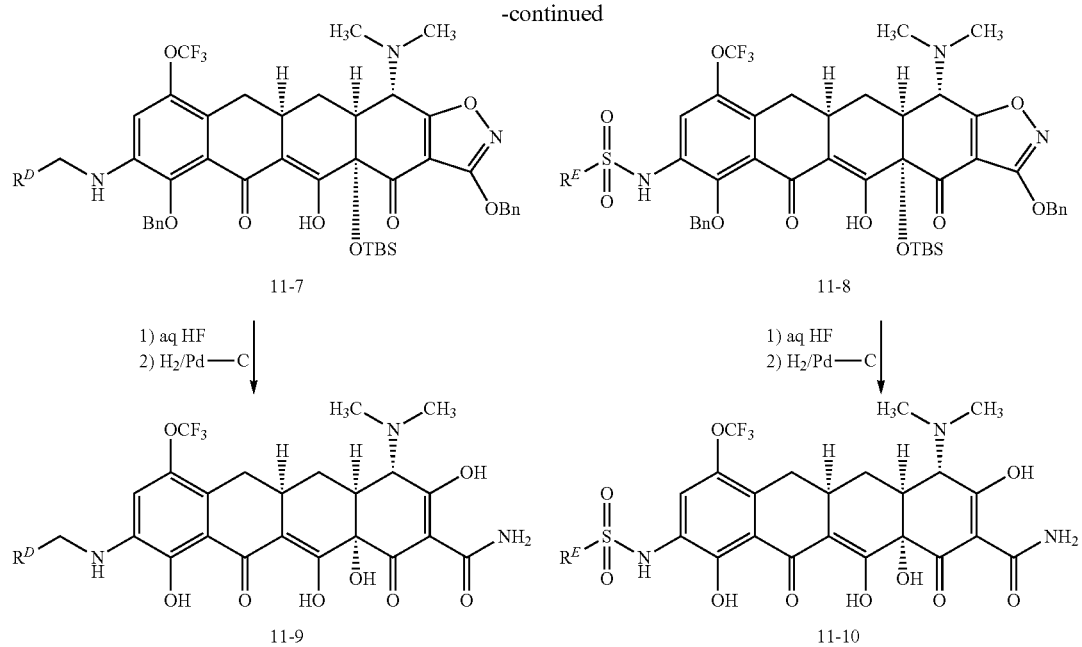

11-7

11-8

1) aq HF
2) H₂/Pd—C 1) aq HF
2) H₂/Pd—C 11-9

11-10

In Scheme 11, "$R^D$" represents $C_1$-$C_6$ alkyl; and "$R^E$" represents $C_1$-$C_6$ alkyl or phenyl.

Phenyl 2-hydroxy-6-methyl-3-nitro-5-(trifluoromethoxy)benzoate (1.1-1)

Compound 10-4 (12.2 mmol) was dissolved in 1,2-dichloroethane (18 mL) and H₂O (18 mL). Tetrabutylammonium bromide (197 mg, 0.61 mmol, 0.05 eq) was added, followed by slow addition of nitric acid (70%, 1.56 mL, 24.4 mmol, 2.0 eq) in order to maintain temperature below 25° C. After stirred at rt for 20 h, the reaction mixture was diluted with dichloromethane and layers were separated. The organic layer was further washed with H₂O, brine, dried (Na₂SO₄) and concentrated to give compound 11-1 as yellow solid, which was pure enough to use directly for the next step.

Phenyl 2-(benzyloxy)-6-methyl-3-nitro-5-(trifluoromethoxy)benzoate (11-2)

11-1 obtained from the above (12.2 mmol) was dissolved in acetone (25 mL). Potassium iodide (101 mg, 0.61 mmol, 0.05 eq), K₂CO₃ (3.37 g, 24.4 mmol, 2 eq), and benzylbromide (1.74 mL, 14.6 mmol, 1.2 eq) were added. The resulting mixture was heated to reflux for 4 h. After cooled to rt, the solution was filtered through a bed of Celite. The solid cake was further washed with three portions of EtOAc. The combined organic solution was concentrated. The residue was dissolved in EtOAc and washed with H₂O, brine, dried (Na₂SO₄) and concentrated to give compound 11-2 as off-white solid, which was used directly for the next step without further purification.

Phenyl 3-amino-2-(benzyloxy)-6-methyl-5-(trifluoromethoxy)benzoate (11-3)

11-2 prepared from the last step (12.2 mmol) was dissolve in THF (73 mL). Solution of Na₂S₂O₄ (12.49 g, 61.0 mmol, 5 equiv) in H₂O (49 mL) was added at 0° C. After stirred at rt for 16 h, layers were separated. The aqueous layer was further extracted with EtOAc three times. The combined organic layers were washed with brine, dried (Na₂SO₄) and concentrated. Further purification with flash chromatography (silica gel, 85:15 hexanes/EtOAc) yielded compound 11-3 as off-white solid (3.45 g): ¹H NMR (400 MHz, CDCl₃) δ7.44-7.34 (m, 7H), 7.28-7.25 (m, 1H), 7.14-7.12 (m, 2H), 6.73 (s, 1H), 5.01 (s, 2H), 3.86 (br s, 2H), 2.29 (s, 3H); MS (ESI) m/z 416.3 (M−H), calcd for $C_{22}H_{17}F_3NO_4$ 416.12.

Phenyl 2-(benzyloxy)-3-(bis(tert-butoxycarbonyl)amino)-6-methyl-5-(trifluoromethoxy)benzoate (11-4).

Di-tert-butyl dicarbonate (4.51 g, 20.66 mmol, 2.5 eq) and DMAP (50 mg, 0.41 mmol, 0.05 eq) were added to the solution of compound 11-3 (3.45 g, 8.26 mmol, 1 eq) in anhydrous DMF (33 mL). The resulting mixture was stirred at rt and the reaction was monitored by LC-MS. After SM was completely consumed, the reaction was diluted with EtOAc. The solution was washed with H₂O three times, brine, dried over Na₂SO₄, filtered and concentrated. Further purification with flash chromatography (silica gel, 95:5 hexanes/EtOAc) yielded compound 11-4 as wax-like solid (4.12 g): ¹H NMR (400 MHz, CDCl₃) δ7.40-7.31 (m, 7H), 7.28-7.25 (m, 1H), 7.15 (s, 1H), 6.98 (d, J=7.8 Hz, 1H), 4.94 (s, 2H), 2.40 (s, 3H), 1.37 (s, 18H); MS (ESI) m/z 616.4 (M−H), calcd for $C_{32}H_{33}F_3NO_8$ 616.22.

Intermediate 11-5.

11-5 was prepared from compound 11-4 and eone 1-6 under similar conditions used in the preparation of compound 2-5 (see Example 2). The crude product was purified by flash chromatography (silica gel, 95:5 to 85:15 hexanes/EtOAc) gave desired product as light yellow foam: ¹H NMR (400 MHz, CDCl₃) δ15.88 (s, 1H), 7.52-7.30 (m, 11H), 5.35 (s, 2H), 4.98 (d, J=9.8 Hz, 1H), 4.79 (d, J=9.8 Hz, 1H), 3.96 (d, J=10.4 Hz, 1H), 3.26 (dd, J=16.5, 4.9 Hz, 1H), 3.01-2.93 (m, 1H), 2.60-2.40 (m, 9H), 2.16-2.13 (m, 1H), 1.34 (s, 18H), 0.81 (s, 9H), 0.26 (s, 3H), 0.13 (s, 3H); MS (ESI) m/z 1006.7 (M+H), calcd for $C_{52}H_{63}F_3N_3O_{12}Si$ 1006.41.

(4aS,11aR,12aS,13S)-8-amino-3,7-bis(benzyloxy)-4a-(tert-butyldimethylsilyloxy)-3-(dimethylamino)-5-hydroxy-10-(trifluoromethoxy)-11a,12,12a,13-tetrahydrotraceno[2,3-d]isoxazole-4,6(4aH,11H)-dione (11-6)

11-6 was prepared from 11-5 under similar conditions used in the preparation of compound 2-6 (see Example 2). Purification of the crude product by flash chromatography (silica gel, 85:15 hexanes/EtOAc) gave desired product as bright yellow foam: $^1$H NMR (400 MHz, CDCl$_3$) δ16.02 (s, 1H), 7.52-7.26 (m, 10H), 6.77 (s, 1H), 5.36 (s, 2H), 4.90 (s, 2H), 3.97 (br s, 3H), 3.12 (dd, J=16.5, 4.9 Hz, 1H), 2.98-2.88 (m, 1H), 2.60-2.40 (m, 9H), 2.16-2.10 (m, 1H), 0.83 (s, 9H), 0.28 (s, 3H), 0.14 (s, 3H); MS (ESI) m/z 806.5 (M+H), calcd for C$_{42}$H$_{47}$F$_3$N$_3$O$_8$Si 806.30.

Compound 264.

Compound 264 was prepared by compound 11-6 and propionaldehyde by similar procedures used in the preparation of Compound 180. The crude product was purified by HPLC on a Waters Autopurification system using a Phenomenex Polymerx™ 10μ RP-γ 100 R column [30×21.20 mm, 10 micron; flow rate, 20 mL/min; Solvent A: 0.05 N HCl/water; Solvent B: CH$_3$CN; injection volume: 4.0 mL (0.05 N HCl/water); gradient: 15→60% B over 15 min; mass-directed fraction collection]. Fractions with the desired MW, eluting at 16.95-18.25 min, were collected and freeze-dried to give product as a yellow solid: $^1$H NMR (400 MHz, CD$_3$OD) δ7.36 (s, 1H), 4.12 (s, 1H), 3.36-3.25 (m, 2H), 3.20-2.90 (m, 9H), 2.39-2.21 (m, 2H), 1.78-1.58 (m, 3H), 1.04 (t, J=7.3 Hz, 3H); MS (ESI) m/z 556.4 (M+H), calcd for C$_{25}$H$_{29}$F$_3$N$_3$O$_8$ 556.18.

Compound 265.

Compound 265 was prepared from 11-6 and isovaleraldehyde by similar procedures used in the preparation of Compound 180. The crude product was purified by HPLC on a Waters Autopurification system using a Phenomenex Polymerx™ 10μ RP-γ 100 R column [30×21.20 mm, 10 micron; flow rate, 20 mL/min; Solvent A: 0.05 N HCl/water; Solvent CH$_3$CN; injection volume: 4.0 mL (0.05 N HCl/water); gradient: 15→60% B over 15 min; mass-directed fraction collection]. Fractions with the desired MW, eluting at 16.75-18.30 min, were collected and freeze-dried to give product as a yellow solid: $^1$H NMR (400 MHz, CD$_3$OD) δ7.32 (s, 1H), 4.11 (s, 1H), 3.48-3.30 (m, 2H), 3.20-2.90 (m, 9H), 2.38-2.21 (m, 2H), 1.80-1.58 (m, 4H), 0.98 (d, J=6.4 Hz, 6H); MS (ESI) m/z 584.4 (M+H), calcd for C$_{27}$H$_{33}$F$_3$N$_3$O$_8$ 584.21.

Compound 266.

Compound 266 was prepared from 11-6 and ethanesulfonyl chloride by similar procedures used in the preparation of Compound 153. The crude product was purified by HPLC on a Waters Autopurification system using a Phenomenex Polymerx™ 10μ RP-γ 100 R column [30×21.20 mm, 10 micron; flow rate, 20 mL/min; Solvent A: 0.05 N HCl/water; Solvent B: CH$_3$CN; injection volume: 4.0 mL (0.05 N HCl/water); gradient: 20→60% B over 15 min; mass-directed fraction collection]. Fractions with the desired MW, eluting at 11.10-12.00 min, were collected and freeze-dried to give product as a yellow solid: $^1$H NMR (400 MHz, CD$_3$OD) δ7.62 (s, 1H), 4.09 (s, 1H), 3.18-2.85 (m, 11H), 2.36-2.19 (m, 2H), 1.69-1.59 (m, 1H), 1.35 (t, J=7.3 Hz, 3H); MS (ESI) m/z 606.3 (M+H), calcd for C$_{24}$H$_{27}$F$_3$N$_3$O$_{10}$S 606.13.

Compound 267.

Compound 267 was prepared from compound 11-6 and isobutanesulfonyl chloride by similar procedures used in the preparation of Compound 153. The crude product was purified by HPLC on a Waters Autopurification system using a Phenomenex Polymerx™ 10μ RP-γ 100 R column [30×21.20 mm, 10 micron; flow rate, 20 mL/min; Solvent A: 0.05 N HCl/water; Solvent B: CH$_3$CN; injection volume: 4.0 mL (0.05 N HCl/water); gradient: 20→60% B over 15 min; mass-directed fraction collection]. Fractions with the desired MW, eluting at 13.40-14.50 min, were collected and freeze-dried to give product as a yellow solid: $^1$H NMR (400 MHz, CD$_3$OD) δ7.61 (s, 1H), 4.10 (s, 1H), 3.18-2.90 (m, 11H), 2.28-2.18 (m, 3H), 1.69-1.59 (m, 1H), 1.05 (d, J=6.8 Hz, 6H); MS (ESI) m/z 634.4 (M+H), calcd for C$_{26}$H$_{31}$F$_3$N$_3$O$_{10}$S 634.16.

Compound 268.

Compound 268 was prepared from compound 11-6 and benzenesulfonyl chloride by similar procedures used in the preparation of Compound 153. $^1$H NMR (400 MHz, CD$_3$OD) δ 7.80 (d, J=8.0 Hz, 2H), 7.63 (s, 1H), 7.58-7.56 (m, 1H), 7.47 (t, J=8.0 Hz, 2H), 4.14 (s, 1H), 3.12-2.90 (m, 9H), 2.29-2.12 (m, 2H), 1.65-1.53 (m, 1H); MS (ESI) m/z 654.1 (M+H).

EXAMPLE 12

Synthesis of Compounds of Formula IV

Scheme 12:

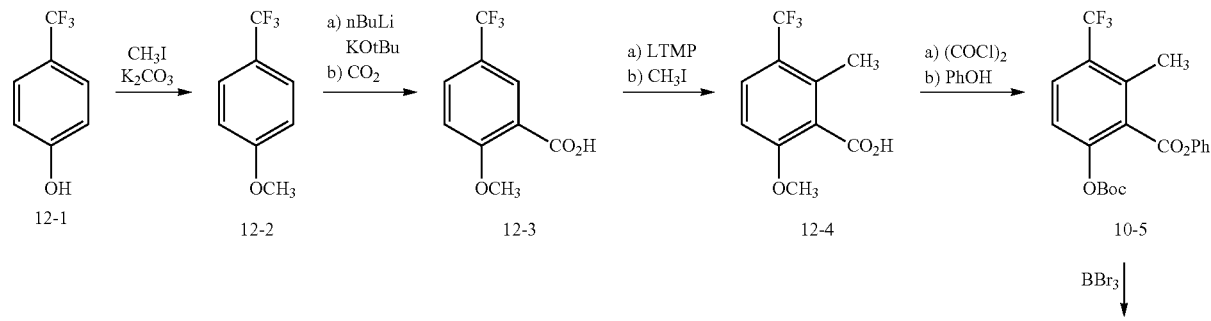

-continued

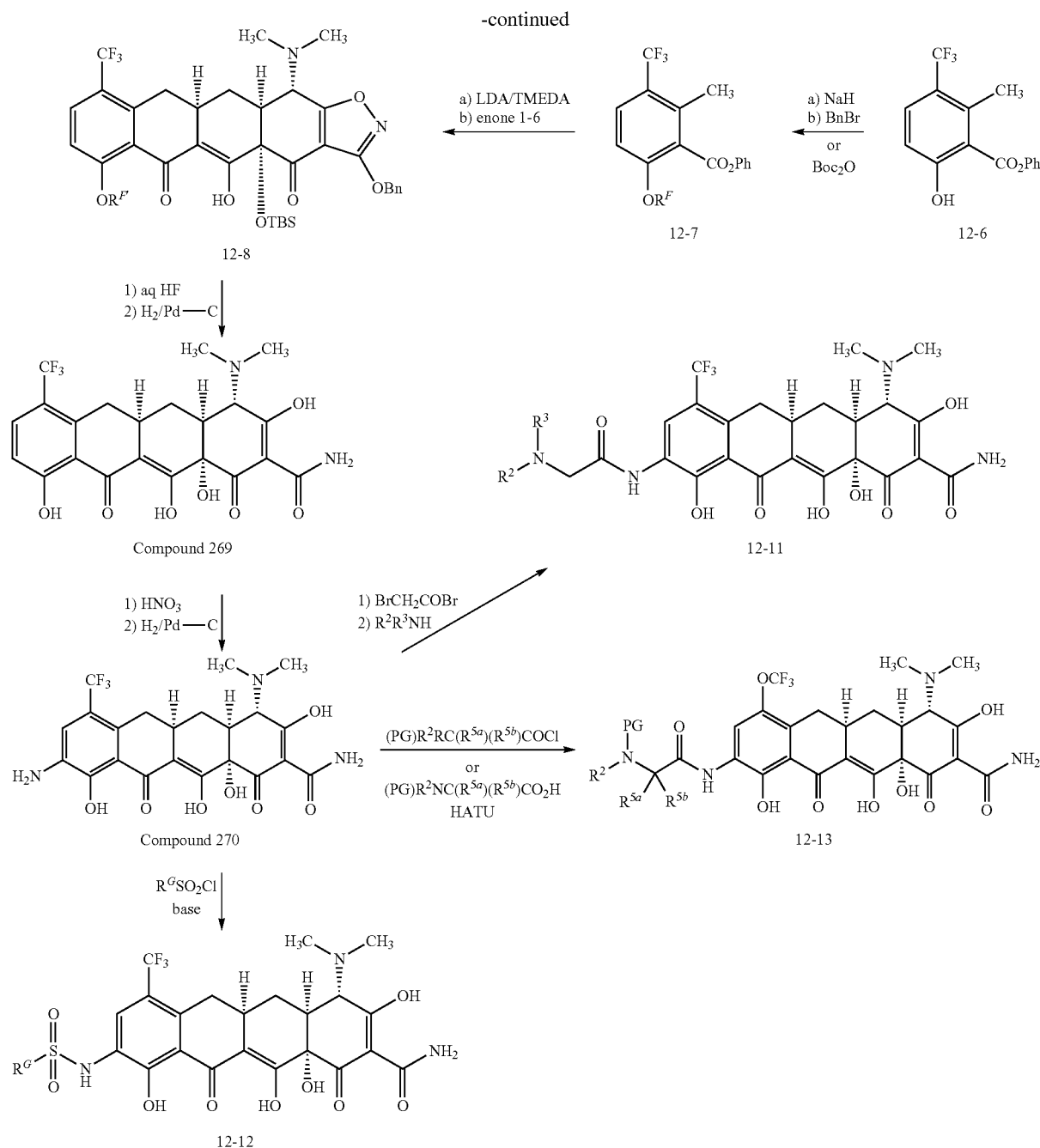

In Scheme 12, "PG" represents a protecting group; "$R^F$" represents benzyl or BOC; "$R^{F'}$" represents benzyl or hydrogen; and $R^G$ represents optionally substituted heterocyclyl.

1-methoxy-4-(trifluoromethyl)benzene (12-2)

To an acetone solution of 4-(Trifluoromethyl)phenol (12-1, 125 g, 0.71 mol) was added potassium carbonate (137 g, 0.99 mol, 1.4 equiv) and MeI (125 mL, 1.99 mol, 2.8 equiv). The reaction was stirred at 25° C. overnight and concentrated. The resulting mixture was diluted with 500 mL of H$_2$O and extracted with t-butylmethyl ether. The combined extracts were dried (Na$_2$SO$_4$) and concentrated to give 110 g of crude 12-2: $^1$H NMR (400 MHz, CDCl$_3$) δ 7.48 (d, J=8.5 Hz, 2H), 6.89 (d, J=8.5 Hz, 2H), 3.78 (s, 3H).

2-methoxy-5-(trifluoromethyl)benzoic acid (12-3)

nBuLi (276 mL, 2.5 M, 0.69 mol, 1.1 equiv) and KOtBu (77 g, 0.69 mol, 1.1 equiv) were added to a THF solution (1 L) of crude 12-2 (110 g) at −78° C. The reaction was stirred at −78° C. for 4 h. Dry CO$_2$ was bubbled into the solution at −78° C. for 1 h. The reaction was allowed to warm to 25° C. over 0.5 h. NaOH (6N, 300 mL) and H$_2$O were added to the resulting reaction mixture. The mixture was extracted with t-butylmethyl ether (400 mL×2). The aqueous layer was acidified with HCl (6N) to pH 1 and extracted with EtOAc (300 mL×4). The combined EtOAc extracts were concentrated and re-dissolved in CH$_2$Cl$_2$. The solution was dried (Na$_2$SO$_4$), filtered through a pad of Celite and concentrated. Flash chromatography on silica gel (1:1 PE/EtOAc) yielded 82 g of compound 12-3 (53% for 2 steps): $^1$H NMR (400 MHz, CDCl$_3$) δ 8.45 (s, 1H), 7.81 (d, J=8.0 Hz, 1H), 7.16 (d, J=8.0 Hz, 1H), 4.13 (s, 3H); MS (ESI) m/z 221.0 (M+H).

6-methoxy-2-methyl-3-(trifluoromethyl) benzoic acid (12-4)

To a THF solution of 2,2,6,6-tetramethylpiperidine (312 mL, 1.85 mol, 5 equiv) was added (740 mL, 2.5 M, 1.85 mol, 5 equiv). The reaction was stirred at 0° C. for 45 min. To the reaction was added a THF solution (800 mL) of crude 12-3 (82 g, 0.37 mol) at 0° C. The reaction was stirred at 0° C. for 4 h. The reaction was cooled to −78° C. and added dropwise to a THF solution (200 mL) of MeI (200 mL, 3.73 mol, 10 equiv) at −78° C. The reaction was allowed to warm to 25° C. over 1 h. The reaction was quenched with HCl (6 N) and extracted with EtOAc. The combined EtOAc extracts were dried (Na$_2$SO$_4$) and concentrated to give the crude product. The crude product was purified by HPLC. Yielded 45 g of compound 12-4 (52%): $^1$H NMR (400 MHz, CDCl$_3$) δ 7.64 (d, J=8.0 Hz, 1H), 6.81 (d, J=8.0 Hz, 1H), 3.90 (s, 3H), 2.48 (s, 3H); MS (ESI) m/z 235.1 (M+H).

Phenyl 6-methoxy-2-methyl-3-(trifluoromethyl) benzoate (12-5)

Oxalyl chloride (66 mL, 0.77 mol, 4 equiv) was added to a CH$_2$Cl$_2$ solution (500 mL, anhydrous) of compound 12-4 (45 g, 0.192 mol). DMF (0.5 mL) was added to the resulting mixture. The reaction was stirred at 25° C. for 1 h and concentrated. The resulting solid was re-dissolved in 500 mL of anhydrous CH$_2$Cl$_2$. Phenol (36.1 g, 0.38 mol, 2 equiv), DMAP (4.6 g, 38 mmol, 0.2 equiv), and triethylamine (105 mL, 0.77 mol, 4 equiv) were added to the reaction mixture. The reaction was stirred at 25° C. for 12 h and concentrated. EtOAc and H$_2$O were added to the residue. The organic layer was washed with NaOH (1 N), H$_2$O, and brine, dried (Na$_2$SO$_4$), and concentrated to give 52.0 g of crude 12-5: $^1$H NMR (400 MHz, CDCl$_3$) δ 7.65-7.75 (m, 1H), 7.40-7.50 (m, 3H), 7.20-7.35 (m, 2H), 6.85-6.90 (m, 1H), 3.95 (s, 3H), 2.54 (s, 3H).

Phenyl 6-hydroxy-2-methyl-3-(trifluoromethyl) benzoate (12-6)

BBr$_3$ (95 g, 0.38 mol, 2 equiv) was added to a CH$_2$Cl$_2$ solution (500 mL) of crude 12-5 (52.0 g,) at −78° C. The reaction was stirred from −78° C. to 25° C. for 1.5 h, quenched with saturated NaHCO$_3$ and concentrated. EtOAc and H$_2$O were added to the reaction mixture. The aqueous layer was extracted with EtOAc. The combined EtOAc extracts were dried (Na$_2$SO$_4$) and concentrated to yield 51 g of crude 12-6.

Phenyl 6-(benzyloxy)-2-methyl-3-(trifluoromethyl) benzoate (12-7-1)

NaH (466 mg, 60% in oil, 11.6 mmol, 1.2 equiv) was added to a DMF solution (30 mL) of crude 12-6 (3 g). The reaction was stirred at 25° C. for 0.5 h. To the resulting reaction was added BnBr (1.6 mL, 13.6 mmol, 1.4 equiv) and stirred at 25° C. for 12 h. The resulting mixture was quenched with H$_2$O and extracted with EtOAc. The combined EtOAc extracts were washed with NaOH (1N), H$_2$O, and brine, dried (Na$_2$SO$_4$), and concentrated to give the crude product. Flash chromatography on silica gel (40:1 hexanes/EtOAc) yielded 3.0 g of compound 12-7-1 (81% 2 steps) as a light yellow solid: $^1$H NMR (400 MHz, CDCl$_3$) δ 7.60-7.70 (m, 1H), 7.15-50 (m, 8H), 7.03-7.10 (m, 2H), 6.85-6.95 (m, 1H), 5.19 (s, 2H), 2.52 (s, 3H).

Phenyl 6-(tert-butoxycarbonyloxy)-2-methyl-3-(trifluoromethyl)benzoate (12-7-2)

Boc$_2$O (82.8 g, 0.38 mol, 2 equiv), DMAP (4.6 g, 38 mmol, 0.2 equiv) were added to a CH$_2$Cl$_2$ solution (150 mL) of crude 12-6 (51 g). The reaction was stirred at 25° C. for 3 h. The resulting mixture was quenched with H$_2$O and extracted with EtOAc. The combined EtOAc extracts were washed with brine, dried (Na$_2$SO$_4$), and concentrated to give the crude product. Flash chromatography on silica gel (30:1 PE/EtOAc) yielded 40.0 g of compound 12-7-2 (53% 2 steps) as a white solid: $^1$H NMR (400 MHz, CDCl$_3$) δ 7.76 (d, J=8.0 Hz, 1H), 7.45-7.41 (m, 2H), 7.30-7.24 (m, 4H), 2.58 (s, 3H), 1.46 (s, 9H); MS (ESI) m/z 397.2 (M+H).

(4 aS,11aR,12aS,13S)-3,7-bis(benzyloxy)-4a-(tert-butyldimethylsilyloxy)-13-(dimethylamino)-5-hydroxy-10-(trifluoromethyl)-11a,12,12a,13-tetrahydrotetraceno[2,3-d]isoxazole-4,6(4aH,11H)-dione (12-8-1)

A THF solution (3 mL) of 12-7-1 (100 mg, 0.26 mmol, 1.5 equiv) and enone 1-6 (84 mg, 0.17 mmol) was added TMEDA (0.23 mL, 1.56 mmol, 9.2 equiv) at −78° C. LDA (2.2 mL, 10% wt suspension, 1.5 mmol, 8.8 equiv) was added to the reaction at −78° C. The reaction was stirred at −78° C. for 30 min and allowed to warm to 25° C. over 1 h, quenched with saturated NH$_4$Cl, and extracted with EtOAc. The combined EtOAc extracts were dried (Na$_2$SO$_4$) and concentrated to yield the crude product. Preparative reverse phase HPLC purification on a Waters Autopurification system using a Sunfire Prep C18 OBD column [5 μm, 19×50 mm; flow rate, 20 mL/min; Solvent A: H$_2$O with 0.1% HCO$_2$H; Solvent B: CH$_3$CN with 0.1% HCO$_2$H; injection volume: 4.0 mL (CH$_3$CN); gradient: 80-100% B over 15 min; mass-directed fraction collection]. Fractions with the desired MW, eluting at 7.8-9.2 mM, were collected and concentrated on a RotaVap at 25° C. to remove most of the acetonitrile. The resulting mostly aqueous solution was extracted with EtOAc. The combined EtOAc extracts were dried (Na$_2$SO$_4$) and concentrated to give 35 mg of pure 12-8-1 (26%).

(4aS,11aR,12aS,13S)-3-(benzyloxy)-4a-(tert-butyldimethylsilyloxy)-13-(dimethylamino)-5,7-dihydroxy-10-(trifluoromethyl)-11a,12,12a,13-tetrahydrotetraceno[2,3-d]isoxazole-4,6(4aH,11H)-dione (12-8-2)

A THF solution (3 mL) of 12-7-2 (500 mg, 1.26 mmol, 3 equiv) and enone (203 mg, 0.42 mmol) was added TMEDA (0.75 mL, 3.78 mmol, 30 equiv) at −78° C. LDA (2.52 mL, 1M, 2.52 mmol, 6 equiv) was added to the reaction at −78° C. The reaction was stirred at −78° C. for 30 min and allowed to warm to 25° C. over 1 h, quenched with saturated NH$_4$Cl, and extracted with EtOAc. The combined EtOAc extracts were dried (Na$_2$SO$_4$) and concentrated to yield the crude product. Preparative reverse phase HPLC purification on a Waters Autopurification system using a Sunfire Prep C18 OBD column and freeze-dried to give 247 mg of pure 12-8-2 (75%): $^1$H NMR (400 MHz, CDCl$_3$) δ 13.95 (s, 1H), 12.15 (s, 1H), 7.64 (d, J=9.2 Hz, 1H), 7.43 (d, J=7.2 Hz, 2H), 7.34-7.28 (m, 3H), 6.84 (d, J=8.8 Hz, 1H), 5.30 (s, 2H), 3.82 (d, J=10.4 Hz, 1H), 3.31-3.25 (m, 1H), 3.05-2.90 (m, 1H), 2.71-2.62 (m, 1H); 2.43 (s, 8H), 0.80 (s, 9H), 0.22 (s, 3H), 0.08 (s, 3H) MS (ESI) m/z 785.3 (M+H).

(4S,4aS,5aR,12aS)-4-(dimethylamino)-3,10,12,12a-tetrahydroxy-1,11-dioxo-7-(trifluoromethyl)-1,4,4a,5,5a,6,11,12a-octahydrotetracene-2-carboxamide (Compound 269)

Aqueous HF (1 mL, 48%) was added to a CH$_3$CN solution (4 mL) of 12-8 (35 mg, 0.045 mmol) in a polypropylene tube at 25° C. The reaction was stirred at 25° C. for 18 h. The resulting mixture was poured into an aqueous solution of K$_2$HPO$_4$ (5 g, dissolved in 30 mL water). The mixture was extracted with EtOAc. The combined EtOAc extracts were dried (Na$_2$SO$_4$) and concentrated to yield 35 mg of crude intermediate.

Palladium on carbon (10 mg, 10 wt %) was added to a HCl/MeOH solution (0.5N, 2 mL) of the above crude intermediate (35 mg). The reaction was purged with hydrogen and stirred under H$_2$ (balloon) at 25° C. for 4 h. The reaction mixture was filtered through a small Celite plug. The filtrate was concentrated to yield the crude product. Preparative reverse phase HPLC purification on a Waters Autopurification system using a Phenomenex Polymerx™ 10μ RP-1 100 A column [10 μm, 150×21.20 mm; flow rate, 20 mL/min; Solvent A: 0.05 N HCl/water; Solvent B: CH$_3$CN; injection volume: 4.0 mL (0.05 N HCl/water); gradient: 0→50% B over 7 min, 50→100% over 3 min, and 100% over 5 min; mass-directed fraction collection]. Fractions with the desired MW, eluting at 6.4-8.2 min, were collected and freeze-dried to yield 6 mg of Compound 269 (28% for 2 steps): $^1$H NMR (400 MHz, CD$_3$OD) δ 7.76 (d, J=8.8 Hz, 1H), 6.95 (d, J=8.8 Hz, 1H), 4.10 (s, 1H), 3.25-2.93 (m, 3H), 3.04 (s, 3H), 2.95 (s, 3H), 2.60-2.48 (m, 1), 2.24-2.17 (iii, 1H), 1.70-1.58 (m, 1H); MS (ESI) m/z 483.21 (M+H).

Alternatively, Compound 269 was prepared from 12-8-2. Aqueous HF (10 mL, 40%) was added to a THF solution (10 mL) of 12-8-2 (247 mg, 0.43 mmol) in a polypropylene tube at 25° C. The reaction was stirred at 25° C. overnight. The resulting mixture was poured into an aqueous solution of K$_2$HPO$_4$ (20 g, dissolved in 100 mL water). The mixture was extracted with EtOAc. The combined EtOAc extracts were dried (Na$_2$SO$_4$) and concentrated to yield 250 mg of the crude intermediate.

Palladium on carbon (150 mg, 10 wt %) was added to a HCl/MeOH solution (0.5N, 6 mL) of the above crude intermediate (250 mg). The reaction was purged with hydrogen and stirred under H$_2$ (balloon) at 25° C. for 1 h. The reaction mixture was filtered through a small Celite plug. The filtrate was concentrated to yield the crude product. Preparative reverse phase HPLC purification on a Waters Autopurification system using a Phenomenex Polymerx™ 10μ RP-1 100 A column and freeze-dried to yield 105 mg of Compound 269 (51% for 2 steps).

(4S,4aS,5aR,12aS)-9-amino-4-(dimethylamino)-3,10,12,12a-tetrahydroxy-1,11-dioxo-7-(trifluoromethyl)-1,4,4a,5,5a,6,11,12a-octahydrotetracene-2-carboxamide (Compound 270)

A mixture of HNO$_3$ (1 μL, 69%) and H$_2$SO$_4$ (0.2 mL) was added to a H$_2$SO$_4$ solution (0.5 mL) of Compound 269 (6 mg, 0.012 mmol) at 0° C. The reaction was stirred at 0° C. for 30 min. The resulting mixture was added dropwise to vigorously stirred diethyl ether (20 mL) The suspension was filtered through a small Celite pad and washed several times with more diethyl ether. The Celite pad was then eluted with MeOH until the eluent became colorless. The yellow MeOH eluent was collected and concentrated under reduced pressure to afford the crude intermediate.

Palladium on carbon (2 mg, 10 wt %) was added to a MeOH solution (1 mL) of the above crude intermediate. The reaction was purged with hydrogen and stirred under H$_2$ (balloon) at 25° C. for 2 h. The catalyst was filtered off with a small Celite pad. The filtrate was concentrated to yield the crude product. Preparative reverse phase HPLC purification on a Waters Autopurification system using a Phenomenex Polymerx™ 10μ RP-1 100 A column [10 μm, 150×21.20 mm; flow rate, 20 mL/min; Solvent A: 0.05 N HCl; Solvent B: CH$_3$CN; injection volume: 4.0 mL (0.05 N HCl/water); gradient: 0→50% B over 7 min, 50→100% over 3 min, and 100% over 5 min; mass-directed fraction collection]. Fractions with the desired MW, eluting at 10-12 min, were collected and freeze-dried to yield 3 mg of pure Compound 270 (49% for 2 steps): $^1$H NMR (400 MHz, CD$_3$OD) δ 7.75 (s, 1H), 4.12 (s, 1H), 3.25-2.92 (m, 3H), 3.03 (s, 3H), 2.95 (s, 3H), 2.64-2.54 (m, 1H), 2.27-2.20 (m, 1H), 1.71-1.60 (m, 1H); MS (ESI) m/z 498.22 (M+H).

Compound 271.

Anhydrous Na$_2$CO$_3$ (16 mg, 0.15 mmol, 6.3 equiv) was added to an anhydrous DMPU/acetonitrile (150 μL/50 μL) solution of Compound 270 (11 mg, 0.024 mmol). Bromoacetyl bromide (2.5 μL, 0.029 mmol, 1.2 equiv) was added to the mixture. The reaction was stirred at 25° C. for 10 min. Pyrrolidine (19 μL, 0.24 mmol, 10 equiv) was added to the reaction mixture. The reaction was stirred at 25° C. for 2 h. The reaction mixture was concentrated and acidified with HCl (0.5 N in MeOH, 0.7 mL). The resulting mixture was added dropwise to vigorously stirred diethyl ether (10 mL). The suspension was filtered through a small Celite pad and washed several times with more diethyl ether. The Celite pad was then eluted with MeOH until the eluent became colorless. The yellow MeOH eluent was collected and concentrated under reduced pressure to afford the crude product. Preparative reverse phase HPLC purification on a Waters Autopurification system using a Phenomenex Polymerx™ 10μ RP-1 100 A column [10 μm, 150×21.20 mm; flow rate, 20 mL/min; Solvent A: 0.05 N HCl; Solvent B: CH$_3$CN; injection volume: 2.0 mL (0.05 N HCl/water); gradient: 0→50% B over 30 min; mass-directed fraction collection]. Fractions with the desired MW were collected and freeze-dried to yield 2.0 mg of pure Compound 271: $^1$H NMR (400 MHz, CD$_3$OD) δ 8.70 (s, 1H), 4.33 (s, 2H), 4.11 (s, 1H), 3.84-3.75 (m, 2H), 3.30-2.90 (m, 5H), 3.03 (s, 3H), 2.95 (s, 3H), 2.60-2.50 (m, 1H), 2.26-2.00 (m, 5H), 1.71-1.58 (m, 1H); MS (ESI) m/z 609.26 (M+H).

Compounds 271-304 were prepared similarly substituting the appropriate amine NHR$^3$R$^3$.

Compound 272.

$^1$H NMR (400 MHz, CD$_3$OD) δ 8.72 (s, 1H), 4.11 (s, 1H), 4.09 (s, 2H), 3.22-2.90 (m, 3H), 3.03 (s, 3H), 2.92 (s, 3H), 2.59-2.49 (m, 1H), 2.25-2.18 (m, 1H), 1.70-1.59 (m, 1H), 1.42 (s, 9H); MS (ESI) m/z 611.25 (M+H).

Compound 273.

$^1$H NMR (400 MHz, CD$_3$OD) δ 8.69 (s, 1H), 4.25 (s, 2H), 4.11 (s, 1H), 3.25-2.88 (m, 3H), 3.03 (s, 3H), 3.01 (s, 6H), 2.95 (s, 3H), 2.59-2.49 (m, 1H), 2.25-2.17 (m, 1H), 1.70-1.58 (m, 1H); MS (ESI) m/z 583.23 (M+H).

Compound 274.

¹H NMR (400 MHz, CD₃OD) δ 8.70 (s, 1H), 4.22 (s, 2H), 4.12 (s, 1H), 3.23-2.92 (m, 3H), 3.05 (s, 3H), 2.96 (s, 3H), 2.91-2.84 (m, 1H), 2.60-2.49 (m, 1H), 2.27-2.19 (m, 1H), 1.71-1.59 (m, 1H), 1.00-0.92 (m, 4H); MS (ESI) m/z 595.24 (M+H).

Compound 275.

¹H NMR (400 MHz, CD₃OD) δ 8.71 (s, 1H), 4.13 (s, 1H), 4.11 (s, 2H), 3.70-3.60 (m, 1H), 3.22-2.93 (m, 3H), 3.05 (s, 3H), 2.95 (s, 3H), 2.59-2.49 (m, 1H), 2.26-2.10 (m, 3H), 1.90-1.79 (m, 2H), 1.78-1.60 (m, 5H); MS (ESI) m/z 623.29 (M+H).

Compound 276.

¹H NMR (400 MHz, CD₃OD) δ 8.72 (s, 1H), 4.12 (s, 3H), 3.25-2.94 (m, 3H), 3.05 (s, 3H), 2.97 (s, 2H), 2.95 (s, 3H), 2.60-2.49 (m, 1H), 2.25-2.20 (m, 1H), 1.71-1.59 (m, 1H), 1.12 (s, 9H); MS (ESI) m/z 625.31 (M+H).

Compound 277.

¹H NMR (400 MHz, CD₃OD) δ 8.72 (s, 1H), 4.12 (s, 1H), 4.10 (s, 2H), 3.25-2.92 (m, 5H), 3.04 (s, 3H), 2.95 (s, 3H), 2.60-2.49 (m, 1H), 2.26-2.18 (m, 1H), 2.12-2.03 (m, 1H), 1.71-1.60 (m, 1H), 1.07 (d, J=6.7 Hz, 6H); MS (ESI) m/z 611.28 (M+H).

Compound 278.

¹H NMR (400 MHz, CD₃OD) δ 8.72 (s, 1H), 4.13 (s, 2H), 4.16 (s, 1H), 3.23-2.93 (m, 5H), 3.04 (s, 3H), 2.96 (s, 3H), 2.60-2.50 (m, 1H), 2.25-2.19 (m, 1H), 1.71-1.60 (m, 1H), 1.20-1.09 (m, 1H), 0.78-0.73 (m, 1H), 0.48-0.41 (m, 1H); MS (ESI) m/z 609.24 (M+H).

Compound 279.

¹H NMR (400 MHz, CD₃OD) δ 8.65 (s, 1H), 4.41-4.34 (m, 2H), 4.35 (s, 2H), 4.24-4.17 (m, 2H), 4.11 (s, 1H), 3.22-2.92 (m, 3H), 3.04 (s, 3H), 2.95 (s, 3H), 2.70-2.60 (m, 1H), 2.59-2.42 (m, 2H), 2.25-2.18 (m, 1H), 1.70-1.59 (m, 1H); MS (ESI) m/z 595.21 (M+H).

Compound 280.

¹H NMR (400 MHz, CD₃OD) δ 8.71 (s, 1H), 4.11 (s, 1H), 4.09 (s, 2H), 3.24-2.94 (m, 3H), 3.05 (s, 3H), 2.96 (s, 3H), 2.80 (s, 3H), 2.60-2.50 (m, 1H), 2.26-2.19 (m, 1H), 1.71-1.60 (m, 1H); MS (ESI) m/z 569.20 (M+H).

Compound 281.

¹H NMR (400 MHz, CD₃OD) δ 8.68 (s, 1H), 4.10 (s, 3H), 3.20-2.93 (m, 10H), 2.56-2.47 (m, 1H), 2.25-2.10 (m, 3H), 1.92-1.85 (m, 2H), 1.73-1.59 (m, 2H), 1.45-1.33 (m, 4H), 1.30-1.16 (m, 1H); MS (ESI) m/z 637.1 (M+H).

Compound 282.

¹H NMR (400 MHz, CD₃OD) δ 8.67 (s, 1H), 4.30 (d, J=16.4 Hz, 1H), 4.19 (d, J=15.6 Hz, 1H), 4.10 (s, 1H), 3.21-2.93 (m, 14H), 2.56-2.48 (m, 1H), 2.22-2.19 (m, 1H), 1.84-1.75 (m, 2H), 1.67-1.57 (m, 1H), 1.02 (t, J=7.2 Hz, 3H); MS (ESI) m/z 611.1 (M+H).

Compound 283.

¹H NMR (400 MHz, CD₃OD) δ 8.66 (d, J=8.4 Hz, 1H), 4.27 (d, J=18.8 Hz, 2H), 4.10 (s, 1H), 3.98-3.94 (m, 1H), 3.47-3.43 (m, 1H), 3.18-2.85 (m, 12H), 2.76-2.71 (m, 2H), 2.54-2.47 (m, 1H), 2.23-2.16 (m, 1H), 1.85-1.53 (m, 6H); MS (ESI) m/z 649.1 (M+H).

Compound 284.

¹H NMR (400 MHz, CD₃OD) δ 8.65 (s, 1H), 4.07 (s, 2H), 4.03 (s, 1H), 3.97-3.90 (m, 2H), 3.12-2.86 (m, 9H), 2.49-2.42 (m, 1H), 2.15-2.11 (m, 1H), 1.57-1.50 (m, 1H); MS (ESI) m/z 637.1 (M+H).

Compound 285.

¹H NMR (400 MHz, CD₃OD) δ 8.72 (s, 1H), 5.50 (d, J=52.0 Hz, 1H), 4.44 (s, 2H), 4.14 (s, 1H), 4.04-3.95 (m, 2H), 3.54-3.47 (m, 2H), 3.23-2.97 (m, 9H), 2.60-2.23 (m, 4H), 1.71-1.62 (m, 1H); MS (ESI) m/z 627.0 (M+H).

Compound 286.

¹H NMR (400 MHz, CD₃OD) δ 8.70 (s, 1H), 4.11 (s, 1H), 4.09 (s, 2H), 3.51-3.44 (m, 1H), 3.19-2.94 (m, 9H), 2.56-2.49 (m, 1H), 2.24-2.19 (m, 1H), 1.68-1.58 (m, 1H), 1.38 (t, J=6.4 Hz, 6H); MS (ESI) m/z 597.2 (M+H).

Compound 287.

¹H NMR (400 MHz, CD₃OD) δ 8.69 (s, 1H), 4.10 (s, 1H), 4.07 (s, 2H), 3.21-2.94 (m, 11H), 2.56-2.50 (m, 1H), 2.25-2.19 (m, 1H), 1.85-1.60 (m, 7H), 1.37-1.22 (m, 3H), 1.12-1.03 (m, 2H); MS (ESI) m/z 651.3 (M+H).

Compound 288.

¹H NMR (400 MHz, CD₃OD) δ 8.71 (s, 1H), 4.32 (s, 2H), 4.14 (s, 1H), 4.10-3.87 (m, 4H), 3.65-3.58 (m, 2H), 3.43-3.36 (m, 2H), 3.23-2.97 (m, 9H), 2.60-2.52 (m, 1H), 2.27-2.23 (m, 1H), 1.70-1.64 (m, 1H); MS (ESI) m/z 625.3 (M+H).

Compound 289.

¹H NMR (400 MHz, CD₃OD) δ 8.72 (s, 1H), 4.14 (s, 1H), 4.13 (s, 2H), 3.19-2.90 (m, 11H), 2.56-2.45 (m, 1H), 2.23-2.15 (m, 2H), 1.92-1.85 (m, 2H), 1.70-1.65 (m, 5H), 1.31-1.22 (m, 2H); MS (ESI) m/z 637.2 (M+H).

Compound 290.

¹H NMR (400 MHz, CD₃OD) δ 8.67 (s, 1H), 5.45 (d, J=52.0 Hz, 1H), 4.40 (s, 2H), 4.09 (s, 1H), 4.00-3.90 (m, 1H), 3.45-3.37 (m, 1H), 3.20-2.92 (m, 11H), 2.53-2.33 (m, 3H), 2.23-2.15 (m, 1H), 1.65-1.55 (m, 1H); MS (ESI) m/z 627.2 (M+H).

Compound 291.

¹H NMR (400 MHz, CD₃OD) δ 8.58 (s, 1H), 5.37 (d, J=56.8 Hz, 1H), 4.36 (m, 4H), 4.02 (s, 1H), 3.17-2.73 (m, 11H), 2.48-2.41 (m, 1H), 2.15-2.11 (m, 1H), 1.60-1.50 (m, 1H); MS (ESI) m/z 613.1 (M+H).

Compound 292.

¹H NMR (400 MHz, CD₃OD) δ 8.68 (s, 1H), 4.15 (s, 1H), 4.11 (s, 2H), 3.21-2.98 (m, 11H), 2.56-2.48 (m, 1H), 2.26-2.19 (m, 1H), 1.82-1.73 (m, 2H), 1.68-1.49 (m, 1H), 1.02 (t, J=7.2 Hz, 3H); MS (ESI) m/z 597.2 (M+H).

Compound 293.

¹H NMR (400 MHz, CD₃OD) δ 8.61 (s, 1H), 4.03 (s, 1H), 3.90 (s, 2H), 3.80-3.72 (m, 1H), 3.15-2.87 (m, 9H), 2.48-2.40 (m, 1H), 2.37-2.11 (m, 5H), 1.90-1.81 (m, 2H), 1.62-1.52 (m, 1H); MS (ESI) m/z 609.2 (M+H).

Compound 294.

¹H NMR (400 MHz, CD₃OD) δ 8.65 (s, 1H), 4.10 (s, 3H), 3.57 (t, J=5.2 Hz, 2H), 3.48 (s, 3H), 3.30-3.25 (m, 2H), 3.18-2.92 (m, 9H), 2.55-2.45 (m, 1H), 2.23-2.15 (m, 1H), 1.65-1.55 (m, 1H); MS (ESI) m/z 613.2 (M+H).

Compound 295.

¹H NMR (400 MHz, CD₃OD) δ 8.16 (s, 1H), 4.33 (d, J=15.6 Hz, 1H), 4.21 (d, J=16.4 Hz, 1H), 4.11 (s, 1H), 3.24-2.93 (m, 14H), 2.58-2.49 (m, 1H), 2.28-2.20 (m, 1H), 1.70-1.58 (m, 1H), 1.40 (t, J=7.4 Hz, 3H); MS (ESI) m/z 597.0 (M+H).

Compound 296.

¹H NMR (400 MHz, CD₃OD) δ 8.57 (s, 1H), 4.19 (s, 2H), 4.05 (s, 1H), 3.35-3.23 (m, 4H), 3.13-2.82 (m, 9H), 2.48-2.39 (s, 1H), 2.28-2.11 (s, 1H), 1.60-1.51 (m, 1H), 1.29 (t, J=7.2 Hz, 6H); MS (ESI) m/z 611.1 (M+H).

Compound 297.

¹H NMR (400 MHz, CD₃OD) δ 8.67 (s, 1H), 4.21 (s, 2H), 4.12 (s, 1H), 3.64-3.61 (m, 2H), 3.19-2.91 (m, 11H), 2.56-2.46 (m, 1H), 2.25-2.17 (m, 1H), 1.97-1.79 (m, 5H), 1.69-1.50 (m, 2H); MS (ESI) m/z 623.2 (M+H).

Compound 298.

¹H NMR (400 MHz, CD₃OD) δ 8.72 (s, 1H), 7.42 (s, 4H), 5.10-5.00 (m, 2H), 4.73-4.62 (m, 2H), 4.57 (s, 2H), 4.13 (s, 1H), 3.21-2.90 (m, 9H), 2.56-1.95 (m, 1H), 2.25-2.20 (m, 1H), 1.68-1.58 (m, 1H); MS (ESI) m/z 657.1 (M+H).

Compound 299.

¹H NMR (400 MHz, CD₃OD) δ 8.68 (s, 1H), 4.12 (s, 1H), 4.09 (s, 2H), 3.22-2.91 (m, 11H), 2.56-2.47 (m, 1H), 2.26-2.17 (m, 1H), 1.69-1.58 (m, 1H), 1.37 (t, J=7.2 Hz, 3H); MS (ESI) m/z 583.1 (M+H).

Compound 300.

$^1$H NMR (400 MHz, CD$_3$OD) δ 8.70 (s, 1H), 6.36 (tt, J=53.5, 3.2 Hz, 1H), 4.23 (s, 2H), 4.13 (s, 1H), 3.69 (td, J=15.3, 2.8 Hz, 2H), 3.23-2.91 (m, 9H), 2.58-2.50 (m, 1H), 2.25-2.19 (m, 1H), 1.70-1.60 (m, 1H); MS (ESI) m/z 619.0 (M+H).

Compound 301.

$^1$H NMR (400 MHz, CD$_3$OD) δ 8.79 (s, 1H), 4.32 (s, 1H), 4.32 (s, 2H), 3.37-3.15 (m, 11H), 2.97-2.89 (m, 1H), 2.78-2.68 (m, 1H), 2.47-2.35 (m, 3H), 2.27-2.18 (m, 1H), 2.16-2.03 (m, 3H), 1.90-1.79 (m, 1H); MS (ESI) m/z 623.2 (M+H).

Compound 302.

$^1$H NMR (400 MHz, CD$_3$OD) δ 8.86 (s, 1H), 4.90-4.80 (m, 1H), 4.62-4.50 (m, 5H), 4.32 (s, 1H), 4.30-4.20 (m, 1H), 3.56 (s, 3H), 3.40-3.12 (m, 9H), 2.80-2.68 (m, 1H), 2.48-2.39 (m, 1H), 1.90-1.79 (m, 1H); MS (ESI) m/z 625.2 (M+H).

Compound 303.

$^1$H NMR (400 MHz, CD$_3$OD) δ 8.73 (s, 1H), 4.75 (tt, J=52.0, 4.8 Hz, 2H), 4.21 (s, 2H), 4.15 (s, 1H), 3.55 (tt, J=26.8, 4.4 Hz, 2H), 3.23-2.87 (m, 9H), 2.60-2.50 (m, 1H), 2.30-2.20 (m, 1H), 1.68-1.64 (m, 1H); MS (ESI) m/z 601.1 (M+H).

Compound 304.

$^1$H NMR (400 MHz, CD$_3$OD) δ 8.79 (s, 1H), 7.49-7.45 (m, 2H), 730-7.28 (m, 3H), 4.71 (s, 2H), 4.11 (s, 1H), 3.18-2.95 (m, 9H), 2.60-2.49 (m, 1H), 2.27-2.18 (m, 1H), 1.70-1.61 (m, 1H); MS (ESI) m/z 631.0 (M+H).

Compounds 307-311 were prepared similarly to 271 substituting bromoacetyl bromide and an amine with an acid chloride (appropriately protected if needed) or a carboxylic acid (appropriately protected if needed) and a coupling reagent such as HATU.

Compound 307.

$^1$H NMR (400 MHz, CD$_3$OD) δ 8.71 (s, 1H), 5.32-5.28 (m, 1H), 4.21-4.17 (m, 1H), 4.14 (s, 1H), 4.07-4.00 (m, 1H), 3.25-2.92 (m, 10H), 2.70-2.61 (m, 1H), 2.59-2.49 (m, 1H), 2.28-2.20 (m, 1H), 1.70-1.60 (m, 1H); MS (ESI) m/z 581.1 (M+H).

Compound 308.

$^1$H NMR (400 MHz, CD$_3$OD) δ 8.54 (s, 1H), 4.07 (s, 2H), 3.46-3.38 (m, 1H), 3.16-2.90 (m, 10H), 2.53-2.43 (m, 1H), 2.33-2.15 (m, 2H), 1.96-1.86 (m, 2H), 1.77-1.55 (m, 4H); MS (ESI) m/z 609.1 (M+H).

Compound 309. $^1$H NMR (400 MHz, CD$_3$OD) δ 8.59 (s, 1H), 5.17-5.12 (m, 1H), 4.11-3.98 (m, 3H), 3.13-2.85 (m, 12H), 2.59-2.42 (m, 3H), 2.18-2.11 (m, 1H), 1.61-1.50 (m, 1H); MS (ESI) m/z 595.1 (M+H).

Compound 310.

$^1$H NMR (400 MHz, CD$_3$OD) δ 8.59 (s, 1H), 4.62-4.57 (m, 1H), 4.12 (s, 1H), 3.51-3.36 (m, 2H), 3.25-2.93 (m, 3H), 3.05 (s, 3H), 2.96 (s, 3H), 2.62-2.49 (m, 2H), 2.25-2.08 (m, 4H), 1.71-1.58 (m, 1H); MS (ESI) m/z 595.25 (M+H).

Compound 311.

$^1$H NMR (400 MHz, CD$_3$OD) δ 8.61 (s, 1H), 4.42-4.37 (m, 1H), 4.13 (s, 1H), 3.82-3.75 (m, 2H), 3.23-2.92 (m, 3H), 3.04 (s, 3H), 3.01 (s, 3H), 2.95 (s, 3H), 2.78-2.62 (m, 1H), 2.62-2.51 (m, 1H), 2.32-2.04 (m, 4H), 1.71-1.60 (m, 1H); MS (ESI) m/z 609.26 (M+H).

Compound 305.

To a solution of Compound 270 (15 mg, 0.024 mmol, 1 equiv) in THF (1 ml) was added sodium carbonate (20 mg, 0.19 mmol, 8 equiv), 3-fluorobenzenesulfonyl chloride (0.036 mmol, 1.5 equiv). The reaction was stirred at rt for 6 h, LC/MS analysis indicated complete consumption of the starting aniline 12. The reaction mixture was then added dropwise into 4 N HCl/MeOH (1 ml) at 0° C. with rapid stirring. The reaction mixture was concentrated and the residue purified by HPLC. The desired product Compound 305 was obtained as a yellow solid after freeze-drying: $^1$H NMR (400 MHz, CD$_3$OD) δ 7.92 (s, 1H), 7.61-7.50 (m, 3H), 7.38-7.32 (m, 1H), 4.10 (s, 1H), 3.19-2.90 (m, 9H), 2.55-2.45 (m, 1H), 2.24-2.46 (m, 1H), 1.68-1.55 (m, 1H); MS (ESI) m/z 656.0 (M+H).

Compound 306.

Compound 306 was prepared similarly to Compound 305 using 1-methyl-1H-pyrazole-3-sulfonyl chloride: $^1$H NMR (400 MHz, CD$_3$OD) δ 8.82 (s, 1H), 8.06 (s, 1H), 7.93 (s, 1H), 4.15 (s, 1H), 3.91 (s, 3H), 3.96-2.95 (m, 9H), 2.59-2.49 (m, 1H), 2.28-2.20 (m, 1H), 1.70-1.60 (m, 1H); MS (ESI) m/z 642.1 (M+H).

EXAMPLE 13

Synthesis of Compounds of Formula V

Scheme 13:

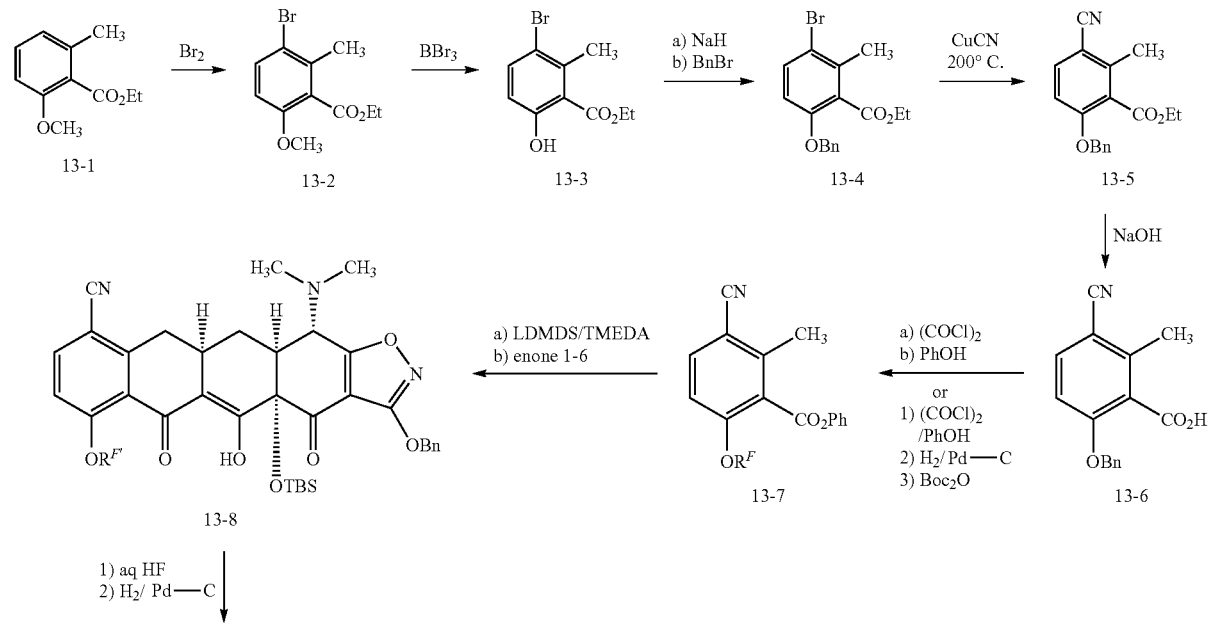

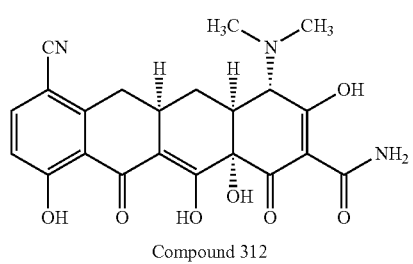

Compound 312

1) HNO₃
2) H₂/Pd—C

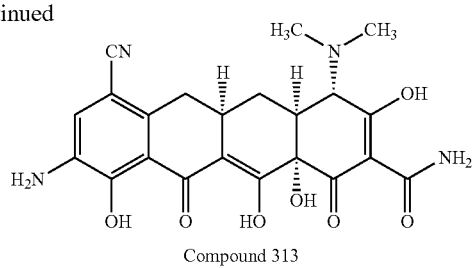

Compound 313

1) BrCH₂COBr
2) R²R³NH

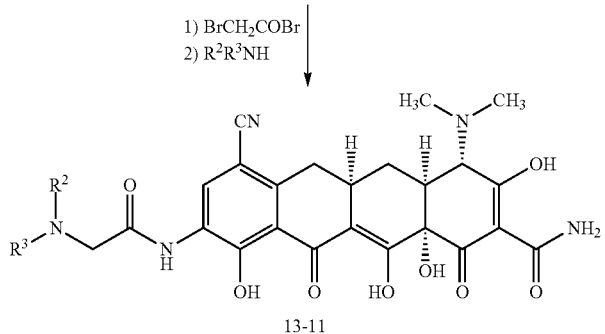

13-11

In Scheme 13, "$R^F$" represents benzyl or BOC; and "$R^{F'}$" represents benzyl or hydrogen.

Ethyl 3-bromo-6-methoxy-2-methylbenzoate (13-2)

To a methylene chloride solution (100 mL) of Ethyl 2-methoxy-6-methylbenzoate (13-1, 5 g, 25.8 mmol, TCI M1120) was added bromine (1.65 mL, 32.2 mmol, 1.25 equiv) at 0° C. The reaction was stirred at 0° C. to 25° C. for 12 h and quenched with sodium thiosulfate solution (5%, 20 mL) and stirred for 20 min. The resulting mixture was extracted with methylene chloride. The combined methylene chloride extracts were dried (Na₂SO₄) and concentrated to give 7.2 g of 13-2: ¹H NMR (400 MHz, CDCl₃) δ 7.47 (d, J=9.2 Hz, 1H), 6.63 (d, J=9.2 Hz, 1H), 4.38 (q, J=7.3 Hz, 2H), 3.78 (s, 3H), 2.30 (s, 3H), 1.35 (t, J=7.3 Hz, 3H).

Ethyl 3-bromo-6-hydroxy-2-methylbenzoate (13-3)

BBr₃ (31 mL, 1.0 M, 30.96 mmol, 1.2 equiv) was added to a methylene chloride solution (100 mL) of crude 13-2 (7.2 g) at −78° C. The reaction was allowed to warm to 25° C. over 2 h. The reaction was stirred from −78° C. to 25° C. for 2 h, quenched with saturated NaHCO₃ and concentrated. EtOAc and H₂O were added to the reaction mixture. The aqueous layer was extracted with EtOAc. The combined EtOAc extracts were dried (Na₂SO₄) and concentrated to yield 7.1 g of 13-3: ¹H NMR (400 MHz, CDCl₃) δ 10.87 (br s, 1H), 7.55 (d, J=9.2 Hz, 1H), 4.43 (q, J=7.3 Hz, 2H), 2.63 (s, 3H), 1.42 (t, J=7.3 Hz, 3H).

Ethyl 6-(benzyloxy)-3-bromo-2-methylbenzoate (13-4)

To a DMF solution (50 mL) of crude 13-3 (7.1 g) was added NaH (1.24 g, 60% in oil, 30.96 mmol, 1.2 equiv) at 0° C. The reaction was stirred at 0° C. for 1 h. To the reaction mixture was added BnBr (4.3 mL, 36.1 mmol, 1.4 equiv) at 0° C. The reaction was stirred at 25° C. for 12 h. The reaction was quenched with NH₄Cl and extracted with EtOAc. The combined EtOAc extracts were washed with H₂O, brine, dried (Na₂SO₄) and concentrated. Flash chromatography on silica gel (30:1 hexanes/EtOAc) yielded 8.0 g of compound 13-4 (89% for 3 steps): ¹H NMR (400 MHz, CDCl₃) δ 7.44 (d, J=9.2 Hz, 1H), 7.25-7.40 (m, 5H), 6.66 (d, J=9.2 Hz, 1H), 5.06 (s, 2H), 4.36 (q, J=7.3 Hz, 2H), 2.32 (s, 3H), 1.32 (t, J=7.3 Hz, 3H).

Ethyl 6-(benzyloxy)-3-cyano-2-methylbenzoate (13-5)

CuCN (770 mg, 8.6 mmol, 3 equiv) was added to a DMF solution (15 mL, anhydrous) of 13-4 (1.0 g, 2.87 mmol) in a sealed tube. The reaction was stirred at 200° C. for 18 min and cooled. The resulting mixture was quenched with H₂O and extracted with EtOAc. The combined EtOAc extracts were washed with H₂O, brine, dried (Na₂SO₄) and concentrated. Flash chromatography on silica gel (10:1 hexanes/EtOAc) yielded 670 mg of compound 13-5 (80%): ¹H NMR (400 MHz, CDCl₃) δ 7.55 (d, J=8.5 Hz, 1H), 7.26-7.40 (m, 5H), 6.83 (d, J=8.5 Hz, 1H), 5.14 (s, 2H), 4.37 (q, J=7.0 Hz, 2H), 2.46 (s, 3H), 1.30 (t, J=7.0 Hz, 3H).

6-(benzyloxy)-3-cyano-2-methylbenzoic acid (13-6)

NaOH solution (5 mL, 3 N) was added to a MeOH/THF solution (5 mL/5 mL) of 13-5 (518 mg, 1.75 mmol) at 55° C. The reaction was stirred from 55° C. for 15 h and concentrated. The resulting mixture was acidified with HCl (6 N) to pH 1 and extracted with EtOAc. The combined EtOAc extracts were dried (Na₂SO₄) and concentrated to yield 530 mg of crude 13-6.

6-(benzyloxy)-3-cyano-2-methylbenzoic acid (13-7-1)

Oxalyl chloride (0.75 mL, 8.75 mmol, 5 equiv) was added to a CH₂Cl₂ solution (5 mL, anhydrous) of crude 13-6 (530 mg). DMF (0.1 mL) was added to the resulting mixture. The reaction was stirred at 25° C. for 1 h and concentrated. The resulting solid was re-dissolved in 5 mL of anhydrous $CH_2Cl_2$. Phenol (330 mg, 3.5 mmol, 2 equiv), DMAP (213 mg, 1.75 mmol, 1 equiv), and triethylamine (1.2 mL, 8.75 mmol, 5 equiv) were added to the reaction mixture. The reaction was stirred at 25° C. for 12 h and concentrated. EtOAc and $H_2O$ were added to the residue. The organic layer was washed with NaOH (1 N), $H_2O$, and brine, dried ($Na_2SO_4$), and concentrated. Flash chromatography on silica gel (10:1 hexanes/EtOAc) yielded 400 mg of compound 13-7-1 (67% for 2 steps): $^1H$ NMR (400 MHz, $CDCl_3$) δ 7.65 (d, J=9.2 Hz, 1H), 7.25-7.45 (m, 8H), 7.06 (d, J=10.2 Hz, 2H), 6.93 (d, J=9.2 Hz, 1H), 5.20 (s, 2H), 2.61 (s, 3H).

Phenyl 6-(tert-butoxycarbonyloxy)-
3-cyano-2-methylbenzoate (13-7-2)

To a solution of compound 13-7-1 (5 g, 0.014 mol) in 1, 4 dioxane/MeOH (25 mL/25 mL) was added Pd/C (1.1 g, 22%), the mixture was purged by bubbling hydrogen through for 5 min and rapidly stirred under 1 atm hydrogen atmosphere at rt for 2 hrs. The catalyst was filtered off with a small Celite pad and washed with more methanol (2 mL×3). The filtrate was concentrated to yield the crude intermediate. Di-tert-butyl dicarbonate (3.3 g, 0.015 mmol, 1.05 equiv), DMAP (20 mg, cat.) were added to a solution of the above intermediate in DCM (100 mL). The resulting mixture was stirred for 1 h at rt and concentrated. The residue was purified by flash-column chromatography to afford the desired product 13-7-2 as a white solid (3.2 g, 62%, two steps): $^1H$ NMR (400 MHz, $CDCl_3$) δ 7.77 (d, J=8.8 Hz, 1H), 7.47 (m, 2H), 7.33 (m, 2H), 7.30 (m, 1H), 7.25 (d, J=7.6 Hz, 1H), 2.71 (s, 3H), 1.47 (s, 9H); MS (ESI) m/z 354.37 (M+H).

(4aS,11aR,12aS,13S)-3,7-bis(benzyloxy)-4a-(tert-butyldimethylsilyloxy)-13-(dimethylamino)-5-hydroxy-4,6-dioxo-4,4a,6,11,11a,12,12a,13-octahydro-tetraceno[2,3-d]isoxazole-10-carbonitrile (13-8-1)

A THF solution (5 mL) of 13-7-1 (400 mg, 1.17 mmol, 1.5 equiv) and enone 1-6 (378 mg, 0.78 mmol) was added TMEDA (1.1 mL, 7.02 mmol, 6.0 equiv) at −78° C. LHMDS (4.7 mL, 1M, 4.66 mmol, 4.0 equiv) was added to the reaction at −78° C. The reaction was stirred at −78° C. for 30 min and allowed to warm to 25° C. over 1 h, quenched with saturated $NH_4Cl$, and extracted with EtOAc. The combined EtOAc extracts were dried ($Na_2SO_4$) and concentrated to yield the crude product. Preparative reverse phase HPLC purification on a Waters Autopurification system using a Sunfire Prep C18 OBD column [5 μm, 19×50 mm; flow rate, 20 mL/min; Solvent A: $H_2O$ with 0.1% $HCO_2H$; Solvent B: $CH_3CN$ with 0.1% $HCO_2H$; injection volume: 4.0 mL ($CH_3CN$); gradient: 80→100% B over 15 min; mass-directed fraction collection]. Fractions with the desired MW, eluting at 5.9-7.0 min, were collected and concentrated on a RotaVap at 25° C. to remove most of the acetonitrile. The resulting mostly aqueous solution was extracted with EtOAc. The combined EtOAc extracts were dried ($Na_2SO_4$) and concentrated to give 153 mg of pure 13-8-1 (27%).

(4aS,11aR,12aS,13S)-3-(benzyloxy)-4a-(tert-butyldimethylsilyloxy)-10-cyano-13-(dimethylamino)-5-hydroxy-4,6-dioxo-4,4a,6,11,11a,12,12a,13-octahydrotetraceno[2,3-d]isoxazol-7-yl tert-butyl carbonate (13-8-2)

To a solution of compound 13-7-2 (402 mg, 1.139 mmol, 2 equiv) and enone 1-6 (282 mg, 0.58 mmol, 1 equiv) was added TMEDA (0.55 mL, 3.5 mmol, 6 equiv) at −78° C. LHMDS (3.3 mL, 1M, 3.3 mmol, 5.6 equiv) was added to the reaction mixture at −78° C. The reaction was stirred at −78° C. for 30 min and allowed to warm to 25° C. over 1 h, quenched with saturated $NH_4Cl$, and extracted with EtOAc. The combined extracts were dried with $Na_2SO_4$ and concentrated to yield the crude product, which was purified by flash-column chromatography to afford the product 13-8-2 as a yellow solid (0.14 g, 32%): $^1H$ NMR (400 MHz, $CDCl_3$) δ 15.41 (s, 1H), 7.85 (d, J=4.0 Hz, 1H), 7.63-7.32 (m, 5H), 7.26-7.20 (m, 1H), 5.44 (s, 2H), 4.01 (d, J=10.8 Hz, 1H), 3.48 (dd, J=16.0 Hz, 4.4 Hz, 1H), 3.21-3.18 (m, 1H), 2.94-2.81 (m, 1H), 2.69-2.63 (m, 1H), 2.71-2.55 (m, 7H), 2.26 (d, J=14.4 Hz, 1H), 1.62 (s, 9H), 0.93 (s, 9H), 0.33 (s, 3H), 0.19 (s, 3H); MS (ESI) m/z 742.37 (M+H).

Compound 312.

Aqueous HF (1 mL, 48%) was added to a $CH_3CN$ solution (4 mL) of 13-8-1 (35 mg, 0.045 mmol) in a polypropylene tube at 25° C. The reaction was stirred at 25° C. for 18 h. The resulting mixture was poured into an aqueous solution of $K_2HPO_4$ (5 g, dissolved in 30 mL water). The mixture was extracted with EtOAc. The combined EtOAc extracts were dried ($Na_2SO_4$) and concentrated to yield 120 mg of the crude intermediate.

Palladium on carbon (50 mg, 10 wt %) was added to a HCl/MeOH solution (0.5N, 2 mL) of the above intermediate (120 mg). The reaction was purged with hydrogen and stirred under $H_2$ (balloon) at 25° C. for 3 h. The reaction mixture was filtered through a small Celite plug. The filtrate was concentrated. Preparative reverse phase HPLC purification on a Waters Autopurification system using a Phenomenex Polymerx™ 10μ RP-1 100 A column [10 μm, 150× 21.20 mm; flow rate, 20 mL/min; Solvent A: 0.05 N HCl/water; Solvent B: $CH_3CN$; injection volume: 4.0 mL (0.05 N HCl/water); gradient: 0-70% B over 7 min, 70→100% over 3 min, and 100% over 5 min; mass-directed fraction collection]. Fractions with the desired MW were collected and freeze-dried to yield 28 mg of Compound 312 (30% for 2 steps): $^1H$ NMR (400 MHz, $CD_3OD$) δ 7.76 (d, J=9.0 Hz, 1H), 6.97 (d, 9.0 Hz, 1H), 4.10 (s, 1H), 3.26-2.91 (m, 3), 3.04 (s, 3H), 2.96 (s, 3H), 2.71-2.62 (m, 1H), 2.27-2.20 (m, 1H), 1.72-1.62 (m, 1H); MS (ESI) m/z 410.22 (M+H).

Alternatively, Compound 312 was prepared from 13-8-2. Compound 13-8-2 (140 mg, 0.19 mmol) was dissolved in THF (5 mL), and HF (5 mL, 40% in water) was added. The resultant yellow solution was stirred at rt overnight. The reaction solution was then slowly added into a solution of $K_2HPO_4$ (3.1 g) in water (20 mL) with rapid stirring. The mixture was extracted with DCM (10 mL×3). The combine extracts were dried over sodium sulfate and concentrated in vacuo to yield the crude intermediate.

To a HCl/MeOH solution (0.5 N, 5 mL) of the above crude intermediate was added Pd/C (30 mg, 20%). The mixture was purged by bubbling hydrogen through for 5 min and rapidly stirred under 1 atm hydrogen atmosphere at rt for 1 hr. The catalyst was filtered off with a small Celite pad and washed with more methanol (5 mL×3). The filtrate was concentrated in vacuo. Preparative HPLC purification on a Polymerx™ column yielded the desired product Compound 312 as a yellow solid (56 mg, 68% two steps).

Compound 313.

A mixture of $HNO_3$ (27 μL, 69%) and $H_2SO_4$ (0.4 mL) was added to a $H_2SO_4$ solution (1 mL) of Compound 312 (150 mg, 0.34 mmol) at 0° C. The reaction was stirred at 0° C. for 30 min. The resulting mixture was added dropwise to vigorously stirred diethyl ether (20 mL). The suspension was filtered through a small Celite pad and washed several times with more diethyl ether. The Celite pad was then eluted with MeOH until the eluent became colorless. The yellow MeOH eluent was collected and concentrated under reduced pressure.

The resulting mixture was re-dissolved in MeOH (15 mL). The Palladium on carbon (20 mg, 10 wt %) was added to the reaction. The reaction mixture was stirred under $H_2$ at 25° C. for 30 min. The reaction mixture was filtered through a small Celite plug. The filtrate was concentrated. Preparative reverse phase HPLC purification on a Waters Autopurification system using a Phenomenex Polymerx™ 10μ RP-1 100 A column [10 μm, 150×21.20 mm; flow rate, 20 mL/min; Solvent A: 0.05 N HCl/water; Solvent B: $CH_3CN$; injection volume: 4.0 mL (0.05 N HCl/water); gradient: 0→50% B over 7 min, 50→100% over 3 min, and 100% over 5 min; mass-directed fraction collection]. Fractions with the desired MW were collected and freeze-dried to yield 62 mg of Compound 313 (40% for 2 steps): $^1$H NMR (400 MHz, $CD_3OD$) δ 7.58 (s, 1H), 4.10 (s, 1H), 3.25-2.93 (m, 3H), 3.03 (s, 3H), 2.93 (s, 3H), 2.75-2.60 (m, 1H), 2.28-120 (m, 1H), 1.71-1.60 (m, 1H); MS (ESI) m/z 455.23 (M+H).

Compound 314.

Anhydrous $Na_2CO_3$ (16 mg, 0.15 mmol, 6.3 equiv) was added to an anhydrous DMPU/acetonitrile (150 μL/50 μL) solution of Compound 313 (11 mg, 0.024 mmol). Bromoacetyl bromide (2.5 μL, 0.029 mmol, 1.2 equiv) was added to the mixture. The reaction was stirred at 25° C. for 10 min, Pyrrolidine (19 μL, 0.24 mmol, 10 equiv) was added to the reaction mixture. The reaction was stirred at 25° C. for 2 h. The reaction mixture was concentrated and acidified with HCl (0.5 N in MeOH, 0.7 mL). The resulting mixture was added dropwise to vigorously stirred diethyl ether (10 mL). The suspension was filtered through a small Celite pad and washed several times with more diethyl ether. The Celite pad was then eluted with MeOH until the eluent became colorless. The yellow MeOH eluent was collected and concentrated under reduced pressure. Preparative reverse phase HPLC purification on a Waters Autopurification system using a Phenomenex Polymerx™ 10μ RP-1 100 A column [10 μm, 150×21.20 mm; flow rate, 20 mL/min; Solvent A: 0.05 N HCl; Solvent B: $CH_3CN$; injection volume: 2.0 mL (0.05 N HCl/water); gradient: 0→50% B over 30 min; mass-directed fraction collection]. Fractions with the desired MW were collected and freeze-dried to yield 4.3 mg of pure 13-11-1: $^1$H NMR (400 MHz, $CD_3OD$) δ 8.62 (s, 1H), 4.34 (s, 1H), 4.12 (s, 1H), 3.3.84-3.76 (m, 2H), 3.30-2.92 (m, 5H), 3.04 (s, 3H), 2.95 (s, 3H), 2.70-2.58 (m, 1H), 2.30-2.01 (m, 5H), 1.72-1.61 (m, 1H); MS (ESI) m/z 566.27 (M+H).

Compounds 315-333 were prepared similarly employing the appropriate amine ($NHR^2R^3$).

Compound 315. $^1$H NMR (400 MHz, $CD_3OD$) δ 8.64 (s, 1H), 4.12 (s, 1H), 4.09 (s, 2H), 3.30-2.92 (m, 3H), 3.05 (s, 3H), 2.95 (s, 3H), 2.71-2.58 (m, 1H), 2.30-2.22 (m, 1H), 1.73-1.62 (m, 1H), 1.42 (s, 9H); MS (ESI) m/z 568.19 (M+H).

Compound 316.

$^1$H NMR (400 MHz, $CD_3OD$) δ 8.63 (s, 1H), 4.26 (s, 1H), 4.13 (s, 1H), 3.30-2.94 (m, 3H), 3.05 (s, 3H), 3.02 (s, 6H), 2.95 (s, 3H), 2.71-2.60 (m, 1H), 2.30-2.23 (m, 1H), 1.73-1.62 (m, 1H); MS (ESI) m/z 540.24 (M+H).

Compound 317.

$^1$H NMR (400 MHz, $CD_3OD$) δ 8.65 (s, 1H), 4.12 (s, 1H), 4.10 (s, 2H), 3.20-2.92 (m, 5H), 3.04 (s, 3H), 2.95 (s, 3H), 2.71-2.62 (m, 1H), 2.30-2.22 (m, 1H), 2.13-2.24 (m, 1H), 1.73-1.63 (m, 1H), 1.08 (d, J=6.7 Hz, 6H); MS (ESI) m/z 568.21 (M+H).

Compound 318.

$^1$H NMR (400 MHz, $CD_3OD$) δ 8.53 (s, 1H), 4.11 (s, 2H), 4.04 (s, 1H), 3.20-2.75 (m, 10H), 2.58-2.52 (m, 1H), 2.19-2.15 (m, 1H),1.62-1.56 (m, 1H), 0.86-0.80 (m, 4H); MS (ESI) m/z 552.1 (M+H).

Compound 319. $^1$H NMR (400 MHz, $CD_3OD$) δ 8.53 (s, 1H), 4.05 (s, 1H), 3.90 (s, 2H), 3.20-2.85 (m, 11H), 2.62-2.48 (m, 1H), 2.19-2.15 (m, 1H), 1.58-1.53 (m, 1H), 1.27 (t, J=7.2 Hz, 3H); MS (ESI) m/z 540.0 (M+H).

Compound 320.

$^1$H NMR (400 MHz, $CD_3OD$) δ 8.64 (s, 1H), 4.15 (s, 1H), 4.11 (s, 2H), 3.30-2.96 (m, 11H), 2.72-2.60 (m, 1H), 2.31-2.28 (m, 1H), 1.88-1.62 (m, 3H), 1.06 (t, J=7.2 Hz, 3H); MS (ESI) m/z 553.9 (M+H).

Compound 321.

$^1$H NMR (400 MHz, $CD_3OD$) δ 8.56 (s, 1H), 4.04 (s, 1H), 4.00 (s, 2H), 3.15-2.85 (m, 11H), 2.62-2.55 (m, 1H), 2.21-2.16 (m, 1H), 1.80-1.50 (m, 8H), 1.30-1.10 (m, 4H); MS (ESI) m/z 608.0 (M+H).

Compound 322.

$^1$H NMR (400 MHz, $CD_3OD$) δ 8.54 (s, 1H), 4.02 (s, 2H), 3.89 (s, 1H), 3.80-3.70 (m, 1H), 3.18-2.85 (m, 9H), 2.60-2.50 (m, 1H), 2.32-2.10 (m, 5H), 1.90-1.80 (m, 2H), 1.67-1.52 (m, 1H); MS (ESI) m/z 566.1 (M+H).

Compound 323.

$^1$H NMR (400 MHz, $CD_3OD$) δ 8.55 (s, 1H), 4.04 (s, 1H), 4.02 (s, 2H), 3.60-3.50 (m, 1H), 3.18-2.78 (m, 9H), 2.60-2.50 (m, 1H), 2.21-2.14 (m, 1H), 2.07 (br s, 2H), 1.76 (br s, 2H), 1.61 (br s, 5H); MS (ESI) m/z 580.1 (M+H).

Compound 324.

$^1$H NMR (400 MHz, $CD_3OD$) δ 8.63 (s, 1H), 4.12 (s, 1H), 4.10 (s, 2H), 3.25-2.93 (m, 10H), 2.69-2.59 (m, 1H), 2.28-2.20 (m, 1H), 2.15-2.12 (m, 2H), 1.96-1.85 (m, 2H), 1.75-1.65 (m, 2H), 1.45-1.31 (m, 5H); MS (ESI) m/z 594.1 (M+H).

Compound 325.

$^1$H NMR (400 MHz, $CD_3OD$) δ 8.62 (s, 1H), 4.29 (d, J=16.0 Hz, 1H), 4.18 (d, J=16.0 Hz, 1H), 4.12 (s, 1H), 3.28-2.92 (m, 14H), 2.70-2.58 (m, 1H), 2.28-2.20 (m, 1H), 1.72-1.53 (m, 1H), 1.38 (t, J=7.2 Hz, 3H); MS (ESI) m/z 554.0 (M+H).

Compound 326.

$^1$H NMR (400 MHz, $CD_3OD$) δ 8.60 (s, 1H), 4.24 (s, 2H), 4.11 (s, 1H), 3.38-3.28 (m, 4H), 3.25-2.98 (m, 9H), 2.68-2.58 (m, 1H), 2.28-2.20 (m, 1H), 1.71-1.62 (m, 1H), 1.36 (t, J=7.2 Hz, 6H); MS (ESI) m/z 568.0 (M+H).

Compound 327.

$^1$H NMR (400 MHz, $CD_3OD$) δ 8.62 (s, 1H), 4.33 (d, J=16.0 Hz, 1H), 4.21 (d, J=16.0 Hz, 1H), 4.14 (s, 1H), 3.30-2.88 (m, 14H), 2.70-2.60 (m, 1H), 2.30-2.22 (m, 1H), 1.90-1.77 (m, 2H), 1.75-1.60 (m, 1H), 1.04 (t, J=7.6 Hz, 3H); MS (ESI) m/z 568.0 (M+H).

Compound 328.

$^1$H NMR (400 MHz, $CD_3OD$) δ 8.51 (s, 1H), 4.30 (br s, 4H), 4.15 (dd, J=9.6, 18.8 Hz, 2H), 4.08 (s, 1H), 3.30-2.88 (m, 9H), 2.64-2.50 (m, 2H), 2.42 (br s, 1H), 2.24-2.15 (m, 1H), 1.70-1.50 (m, 1H); MS (ESI) m/z 552.0 (M+H).

Compound 329.

$^1$H NMR (400 MHz, $CD_3OD$) δ 8.57 (s, 1H), 4.07 (s, 1H), 4.04 (s, 2H), 3.46-3.41 (m, 1H), 3.23-2.82 (m, 9H), 2.62-2.55 (m, 1H), 2.25-2.20 (m, 1H), 1.65-1.52 (m, 1H), 1.35 (d, J=6.4 Hz, 6H); MS (ESI) m/z 554.0 (M+H). Compound 330.
$^1$H NMR (400 MHz, $CD_3OD$) δ 8.54 (s, 1H), 5.50-5.38 (m, 1H), 4.35 s, 2H), 4.04 (s, 1H), 4.00-3.71 (m, 2H), 3.50-3.28

(m, 2H), 3.29-2.82 (m, 9H), 2.60-2.24 (m, 4H), 1.66-1.50 (m, 1H); MS (ESI) m/z 584.0 (M+H).

EXAMPLE 14

Antibacterial Activity

The antibacterial activities for the compounds of the invention were studied according to the following protocols.

Minimum Inhibitory Concentration (MIC) Assay

MICs were determined according to the Clinical and Laboratory Standards Institute (CLSI) guidances (e.g., CLSI. Performance standards for antimicrobial susceptibility testing; nineteenth information supplement. CLSI document M100-S19, CLSI, 940 West Valley Road, Suite 1400, Wayne, Pa. 19087-1898, USA, 2009). Briefly, frozen bacterial strains were thawed and subcultured onto Mueller Hinton Broth (MHB) or other appropriate media (*Streptococcus* requires blood and *Haemophilus* requires hemin and NAD). Following incubation overnight, the strains were subcultured onto Mueller Hinton Agar and again incubated overnight. Colonies were observed for appropriate colony morphology and lack of contamination. Isolated colonies were selected to prepare a starting inoculum equivalent to a 0.5 McFarland standard. The starting inoculum was diluted 1:125 using MHB for further use. Test compounds were prepared by dilution in sterile water to a final concentration of 5.128 mg/mL. Antibiotics (stored frozen, thawed and used within 3 hours of thawing) and compounds were further diluted to the desired working concentrations.

The assays were run as follows. Fifty μL of MHB was added to wells 2-12 of a 96-well plate. One hundred μL of appropriately diluted antibiotics was added to well 1. Fifty μL of antibiotics was removed from well 1 and added to well 2 and the contents of well 2 mixed by pipetting up and down five times. Fifty μL of the mixture in well 2 was removed and added to well 3 and mixed as above. Serial dilutions were continued in the same manner through well 12. Fifty μL was removed from well 12 so that all contained 50 μL. Fifty μL of the working inoculum was then added to all test wells. A growth control well was prepared by adding 50 μL of working inoculum and 50 μL of MHB to an empty well. The plates were then incubated at 37° C. overnight, removed from the incubator and each well was read on a plate reading mirror. The lowest concentration (MIC) of test compound that inhibited the growth of the bacteria was recorded.

EXAMPLE

| | 1 | 2 | 3 | 4 | 5 | 6 | 7 | 8 | 9 | 10 | 11 | 12 |
|---|---|---|---|---|---|---|---|---|---|---|---|---|
| [Abt] | 32 | 16 | 8 | 4 | 2 | 1 | 0.5 | 0.25 | 0.125 | 0.06 | 0.03 | 0.015 |
| grow | − | − | − | − | − | + | + | + | + | + | + | + |

[abt] = antibiotic concentration in the well
Grow = bacterial growth (cloudiness)

Interpretation: MIC=2 μg/mL
Protocol for Determining Inoculum Concentration (Viable Count)

Ninety μl of sterile 0.9% NaCl was pipetted into wells 2-6 of a 96-well microtiter plate. Fifty 50 μl of the inoculum was pipetted into well 1. Ten μL from was removed from well 1 and added it to well 2 followed by mixing. Ten μL was removed from well two and mixed with the contents of well 3 and so on creating serial dilutions through well 6. Ten μL was removed from each well and spotted onto an appropriate agar plate. The plate was placed into an incubator overnight. The colonies in spots that contain distinct colonies were counted. Viable count was calculated by multiplying the number of colonies by the dilution factor.

| | Spot from Well | | | | | |
|---|---|---|---|---|---|---|
| | 1 | 2 | 3 | 4 | 5 | 6 |
| Dilution Factor | $10^2$ | $10^3$ | $10^4$ | $10^5$ | $10^6$ | $10^7$ |

Bacterial Strains

Fifteen bacterial strains, listed below, were examined in minimum inhibitory concentration (MIC) assays.

| ID | Organism | Source | Resistance | Comments | Gram Rx |
|---|---|---|---|---|---|
| SA100 | S. aureus | ATCC 13709 | MSSA | Smith strain | positive |
| SA101 | S. aureus | ATCC 29213 | MSSA | control | positive |
| SA158 | S. aureus | MR, SK75 | tetK (efflux) | | positive |
| SA161 | S. aureus | Micromyx, LLC | tet(M) ribosomal protection | | positive |
| EF103 | E. faecalis | ATCC 29212 | tet-I/R | control | positive |
| EF159 | E. faecalis | MR, DS160 | tet(M) (rib protect) | cip-R, ery-I | positive |
| SP106 | S. pneumoniae | ATCC 49619 | wt | control | positive |
| SP160 | S. pneumoniae | MR, 54 | tet(M) (rib protect) | pen-R, ery-R | positive |
| EC107 | E. coli | ATCC 25922 | wt | control | negative |
| EC155 | E. coli | MR, 10 | tet(A) (efflux) | | negative |
| KP109 | K. pneumoniae | ATCC 13883 | wt | | negative |
| KP153 | K. pneumoniae | MR, 1 | tet(A) (efflux) | cip-R, gen-R | negative |
| EC108 | E. cloacae | ATCC 13047 | wt | | negative |
| AB110 | A. baumanii | ATCC 19606 | wt | | negative |
| PA111 | P. aeruginosa | ATCC 27853 | wt | control | negative |

MSSA = methicillin susceptible S. aureus
wt = wild type
ATCC = American Type Culture Collection
MR = Marilyn Roberts, University of Washington
tet = tetracycline
tet-I/R = tetracycline intermediate/resistant mechanism no specified
cip = ciprofloxacin
R = resistant
gen = gentamicin
ery = erythromycin
pen = penicillin Results Values of minimum inhibition concentration (MIC) for the compounds of the invention are provided in Table 5.

TABLE 5

MIC Values for Compounds of the Invention Compared to Sancycline, Minocycline and Tigecycline.

| Cmpd | SA101 29213 | SA100 13709 | SA161 MRSA, tetM | SA158 tetK | EF103 29212 | EF159 tetM | SP106 49619 | SP160 tetM |
|---|---|---|---|---|---|---|---|---|
| 100 | B | B | B | B | B | B | B | C |
| 101 | B | B | A | B | B | B | A | B |
| 102 | B | B | B | B | B | B | B | A |
| 103 | B | B | B | B | B | B | A | A |
| 104 | B | B | B | B | B | B | A | A |
| 105 | B | B | B | B | B | B | A | A |
| 106 | A | B | B | B | A | B | A | A |
| 107 | B | B | B | B | B | B | A | A |
| 108 | B | B | C | B | B | B | B | B |
| 109 | B | B | B | B | B | B | A | A |
| 110 | C | C | C | C | B | C | C | C |
| 111 | C | C | B | B | B | B | C | B |
| 112 | B | B | B | B | B | B | A | A |
| 113 | C | C | B | B | B | B | C | B |
| 114 | B | A | B | B | B | B | A | A |
| 115 | B | B | A | B | B | B | A | A |
| 116 | B | B | B | B | B | B | C | B |
| 117 | C | B | B | B | B | B | C | B |
| 118 | C | C | B | B | B | B | B | B |
| 119 | C | C | C | C | B | B | C | B |
| 120 | B | B | B | B | B | B | A | B |
| 121 | B | B | B | C | B | B | B | B |
| 122 | C | B | B | C | B | B | B | B |
| 123 | B | B | B | B | B | B | A | B |
| 124 | B | B | B | C | B | B | B | B |
| 125 | B | B | B | B | B | B | B | B |
| 126 | B | A | B | B | A | B | A | A |
| 127 | B | B | B | B | B | B | A | A |
| 128 | B | B | B | B | A | B | A | B |
| 129 | B | B | B | B | B | B | B | B |
| 130 | B | B | B | B | B | B | A | A |
| 131 | B | B | B | B | B | B | A | A |
| 132 | B | B | B | B | A | B | A | A |
| 133 | B | B | B | B | B | B | A | A |
| 134 | C | C | B | B | B | B | C | B |
| 135 | B | B | B | B | A | B | A | A |
| 136 | B | B | B | B | A | B | A | A |
| 137 | B | B | B | B | B | B | B | B |
| 138 | B | B | B | B | B | B | B | B |
| 139 | B | B | B | B | B | B | C | C |
| 140 | C | C | B | C | B | B | C | B |
| 141 | C | C | B | B | B | B | C | B |
| 142 | B | B | B | B | B | B | A | B |
| 143 | B | B | B | B | B | B | B | B |
| 144 | C | B | B | B | B | B | B | A |
| 145 | B | B | A | B | B | A | A | A |
| 146 | A | A | A | A | A | A | A | A |
| 147 | A | B | A | B | B | A | A | A |
| 148 | B | B | A | B | B | A | A | A |
| 149 | C | C | B | B | B | B | C | B |
| 150 | B | B | B | B | B | B | B | B |
| 151 | C | B | B | B | B | B | B | B |
| 152 | B | B | B | B | B | B | A | A |
| 153 | B | B | B | B | B | B | C | B |
| 154 | A | A | A | B | A | B | A | B |
| 155 | C | C | C | C | C | C | C | C |
| 156 | C | B | B | B | B | B | B | B |
| 157 | B | B | B | B | B | B | B | B |
| 158 | C | B | B | B | B | B | B | B |
| 159 | C | B | B | B | B | B | B | B |
| 160 | B | B | B | B | B | B | B | B |
| 161 | B | B | B | B | B | B | B | B |
| 162 | B | C | B | B | B | B | B | B |
| 163 | C | B | B | B | B | B | B | B |
| 164 | C | C | C | C | B | B | C | C |
| 165 | B | B | B | C | B | B | C | B |
| 166 | B | B | B | B | B | B | B | B |
| 167 | B | B | B | B | B | B | C | B |
| 168 | B | B | B | B | B | B | B | B |
| 169 | B | A | B | B | B | B | A | B |
| 170 | B | B | B | B | B | B | A | B |
| 171 | B | B | B | B | B | B | B | B |
| 172 | C | B | B | B | B | B | B | B |

TABLE 5-continued

MIC Values for Compounds of the Invention Compared to Sancycline, Minocycline and Tigecycline.

| | | | | | | | | |
|---|---|---|---|---|---|---|---|---|
| 173 | B | B | B | B | B | B | A | B |
| 174 | B | B | B | B | B | B | B | B |
| 175 | B | B | B | C | B | B | B | B |
| 176 | B | B | B | B | B | B | B | B |
| 177 | C | B | B | B | B | B | C | B |
| 178 | C | C | C | C | C | C | C | C |
| 179 | C | C | B | B | B | B | B | B |
| 180 | C | C | C | C | C | C | C | C |
| 181 | C | C | C | C | C | C | C | C |
| 182 | C | C | C | C | C | C | C | C |
| 183 | C | C | C | C | C | C | C | C |
| 184 | C | C | C | C | C | C | C | C |
| 185 | C | C | C | C | C | C | C | C |
| 186 | C | C | C | C | C | C | C | C |
| 187 | B | B | B | B | B | B | C | B |
| 188 | C | C | C | C | C | C | C | C |
| 189 | C | C | C | C | C | C | C | C |
| 190 | C | C | C | C | C | C | C | B |
| 191 | C | B | B | B | B | B | B | B |
| 192 | B | B | B | B | B | B | B | B |
| 193 | C | C | B | B | B | B | C | B |
| 194 | C | C | B | B | B | B | C | B |
| 195 | C | B | B | B | B | B | B | B |
| 196 | C | C | C | C | C | B | C | B |
| 197 | B | B | B | B | B | B | B | B |
| 198 | B | B | B | B | B | B | C | B |
| 199 | C | C | C | C | B | C | C | B |
| 200 | C | C | C | C | C | C | C | C |
| 201 | C | C | C | C | B | C | C | B |
| 202 | C | C | C | B | B | B | C | B |
| 203 | C | C | B | B | B | B | C | B |
| 204 | C | C | C | C | B | C | C | B |
| 205 | C | C | C | C | C | C | C | C |
| 206 | C | C | C | C | C | C | C | C |
| 207 | B | B | B | B | B | B | B | B |
| 208 | C | C | C | C | C | C | C | C |
| 209 | A | A | B | B | B | B | B | B |
| 210 | A | A | A | B | A | A | A | A |
| 211 | C | B | B | C | B | B | C | B |
| 212 | A | A | B | B | A | B | A | B |
| 213 | B | B | B | B | A | B | A | A |
| 214 | B | B | B | B | B | B | B | B |
| 215 | B | B | B | B | B | B | B | B |
| 216 | C | C | B | B | B | B | C | B |
| 217 | B | B | B | B | B | B | A | A |
| 218 | A | A | A | B | A | A | A | A |
| 219 | B | B | B | B | B | B | C | B |
| 220 | A | A | A | B | A | A | A | A |
| 221 | B | B | B | B | B | B | A | A |
| 222 | B | B | C | B | B | B | A | B |
| 223 | B | B | B | B | B | B | B | B |
| 224 | A | A | B | B | A | A | A | A |
| 225 | B | B | B | B | B | B | B | B |
| 226 | B | B | B | B | B | B | A | A |
| 227 | B | B | B | B | B | B | B | B |
| 228 | C | C | C | C | B | C | B | B |
| 229 | C | C | C | C | C | C | C | C |
| 230 | B | B | B | B | A | B | A | A |
| 231 | B | B | B | B | B | B | C | B |
| 232 | B | B | B | B | B | B | B | B |
| 233 | B | B | B | B | B | B | B | B |
| 234 | B | B | B | B | B | B | A | B |
| 235 | B | B | B | B | B | B | B | B |
| 236 | B | B | B | B | B | B | B | B |
| 237 | B | B | B | B | B | B | B | B |
| 238 | B | B | B | B | B | B | C | C |
| 239 | B | B | B | B | B | B | A | B |
| 240 | B | B | B | B | B | B | B | B |
| 241 | B | B | B | B | B | B | B | B |
| 242 | B | B | B | B | B | B | B | B |
| 243 | B | A | B | B | B | B | B | B |
| 244 | A | A | A | B | A | A | A | A |
| 245 | B | B | B | B | A | B | A | A |
| 246 | B | B | B | B | B | B | A | A |
| 247 | B | B | A | B | B | B | C | C |
| 248 | B | B | A | B | B | B | C | C |
| 249 | B | C | B | B | C | B | C | C |

TABLE 5-continued

MIC Values for Compounds of the Invention Compared to Sancycline, Minocycline and Tigecycline.

| | | | | | | | | |
|---|---|---|---|---|---|---|---|---|
| 250 | B | B | A | B | B | B | C | C |
| 251 | B | A | A | B | B | B | C | C |
| 252 | B | B | A | B | B | B | C | C |
| 253 | B | B | B | B | B | B | C | C |
| 254 | B | B | B | C | B | B | C | B |
| 255 | C | B | B | C | B | B | C | B |
| 256 | B | B | B | B | B | B | C | C |
| 257 | B | A | B | B | A | A | A | A |
| 258 | A | A | A | B | A | A | A | A |
| 259 | B | B | B | B | B | A | B | A |
| 260 | B | A | B | B | A | A | A | B |
| 261 | A | A | B | B | A | A | A | A |
| 262 | C | C | C | C | C | C | C | C |
| 263 | B | B | B | B | B | B | A | A |
| 264 | B | B | B | B | B | B | C | C |
| 265 | C | B | B | B | B | B | C | C |
| 266 | B | B | B | B | B | B | B | B |
| 267 | B | B | B | B | B | B | B | B |
| 268 | C | C | B | B | B | B | C | C |
| 269 | B | B | B | B | B | B | C | B |
| 270 | A | A | B | B | B | B | A | B |
| 271 | B | B | B | B | B | B | A | A |
| 272 | B | B | B | B | B | B | A | A |
| 273 | B | B | B | B | B | B | A | A |
| 274 | C | B | B | B | B | B | B | B |
| 275 | B | B | B | B | B | B | A | B |
| 276 | C | B | B | B | B | B | B | C |
| 277 | C | B | B | B | B | B | B | A |
| 278 | C | C | B | C | B | B | A | B |
| 279 | B | B | B | B | A | B | A | A |
| 280 | C | B | B | C | B | B | B | B |
| 281 | B | B | B | B | B | B | B | B |
| 282 | B | A | B | B | B | B | B | B |
| 283 | B | B | B | B | B | B | B | B |
| 284 | C | B | B | C | B | B | C | B |
| 285 | B | B | B | B | B | B | B | B |
| 286 | A | A | B | B | A | B | B | B |
| 287 | B | B | B | B | B | B | C | B |
| 288 | C | B | B | B | B | B | B | B |
| 289 | B | B | B | B | B | B | B | B |
| 290 | B | B | B | B | B | B | B | B |
| 291 | B | B | B | B | B | B | A | B |
| 292 | A | A | B | B | A | B | A | A |
| 293 | B | A | B | B | A | B | A | A |
| 294 | A | A | B | C | B | B | A | B |
| 295 | A | A | B | B | A | A | B | B |
| 296 | B | B | B | B | B | A | A | B |
| 297 | B | B | B | B | B | B | B | B |
| 298 | B | B | B | B | B | B | C | B |
| 299 | B | A | B | B | A | B | A | A |
| 300 | C | B | B | C | B | B | C | B |
| 301 | B | B | B | B | B | B | B | B |
| 302 | B | A | B | B | A | B | A | A |
| 303 | B | B | B | C | B | B | A | B |
| 304 | C | B | B | B | B | B | C | C |
| 305 | C | C | B | B | B | B | C | C |
| 306 | C | C | C | C | C | C | C | B |
| 307 | B | B | B | B | B | B | A | B |
| 308 | B | B | B | B | A | A | A | A |
| 309 | A | A | A | B | A | A | A | A |
| 310 | B | B | B | B | B | B | B | B |
| 311 | A | B | A | B | A | A | A | A |
| 312 | A | A | B | B | B | B | A | B |
| 313 | B | B | C | C | B | C | C | C |
| 314 | C | B | B | B | B | B | B | B |
| 315 | C | C | B | B | B | B | B | B |
| 316 | C | B | B | C | B | B | B | B |
| 317 | C | B | B | C | B | B | B | B |
| 318 | C | C | C | C | B | C | B | B |
| 319 | C | C | C | C | B | B | C | B |
| 320 | C | C | C | C | B | B | B | B |
| 321 | C | C | C | C | B | B | B | B |
| 322 | C | C | C | C | B | B | B | B |
| 323 | B | B | B | B | B | B | B | B |
| 324 | C | B | B | B | B | B | B | B |
| 325 | C | B | C | B | B | B | A | B |
| 326 | C | B | C | B | B | B | B | B |

TABLE 5-continued

MIC Values for Compounds of the Invention Compared to Sancycline, Minocycline and Tigecycline.

| | | | | | | | | |
|---|---|---|---|---|---|---|---|---|
| 327 | C | B | B | B | B | B | B | B |
| 328 | C | C | B | C | B | B | B | B |
| 329 | C | C | C | C | B | B | C | B |
| 330 | C | C | C | C | C | C | C | C |
| 331 | C | B | B | B | B | B | B | B |
| 332 | C | B | C | B | B | B | A | B |
| 333 | C | C | C | C | C | C | C | C |
| 334 | B | B | C | B | B | B | A | B |
| 335 | B | B | B | B | B | B | A | B |
| Minocycline | 0.06 | 0.06 | 8 | 0.03 | 1 | 16 | 0.016 | 2 |
| Sancycline | 0.5 | 1 | NT | 4 | 8 | 8 | 0.25 | 8 |
| Tigecycline | 0.06 | 0.06 | 0.125 | 0.06 | 0.03 | 0.06 | 0.016 | 0.016 |

| Cmpd | EC107 25922 | EC155 tetA | AB110 19606 | PA111 27853 | EC108 13047 | KP109 13883 | KP153 tetA |
|---|---|---|---|---|---|---|---|
| 100 | B | B | B | C | B | B | B |
| 101 | B | B | C | B | B | B | B |
| 102 | B | B | C | A | B | B | B |
| 103 | B | B | B | C | B | B | B |
| 104 | B | B | B | C | B | B | B |
| 105 | B | B | B | B | B | B | B |
| 106 | B | B | B | B | B | B | B |
| 107 | B | B | C | B | B | B | B |
| 108 | B | B | C | C | B | B | B |
| 109 | B | B | C | C | B | B | B |
| 110 | C | C | C | C | C | C | C |
| 111 | C | C | C | C | C | C | C |
| 112 | B | B | C | C | B | B | B |
| 113 | C | C | C | C | C | C | C |
| 114 | B | B | C | C | B | B | B |
| 115 | B | B | B | C | B | B | B |
| 116 | C | C | C | C | C | C | C |
| 117 | C | C | C | C | C | C | C |
| 118 | B | B | C | C | C | B | B |
| 119 | C | C | C | C | C | C | C |
| 120 | B | B | C | A | B | B | B |
| 121 | B | C | C | C | B | B | C |
| 122 | C | C | C | C | C | C | C |
| 123 | B | B | C | C | B | B | B |
| 124 | B | B | C | C | B | B | B |
| 125 | B | A | A | B | B | B | B |
| 126 | B | B | C | B | B | B | B |
| 127 | B | B | B | C | B | B | B |
| 128 | B | B | A | C | B | B | B |
| 129 | B | B | B | C | B | B | B |
| 130 | B | B | A | C | B | B | B |
| 131 | B | B | C | C | B | B | B |
| 132 | B | B | B | C | B | B | B |
| 133 | B | B | B | C | B | B | B |
| 134 | C | C | C | C | C | C | C |
| 135 | B | B | A | C | B | B | B |
| 136 | B | B | B | C | B | B | B |
| 137 | B | B | B | C | B | B | B |
| 138 | B | B | B | C | C | B | B |
| 139 | C | C | C | C | C | C | C |
| 140 | C | C | C | C | C | C | C |
| 141 | B | C | C | C | C | C | C |
| 142 | B | B | C | B | B | B | B |
| 143 | B | B | C | C | B | B | B |
| 144 | B | B | C | C | B | B | B |
| 145 | B | B | B | B | B | B | B |
| 146 | B | B | A | B | A | B | B |
| 147 | B | B | B | B | A | B | B |
| 148 | B | B | A | C | B | B | B |
| 149 | B | B | C | C | B | B | B |
| 150 | B | C | C | C | B | B | B |
| 151 | B | B | C | C | B | B | B |
| 152 | B | B | C | C | B | B | B |
| 153 | B | C | C | C | C | C | C |
| 154 | B | C | C | C | B | B | C |
| 155 | C | C | C | C | C | C | C |
| 156 | C | C | C | C | C | C | C |
| 157 | C | C | C | C | C | C | C |
| 158 | B | C | C | C | C | C | C |
| 159 | B | C | C | C | C | C | C |
| 160 | C | C | C | C | C | C | C |

TABLE 5-continued

MIC Values for Compounds of the Invention Compared to Sancycline, Minocycline and Tigecycline.

| | | | | | | | |
|---|---|---|---|---|---|---|---|
| 161 | C | C | C | C | C | C | C |
| 162 | C | C | C | C | C | C | C |
| 163 | B | C | C | C | C | C | C |
| 164 | C | C | C | C | C | C | C |
| 165 | C | C | C | C | C | C | C |
| 166 | B | C | C | C | C | B | C |
| 167 | B | C | C | C | C | C | C |
| 168 | B | C | C | C | C | C | C |
| 169 | B | C | C | C | B | B | C |
| 170 | B | C | C | C | C | C | C |
| 171 | B | C | C | C | C | C | C |
| 172 | C | C | C | C | C | C | C |
| 173 | B | C | C | C | C | C | C |
| 174 | B | C | C | C | C | C | C |
| 175 | B | C | C | C | B | B | C |
| 176 | C | C | C | C | C | C | C |
| 177 | C | C | C | C | C | C | C |
| 178 | C | C | C | C | C | C | C |
| 179 | B | B | C | C | B | B | B |
| 180 | C | C | C | C | C | C | C |
| 181 | C | C | C | C | C | C | C |
| 182 | C | C | C | C | C | C | C |
| 183 | C | C | C | C | C | C | C |
| 184 | C | C | C | C | C | C | C |
| 185 | C | C | C | C | C | C | C |
| 186 | C | C | C | C | C | C | C |
| 187 | C | C | C | C | C | C | C |
| 188 | C | C | C | C | C | C | C |
| 189 | C | C | C | C | C | C | C |
| 190 | C | C | C | C | C | C | C |
| 191 | B | C | C | C | C | B | B |
| 192 | B | B | C | C | B | B | B |
| 193 | B | B | C | C | C | C | B |
| 194 | B | B | C | C | C | B | B |
| 195 | B | C | C | C | B | B | C |
| 196 | C | C | C | C | C | C | C |
| 197 | B | C | C | C | C | B | C |
| 198 | C | C | C | C | C | C | C |
| 199 | C | C | C | C | C | C | C |
| 200 | C | C | C | C | C | C | C |
| 201 | C | C | C | C | C | C | C |
| 202 | C | C | C | C | C | C | C |
| 203 | C | C | C | C | C | C | C |
| 204 | C | C | C | C | C | C | C |
| 205 | C | C | C | C | C | C | C |
| 206 | C | C | C | C | C | C | C |
| 207 | B | B | B | C | C | B | B |
| 208 | C | C | C | C | C | C | C |
| 209 | B | B | B | B | B | B | B |
| 210 | B | B | B | B | B | B | B |
| 211 | C | C | C | C | C | C | C |
| 212 | B | C | B | C | B | B | C |
| 213 | B | B | A | A | B | B | B |
| 214 | B | B | A | C | B | B | B |
| 215 | B | B | B | C | B | B | B |
| 216 | B | B | C | C | C | B | B |
| 217 | B | B | B | B | B | B | B |
| 218 | B | B | B | B | B | B | B |
| 219 | C | C | C | C | C | C | C |
| 220 | B | B | A | B | B | B | B |
| 221 | B | C | B | C | B | B | C |
| 222 | B | C | C | C | C | B | C |
| 223 | B | B | B | C | B | B | B |
| 224 | B | B | B | B | B | B | B |
| 225 | B | B | B | C | B | B | B |
| 226 | B | B | C | C | B | B | B |
| 227 | B | C | C | C | C | C | C |
| 228 | C | C | C | C | C | C | C |
| 229 | C | C | C | C | C | C | C |
| 230 | B | B | B | C | B | B | B |
| 231 | B | B | C | C | B | B | B |
| 232 | B | B | B | C | B | B | B |
| 233 | B | B | B | C | B | B | B |
| 234 | B | B | B | C | B | B | B |
| 235 | C | C | C | C | C | C | C |
| 236 | B | B | B | C | B | B | B |
| 237 | B | B | B | C | B | B | B |

TABLE 5-continued

MIC Values for Compounds of the Invention Compared to Sancycline, Minocycline and Tigecycline.

| | | | | | | | |
|---|---|---|---|---|---|---|---|
| 238 | C | C | C | C | C | C | C |
| 239 | B | C | B | C | B | B | C |
| 240 | B | C | C | C | C | C | C |
| 241 | B | C | C | C | C | C | C |
| 242 | B | B | B | C | C | B | B |
| 243 | B | B | A | B | B | B | B |
| 244 | B | B | A | B | B | B | NT |
| 245 | B | B | B | C | B | B | B |
| 246 | B | B | B | C | B | B | B |
| 247 | C | C | C | C | C | C | C |
| 248 | C | C | C | C | C | C | C |
| 249 | C | C | C | C | C | C | C |
| 250 | C | C | C | C | C | C | C |
| 251 | C | C | C | C | C | C | C |
| 252 | C | C | C | C | C | C | C |
| 253 | C | C | C | C | C | C | C |
| 254 | C | C | C | C | C | C | C |
| 255 | C | C | C | C | C | C | C |
| 256 | C | C | C | C | C | C | C |
| 257 | B | B | C | B | B | B | B |
| 258 | A | B | A | B | B | B | B |
| 259 | B | B | B | C | B | B | B |
| 260 | B | B | C | A | B | B | B |
| 261 | B | B | C | B | B | B | B |
| 262 | C | C | C | C | C | C | C |
| 263 | B | B | A | C | B | B | B |
| 264 | C | C | C | C | C | C | C |
| 265 | C | C | C | C | C | C | C |
| 266 | B | C | C | C | C | B | C |
| 267 | B | C | C | C | C | C | C |
| 268 | C | C | C | C | C | C | C |
| 269 | B | B | B | C | C | B | B |
| 270 | B | B | B | B | B | B | B |
| 271 | B | B | C | C | B | B | B |
| 272 | B | B | C | C | B | B | B |
| 273 | B | B | C | C | B | B | B |
| 274 | B | C | C | C | B | B | C |
| 275 | B | B | C | B | B | B | B |
| 276 | B | B | C | C | B | B | B |
| 277 | B | B | C | B | B | B | B |
| 278 | B | B | C | C | C | B | B |
| 279 | B | B | C | B | B | B | B |
| 280 | B | C | C | C | C | B | C |
| 281 | B | B | A | C | B | B | B |
| 282 | B | B | B | C | B | B | B |
| 283 | B | B | A | C | B | B | B |
| 284 | C | C | C | C | C | C | C |
| 285 | B | C | C | C | C | B | C |
| 286 | B | B | B | B | B | B | B |
| 287 | B | B | B | C | B | B | B |
| 288 | C | C | C | C | C | C | C |
| 289 | B | B | B | C | B | B | B |
| 290 | B | C | C | C | C | B | C |
| 291 | B | C | C | C | C | B | C |
| 292 | B | B | B | B | B | B | B |
| 293 | B | B | A | B | B | B | B |
| 294 | B | B | C | C | B | B | C |
| 295 | B | B | A | B | B | B | B |
| 296 | B | B | B | C | B | B | B |
| 297 | B | B | B | C | B | B | B |
| 298 | B | C | C | C | C | C | C |
| 299 | B | C | C | A | B | B | C |
| 300 | B | C | C | C | C | C | C |
| 301 | B | B | B | C | B | B | B |
| 302 | B | C | C | C | B | B | C |
| 303 | B | C | C | C | C | B | C |
| 304 | C | C | C | C | C | C | C |
| 305 | C | C | C | C | C | C | C |
| 306 | C | C | C | C | C | C | C |
| 307 | B | C | C | B | B | B | C |
| 308 | B | B | C | B | B | B | B |
| 309 | B | B | B | C | B | B | B |
| 310 | B | C | C | C | B | B | C |
| 311 | B | B | A | C | B | B | B |
| 312 | B | C | A | B | B | B | B |
| 313 | B | C | C | C | B | B | C |
| 314 | B | C | C | C | B | C | C |

TABLE 5-continued

MIC Values for Compounds of the Invention Compared to Sancycline, Minocycline and Tigecycline.

| | | | | | | | |
|---|---|---|---|---|---|---|---|
| 315 | B | C | C | C | C | C | C |
| 316 | B | C | C | C | C | C | C |
| 317 | B | C | C | C | B | C | C |
| 318 | C | C | C | C | C | C | C |
| 319 | C | C | C | C | C | C | C |
| 320 | B | C | C | C | C | C | C |
| 321 | B | B | C | C | C | B | B |
| 322 | B | C | C | C | C | C | C |
| 323 | B | C | C | C | B | B | C |
| 324 | B | C | C | C | C | C | C |
| 325 | B | C | C | C | B | B | C |
| 326 | B | C | C | C | B | B | C |
| 327 | B | C | C | C | B | B | C |
| 328 | B | C | C | C | C | C | C |
| 329 | C | C | C | C | C | C | C |
| 330 | C | C | C | C | C | C | C |
| 331 | B | C | C | C | C | C | C |
| 332 | B | C | C | C | C | B | B |
| 333 | C | C | C | C | C | C | C |
| 334 | B | C | C | C | B | B | C |
| 335 | B | C | C | C | B | B | C |
| Minocycline | 0.5 | 8 | 0.06 | 16 | 2 | 1 | 8 |
| Sancycline | 8 | 32 | 0.25 | >32 | 8 | 8 | 32 |
| Tigecycline | 0.03 | 0.5 | 0.25 | 8 | 0.25 | 0.125 | 1 |

A = lower than or equal to lowest MIC among three control compounds;
B = greater than lowest MIC among three control compounds, but lower than highest MIC among three control compounds;
C = greater than MIC of all three control compounds.

EXAMPLE 15

In Vivo Activities

Murine Systemic Infection Model with Intraperitoneal Challenge of *S. aureus*

In the model, CD-1 female mice (18-20 grams) were injected intraperitoneally with *S. aureus* ATCC 13709 (Smith) ($1-2\times10^6$/mouse) mixed with 5% hog gastric mucin, a bacterial inoculum previously established through virulence studies required to achieve 90-100% lethality within 24-48 hours. Typically, six mice were treated intravenously per dose group one hour post-challenge with either compound 101, compound 105, compound 145, compound 153, compound 166, and compound 218, tetracycline or tigecycline at doses ranging from 0.05-10 mg/kg. After 48 hours, percent survival was calculated and the dose (mg/kg) effecting 50% survival, the protective dose 50% ($PD_{50}$), was reported along as calculated by Probit analysis.

Results

The $PD_{50}$ values of compound 101, compound 105, compound 145, compound 153, compound 166, and compound 218 and comparators tigecycline and tetracycline in the *S. aureus* ATCC 13709 mouse septicemia model are described in Table 6.

TABLE 6

| Cmpd # | $PD_{50}$ mg/kg, i.v., SA Smith Septicemia |
|---|---|
| 218 | 1.4 |
| 153 | >10 |
| 166 | 4.3 |
| 145 | 0.35 |
| 101 | 0.36 |
| 105 | 0.25 |
| Tigecycline | 0.97 |
| Tetracycline | 1.0 |

What is claimed is:

1. A compound of Structural Formula I:

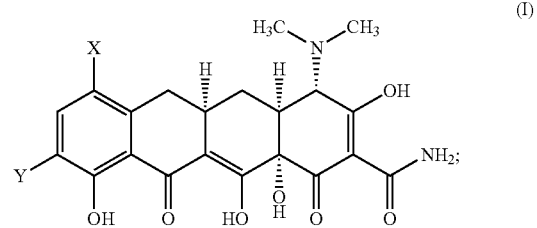

or a pharmaceutically acceptable salt thereof, wherein:
X is —$CF_3$;
Y is selected from —NH—C(O)—$(CH_2)_{1-4}$—$N(R_2)(R_3)$, —N(H)—C(O)-heterocyclyl, —N(H)—C(O)-carbocyclyl, NH—$S(O)_2$—($C_1$-$C_6$) alkyl, wherein:
   each $R^2$ is independently selected from hydrogen, and ($C_1$-$C_3$)alkyl;
   each $R^3$ is independently selected from hydrogen, ($C_1$-$C_6$)alkyl, —($C_0$-$C_6$) alkylene-carbocyclyl, —($C_0$-$C_6$) alkylene-heterocyclyl;
   or $R^2$ and $R^3$, taken together with the nitrogen atom to which they are bound form a heterocyclyl, wherein the heterocyclyl optionally comprises 1 to 4 additional heteroatoms independently selected from N and S;
wherein:
   each carbocyclyl is independently a 3-12 membered saturated or unsaturated aliphatic ring or a 6-12 membered aromatic ring;
   each heterocyclyl is independently a 4-12 membered saturated or unsaturated aliphatic ring containing 1, 2, 3, 4 or 5 heteroatoms independently selected from N, O or S or a 5-12 membered heteroaryl containing 1, 2, 3 or 4 heteroatoms independently selected from N, O, and S;

each carbocyclyl or heterocyclyl is optionally and independently substituted with one or more substituents independently selected from chloro, fluoro, $(C_1-C_4)$alkyl, —OH, —O—$(C_1-C_4)$alkyl, fluoro-substituted-$(C_1-C_4)$alkyl, —C(O)—$(C_1-C_4)$alkyl, —C(O)-(fluoro-substituted-$(C_1-C_4)$alkyl, and —N($R^G$)($R^G$);

each alkyl is optionally and independently substituted with one or more substituents independently selected from fluoro, chloro, —O—$(C_1-C_4)$alkyl, and fluoro-substituted-$(C_1-C_4)$alkyl; and each $R^G$ is hydrogen or $(C_1-C_4)$alkyl, wherein each alkyl in the group represented by $R^G$ is optionally and independently substituted with one or more substituents independently selected from —$(C_1-C_4)$alkyl, $(C_3-C_6)$ cycloalkyl, halo, —OH, —O—$(C_1-C_4)$alkyl, and —$(C_1-C_4)$alkylene-O—$(C_1-C_4)$alkyl.

2. The compound of claim 1, wherein:
Y is selected from —NH—C(O)—CH$_2$—N($R^2$)($R^3$),

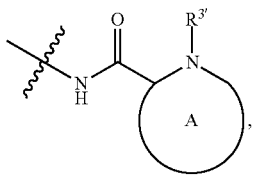

—NH—C(O)-phenyl, —NH—C(O)-thienyl and —NH—S(O)$_2$—$(C_1-C_6)$alkyl, wherein:
each $R^2$ is independently selected from hydrogen, and $(C_1-C_2)$alkyl; and
each $R^3$ is independently selected from hydrogen, $(C_1-C_6)$alkyl, and —$(C_0-C_1)$alkylene-cycloalkyl; or
$R^2$ and $R^3$ taken together with the nitrogen atom to which they are bound form a saturated heterocyclyl;
ring A represents a 4-7 membered saturated heterocyclyl;
$R^{3'}$ is hydrogen or methyl;
each cycloalkyl, phenyl or heterocyclyl is optionally and independently substituted with one or more substituents independently selected from fluoro, $(C_1-C_4)$alkyl, —O—$(C_1-C_4)$alkyl, fluoro-substituted-$(C_1-C_4)$alkyl, and —N($R^2$)($R^2$); and
each alkyl is optionally and independently substituted with one or more substituents independently selected from fluoro, —O—$(C_1-C_4)$alkyl, and fluoro-substituted-$(C_1-C_4)$alkyl.

3. The compound of claim 1, wherein:
Y is selected from —NH—C(O)—CH$_2$—N($R^2$)($R^3$), and

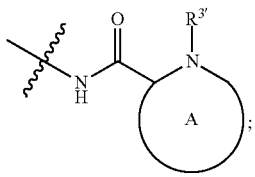

each $R^2$ is independently selected from hydrogen and —CH$_3$;
each $R^3$ is independently selected from $(C_1-C_6)$alkyl and —$(C_0-C_1)$alkylene-carbocyclyl, wherein the $(C_1-C_6)$ alkyl is optionally substituted with fluoro or —OCH$_3$; or $R^2$ and $R^3$, taken together with the nitrogen atom to which they are bound form a saturated heterocyclyl optionally substituted with fluoro or —OCH$_3$; and ring A represents a 4-7 membered saturated heterocyclyl;
$R^{3'}$ is hydrogen or methyl;
each carbocyclyl or heterocyclyl is optionally and independently substituted with one or more substituents independently selected from fluoro, $(C_1-C_4)$alkyl, —O—$(C_1-C_4)$alkyl, fluoro-substituted-$(C_1-C_4)$alkyl, and —N($R^G$)($R^G$); and each alkyl is optionally and independently substituted with one or more substituents independently selected from fluoro, —O—$(C_1-C_4)$alkyl, and fluoro-substituted-$(C_1-C_4)$alkyl.

4. The compound of claim 1, or a pharmaceutically acceptable salt thereof, wherein:
Y is

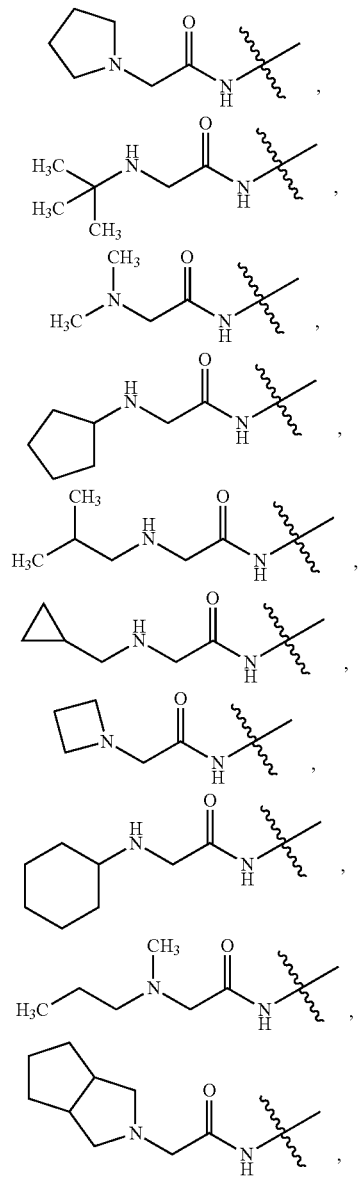

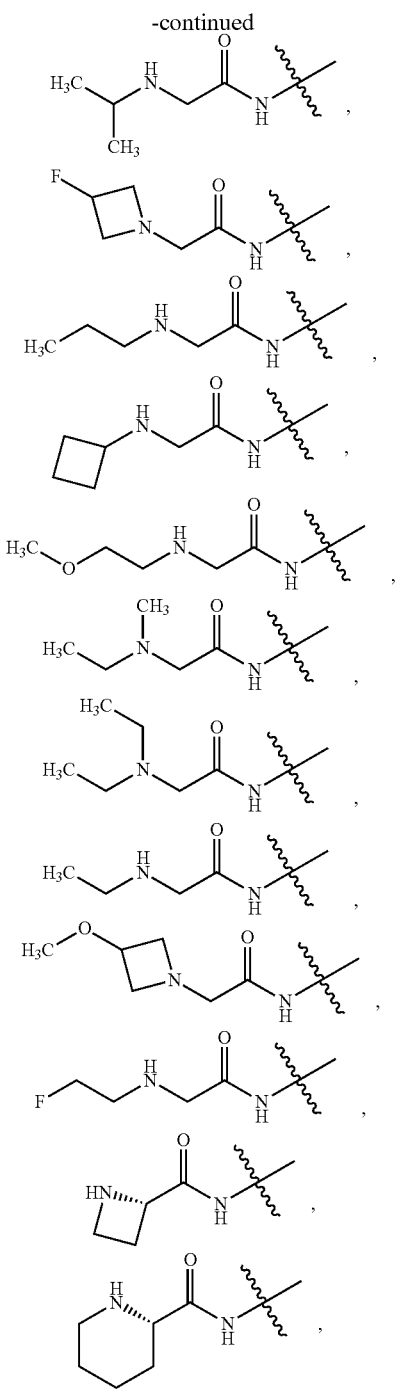

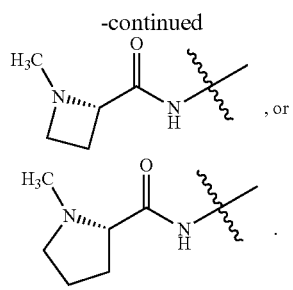

5. A pharmaceutical composition, comprising a pharmaceutically acceptable carrier or diluent and a compound of claim 1, or a pharmaceutically acceptable salt thereof.

6. A method for treating a bacterial infection or colonization in a subject, comprising administering to the subject an effective amount of a compound of claim 1, or a pharmaceutically acceptable salt thereof.

7. The method of claim 6, wherein the infection is caused by a Gram-positive bacteria.

8. The method of claim 7, wherein the Gram-positive bacteria is selected from the group consisting of *Staphylococcus* spp., *Streptococcus* spp., *Propionibacterium* spp., *Enterococcus* spp., *Bacillus* spp., *Corynebacterium* spp., *Nocardia* spp., *Clostridium* spp., *Actinobacteria* spp., and *Listeria* spp.

9. The method of claim 6, wherein the infection is caused by a Gram-negative bacteria.

10. The method of claim 9, wherein the Gram-negative bacteria is selected form the group consisting of Enterobactericeae, Bacteroidaceae, Vibrionaceae, Pasteurellae, Pseudomonadaceae, Neisseriaceae, Rickettsiae, Moraxellaceae any species of *Proteeae, Acinetobacter* spp., *Helicobacter* spp., and *Campylobacter* spp.

11. The method of claim 6, wherein the infection is caused by a bacteria selected from the group consisting of rickettsiae, chlamydiae, *Legionella* spp. and *Mycoplasma* spp.

12. The method of claim 6, wherein the infection is caused by more than one bacteria.

13. The method of claim 6, wherein the infection is caused by a bacteria resistant to one or more antibiotics.

14. The method of claim 13, wherein the infection is caused by a bacteria resistant to tetracycline.

15. The method of claim 13, wherein the infection is caused by a bacteria resistant to methicillin.

16. The method of claim 13, wherein the infection is caused by a bacteria resistant to vancomycin.

17. The method of claim 13 wherein the infection is caused by a bacteria resistant to a quinolone or fluoroquinolone.

18. The method of claim 13 wherein the infection is caused by a bacteria resistant to tigecycline.

* * * * *